(12) United States Patent
Litman et al.

(10) Patent No.: US 7,038,030 B2
(45) Date of Patent: May 2, 2006

(54) BIVM (BASIC, IMMUNOGLOBULIN-LIKE VARIABLE MOTIF-CONTAINING) GENE, TRANSCRIPTIONAL PRODUCTS, AND USES THEREOF

(75) Inventors: Gary W. Litman, Gulfport, FL (US); Noel A. Hawke, Durham, NC (US); Jeffrey A. Yoder, St. Petersburg, FL (US); Donna D. Eason, Bradenton, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/417,476

(22) Filed: Apr. 16, 2003

(65) Prior Publication Data

US 2004/0002102 A1    Jan. 1, 2004

Related U.S. Application Data

(60) Provisional application No. 60/373,146, filed on Apr. 16, 2002.

(51) Int. Cl.
*C07H 21/02*    (2006.01)
*C07H 21/04*    (2006.01)

(52) U.S. Cl. .................. 536/23.1; 536/24.3; 536/24.33; 424/265.1

(58) Field of Classification Search ............... 536/23.1, 536/24.3, 24.33; 424/265.1; 435/4
See application file for complete search history.

(56) References Cited

U.S. PATENT DOCUMENTS 5,645,995 A * 7/1997 Kieback ................... 435/6
6,639,063 B1 * 10/2003 Edwards et al. ........... 536/23.5

OTHER PUBLICATIONS

Christian et al., An Evaluation of the Assembly of an Approximately 15-Mb Region on Human Chromosome 13q32-q33 Linked to Bipolar Disorder and Schizophrenia, Genomics 79(5):635-658 (May 2002).*
Image 785450; GenBank AA449273.
Hawke, N.A. et al. "Expanding our Understanding of Immunoglobulin, T-cell Antigen Receptor, and Novel Immune-Type Receptor Genes: a Subset of the Immunoglobulin Gene Superfamily" *Immunogenetics*, 1999, 50:124-133.
Abbaszadega, M. "Advanced Detection of Viruses and Protozoan Parasites in Water" *Rev. Biol. Biotech.*, 2001, 1(2):21-26.
Yoder and Litman, GenBank AF411393.
McArthur, A.G. "The *Giardia* Genome Project Database" *FEMS Microbiol. Lett.*, 2000, 189:271-273.

* cited by examiner

*Primary Examiner*—James Housel
*Assistant Examiner*—Stacy B. Chen
(74) *Attorney, Agent, or Firm*—Saliwanchik, Lloyd & Saliwanchik

(57) ABSTRACT

The subject invention provides polynucleotide sequences, designated BIVM, and transcriptional/translational products obtained from the polynucleotide sequences of the invention. The subject invention also provides polynucleotide and polypeptide sequences provided by SEQ ID NOs:1–28. Also provided are methods of detecting the presence of BIVM nucleic acids or polypeptides in samples suspected of containing BIVM genes, BIVM transcriptional products, or BIVM translational products. These methods are also useful for the detection of BIVM orthologs. Other embodiments provide polypeptide and/or nucleic acid vaccines for the induction of an immune response to in an individual. Kits for detecting the presence of BIVM genes, orthologs thereof, BIVM polypeptides, or BIVM transcriptional products are also provided.

15 Claims, 15 Drawing Sheets

FIG. 1A

Figures 2, 3A:
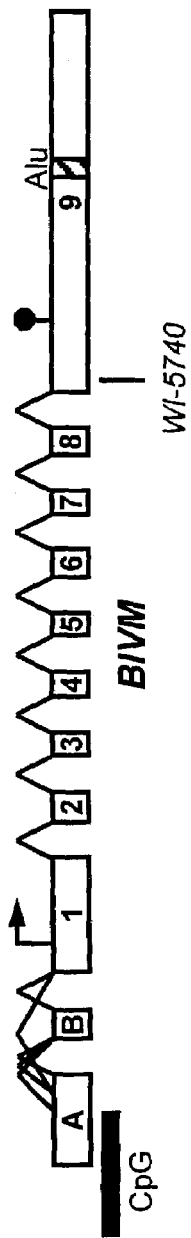

```
AGTAACGCCTTCTCCAAGTGGATGGCGGGGTGGACACGCGTCCCGGCGCCCCGGGCTCCC   60
TGGGATATGTAGTTCGCGACAGGACGAGCGGAAATACTGCCAGGATTTTACCACCTCTCG  120
CCCATTTATTTACTTCTCGGTCACCGCTTTCGGGGGACAGATAAACACCACAGATGCCCA  180
TCAAAGGGGCGCACGGGTCTGGAGGCGCAGCTCAGGTTTTTGCGTTGGTCACCCTGCCCT  240
CCGCACGTGGAGAGGGCAGGCATAAAGCACCTTGAAAGGAAGGTGCTGTCAATGCTATCC  300
GACGACCTGTCGCCGGGCACCGCAGCATCCTCGCTCGCTCCGATGGGACGAGGGACGCCG  360
GCCCCAGGGTAACAGGAGGCGCCTCGCCGGCCGCGCGCTGGATGCTGTGATCCAGGTCCG  420
GAGCCGGGTTCCGCCGCGGCCGCAGCGACCCGACCCCACCCGACAGGCCAGAGGAATCAG  480
TTTAGACTTGAAATTCAGTTTTTTCCTGAAACTGATCAGAAGTTAGTGACACCTTGATTGG  540
ATCCGTTTTTCTGTCAGGAGCTCATTTTGCAGCTCTCAAGCTTTTATAGCATGCTGTAAA   600
CAATTGTCAAAGTTGTTTATCAAGAAACAGATAGAGTTGCAACTTGTTTCTAGTAATAGA  660
AACTTTTACACTGCATTCAATGCCTAACGTTGCAGAAACAGAAAGGTCAAATGATTCTGG  720
```

```
  1                      M  P  N  V  A  E  T  E  R  S  N  D  S  G
     AAATGGTGAGCACAAATCTGAGAGAAAGTCACCTGAAGAGAATCTACAAGGTGCTGTAAA   780
 15   N  E  H  K  S  E  R  K  S  P  E  E  N  L  Q  G  A  V  K
     ATCTTTCTGCACAAGTGCCTCAGGAGCACCCTTGGGTCCCAAAGGAGATGGTCATTATCC   840
 35   S  F  C  T  S  A  S  G  A  P  L  G  P  K  G  D  G  H  Y  P
     ATGGAGTTGTCCAGTGACTCATACACGGGAAAAAATTTATGCCATCTGTTCGGACTATGC   900
 55   W  S  C  P  V  T  H  T  R  E  K  I  Y  A  I  C  S  D  Y  A
     CTTTCTCAACCAGGCGACCTCAATCTATAAAACTCCAAATCCATCCCGCTCTCCTTGCCT   960
 75   F  L  N  Q  A  T  S  I  Y  K  T  P  N  P  S  R  S  P  C  L
     CCCTGATAGTACCTCTTTATCTGCTGGAAATAATTCATCAAGATACATTGGTATCCCGAC  1020
 95   P  D  S  T  S  L  S  A  G  N  N  S  R  Y  I  G  I  P  T
     TAGTACATCGGAAATTATCTACAATGAAGAAAATAGCTTGGAAAACTTATCCAACAGCCT  1080
115   S  T  S  E  I  I  Y  N  E  E  N  S  L  E  N  L  S  N  S  L
     GGGCAAGCTACCTCTCGCATGGGAAATTGATAAATCTGAATTTGATGGGGTGACCACAAA  1140
135   G  K  L  P  L  A  W  E  I  D  K  S  E  F  D  G  V  T  T  N
     TTCGAAACACAAATCAGGCAATGCAAAGAAACAAGTTTCCAAGAGAAAAACTTCAGATAA  1200
155   S  K  H  K  S  G  N  A  K  K  Q  V  S  K  R  K  T  S  D  K
     AAAGGGAAGATATCAGAAGGAATGTCCTCAGCATTCTCCTCTTGAAGATATTAAACAGCG  1260
175   K  G  R  Y  Q  K  E  C  P  Q  H  S  P  L  E  D  I  K  Q  R
     GAAAGTATTAGACCTCAGACGATGGTACTGCATAAGCCGACCACAGTATAAGACTTCTTG  1320
195   K  V  L  D  L  R  R  W  Y  C  I  S  R  P  Q  Y  K  T  S  C
     TGGCATCTCTTCATTAATTTCTTGTTGGAATTTCTTATACAGCACAATGGGAGCTGGAAA  1380
215                      W  N  F  L  Y  S  T  M  G  A  G  N
     CCTTCCACCTATTACCCAAGAAGAAGCTTTACATATTCTGGGCTTTCAACCTCCATTTGA  1440
235   L  P  P  I  T  Q  E  E  A  L  H  I  L  G  F  Q  P  P  F  E
     AGATATTAGGTTTGGTCCTTTCACGGGGAATACAACACTTATGAGGTGGTTTAGACAAAT  1500
255   D  I  R  F  G  P  F  T  G  N  T  T  L  M  R            I
     TAATGACCACTTCCATGTAAAAGGATGCTCTTATGTTCTATATAAGCCTCATGGGAAGAA  1560
275   N  D  H  F  H  V  K  G  C  S  Y  V  L  Y  K  P  H  G  K  N
     TAAAACAGCAGGAGAAACTGCTTCAGGGGCCCTGTCAAAGTTAACCCGTGGATTGAAAGA  1620
295   K  T  A  G  E  T  A  S  G  A  L  S  K  L  T  R  G  L  K  D
     TGAATCGCTGGCTTATATCTATCATTGCCAAAATCATTATTTTTGTCCAATTGGCTTCGA  1680
315   E  S  L  A  Y  I        Q  N  H        P  I  G  F  E
     AGCAACCCCTGTTAAAGCTAATAAAGCATTCAGCAGGGGACCTCTCTCACCACAGGAAGT  1740
335   A  T  P  V  K  A  N  K  A  F  S  R  G  P  L  S  P  Q  E  V
     TGAATATTGGATCTTAATTGGAGAATCAAGTAGAAAACATCCTGCCATTCACTGTAAAAA  1800
```

FIG. 1B

```
335 A  T  P  V  K  A  N  K  A  F  S  R  G  P  L  S  P  Q  E  V
    TGAATATTGGATCTTAATTGGAGAATCAAGTAGAAAACATCCTGCCATTCACTGTAAAAA   1800
355 E  Y  W  I  L  I  G  E  S  S  R  K  H  P  A  I  H  C  K  K
    ATGGGCAGATATTGTTACTGATCTAAACACTCAAAATCCAGAATACCTGGATATCCGGCA   1860
375 W  A  D  I  V  T  D  L  N  T  Q  N  P  E  Y  L  D  I  R  H
    CTTAGAGAGGGGACTGCAGTATAGAAAAACAAAGAAGGTTGGGGGAAATTTGCATTGCAT   1920
395 L  E  R  G  L  Q  Y  R  K  T  K  K  V  G  G  N  L  H  C  I
    CATAGCATTCCAGAGACTTAACTGGCAAAGATTTGGCCTTTGGAACTTTCCATTTGGAAC   1980
415 I  A  F  Q  R  L  N  W  Q  R  F  G  L  W  N  F  P  F  G  T
    CATTAGACAAGAATCACAACCTCCAACACATGCCCAGGGAATTGCCAAATCTGAGAGTGA   2040
435 I  R  Q  E  S  Q  P  P  T  H  A  Q  G  I  A  K  S  E  S  E
    AGACAATATTTCCAAGAAGCAGCATGGGCGTCTGGGCCGGTCTTTCAGTGCTAGTTTCCA   2100
455 D  N  I  S  K  K  Q  H  G  R  L  G  R  S  F  S  A  S  F  H
    TCAGGACTCGGCATGGAAAAAGATGTCTAGTATCCATGAGAGAAGGAACAGTGGTTACCA   2160
475 Q  D  S  A  W  K  K  M  S  S  I  H  E  R  R  N  S  G  Y  Q
    GGGTTACAGTGATTACGATGGGAATGATTGACTATGCTTGCTACTGAACAGCTGGCATTA   2220
495 G  Y  S  D  Y  D  G  N  D
    TATATGAAACTGCTATATACAGGACTGTATAAAGACAGTAGAAGATTTTAGTAAGCCTAC   2280
    ATTAAATAGGAGCAGATCTTGTGGTATAAAAAATAACCTTGTAGTTCTCCAGATACTAAG   2340
    CTTGTATATGATTATGGTGGGTGATTTCAGATATATAAGCAGATAAGCACAGATTATTGT   2400
    CCTTTCAAGTTAAGAGTATATAATCTGGACAGAAAATTTCACAAAATTCAATAAAATTAC   2460
    AACTGTTGTCTAAATAAGTGAAACACAAATTCACTTAATAGCATCAAGATTTGAAATACT   2520
    TAAGCATGAAGTGACTTTTATAATGACTCGATCCCTAGACATTTGTTACAGATAGTTTTA   2580
    TGCCTAAGACCAAGATGTAAAGTACCATCTGCCCTTAAAAAAAATTGGGGCTGTCAATTT   2640
    CTAGTTTTCACTCATGGTTAACACGCATTTAAAATTATTTCATGAGTCTAGTAGTTCTTT   2700
    GATTTATAGCAGGATCTTGCTTGCCTCATTTGTTTCCTGGTTATGTTCTTAGGATTCTGA   2760
    CTAAGAGGCAAAAGAGAAAAGACTCAAGAAACTGATCCTGgagatcgagaccatcctggc   2820
    taacatggtgaaaccccgtctctactaaacatacaaaaaattagccgggtgtagtggtgg   2880
    gcacctgtagtcctagctactcgagaggctgaggcaggagaatggcgtgaacccgggagg   2940
    tggagcttgcagtgagcggagatcgcgccactgcactccagcctgggcgacagggcaaga   3000
    ctctgtctcAAAAAAAAAAAAAAAAAAAAAAGACGGATCCTTTTTTTTGGTGCAAATGGGT   3060
    GACTTAGTGCATTGATTCAGATTTTTAAAATTTCTTGATGTGGTTTGTAATAATCAAATA   3120
    TTGACAAGAACCTTAGGTCTCGAAAGACTTTTATAAGTCTAGATGACGTTTGCCTTAGGG   3180
    GTAAAGTAAAAGAACAATTGGCACCTTAAGTTTCTATACCCAAGGTTATCTGTGAAATGA   3240
    GATCTCCTGATATTTGATTGCTTTCTCAGTATGGAGTCATATGTTGATAACAGTACTGAA   3300
    GATGCATAAGAAATGCCCAAGTCACTCAGAGGACAACTACCCATATTCCAGACTCTGAGC   3360
    TGTTTCCTTTTTAAAAATCATATAGACAATTAGCTGTTTGAAGTGAGTATTAAATATTTC   3420
    AGAAGTGTGAATTTCATGTATTTGAGCTCCTCTAGTTGCTGTTGGTTTTTCTTCTGCTGC   3480
    CAACCTGTGACTCACAAATGACTAGGATCTCTTGTTCTTTAATTTTAGGGTCTTGTTCCA   3540
    GGACTCAAATCAGTAACTTGGTGATTACAAGGTGCTGAATGTGTTGGTAACCATATCGCA   3600
    ATACACCTCAAGGAAAAGGTTCAGATTTTTATTTTTAAAATATTTTCATTTTTTCTTGA   3660
    ATTTTATATCCGTTTGTTCACTCGTACATGCCTAGCCTACAGAAGGGGATATATATTATG   3720
    AAATGGTCATTTTTCTGAAGAGAATATTTTGCTTGAAATGCAAAGGACTGAAAGAGATTT   3780
    GTAGGTTGTTGATTTTGTTACTTCATACTGGAACTTTTAAAAAGATTTCATCAAATAAAG   3840
    TTTTGTTTTCTACTTTT                                              3857
```

FIG. 1C

FIG. 3B

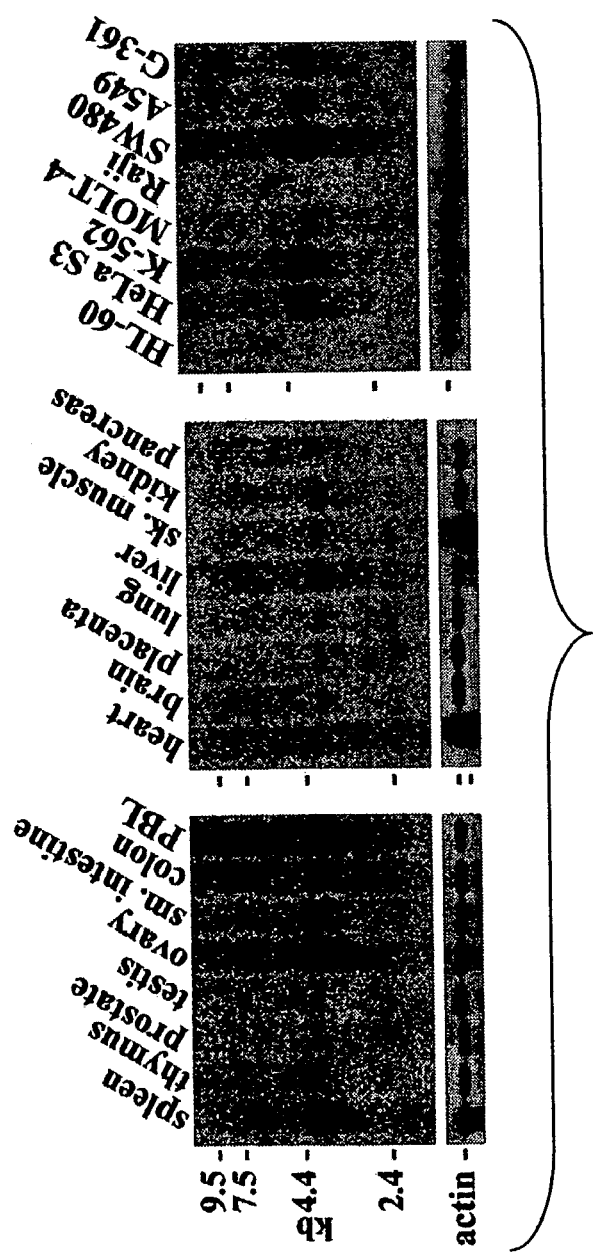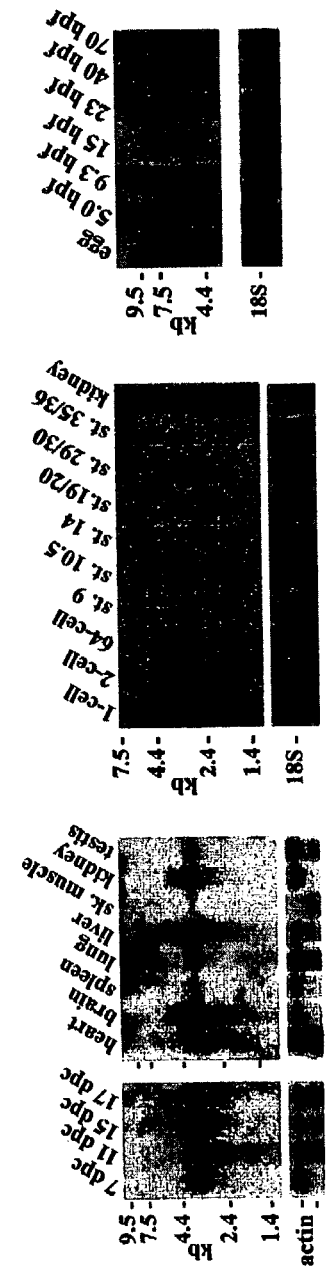
FIG. 5A
FIG. 5B
FIG. 5C
FIG. 5D

```
    GCACATCTTGCAGGTCAAAACGAACACCCCCTCCTTCGATATCCTCTCAGACCCTACACT   60
    CTCAATTGTGTTACAGACCGGGCATGGGAAGAACTTGCTACGGCCGGCTTTCTTAGGGGG  120
    CGCCGCCCTTGTCCTCTTCTTCTTTCCCATCCTCCTGTCCTCTTTTTGTGACTGTTTGTG  180
    ACTAGACGCCGTTTCTAACAAAATTGCCAAGCATGTATGCAAAATTAAAATGGAAAGATA  240
1                                                  M  E  R  Y
    CCCCAGACAACGGTTAGACGACGGCAGGTGGCAGTGCGTGGCAGCGCAGTACAGATACTC  300
5    P  R  Q  R  L  D  D  G  R  W  Q  C  V  A  A  Q  Y  R  Y  S
    CTGCGCCATCTCATGCCTTGTGAGCATATTCAATCATCTCTTCAACAGAGACATGACCCT  360
25   C  A  I  S  C  L  V  S  I  F  N  H  L  F  N  R  D  M  T  L
    GGACGAGTGTATTGCTATTCTCTTTCCAGACCTGAAAGAAGACCCACGACACTATGATTT  420
45   D  E  C  I  A  I  L  F  P  D  L  K  E  D  P  R  H  Y  D  F
    TGGACCTCAGGCTTCTAACAGTGCTGTTCAAAGCTGGTTCAAGACCCTCTGCATGCACTA  480
65   G  P  Q  A  S  N  S  A  V  Q  S  W  F  K  T  L  C  M  H  Y
    TGGCCTTTCTGGCACCTCTTGCACGATATACAAGGAGCAGGGCAGAACGAGAACTGCGTG  540
85   G  L  S  G  T  S  C  T  I  Y  K  E  Q  G  R  T  R  T  A  C
    TAGCAAGCAAGAGGCACTTAAGAATATCATCACTGCTTTGAATACGCCAAGATGTGCGTT  600
105  S  K  Q  E  A  L  K  N  I  I  T  A  L  N  T  P  R  C  A  L
    ACTGTATCACTGCTTGAACCATTACTGCATAATCGTAGGCTATATAATAAGTCCATCTAC  660
125  L  Y  H  C  L  N  H  Y  C  I  I  V  G  Y  I  I  S  P  S  T
    GCCTAATAGACCAAGTAATCATTGCGTCTTCAGCGGGGATGATGGATGCACCCTCAAGCT  720
145  P  N  R  P  S  N  H  C  V  F  S  G  D  D  G  C  T  L  K  L
    CCTGTGTGCAGACGGCACAGAAGCCGAGGACGTGGACGATAGTAATATTTGGTTAATAGT  780
165  L  C  A  D  G  T  E  A  E  D  V  D  D  S  N  I  W  L  I  V
    GGCAGACTGTGGGAAAGGAACTGCTCCCCTTAGGTCACTGACCTGGGAATTTGTACATAA  840
185  A  D  C  G  K  G  T  A  P  L  R  S  L  T  W  E  F  V  H  K
    AGATATATCTACCCGACCTCCGTATGCATATAACGCTAGGTGCCCTGAGAGAGGACTGCT  900
205  D  I  S  T  R  P  P  Y  A  Y  N  A  R  C  P  E  R  G  L  L
    AAGGAAAACAGAATCAAAGGGATATATACCAGTTGAGATAGACTCAGTGCTTGTTAACAG  960
225  R  K  T  E  S  K  G  Y  I  P  V  E  I  D  S  V  L  V  N  S
    CACGGGAGTATCCACCTGTGTTAGATCTGGTGGCGTCATCAAGGGATCGTCGCACTGCAT 1020
245  T  G  V  S  T  C  V  R  S  G  G  V  I  K  G  S  S  H  C  I
    CATTGGATTTGTTAGTGACTAGAGCCCCGTTTATTACTCCCGGACGAAAGTATAACTATT 1080
265  I  G  F  V  S  D  *
    AACACCACAAGCACAACGATAGCTCCAGTAGAGCAGAGCCGAAGCACTTGAGGCAGCGAG 1140
    GCCTCCAAATACCCACATAGAACGTCACAGATGATAGCTGTCCATGTCGCAATTGACAAG 1200
    GTTAACGGGAAGGTTGAAACAGGCGAGGGCGTCCATCTGGTACGTTGTACTTTGGTTGTT 1260
    GAATATTGAACTGTTGTAAGTGTTGATTTGCTGGGTATATCTATTGCTTATGTACCGAAA 1320
    AAGGGCATTGCAAACGTCATATATTGCATCTATCTGATGAACACAGACCCCAGTTTTTTG 1380
    AAGATTTGCAAGTCTTCTTTGTGGTGGGGCATTCATATATGAATAAGAGCAGACTTCTCC 1440
    GCAGGCAAAGGACATGGACTGAATGGCATGCTCGTAACCAGTTAGGTCCAGTGCTTTGGT 1500
    TCGTGCATAGTATTTAAAGACCTTCTGAAGAAGGATGGTTTGAAATAGGGTCGTCCTGTC 1560
    CACACAGTCCAGGCAGTTTATCCGCGGATAGCACTTCTGAACAAAGTCAGGAAGAGCAAC 1620
    TCCGACATCACCGCTAGGAACTAGAACTGTGCTTGTGGCTATGTCATCTGCTAACTGGTG 1680
    ATACTCTGTGTTGCTGTGTCTACGTATGTTGTAGTTCATCAACTTAACGTTGAGGGAGTT 1740
    CTTGCGGCGAGAATCAGCAGTTTTCTCATAGACTCGGTAAAGAACGCCGTCAGAGCCGC 1800
    TCATCGGCGGTCTCAAGGCTTTTCTTTTCACTGGCAGCAATGGAGTCATCCAAAAGATCG 1860
    ACTTCATTTTTGAGGAGGTTGACGATAAGTATCTCTGCGTCTGCAGTCACTAAGTTACCC 1920
    AATAGAAGGCTTATATGCCTTTGCAAGAGACTACTAAACTGAGCGAGGCCCTGCTCTTCA 1980
    TGAGCCCCATCTGGGAAGCGTATGGCAGGAGTGAACTTGTAAGTAAAAAAAAAAAAAAAA 2040
```

FIG. 7A

```
BIVM   189 EDIKQRKVLDLRRWYCISRPQYKTSCGISSLISCWNFLYSTMGAGNLPPI
BIVML    1 MRYPRQRLDDGRWQCVAA-QYRYSCAISCLVSIENHLFNRDMT-----L

M2
BIVM   239 TQEEAVHILGFQPPFEDIRFGPFTGNITIMRWFROINDHRHVKGCSYVLY
BIVML   45 DECIAILFPDLKEDPRHYDFGPQASNSAVQSWFKTLCMHYGISGTSCTIY

M3b
BIVM   289 KPHGKNKTAGETASGAISKITRGLKDESLAYTYHCQNHYFCPIGFEATPV
BIVML   94 KEQGRTRTACSKQE-ALKNIITALNTPRCALYHCLNHYCIIVGYIISPS

BIVM   339 KANKAFSRGPLSPQEVEYWILIGESSRKHPAIHCKKWADIVTDINTQNPE
BIVML  119 TPN--------------------RPSNHCVFSCDDGCTLKLLCAD

BIVM   389 YLDIRHIERGLQVRKTKKVGGNLICIIAFQRLNWQRFGLWNFPFGTIRQE
BIVML  166 GTPAEDVLDSNIRLIVADCG---KGTAPLRSLTWEFVHKDISTRPPYAYN

BIVM   439 SQPPTHAQGIAKSESEDNISKKQHGRLGRSFSASFHQDSAWKKMSSIHER
BIVML  212 ARCP-ERGLFRKIESKGYIPVEIDSVLVNSTGVSTCVRSGGVIKGSSHC-

BIVM   489 RNSCYQGYSDYDGND
BIVML  264 -IIG--FVSD
```

FIG. 7B

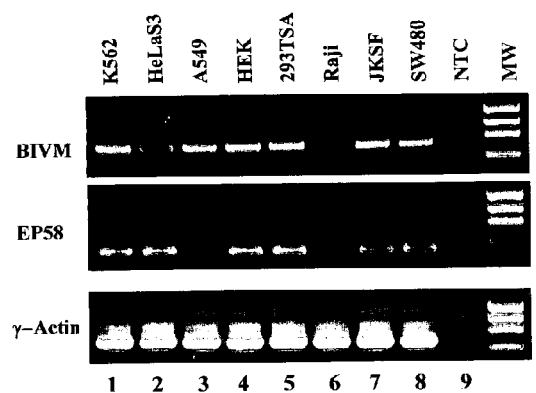
Fig. 1 RT
FIG. 8
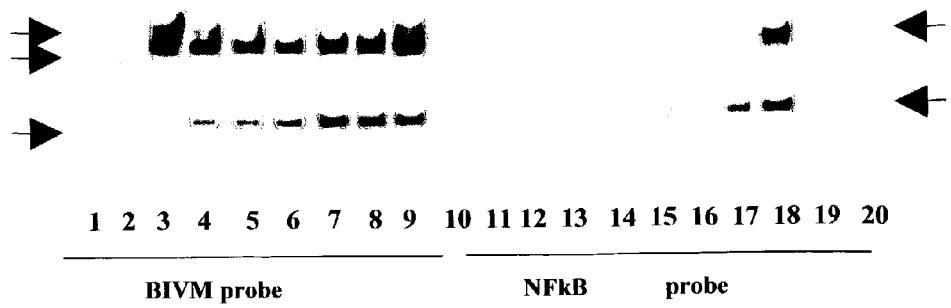
FIG. 10

SEQUENCE LISTING

```
<160> NUMBER OF SEQ ID NOS: 64

<210> SEQ ID NO 1
<211> LENGTH: 3857
<212> TYPE: DNA
<213> ORGANISM: Homo sapiens
<220> FEATURE:
<221> NAME/KEY: misc_feature
<222> LOCATION: (1)..(473)
<223> OTHER INFORMATION: Exon A - untranslated
<220> FEATURE:
<221> NAME/KEY: misc_feature
<222> LOCATION: (474)..(557)
<223> OTHER INFORMATION: Exon B - untranslated
<220> FEATURE:
<221> NAME/KEY: misc_feature
<222> LOCATION: (558)..(1157)
<223> OTHER INFORMATION: Exon 1
<220> FEATURE:
<221> NAME/KEY: misc_feature
<222> LOCATION: (680)..(682)
<223> OTHER INFORMATION: Translation initiation codon (ATG)
<220> FEATURE:
<221> NAME/KEY: misc_feature
<222> LOCATION: (1158)..(1284)
<223> OTHER INFORMATION: Exon 2
<220> FEATURE:
<221> NAME/KEY: misc_feature
<222> LOCATION: (1285)..(1380)
<223> OTHER INFORMATION: Exon 3
<220> FEATURE:
<221> NAME/KEY: misc_feature
<222> LOCATION: (1381)..(1485)
<223> OTHER INFORMATION: Exon 4
<220> FEATURE:
<221> NAME/KEY: misc_feature
<222> LOCATION: (1486)..(1580)
<223> OTHER INFORMATION: Exon 5
<220> FEATURE:
<221> NAME/KEY: misc_feature
<222> LOCATION: (1581)..(1713)
```

```
<223> OTHER INFORMATION: Exon 6
<220> FEATURE:
<221> NAME/KEY: misc_feature
<222> LOCATION: (1714)..(1800)
<223> OTHER INFORMATION: Exon 7
<220> FEATURE:
<221> NAME/KEY: misc_feature
<222> LOCATION: (1801)..(1897)
<223> OTHER INFORMATION: Exon 8
<220> FEATURE:
<221> NAME/KEY: misc_feature
<222> LOCATION: (1898)..(3857)
<223> OTHER INFORMATION: Exon 9
<220> FEATURE:
<221> NAME/KEY: misc_feature
<222> LOCATION: (2189)..(2191)
<223> OTHER INFORMATION: Translation termination codon (TGA)
<220> FEATURE:
<221> NAME/KEY: misc_feature
<222> LOCATION: (2801)..(3009)
<223> OTHER INFORMATION: Alu sequence

<400> SEQUENCE: 1
agtaacgcct tctccaagtg gatggcgggg tggacacgcg tcccggcgcc ccgggctccc      60
tgggatatgt agttcgcgac aggacgagcg gaaatactgc caggatttta ccacctctcg     120
cccatttatt tacttctcgg tcaccgcttt cggggacag ataaacacca cagatgccca      180 tcaaagggc gcacgggtct ggaggcgcag ctcaggtttt tgcgttggtc accctgccct     240
ccgcacgtgg agagggcagg cataaagcac cttgaaagga aggtgctgtc aatgctatcc     300
gacgacctgt cgccgggcac cgcagcatcc tcgctcgctc cgatgggacg agggacgccg     360 gccccaggt aacaggaggc gcctcgccgg ccgcgcgctg gatgctgtga tccaggtccg     420
gagccgggtt ccgccgcggc cgcagcgacc cgaccccacc cgacaggcca gaggaatcag     480
tttagacttg aaattcagtt tttcctgaaa ctgatcagaa gttagtgaca ccttgattgg     540
atccgttttt ctgtcaggag ctcattttgc agctctcaag cttttatagc atgctgtaaa     600
caattgtcaa agttgtttat caagaaacag atagagttgc aacttgtttc tagtaataga     660
aacttttaca ctgcattcaa tgcctaacgt tgcagaaaca gaaaggtcaa atgattctgg     720
aaatggtgag cacaaatctg agagaaagtc acctgaagag aatctacaag gtgctgtaaa     780
atctttctgc acaagtgcct caggagcacc cttgggtccc aaaggagatg gtcattatcc     840
atggagttgt ccagtgactc atacacggga aaaaatttat gccatctgtt cggactatgc     900
ctttctcaac caggcgacct caatctataa aactccaaat ccatcccgct tccttgcct     960 ccctgatagt acctctttat ctgctggaaa taattcatca agatacattg gtatcccgac    1020
tagtacatcg gaaattatct acaatgaaga aaatagcttg gaaaacttat ccaacagcct    1080
gggcaagcta cctctcgcat gggaaattga taaatctgaa tttgatgggg tgaccacaaa    1140
ttcgaaacac aaatcaggca atgcaaagaa acaagtttcc aagagaaaaa cttcagataa    1200
aaagggaaga tatcagaagg aatgtcctca gcattctcct cttgaagata ttaaacagcg    1260
gaaagtatta gacctcagac gatggtactg cataagccga ccacagtata agacttcttg    1320
tggcatctct tcattaattt cttgttggaa tttcttatac agcacaatgg gagctggaaa    1380
ccttccacct attacccaag aagaagcttt acatattctg ggctttcaac ctccatttga    1440
agatattagg tttggtccctt tcacggggaa tacaacactt atgaggtggt ttagacaaat    1500
taatgaccac ttccatgtaa aaggatgctc ttatgttcta tataagcctc atgggaagaa    1560
taaaacagca ggaaaactg cttcaggggc cctgtcaaag ttaacccgtg gattgaaaga    1620
tgaatcgctg gcttatatct atcattgcca aaatcattat ttttgtccaa ttggcttcga    1680
```

```
agcaacccct gttaaagcta ataaagcatt cagcagggga cctctctcac cacaggaagt    1740
tgaatattgg atcttaattg gagaatcaag tagaaaacat cctgccattc actgtaaaaa    1800
atgggcagat attgttactg atctaaacac tcaaaatcca gaatacctgg atatccggca    1860
cttagagagg ggactgcagt atagaaaaac aaagaaggtt gggggaaatt tgcattgcat    1920
catagcattc cagagactta actggcaaag atttggcctt tggaactttc catttggaac    1980
cattagacaa gaatcacaac ctccaacaca tgcccaggga attgccaaat ctgagagtga    2040
agacaatatt tccaagaagc agcatgggcg tctgggccgg tctttcagtg ctagtttcca    2100
tcaggactcg gcatggaaaa agatgtctag tatccatgag agaaggaaca gtggttacca    2160
gggttacagt gattacgatg gaatgattg actatgcttg ctactgaaca gctggcatta    2220
tatatgaaac tgctatatac aggactgtat aaagacagta gaagatttta gtaagcctac    2280
attaaatagg agcagatctt gtggtataaa aaataacctt gtagttctcc agatactaag    2340
cttgtatatg attatggtgg gtgatttcag atatataagc agataagcac agattattgt    2400
cctttcaagt taagagtata taatctggac agaaaatttc acaaaattca ataaaattac    2460
aactgttgtc taaataagtg aaacacaaat tcacttaata gcatcaagat ttgaaatact    2520
taagcatgaa gtgacttta taatgactcg atccctagac atttgttaca gatagtttta    2580
tgcctaagac caagatgtaa agtaccatct gcccttaaaa aaaattgggg ctgtcaattt    2640
ctagttttca ctcatggtta acacgcattt aaaattattt catgagtcta gtagttcttt    2700
gatttatagc aggatcttgc ttgcctcatt tgtttcctgg ttatgttctt aggattctga    2760
ctaagaggca aaagagaaaa gactcaagaa actgatcctg gagatcgaga ccatcctggc    2820
taacatggtg aaacccgtc tctactaaac atacaaaaaa ttagccgggt gtagtggtgg    2880
gcacctgtag tcctagctac tcgagaggct gaggcaggag aatggcgtga acccgggagg    2940
tggagcttgc agtgagcgga gatcgcgcca ctgcactcca gcctgggcga cagggcaaga    3000
ctctgtctca aaaaaaaaa aaaaaaaaa gacggatcct ttttttttggt gcaaatgggt    3060
gacttagtgc attgattcag atttttaaaa tttcttgatg tggtttgtaa taatcaaata    3120
ttgacaagaa ccttaggtct cgaaagactt ttataagtct agatgacgtt tgccttaggg    3180
gtaaagtaaa agaacaattg gcaccttaag tttctatacc caaggttatc tgtgaaatga    3240
gatctcctga tatttgattg ctttctcagt atggagtcat atgttgataa cagtactgaa    3300
gatgcataag aaatgcccaa gtcactcaga ggacaactac ccatattcca gactctgagc    3360
tgtttccttt ttaaaaatca tatagacaat tagctgtttg aagtgagtat taaatatttc    3420
agaagtgtga atttcatgta tttgagctcc tctagttgct gttggttttt cttctgctgc    3480
caacctgtga ctcacaaatg actaggatct cttgttcttt aattttaggg tcttgttcca    3540
ggactcaaat cagtaacttg gtgattacaa ggtgctgaat gtgttggtaa ccatatcgca    3600
atacacctca aggaaaaggt tcagattttt atttttaaaa tattttcatt tttttcttga    3660
atttatatc cgtttgttca ctcgtacatg cctagcctac agaagggat atatattatg    3720
aaatggtcat ttttctgaag agaatatttt gcttgaaatg caaaggactg aaagagattt    3780
gtaggttgtt gattttgtta cttcatactg gaacttttaa aaagatttca tcaaataaag    3840
ttttgttttc tactttt                                                  3857
```

<210> SEQ ID NO 2
<211> LENGTH: 503
<212> TYPE: PRT

-continued

<213> ORGANISM: Homo sapiens

<400> SEQUENCE: 2

```
Met Pro Asn Val Ala Glu Thr Glu Arg Ser Asn Asp Ser Gly Asn Gly
1               5                   10                  15

Glu His Lys Ser Glu Arg Lys Ser Pro Glu Glu Asn Leu Gln Gly Ala
            20                  25                  30

Val Lys Ser Phe Cys Thr Ser Ala Ser Gly Ala Pro Leu Gly Pro Lys
        35                  40                  45

Gly Asp Gly His Tyr Pro Trp Ser Cys Pro Val Thr His Thr Arg Glu
    50                  55                  60

Lys Ile Tyr Ala Ile Cys Ser Asp Tyr Ala Phe Leu Asn Gln Ala Thr
65                  70                  75                  80

Ser Ile Tyr Lys Thr Pro Asn Pro Ser Arg Ser Pro Cys Leu Pro Asp
                85                  90                  95

Ser Thr Ser Leu Ser Ala Gly Asn Asn Ser Ser Arg Tyr Ile Gly Ile
            100                 105                 110

Pro Thr Ser Thr Ser Glu Ile Ile Tyr Asn Glu Glu Asn Ser Leu Glu
        115                 120                 125

Asn Leu Ser Asn Ser Leu Gly Lys Leu Pro Leu Ala Trp Glu Ile Asp
130                 135                 140

Lys Ser Glu Phe Asp Gly Val Thr Thr Asn Ser Lys His Lys Ser Gly
145                 150                 155                 160

Asn Ala Lys Lys Gln Val Ser Lys Arg Lys Thr Ser Asp Lys Lys Gly
                165                 170                 175

Arg Tyr Gln Lys Glu Cys Pro Gln His Ser Pro Leu Glu Asp Ile Lys
            180                 185                 190

Gln Arg Lys Val Leu Asp Leu Arg Arg Trp Tyr Cys Ile Ser Arg Pro
        195                 200                 205

Gln Tyr Lys Thr Ser Cys Gly Ile Ser Ser Leu Ile Ser Cys Trp Asn
    210                 215                 220

Phe Leu Tyr Ser Thr Met Gly Ala Gly Asn Leu Pro Pro Ile Thr Gln
225                 230                 235                 240

Glu Glu Ala Leu His Ile Leu Gly Phe Gln Pro Phe Glu Asp Ile
                245                 250                 255

Arg Phe Gly Pro Phe Thr Gly Asn Thr Thr Leu Met Arg Trp Phe Arg
            260                 265                 270

Gln Ile Asn Asp His Phe His Val Lys Gly Cys Ser Tyr Val Leu Tyr
        275                 280                 285

Lys Pro His Gly Lys Asn Lys Thr Ala Gly Glu Thr Ala Ser Gly Ala
    290                 295                 300

Leu Ser Lys Leu Thr Arg Gly Leu Lys Asp Glu Ser Leu Ala Tyr Ile
305                 310                 315                 320

Tyr His Cys Gln Asn His Tyr Phe Cys Pro Ile Gly Phe Glu Ala Thr
                325                 330                 335

Pro Val Lys Ala Asn Lys Ala Phe Ser Arg Gly Pro Leu Ser Pro Gln
            340                 345                 350

Glu Val Glu Tyr Trp Ile Leu Ile Gly Glu Ser Ser Arg Lys His Pro
        355                 360                 365

Ala Ile His Cys Lys Lys Trp Ala Asp Ile Val Thr Asp Leu Asn Thr
    370                 375                 380

Gln Asn Pro Glu Tyr Leu Asp Ile Arg His Leu Glu Arg Gly Leu Gln
385                 390                 395                 400
```

```
Tyr Arg Lys Thr Lys Lys Val Gly Gly Asn Leu His Cys Ile Ile Ala
            405                 410                 415

Phe Gln Arg Leu Asn Trp Gln Arg Phe Gly Leu Trp Asn Phe Pro Phe
            420                 425                 430

Gly Thr Ile Arg Gln Glu Ser Gln Pro Pro Thr His Ala Gln Gly Ile
            435                 440                 445

Ala Lys Ser Glu Ser Glu Asp Asn Ile Ser Lys Lys Gln His Gly Arg
450                 455                 460

Leu Gly Arg Ser Phe Ser Ala Ser Phe His Gln Asp Ser Ala Trp Lys
465                 470                 475                 480

Lys Met Ser Ser Ile His Glu Arg Arg Asn Ser Gly Tyr Gln Gly Tyr
                485                 490                 495

Ser Asp Tyr Asp Gly Asn Asp
            500

<210> SEQ ID NO 3
<211> LENGTH: 96898
<212> TYPE: DNA
<213> ORGANISM: Homo sapiens
<220> FEATURE:
<221> NAME/KEY: misc_feature
<222> LOCATION: (466)..(702)
<223> OTHER INFORMATION: Inverse complement of MGC5302 Exon 6
<220> FEATURE:
<221> NAME/KEY: misc_feature
<222> LOCATION: (823)..(997)
<223> OTHER INFORMATION: Inverse complement of MGC5302 Exon 5
<220> FEATURE:
<221> NAME/KEY: misc_feature
<222> LOCATION: (2904)..(2985)
<223> OTHER INFORMATION: Inverse complement of MGC5302 Exon 4
<220> FEATURE:
<221> NAME/KEY: misc_feature
<222> LOCATION: (3164)..(3366)
<223> OTHER INFORMATION: Inverse complement of MGC5302 Exon 3
<220> FEATURE:
<221> NAME/KEY: misc_feature
<222> LOCATION: (6395)..(6570)
<223> OTHER INFORMATION: Inverse complement of MGC5302 Exon 2
<220> FEATURE:
<221> NAME/KEY: misc_feature
<222> LOCATION: (8013)..(8312)
<223> OTHER INFORMATION: Genomic fragment identified as part of CpG
      island (Genbank Z59762)
<220> FEATURE:
<221> NAME/KEY: misc_feature
<222> LOCATION: (8059)..(8572)
<223> OTHER INFORMATION: Inverse complement of MGC5302 Exon 1
<220> FEATURE:
<221> NAME/KEY: misc_feature
<222> LOCATION: (8233)..(8235)
<223> OTHER INFORMATION: Inverse complement of MGC5302 translation
      initiation codon (ATG)
<220> FEATURE:
<221> NAME/KEY: misc_feature
<222> LOCATION: (8614)..(9086)
<223> OTHER INFORMATION: BIVM Exon A - untranslated
<220> FEATURE:
<221> NAME/KEY: misc_feature
<222> LOCATION: (9019)..(9033)
<223> OTHER INFORMATION: BIVM Exon A alternative splice donor site
<220> FEATURE:
<221> NAME/KEY: misc_feature
<222> LOCATION: (9077)..(9091)
<223> OTHER INFORMATION: BIVM Exon A splice donor site
<220> FEATURE:
<221> NAME/KEY: misc_feature
<222> LOCATION: (14862)..(14876)
<223> OTHER INFORMATION: BIVM Exon B splice acceptor site
<220> FEATURE:
<221> NAME/KEY: misc_feature
<222> LOCATION: (14872)..(14955)
```

```
<223> OTHER INFORMATION: BIVM Exon B - untranslated
<220> FEATURE:
<221> NAME/KEY: misc_feature
<222> LOCATION: (14946)..(14960)
<223> OTHER INFORMATION: BIVM Exon B splice donor site
<220> FEATURE:
<221> NAME/KEY: misc_feature
<222> LOCATION: (16309)..(16309)
<223> OTHER INFORMATION: n = a, c, g, or t.
<220> FEATURE:
<221> NAME/KEY: misc_feature
<222> LOCATION: (16701)..(16715)
<223> OTHER INFORMATION: BIVM Exon 1 splice acceptor site
<220> FEATURE:
<221> NAME/KEY: misc_feature
<222> LOCATION: (16711)..(17310)
<223> OTHER INFORMATION: BIVM Exon 1
<220> FEATURE:
<221> NAME/KEY: misc_feature
<222> LOCATION: (16833)..(16835)
<223> OTHER INFORMATION: BIVM translation initiation codon (ATG)
<220> FEATURE:
<221> NAME/KEY: misc_feature
<222> LOCATION: (17301)..(17315)
<223> OTHER INFORMATION: BIVM Exon 1 splice donor site
<220> FEATURE:
<221> NAME/KEY: misc_feature
<222> LOCATION: (25983)..(25997)
<223> OTHER INFORMATION: BIVM Exon 2 splice acceptor site
<220> FEATURE:
<221> NAME/KEY: misc_feature
<222> LOCATION: (25993)..(26119)
<223> OTHER INFORMATION: BIVM Exon 2
<220> FEATURE:
<221> NAME/KEY: misc_feature
<222> LOCATION: (26110)..(26124)
<223> OTHER INFORMATION: BIVM Exon 2 splice donor site
<220> FEATURE:
<221> NAME/KEY: misc_feature
<222> LOCATION: (30592)..(30606)
<223> OTHER INFORMATION: BIVM Exon 3 splice acceptor site
<220> FEATURE:
<221> NAME/KEY: misc_feature
<222> LOCATION: (30602)..(30697)
<223> OTHER INFORMATION: BIVM Exon 3
<220> FEATURE:
<221> NAME/KEY: misc_feature
<222> LOCATION: (30688)..(30702)
<223> OTHER INFORMATION: BIVM Exon 3 splice donor site
<220> FEATURE:
<221> NAME/KEY: misc_feature
<222> LOCATION: (31298)..(31312)
<223> OTHER INFORMATION: BIVM Exon 4 splice acceptor site
<220> FEATURE:
<221> NAME/KEY: misc_feature
<222> LOCATION: (31308)..(31412)
<223> OTHER INFORMATION: BIVM Exon 4
<220> FEATURE:
<221> NAME/KEY: misc_feature
<222> LOCATION: (31403)..(31417)
<223> OTHER INFORMATION: BIVM Exon 4 splice donor site
<220> FEATURE:
<221> NAME/KEY: misc_feature
<222> LOCATION: (31620)..(31634)
<223> OTHER INFORMATION: BIVM Exon 5 splice acceptor site
<220> FEATURE:
<221> NAME/KEY: misc_feature
<222> LOCATION: (31630)..(31724)
<223> OTHER INFORMATION: BIVM Exon 5
<220> FEATURE:
<221> NAME/KEY: misc_feature
<222> LOCATION: (31715)..(31729)
<223> OTHER INFORMATION: BIVM Exon 5 splice donor site
<220> FEATURE:
<221> NAME/KEY: misc_feature
<222> LOCATION: (41120)..(41134)
<223> OTHER INFORMATION: BIVM Exon 6 splice acceptor site
<220> FEATURE:
<221> NAME/KEY: misc_feature
```

```
<222> LOCATION: (41130)..(41262)
<223> OTHER INFORMATION: BIVM Exon 6
<220> FEATURE:
<221> NAME/KEY: misc_feature
<222> LOCATION: (41253)..(41267)
<223> OTHER INFORMATION: BIVM Exon 6 splice donor site
<220> FEATURE:
<221> NAME/KEY: misc_feature
<222> LOCATION: (44021)..(44035)
<223> OTHER INFORMATION: BIVM Exon 7 splice acceptor site
<220> FEATURE:
<221> NAME/KEY: misc_feature
<222> LOCATION: (44031)..(44117)
<223> OTHER INFORMATION: BIVM Exon 7
<220> FEATURE:
<221> NAME/KEY: misc_feature
<222> LOCATION: (44108)..(44122)
<223> OTHER INFORMATION: BIVM Exon 7 splice donor site
<220> FEATURE:
<221> NAME/KEY: misc_feature
<222> LOCATION: (48198)..(48212)
<223> OTHER INFORMATION: BVIM Exon 8 splice acceptor site
<220> FEATURE:
<221> NAME/KEY: misc_feature
<222> LOCATION: (48208)..(48304)
<223> OTHER INFORMATION: BIVM Exon 8
<220> FEATURE:
<221> NAME/KEY: misc_feature
<222> LOCATION: (48295)..(48309)
<223> OTHER INFORMATION: BIVM Exon 8 splice donor site
<220> FEATURE:
<221> NAME/KEY: misc_feature
<222> LOCATION: (49127)..(49141)
<223> OTHER INFORMATION: BIVM Exon 9 splice acceptor site
<220> FEATURE:
<221> NAME/KEY: misc_feature
<222> LOCATION: (49137)..(51096)
<223> OTHER INFORMATION: BIVM Exon 9
<220> FEATURE:
<221> NAME/KEY: misc_feature
<222> LOCATION: (49428)..(49430)
<223> OTHER INFORMATION: BIVM translation termination codon (TGA)
<220> FEATURE:
<221> NAME/KEY: misc_feature
<222> LOCATION: (50039)..(50248)
<223> OTHER INFORMATION: Alu sequence
<220> FEATURE:
<221> NAME/KEY: misc_feature
<222> LOCATION: (55216)..(55975)
<223> OTHER INFORMATION: ERCC5 Exon 1
<220> FEATURE:
<221> NAME/KEY: misc_feature
<222> LOCATION: (61682)..(61860)
<223> OTHER INFORMATION: ERCC5 Exon 2
<220> FEATURE:
<221> NAME/KEY: misc_feature
<222> LOCATION: (63321)..(63437)
<223> OTHER INFORMATION: ERCC5 Exon 3
<220> FEATURE:
<221> NAME/KEY: misc_feature
<222> LOCATION: (63851)..(63939)
<223> OTHER INFORMATION: ERCC5 Exon 4
<220> FEATURE:
<221> NAME/KEY: misc_feature
<222> LOCATION: (65614)..(65678)
<223> OTHER INFORMATION: ERCC5 Exon 5
<220> FEATURE:
<221> NAME/KEY: misc_feature
<222> LOCATION: (67834)..(67984)
<223> OTHER INFORMATION: ERCC5 Exon 6
<220> FEATURE:
<221> NAME/KEY: misc_feature
<222> LOCATION: (71070)..(71283)
<223> OTHER INFORMATION: ERCC5 Exon 7
<220> FEATURE:
<221> NAME/KEY: misc_feature
<222> LOCATION: (71592)..(72669)
<223> OTHER INFORMATION: ERCC5 Exon 8
<220> FEATURE:
```

```
<221> NAME/KEY: misc_feature
<222> LOCATION: (75231)..(75477)
<223> OTHER INFORMATION: ERCC5 Exon 9
<220> FEATURE:
<221> NAME/KEY: misc_feature
<222> LOCATION: (75826)..(75944)
<223> OTHER INFORMATION: ERCC5 Exon 10
<220> FEATURE:
<221> NAME/KEY: misc_feature
<222> LOCATION: (76194)..(76411)
<223> OTHER INFORMATION: ERCC5 Exon 11
<220> FEATURE:
<221> NAME/KEY: misc_feature
<222> LOCATION: (77677)..(77822)
<223> OTHER INFORMATION: ERCC5 Exon 12
<220> FEATURE:
<221> NAME/KEY: misc_feature
<222> LOCATION: (81763)..(81965)
<223> OTHER INFORMATION: ERCC5 Exon 13
<220> FEATURE:
<221> NAME/KEY: misc_feature
<222> LOCATION: (82824)..(82908)
<223> OTHER INFORMATION: ERCC5 Exon 14
<220> FEATURE:
<221> NAME/KEY: misc_feature
<222> LOCATION: (84870)..(85560)
<223> OTHER INFORMATION: ERCC5 Exon 15

<400> SEQUENCE: 3
```

| | | | | | |
|---|---|---|---|---|---|
| ctagacagag | aaagcaaacc | ctaattccca | gacagaacat | ttggatgagt | ttcacgtcat | 60 |
| tccccaccag | aaggcctggt | aagaaacaag | tagtttatat | cttccttatt | ctgttgtgat | 120 |
| aacatggctc | tgggaaaaag | tatttgtaaa | atgacttaca | tgtaagtatt | aataaaaaca | 180 |
| tatttggagg | tgacatgtgc | ttatctcaag | ggttagctgg | aaaaaaatta | tagctctatc | 240 |
| caggctccaa | actcccttga | tgcgcattta | atatcaagac | tgggcagtga | gggcagaccc | 300 |
| tggttgccaa | aacagtcccc | agcaccccca | tgtctcaata | ttcgctcaat | tttgtgctaa | 360 |
| cttctcccac | ctcttgaaat | ttgcaggcct | taatttccct | tcccaaagca | ctatgtacaa | 420 |
| atacattaga | aaaacaaaaa | agattagcta | ctgattaagt | catccttga | agaaatcaaa | 480 |
| aaatgaaata | tgtttcacaa | tgggaccata | caggttttca | tcgtgtttaa | agaagaaaaa | 540 |
| gttggtgaaa | gcagcgtcta | tgagttctgg | gtgttttcta | ctgagtttaa | ccagctcgag | 600 |
| tctctctttg | cggctgtctc | gccctctcca | gacggcagtg | gaattttgc | tttcccaggg | 660 |
| aggacccgtg | ttagcttgca | cggacatcat | atccagactt | accctagaag | acaaagtgca | 720 |
| acagattttc | ctcccaaatc | atcatatcac | aaaggttgtt | gcaaaagaac | tcaccaaaga | 780 |
| aagaaaacca | aggctctggg | ccaaccctga | cttatctctc | accggcccat | ggtttccaga | 840 |
| acagaatcag | tcaaatcgta | cgtaggcatc | acgatatcct | tggaatctgt | ggagccacac | 900 |
| caggaaaaga | tcggatggat | gtttgaattg | gatttctttt | tttccaaagg | ccagtctccc | 960 |
| aaattaacaa | agagctccac | atctggcatc | ttcacctaga | aaaacaaaa | cgaggagctt | 1020 |
| attcacattt | cctgcattgg | ataatacatt | gtatttatca | atttaaattt | gaaattgcat | 1080 |
| taatgaaagg | ccaatgttac | atgtttcagg | taataataat | taccttggtt | tgaatagtgg | 1140 |
| gcaatgtttc | agaatatggt | cacatgtata | agtattctat | gctccctatg | aaagggatga | 1200 |
| aactgcaaaa | gtaatctctg | ttctaatact | gcgaacagcc | tctaagatga | tcaaagagaa | 1260 |
| ggagaattat | tggaaaataa | tttaaaaaat | agcacttggg | actctaaccc | tagttttcctg | 1320 |
| ctagtgagcc | agatggttcc | atttttaaaaa | acatacacca | ggtaggtggt | gggaccagga | 1380 |
| tttgaactca | ggaagcccaa | caccaacagc | aacgtagtaa | gtttcaagct | atgcttcctt | 1440 |
| cctctactgg | caaatggcat | gaatatgtaa | agaggatatg | ttttatctag | tcacagaaaa | 1500 |

```
tgtttagagt atttacaaaa caacagatat acatttttaa ggccagaaaa gcactgacca   1560
gtctgagaag catcttgaga aaccgaagtc ctgaagaaca ttctcatttt cccatggatt   1620
gacaaagagg agcaagagaa gtatgacggt actctgatgt cttagtttaa aggaggctta   1680
atattgatgc tatataacta cctacattca gaattaacag actgtaagtg ctttgaaatc   1740
ttgaaaaaaa ggcattatga ttttccatga gtagtttaat caagatatac atgcaaatta   1800
ttcaacaaat aaatataata gattacaaat aaatatacat ttggtaaaaa tgttggtaga   1860
gtctttcaca tccaccattt taacattact ttcaaaccat tccactagaa cccaacaaaa   1920
gcccattatc ccaaggaatg ggattcagta caaggcaagt catctttgga ctcagagtta   1980
gtttagtacc aaaataattt tatgataagg cattttcctt tcctctataa aatattgtgt   2040
ccctgcaaaa gatatgctga agtcttaaat cccagtgtct cagaatgacc ttatttggaa   2100
atagggttgt tgcagatatt agttagcatg aggtcatact ggagtaggct gggccattaa   2160
tccactatgc tgtgtcctta taagaagaga cccagagaca tgaggggaga agcccacgtg   2220
atgacagagg cagagatggg aggatgcagc tgcaaaccaa ggaacaccaa agatggaggg   2280
ccactgacag cagccaggaa gaggcaggaa aggaaaggaa aggatcatct cagagggagc   2340
tggcctcctg acactttaat tttttttggg ggggacagg atctcactct tgtcacccag   2400
gccttgggag tgcagtggcg tgatctcggc tcatgcagcc tcgacctcct aggttcaagc   2460
gatcttcctg cctcagctcc ccattagctg aaactactac aggctaattt ttgtattttt   2520
tgtagagaca ggtcttcacc atgttgccca gcctggtctc aagctcctgg gctcaagtga   2580
tccacccgct ttgacctcct aaagtgctag gattacaggc gtgagccatg gcacctagct   2640
gacactttga ttttggacat ctggcctcca taactgccag agaatacatt tctgttattt   2700
taaggcttcc agtttgtagc actttgttac ggcagcccta ggaaacaaac gcaggtacct   2760
gaaataacag aaagcttcag aatagtatta tcataaggct ccagaagaga ataccctgat   2820
agtgtataat ttgtattttg aaaaattatc ctgtaaaatc tgggcttaaa ttatctatta   2880
cagctaagag aaaatatata cttacctttc tagtcaaaga aagtagtatg gcatccatga   2940
aaattctaaa acctacatgt tcaccatgag tcttgatata aacctaaaag agaatttacc   3000
atttattatg ttagtctaaa gacgctggca gacttcactg aggaaaagct tgtcacagtg   3060
ctcattcgaa tgatgtttat aaaatgattt agctaattgt agccaaatgt tcaaaacaag   3120
aaaaaaaatc actaaaacaa acaagcaaaa aatcatgtgt tgtaccttgt tatcctttaa   3180
ggtgtagtga cataggctct gcctctgtcc aaatcttttt gggatttcta ctgcaatctt   3240
ttctggatcc acagcaggga aatgtgccag atctctctga atctgagcaa tggtttcagg   3300
gcagttcatc tcccgtagcc aggctgcact atcttgcaga ggacagtcac agttctcatg   3360
gtaaaccggc cctatttaca taagaataac aaagtacaac agtgatcatt tcactcagca   3420
tcgaaacttt gtaataaaca tctataatgt ggcttcatga attttgctta gttacatagg   3480
aagagcattt tcattgaaaa cacattttaa gagaattaca ggccagcaag gttggctcat   3540
gtcggtaatc ccagcacttt gggaggctga ggcaggaaga cagcctgagc ccaggagttc   3600
gggagcagcc tggcaacac agggagacca tgtctctaca aaaataaaa aattagctgg   3660
gtgcgttggc atgcacctgt ggtttcagct acttgggagg ctgacgtggg aggatcactt   3720
gagcccagga ggttgaagct gcagtgagcc atgtttgcgc cactccatcc tgggcaagac   3780
agtgagagcc cgtttcaaag aaaaaaaaag taatacattt ttactatact ggggcattgc   3840
```

```
aagtaagtca gccttctact ctgacagctc ttcacagtga agttttgtga tattttcata   3900
ataataaggt ctactttgca tgagttcaaa agaaaggaaa tagaggctgg gtgcagtggc   3960
tcacgtctgt aataccagca ctttgggagg ctgaggtggg tggataactt gaggtcagga   4020
gtttgagacc agcctggcca acatgttgaa accccatctc tactaaaaat acaaaaaagt   4080
ttagctgggt atggtggtgt gtgcctgaaa tctcagctac tcaggaggct gaggcatgac   4140
aatagcttga atctgggagg tgaaggttgc agtgagcgga gattgtgcca ctgtgctcca   4200
gcttggggga cagagtgaga ctcttgtttc aaaaaataaa agaaagacaa cagatacttg   4260
gtttatgtct atggtaatat tacagctcat tattccttat gttttgcaga ctgaagaata   4320
accaaatact ggtaaaaggg tatcagagga gcatacctat tttaatgaaa gacaaaagtg   4380
atatgattta ctattttgat ggtctgttat acaaacaggt tcttaaagtg tctaaggtac   4440
ttttctcaat aagtaaatca tcaataacag caaaaataaa caaggaactg ctattctttt   4500
tttttttttt tttaagaatt attaaggagg aaaagtaggc tgggttcttg gctcatgcct   4560
gtaatcccag cactttggga ggctgaggcg ggcggatcac gaggtcagga gatcgagacc   4620
atcctggtca acatggtgaa accccgtctc tactaaaaat acaaaaatta gccaggtgtt   4680
gtggcgcgtc cctgtagtct cagctatttg ggtggctgag gcagcagaat cgcttgaacc   4740
cgggaggcag agcttgcagt gagccgagat tgcaccactg cactctaggc tagtgacaga   4800
gcgagacatc gtctcaaaaa aaaaaaaaa aaaaaagca aagtagctg gtacagtgg     4860 ctcacgcctg taatcctagc actttgggag actgaggtgg gcagatcact tgagctccag   4920
ggttcgggac cagtctgagc aacatggcaa accctgtttt ctacaaaaaa tacaaaaatt   4980 agtgggcat ggtggtgagt gcctgtagtc ccagctactc atgcagctga ggtgggagga    5040
ttgcttgaac ccaggaggtc gaggctgcag taagcagtga ttgcaccact gcactccagc   5100
ctgggcaaca gagcgagacc ctgtctcaac aacaacggca acaaaaagaa gcaaagtaa    5160 ttctcaaaac agtccacttc actaatttta taacaaatta attacagtct gcactgaggt   5220
ttttactgtt attcctttt ataattctca gatcccacct aacccaggca gtggctgaca    5280
atggaatatc tttttaaggt ttagtgggtg atactgtacc aggctgtact ggcagaatgt   5340
aggaaaggaa cctagacact cttgaaaagt gtttaccttt tcttacttct ctgcagagtt   5400
cacaaaaata aaaaaaaaaa agtttacttt tcttggggtt gttaaggggg ggacaagatt   5460
tctgcctttg tatatacact gcttccctac tgtcttgtgg tactgtcgcc tgtaagaggg   5520
aaggagatgg ctctaggtaa taaaactgta ctctcatcct atataagaaa catcagaatg   5580
gccgagcatg gtggctcaca cctgtaatcc cagcactttg ggagactgag gcaggcagat   5640
catgaggtca agagatcgaa accatcctgg tcaacatggt gaaatcctgt ctctactaaa   5700
aatacaaaaa ttagcctggc atggtggtgc gtgcctgtaa tcccagctac atgggaggct   5760
aaggcaggat aatcgcttga acccggaagg cggagcttgc agtgagccaa gactgcgcca   5820
ttgcactcca gccttgtgac agagcgagac tctgcctcaa aaaaaaaaa aaaaaataa     5880 ataaataaat aaataaataa atgtcagaga atttctctgg gaaaatggca ttggaacaaa   5940
gacaaaaaaa caaccaccag tgcgctcctt gtctttcgag ctatctccct tcctgaagtg   6000
atctacctaa tttcaataac acttatcagt tacttaagtc atatatttcc aattaagaaa   6060
gtatcatata tgagcatgaa cacagcttga ttattcttgc taatgtatgt cttcgcggag   6120
taaattctct actaatatgt tccttgctct ttagcaaatc agaatttccg ttcaaatctt   6180
gaatgtcttt ttaccaggac tcataactta gctttcaagt agaaagcctt tattttctt    6240
```

-continued

```
ctttcagtaa aaaaaaaaaa aaaaatatat atatatatat atatatcatg ccaagttgtt    6300
tttgttgatg gaataacata tattatttta ttcaaatact gctgttataa aattatattc    6360
caaattacct tttaaaatat atggggattt ggccacatgt tgcccttgga atttaatttc    6420
caccttcaga tttttgtagc ttgcatacat tctgtatctt actatgaagg acccatcttt    6480
tcggtctaaa acctggactc caactctagt gaattgctcc tctggtgctg agactttcac    6540
ctggaagacc ttttcgcctg gagaagatgt gaatctgtga tgaaaaggca atgggggaga    6600
taaacagatt ttaacgaaca aacacacaaa ggttatgctc ttcagtctgg aaacttgatt    6660
attctcctcc acattcttcc tctaacatat gattgcttct tcttctctta tgcttttagt    6720
accagaatga atatgatgga tcagagattt aaaaaaatga ggatgacaat ggccaagata    6780
acatgaaaca gtttcattaa acagtcacaa tggagtatgt taagactatt aatctatata    6840
agcacagaac atactcatgc attccatatg gaaaaatatt cttactaact tatttcatgc    6900
tatcacatct ggatatttgt gatcaaatga tgctcccaaa gataatgatc ttattttgaa    6960
aaatctctgc caatgaatct ttacaatatc agtattataa atcacgctca ggcctggcac    7020
tgtggcccat gcctactatc tcaacatctt gggaggccaa ggagggaaga ctgcttgagg    7080
ccaggagttc gagatcagcc tgggcaacaa ggtgagatcc tgtctctaca ataataata    7140 ataataataa aaaacaaata gccaggcgag gtggcacacg cctgtagtcc caactactag    7200
ggaggctgag gtgggaggat agcttcagcc tgggaggttg agggtacagt gagctgtgat    7260
tgcaccactg cactccagac taggctagga agtgaaaccc tgtcttaaaa aaaaaaaact    7320
cacgctcagc catgggcaaa agcaaagtag taggtagtgt atcatctttt gccaaataac    7380
aaaatttaca acctgccttt tacttgacaa ccttttattc cagtattttt ttctgtatga    7440
aatacacaca gtcagcatcc accaataata gagacaatca tttcagaagt ataggaatta    7500
taaaaataag ttttaagtat gatgttaaag tattaaattc attggaacaa atatttgtt    7560 acaatcatat aggagattaa tacttcgata cttccttcc gaactctgaa gtttcaaata    7620
gtacttcatt tttcttttc agtttcaaaa catgcttacc tgcagatgtc tccttgaaaa    7680
ttgagggccg caccagagaa agatgaagcc catcaagtct ctaacaacta ggtttaaatc    7740
ccttataata gcttatgcga aaagtagtta gaaacagtat ttccagcaaa gtggagggac    7800
tttgtcttgc cctgataatg tgggaatctg aatcaaaatt gctaggagat tatttatat    7860 gttatataca atacattata ttgcatatat tataattcgg aacaatttct acagctacag    7920
agaaaaatgg gtaaccaaat atcctggaat ataaactgct gtggagaaac gagttcttgg    7980
aaagaaaaat cttaaaggga gaaacagatt taaccgccat ccaaaatagg taaggagccg    8040
tttctcgact tacttattcc ctgatgtatc cactgcctga atatagaaat agcgggcggg    8100
aaggacgacg tctgctttta gcccgggtcc ccatatttcg ctcttctccg ggctcagctg    8160
cctttctccg ccggtctcgg cgagtgctgg aactgtcgcc agaagaagc aataaagtag    8220 caaagtgcca acatttaca agacggactc tcgaaatgat ccaccgataa atgaagaagt    8280
gtaagaggtg gacagaagca gccgagcctt cggcagggac ccgccggccg atcgcagcag    8340
ccaacgcgac tgcaaaggtt gccgcccggc gtgcagggca ggcgcgcggg tctccgcgac    8400
cccaggacaa tcaaagcccg tgccccggcg cgcccaggtg agggtcccct ggcgttctgc    8460
tgtcccggcc gagaaccgcg ctgctcctct ctctcaggac aatgatgaac ttgagttgct    8520
cctgccactg gagcatcatt tgggagcgaa tccgtctcag gttccagcca aggtgtaggg    8580
```

```
cgagggatt  ggcccgtgcg  tcgggccagg  ctcagtaacg  ccttctccaa  gtggatggcg    8640
gggtggacac  gcgtcccggc  gccccgggct  ccctgggata  tgtagttcgc  gacaggacga    8700
gcggaaatac  tgccaggatt  ttaccacctc  tcgcccattt  atttacttct  cggtcaccgc    8760
tttcggggga  cagataaaca  ccacagatgc  ccatcaaagg  ggcgcacggg  tctggaggcg    8820
cagctcaggt  ttttgcgttg  gtcaccctgc  cctccgcacg  tggagagggc  aggcataaag    8880
caccttgaaa  ggaaggtgct  gtcaatgcta  tccgacgacc  tgtcgccggg  caccgcagca    8940
tcctcgctcg  ctccgatggg  acgagggacg  ccggccccag  ggtaacagga  ggcgcctcgc    9000
cggccgcgcg  ctggatgctg  tgatccaggt  ccggagccgg  gttccgccgc  ggccgcagcg    9060
acccgacccc  acccgacagg  ccagaggtac  cccggggcgg  ggggcagggg  ccgaggtggc    9120
ggccggctgt  gcgctctgag  cgcctggccc  tccgctgggc  acctgggcgc  cgccagcccg    9180
gcctgctgcc  gctctacgcg  cagccacctg  ggcattcaaa  attttttactt  aattcgatac    9240
cggcctgggc  tgccaggggt  catcgcctct  ccgagccccg  tggcgtccag  atggaggcca    9300
ctgcatgggt  gcgcgctctc  ccgggaagga  gtaggggaa   gagctgtgtc  gcgggggaa    9360
gagaagcgca  agggaaagaa  gggcctagcc  ctctggtgaa  caaagctcga  ttaggaggtg    9420
tccatgtgga  taccggtgac  ccctgtgcgg  ccgtcggtct  ccacgccacg  ctgggcaggg    9480
tccgggaacc  agcgcgcagc  ggccgtcgcc  ttccccctgca cgccagcacc  cgggtctggg    9540
ccgccgccag  gagtcacggg  ctcaccgccc  tggtcagctt  ggcagtcgga  cccggagccg    9600
cctcctctgc  ctgcctccct  cttgccagct  gccccgaaaa  cccagaagag  ccggtggctc    9660
cgagccaagg  cgggcctggt  tcggcgccag  gaaaggggt   ttcttcctca  ttttctttg    9720
tgcaattgtc  attattaatg  ataccgactc  gtttactcaa  acagtcgaat  cggagccca    9780
gctcttagcc  cggatgcagc  aattgcccgt  gggcccccctt taacaccaac  agcgtccccg    9840
gggcccgggg  caagcatgtt  cgaggcggtc  accccgggc   tcggcgcgc   tcccctggc    9900
ggagagcctc  gtcttccggc  cggtgaggga  aggtagagga  gggagtaggg  gcgaggaggc    9960
ctcggcggcc  cttgggctct  gcgggctggg  gactcgggt   gcccgcgaca  cgcgcggagg  10020
cgcgggctgg  gttggccacg  ggcagggagc  gcagccgcgc  tccttcctct  ctgcccgcgt  10080
cgcctccgcg  cgcactggtt  ctgcgcggcg  gggcttggcc  tgcgcgactg  tctactccgt  10140
cccggcggcc  tcggagcccg  gccgagcggc  gagcttgtca  gaggacggtg  gtggaaacgc  10200
tcccggcctc  cccaggggcg  cgggctggag  gctggcgcca  ggcgcggagg  actcccggta  10260
tcttttgaca  ggctggcgcc  tcggctctgg  ggacccgcag  gtctgaaggg  gaggaaggg   10320
cctggagggc  gcgggaggac  accggtgggg  aaggggtggca ttagctcggc  cggggctat   10380
gcgcctctgg  tttcgccctc  ccgcgcatat  tcgaccctta  cgaggtcacc  ggaatgcccc  10440
tgctcctcag  ttgccttcta  tacaggatat  cgatcagggt  attttgttat  acgaaaaggc  10500
tttactgaag  aggttttag   atgtgtttgg  ttctctcata  aacttgatac  ttgagaatac  10560
agacaaaata  taacctgaaa  agactacaac  ctaggcgatg  aagattggct  ttacaaatgg  10620
acgtttattt  tacagaacac  ttcgttcagt  gactttgaac  aatcatgact  ctggcggtgc  10680
ttttaaact   tgccattta   taaattttg   ctttgcatac  gagcaaacca  tatttctatt  10740
gcttatgaca  tgatttatg   agtaagctat  tagttgagcc  tgaggtcctg  cagtcattct  10800
tagtagtaaa  ttttttttt   tttttttg   agacggagtt  ttgctctgat  cgcccaggct  10860
ggagtgcaat  ggtgcaactg  taacctccac  ctctggtgtt  cagcgattct  ccagccttgc  10920
ctcctgagta  gctgggccta  cacgcatgcg  ccaccatgca  cggctaattt  tgtatttttt  10980
```

```
tatttttttat tttttttttag tagaaacggg tctcaccatg ttggccaggc tggcctcaaa    11040
ctcctgacct cagatgatcc acccgcctca gcctcccaaa gtgctgggat tacaggtgtg    11100
agccaccacg ccggcttagt aaatcttaat atagcaacac ctcacttgcc tggaagaggg    11160
aaccgcaatc aatcaaaatg agggcctaca gtaatgcctg gcatgatgca aacacttaaa    11220
aattatctgt tgaatgagac gtctacaaat cctaggccct ggggatacaa taatctggaa    11280
aaccagactt gcaggatgca gacgttgatc atatgaacag atatgcacag aagtaagtgt    11340
aaaattgcca cctggtaaga cctgtgtgag gaaggtacta gagtctgtac cgggtcacct    11400
ggcctagttt gagaagccaa gaaggtttcc cccagaaagt gacatttgag ctgacattgg    11460
aaagatgaat gggaatgagc taagtaaggg agacagtatt gggagaacca aaaagtaatg    11520
tggagcttgg ggggtggggg aaaggaatga gatggagcta accagataga tctagggacc    11580
atcaggagtt ggccttttgt tctaagagca gaggctttca ggcagaggag ttctgtgatc    11640
atatatatgt agcaaacttt attttctaat atctctgcac aggtcaggtt agaagtgtca    11700
actcactggg aatagtttat aaatagagaa acaaaaggag ataaaagatg agtcaaaaca    11760
gtgacagctg cagcctatta agtggaggga caaactgcct ctctatagct cagtattgtc    11820
tataatgatt ctgttattag tattatcagt aataaattgt gcttagtgta ctttaagaaa    11880
gctagaatct gagcatgcaa taatagaagc ccccttggcc tcttgggggct ctcactatag    11940 tggagagaat agacgtgaga cagtgtggaa agaaagtaaa cactagcagt gtttgggtcg    12000
tgggatttgg gtaatttcca ttttcctgta atatcttttg gtactttgca ttttttttgta    12060 atgttttact tataaaatct atgaatatta cattttcaaa gagaaattta catatagttt    12120
ccaatgagaa tgtttcatgc ccttggattt tagtgacagt caatataaaa tgcatcctta    12180
tattgatgat cttcattttt tttttgctaa aacttcgacc aaataaatca tcttgttccg    12240
tgaccattat ttaaaagcaa acaaactaaa aacacaaaca aaccagactg ttactttttt    12300
ctctctttcc tttttttttt ttttttttga cacagagtct tgctttgttg cccaggctag    12360
agtgcagtgg tgtgatcata gctcactgca gcctcaaact cctggcctca agtgattctt    12420
ttgcctcagc ctcccaaagc atagatatta caggtatgag ccactgtgcc tggctcacac    12480
tgttactctt tttattaatc tagtgctgtg ttctatcttt agcgtccagg aagcttaccc    12540
ccaacttttg tgcttaaatg cagtcatttc cctttgccta tgtttttgat aagaatattc    12600
tccatggctg ggcatggtgg cttgtgcctg taatgccagc aatttgggag gctgaggcgg    12660
gaggattgct tgaagccaag aggtcaagac cagcctaggc aacatagcaa gaccctgttt    12720
cttaaaaaaa aaaaaaaaaa aggttattct atatatgttc caaatgagca tacttttaca    12780
atccctgcca ggtgcagtgg ctcattccta taatcccagc actttggggg gccgaggcca    12840
gcagatcacc tgaggtcagg agttccagac cagcctggcc aacgtggtga acccccatct    12900
ctactaaaaa tacaaaaatt agccaggcat ggtggcacct gcctgtaatt ccagctactc    12960
cagaggctga ggcaggagaa tctcttgaat ccaggagaca gaggttgcag tgagctgaga    13020
tccggccatt gcactccagc ctgggcaaca gagtgagatt ccatttaaaa aaatcaaatc    13080
aaatccctac actgtcacac agagagctgg tcccacaggc aaaattccat tcagtgtgag    13140
gaaggaagcc ctgggaaagt ggaagccaag tctgagatga ggatataaaa ggggcagggc    13200
ctggaacatt tccgtctcgc caccaaactc actctaataa cctttgtcta ttgcctctca    13260
ccgagactat atgctctttc attcctcacc tcgcacagcc cacccccacg accccaatac    13320
```

```
cacaaatacc tacctctctg tccaccacac tgatgtagag aaaggcatga aggtcacaga    13380
tgagaagtag aaaatgctat gttaggacat ctgctgagaa tcagagcaac tctgtcttcc    13440
aaaaagacaa gagtttggtc tgaacaacgc caggtactga gcttccctct gccatcaccg    13500
ttgcaccacc agatgaataa ggagagagca ccacttccac ttgaggaccc actacaacta    13560
ctccaagaat ttttttttacc aaaagaaagt gaaagttttc aaagtgaaac cacaggaggt    13620
tccacctttc gtggtaatat tcctatccaa ctgaccctct tgcaaacaac tataaactct    13680
gcacaaatta ttttaaaact gaagagtttt tgtttgttt gttcgtttcg agacaagatg    13740
gagtgcaggt cacccaggct ggagtgcagt ggcgcgatct tggctcaacg caacctccac    13800
cttcgagcct caagcaattc tgcctcagcc tcccgagtag ctgggattac aggcatgcgt    13860
cactaccgcc tggctaattt ttatctttt tttgagatgg agtttcactc tgtcacccag    13920
gctggagtgc aatggcagga tctcagctca ctgcaacctc cacctcctgg gttcaggccg    13980
ttctcctgcc tcagcctcgc aagtagctgt gattacaggt gcgcgccatc atgcccagct    14040
aatttttttg tgttttttag tagagacagg gtttcaccct gtgtgccagg ctggtctcga    14100
actctgacct catgatccac cgcctcggc ctcctacagt gctgggatta caggtgtgag    14160
ccactgcacc cggcccttac tgtctggcta attttttaaat tttcagtcga gatggggttt    14220
caccatattg gccaggctag tcttgaactc ctgacctcaa atgatccacc cgcctcagcc    14280
tcccaaagtg ctgggattac aggcatgagc caccacacca ggcctaaaaa ctgaaggttt    14340
gaatagagaa aaagcatgct ttaaaagtaa agaaaatgga atttttgccta gcatatgtgg    14400 agtcctaata tgcagctctg tttccttaaa ttccatgaaa gccatgcagt acctttgcta    14460
gtttctcctc acagatcagg ataacctagg gggctcttgt gtgaatcgtc ttctatttct    14520
tgcagcctaa ctcataggct ttcgttgttc aatatttgta tgatggtttt gatactattt    14580
ttggtaaccc atgacagtta ttttattttc taattttttta agtaagcaaa tgggcagaga    14640
tattaactgg taaaagtcca actgatcacc cagggtggac tgaatctctc aactgatgct    14700
ctgttgctgg agccctgaga aacccgcata ccctgcccgg gcacctgcct gggggttgtct    14760 gctgcgtgtc ctgggatggt tcaattcacc aaggacttcc tctggtataa atcttcagct    14820
tccttgcatg ccctcagttg ctatttaagc tttctgtttt cttccctaaa ggaatcagtt    14880
tagacttgaa attcagtttt tcctgaaact gatcagaagt tagtgacacc ttgattggat    14940
ccgttttcct gtcaggtgat gaatctttgg aaaatttact ttctgtattc tgtgtttatt    15000
taaatctgtg gccgttattc atcatgtatc ctttatgcct atgtacgtaa aaaatcttgc    15060
taatacatta ttttttagac aactttatg aggtataatt cacacaccat ataatttacc    15120
cattaagtta tgcaattcat tggcttttag ggtatttaca agttgtgtgt tcattgccac    15180
aatcatttat agaatattat cattattaca aaaagaaact ccatcacccc caaacccccaa    15240 gccctaggaa accatgaatc tactttctgt ctgcatagat ttgcctgttc tggacatgtt    15300
atataaatag aataatacac tatctggtcc tttgtgacga tcttctttta ctcactataa    15360
tgttttcggg gttcatccat gttgtagcat gggtcagtac ttcatttctt tttattgcca    15420
aataatattc cattgtatgg ataaccaca ttttattttat acattcctca gttggtggac    15480 atttggggttt tttccatttt ttggccatta tgaataatgc tgctattaac atttgtgtga    15540
agatgtattt tcatctgtca cggatatata ccttggcatg aaattgctgg accatatggt    15600
aactctgttt aattgttgga agaactgttt tccaaagcaa ctggaccatt ttacatttcc    15660
attagcaatg tatgagggtt atgatttctc cacgtcctca ccaacatttt tgattatagc    15720
```

-continued

```
cattctagcg tgtgtgaggt gttaatctca ttgtggtttt gatttgtatt tccatgatgg   15780
ctaatgatac tgagcatctt ttcatgtgct tattggccat ttattttat ttttgataca    15840 gtctcgctct gttgcccagg ctagagtgta gtggcgcgat ctcggctcac tgcaacctct   15900
acctcccagg ttcaagtgag tcttatgtct cagcctcctg agtagctggg actacaggca   15960
tgtgccacca tgcctggcta atttttgtat ttttagaagg acggggtttt caccatgttg   16020
gccaggctgg tctcgaactc ctgacccaa gtgatccacc tgccttggcc tcccaaagtg     16080
ctggattaca ggtgtgagtg actgcgcctg gccttattgg caatttctgt actgattttg   16140
gagaagacac tattcagata ctttgcccat ttttaaaaat tgggctattt gctggccggg   16200
catggtggct cacatctgta attccagcac tttgggaggc agaggtgggc agatcacttg   16260
aggtcgggat tttgagacca gcctgaccaa gatggagaaa aacatctnt actaaaaata    16320 caaaattagc cgggcgtggt ggcgcatgcc tgtaatccca gctacttggg aggctgaggc   16380
aggagaatca cttgaacccg ggaggcggag gttgcggtga gccgagattg tgccattgca   16440
ctccagcctg ggcaacaaga gtgaaactcc atctcaaaaa aaaaaaaatt gggctatttg   16500 cttttttaatt atttttaat tatttgaaaa taatttaatg catatttag actaatttaa     16560 aaaataagat agtgattgtg actccagtca tatagtagtt gtaaaattaa tatagaatga   16620
aggcatatgt atgcataaaa cttgctatgc tttttagtgg ctctttgtgt atctggtgga   16680
ttgttgatca ttcttttttcc ttcctcttag gagctcattt tgcagctctc aagcttttat  16740
agcatgctgt aaacaattgt caaagttgtt tatcaagaaa cagatagagt tgcaacttgt   16800
ttctagtaat agaaactttt acactgcatt caatgcctaa cgttgcagaa acagaaaggt   16860
caaatgattc tggaaatggt gagcacaaat ctgagagaaa gtcacctgaa gagaatctac   16920
aaggtgctgt aaaatctttc tgcacaagtg cctcaggagc acccttgggt cccaaaggag   16980
atggtcatta tccatggagt tgtccagtga ctcatacacg ggaaaaaatt tatgccatct   17040
gttcggacta tgccttttctc aaccaggcga cctcaatcta taaaactcca aatccatccc   17100
gctctccttg cctccctgat agtacctctt tatctgctgg aaataattca tcaagataca   17160
ttggtatccc gactagtaca tcggaaatta tctacaatga agaaaatagc ttggaaaact   17220
tatccaacag cctgggcaag ctacctctcg catgggaaat tgataaatct gaatttgatg   17280
gggtgaccac aaattcgaaa cacaaatcag gtaaggaggg agccatgaag ttcatatgtg   17340
aaaataatga gaaacaaac actatgtctt gtttaatctt gccattacac atagtttcct    17400
tgtataatac tagataagga acatggctat catcttgtct gtcaatgtag ttttaggaaa   17460
gtaaccttga cgtagggcat gtagttcatt gcggggcttc cactggaaac ttcaagcata   17520
agctttgtat caaatatttt gagagatttg aaaatctaat aatgtaaaat attataaaca   17580
gatggtagct tagaaaatga aatgttaata acatggctag ataacttac tactgtttca     17640 tagtttata ggcacatgaa gttgtatttc ctgaccaaac atctttttt cctgctatat      17700 aatgttttag cttttttgt tgttaaaatt ttttaggcac ccagcaaagc ctccatgtac     17760
caccaagtgg gttgtgtact gctcaattta agaggatgct gtttaccgag gttgtgcata   17820
actttcacag ttgcaatggg gtggtcctat ggcagataga aatactttac acttcttttct  17880 tttgaattca aagtaataca ggaattttat gaggcaggta ctgttagccc catttgtagg   17940
tgaagaaatt gaggcttaga agggataaat ctctagaccg aagttgcaga gttaataaga   18000
ggaggtcaaa ctaggatttg tatttacttc tagtcttctc tgatgatttt ataaaacctt   18060
```

```
aatgcttctg cttgtttatc tgcaaaatca atttgtttca tagaatttta ggtaaatttg    18120
taattcttaa gggtaggagg gggattttgc ttttttttgtc taaatttgta ggtaatgagt    18180
ctgcaatttt cttttttgtct aatgcctttg gccagttttg gaattagggc tatgcaaatc    18240
ttctaagaaa agttgggaag tgtttttttcc tcctgttttc tgaggatttt cagagagata    18300
ttaaaatctg tatttataat tatggagttg tcttgatttc tgttaatttc tgacaaattt    18360
taatttgtcc atgtcattta agttgtcaaa tttgggggct taaagttaat gttatccctc    18420
taacatctaa ggaatctttg ttgacaactc cttttgcatc ctaatactgg taattaattt    18480
attttctcta ttttttttaa aactgatcaa tctagctagg agtttatcaa ttttgttaat    18540
cttttcaaat aactagcttt tgttaatttt ctcaattgtt tgttttctat ttcattggtt    18600
tctgctcttt attatttgct tcctctgact tactttgggt ttattttgtt cttcattttc    18660
tgacttctta agatggaagc ttagatcatt gattttagac ttttctacca taagcataga    18720
atactccaaa ttgctaagta ctgctttagc tgcagctcac aaattttgat atgcttatta    18780
ttattactta attggaaata ttttctaatt tcctttgcaa tttattcttt gatacatgta    18840
ttacttagat gtatgctgtt taatttctag atattaatag ttttttctaaa tattgatttc    18900 tagtttagtt ccattgtgga cagagggcat atgctctcag tcttttttaaa tttactgaga    18960 cttgttttat gacccaacat atggtctatc ttggtgaatg tgccatgtgc acttgaaaag    19020
aatgtgcatt ctgcagtcat tgggagtatc tataaatatt aattatgtcg aagtgtttga    19080
aagtgtcatt cacatctttt gtgtctccgc ttaacttgtg tcttgttcta tcaattacca    19140
aaagaagggt gttaaaaatc ttcaactatg attgtgaagt tgtcttttct ccatttaatt    19200 tctttttttaa aaactaatac atgtctaata acagaaaatt tactgtctta accatttta    19260 cgtgtacagt ttagtggcat taagtacatt tacgttgttg tgcaaccatc atcactattc    19320
atctccaaat ctcttttcctt ttcttttctt tctttttttt ttttttctga cagagagtct    19380
cgctctgtcg cccaggctgg agtgcagtgg cgcgatctcg gctcactgca agctccgcct    19440
cccgggttca caccattctc ctgcctcagc ctcccgagta cctgggacta caggcgcctg    19500
tcaccgtgcc cggctacttt tttgtatttt tagtagggtc ggggtttcac cgtggtctcg    19560
acctcctgac ctcgtgatcc gcccgcctcg gcctcccaaa gtgctgggat tacaggcgtg    19620
agccaccccg cccagcccct cttttcatct tacaaaataa actttgtacc cattaaacaa    19680
taaatcctca ttccttctcc tcacagtccc tggaaaccac aatttttactt tttgtcactg    19740 tgaatttgac tattctaggt accttatgta agtgaaatca tatagtattt gtcttttat    19800 gactggttta tttatagcca cccctgctct cttctgggtg ctatttgctt tggaatactt    19860
atttccatcc ttttactttc agcctatttg tatctctaga tctaaagtga gtgtttcaga    19920
gacagcatat agttagctaa tttttttctgt ttctgttttt gtgtgtgaac ccacgtatac    19980
aaaaacatat ttttaaaaaa atgcattctg ccagtctcta tgttttgagt ggagaattta    20040
atccatttac atttgaagta atcactgata aggagagact tgtcatttta gtacttgtta    20100
tttatatgta aacactctgt tcctatactg cttcgtccac acttaacttt cagttattga    20160
tgttatcaaa ttacaaattt atatattgtg tgtctgaaaa cataaactaa taatttttat    20220
gtattaatct cttaaataat gtggaaaaca aaatgtggag ttacaaacca aagttattat    20280
aataatagct tttttatttt tatttttttat tttgaaatag ggtcttgctc tcttgcccag    20340
gctggagtgc agtggcacga ccatggctta ctgcagcctt gacctcaggc ttaagcaatc    20400
ctcccacttc agccttctga gtagctggga ctacaggtgc acatcaccac gactggctaa    20460
```

```
tttttaatat ttttttgtag agatagagtc tcactatgtt gccagggtg  gtcttgaact   20520 cctgggctca agcaatcctc ctgcctcggc cttccaaagt gctgggaata caggcatgag   20580
ccactgctcc tggcctacta ctagctttta agctaataat aatttctcaa aaatgtatta   20640
gtctcataaa tcatatagaa tacaaaaact ggagttgcaa actaacaaaa taacactggc   20700
ttttataatt gttcgtgtat taccttcact gaggtaaatt tatttcttcc tatggctttg   20760
aggtactagc taatgtcctt tcatttcaac cagcaggaat cctttagca  ttccttacag   20820 ggcaagtcta gtggtaataa actccttcag ttttttgtttg tctgggaatg tctgagtttc   20880
ttcttcactt ttgaaggaca gttttgctgg atttagaatt cttgtttgaa tttttttttt   20940
atttcagcac tttgaatata tcagcccact tccttctggc ttccaaagtt tctgatgaga   21000
aatctgttga tattcttatt aacagtccat tgtatgtgat gagttgcttc tcttgtgttg   21060
cttttaagag tctttgtctt tttgcaattt ttaaattttt tatttgatac ggagttttgt   21120
tcttgttgcc caggttggag tgcaatggca cgatcttggc tcaccacaac ctccaccttc   21180
tgggttcaag caattctcct gcctcagcct cccaagtagc tgggattaca ggcgtgcgcc   21240
accatgcctg gctaattttg tattttagt  agagacggag tttctccatg ttggtcaggc   21300
tggtcttgaa ctcctgacct caggtcatcc gcctgcctca gcctcccaaa gtgctgggat   21360
tacaggcgtg agccaccgtg cccagccttg caatttatt  ataacatata ttggtgtggg   21420
tctttctaag ttcatcctat ttggaatttg ttgagtttct tggatgttta tattcatgtt   21480
ttttaaatca aatttggaaa gttttaggc  attatttgtt tggataatct cctacccctt   21540
tttcagtgtc ttctccttct ggaacttctg caatgtatag gttggtccac tcgatggtgt   21600
ccccaggtcc cttaaggtct gttttacttt cttcagacct ttttttttct gttcctcata   21660
ctcaattatt tcagttttcc catcttcaag gtcactaatt tttctgcctg ctcaaaactg   21720
cctttgaatc actctagtga gtttttcatt tcagttatta tatttttcag cccaagaatt   21780 tattttttggt tttaagtttt ctatctcttc attgatattt ccatgttctt catacataca   21840
tctttcgtta gttcttttgg catctttaag atagtggttt taaagtccctt gtctagcaag   21900 tctgccattt ggtctttcca ggatggtttc tgttggttta tatatttttt tgtttctttg   21960
aatgggcctt attctgtttc ttgtgatttt ttgttgttgt tgttgttgga aactagacat   22020
tcaaatatta tttaataatg cagtaactct ggaaatcaat acccatcttt cccagagttt   22080
gttgatttta gttttttgttt tttgattgct ataggctgtt tctatgctgg taatcaacct   22140
gaggtataca tttaagggct ctcagggaa  aagcccctgc ctttctctga gtgtgtacag   22200
tgattttcta catttccctg tataagtgat tgcttttgaa tatactgttt ttgaaatgtc   22260
tggctcccca aacagaaaat ggagaggaaa aaaacagaa  caaaaaaacc acaccaaagg   22320
tgctggcccc ttaagtcctc tggaagttgc ttctgttgta gtgggaggg  cttgcaacat   22380 tggagggaga gttgcaacaa tggctgcccc cctgtatctg tgctttcaag atcagaagca   22440
gcagtcagca atcagaacac agatttccaa ttttcatagg acatggacct tttttgcccac   22500 catggttccc acaaactgcc tgaagcttct ccaggagcat atgcacagtt tcttggactt   22560
ggggataggt agttgtacct tgctatgtgc tgaaattgac caaaatttgc atttactgtt   22620
caggacttcc tctgaaagtt gcaatccttt gaatagactc tggaattcca aaataattac   22680
atcagacaga ttctgccagt gcagttgtct aggtggggag acagattcct ggtgcctcct   22740
acactgcact taattctgtt aattttttta aaatgtaat  ttgaagctct gttattaagt   22800
```

```
tcacatacat ttatgagatt taggccttct tcctgaattg acccttttat cattatgaaa    22860
tatatttcgt tattcctgga agtatttctt gttctgaaag ttactttgtt tgatattaat    22920
aaagctcctc agctttattt tgattatatt tgcatggtat atatttttcc atctatttat    22980
tttagttcta gaatttacat ttttatagct tctatttctc atctgagatt tgctatattt    23040
ttcatttatt acaagagcat tttatctatg tcataatgca gagttataat atctacttta    23100
atttcttatc tgcaaatttc aaaatctggc taatctcaca gtaggcctta tcttttttct    23160
tgagaatgag tcatatttt cactttcctt atatgttcta taattttgca ttgtatccta    23220
gagagtggga ctattatgtt atggcaactc tggtatattc cttcaaagtg ttgatttttt    23280 tttggtttg ggaggcagtt aatttggttg aactaaaact gtaaattctg tctccttggt    23340
acagctccaa ccatctcagt tcagctcttt tagctgtgtt gcttgaattt gctccttaca    23400
tgcatggtcc aggggtcagt ccaaggtttg ggccaaattt atacacagaa tttgggcccc    23460
ctcttctctg tggctctctt ctttctgggt ttcctctcac ctcactttca gtgatggtga    23520
ttgcacagga ctctgtcctt tggttcttcc agtaaaaaaa gacagtggat tttctgcttt    23580
tgtttgctct tctcatacct ttttctaaaa gtcagtgtgg tgaatacata tatttgtgtg    23640
tgtatgtgtc tgtgtgtgtc tgtctgtctg tgtgtgtgtt tggtgttgag gctgtgtgtg    23700
tgtgctgtgg gtagggtgag gaatggaaga aggaactcag taatgagaag gagcagtggg    23760
cgaaggttct tgaagctgat gtgatggaag gcagaaggtg caggtgttgc tcttctatgt    23820
tcccatctca aacggcgctt tcactttgat gtggcttctt tccctcaagt caaatgaact    23880
tttgcctgtg ggaccagctc tttctgtggc agtgcgggca ttttatgaag tacgctcatt    23940
tgggccgtat atgctaattg atcccagggg caatccgaga ttcaacaaaa agagaatagg    24000
gggcaaggtc atggaaccct agaggaaagt gtgagtacag actgttggca gagcctatca    24060
aggtcacaca tttctatgtt tcattagctt taacatttta agtggctggg aaaactactt    24120
agggaattaa gtcattatta ggcagtgaag acatctcaag aaatgttaga aactaattct    24180
tctgttatct gactctgtaa gagtcatttt accagtcaag gaaatttggc acaatgagat    24240
ttggcacagt tgctcacctt tgccagtgat gttcagctct gtgaaaagtg tgttctctgt    24300
aaaaacttag aaaaaataat taaaagggtc acgcatgatg gctcacactt gtaatcccag    24360
cattttgtga ggctgaggca ggtggattgc ttgagctcag gagtttgaga ccaacctggg    24420
caacatagtg agaccctgac tttgttaaaa atacaaaaat tagctgggca tggtcgcacg    24480
cacttgtggt cccaggtact cctgaggctg atgtaggagg attgcttgag ccccggaggc    24540
agaggttgca atgagtggag attgcgtcac tgcactcttg tctgggcaac aaagcaagac    24600
cttgtctcaa aacaaacaaa caaacaaaca aacaaaaga ataattaaaa ggaaggcgaa    24660
acattgtttc ttgactttat agtcttcatt attattacat ttttacagaa attccctgtg    24720
taataatagt tcctgagttc cagctgttcg taggtgtcaa atggtttctc tgtatagtat    24780
cttgaaggaa taaaactgat ctcttttccat gtttgcttac taggcatata tgtatataat    24840 ctatttata atttatgaat gactcataaa aatgaaatat tagccttcag ttaattttta    24900
taacagaact gttttaaaat agaatatgtg tgaaatatta agtatttga gcatagctat    24960 ctgaaatctt aatagtattt taatgaaatg aggcttggat gttatttatt gatattttac    25020
tttatataat ttttactag atacttcact aacgatttag aaataaaact tataaaaata    25080 aaagtatag ggatggatac cccattctcc atgatgtggt tatttcacat tgcatgcttg    25140
tatcaaaaca tcttatgtac ccctaagcat gtacacctac tatgtactct caaaaattaa    25200
```

```
aaaaaattaa aaagtacaaa ttctcactct tacttttggc ttccttttgt ctagctccca    25260 attctcccctt ccccagtagt aaccactgtt gtttgccttg agggtctttt ggagaatgtt   25320
tgtatgtgtg tgcatgtatg agtgtgtgtg cacatgcata catagatgca tacatgcaca    25380
caggaggctt gctttcatt ctagtttctg tgctagagtt gcattttagt aatgtatatg    25440
tgtgcatcat tcttcattca ttctgtcgtc tctgtcggtc cagagatatt tttaaacatc    25500
acatcatcac attaatggat ctggtgcttt tactttctta acagagttgc tttaatttgg    25560
ttttattgtt ttatagaaag ccttcatttt ctggaaagtg gtctagttaa atttttttac   25620
tgtcgataat ttgattttcc ggatgtggct aaagatttag tgattgactg ttccaccagc   25680
taagtgacta gctctggaat tggagtataa aacctgaca cgaaatagga ttcatggttg    25740
tttaaatttg tttttattat ttctctttaa ggtaggggac tattattgaa aatacatgta   25800
ttacttcatt gtgtttgcaa atatcacttt tagaacctgt ggcagttatt tatttgttat   25860 tatttttct ttgcactttc tcagcagaat tattaaggca gttacttctt aattttggtg    25920
cataattaat ttttgtcatt tcagtttact tcatcttaag cattttgctt atttttatact  25980 cttgtattct aggcaatgca aagaaacaag tttccaagag aaaaacttca gataaaaagg   26040
gaagatatca gaaggaatgt cctcagcatt ctcctcttga agatattaaa cagcggaaag   26100
tattagacct cagacgatgg tgatgttatc agtttttatt tttttcattt ttgaaatatg   26160
taatatatgt tggcaataac gtagcagttt acaaattaat acattatatg tatcataaat    26220
atttttattt ctaaaattat taccaggatt tctgaatatt taaagtcacc acaaatgttt   26280
gaagtagatt aataatgagt tatgctggtc tttcccaaac tcggcttatt attagagtca    26340
tctgtgtgac tccacgtaac tgccatgtag atttaacaat gattaacctt ttgatgtagt    26400
taaatactta gcttttcatt gctgaagaat tttcaagtaa gtgactgatt tttattatat    26460
ttcatctcaa gttacctaag tatgcatctc taaaaaatga ctttttttcta cttaaccaca   26520 atacttttgt catacttaat aagattaacg atatttccct agtgtctaat tcccaggcta    26580
aattcacgtt tcccagattg ttctgaaaag gtcttcacat ctgtttgttc aaagtgggac    26640
ccagttgtga accacatgtt tgcttgtcat gacccataat tctctcaatc taggtcagtc    26700
tccaccccac tttccccctt gtcttttaaa aattctatta ttttaatcga caaatgagaa    26760
taataaagat tgacttattg aagagacttg gccagatatt ttatagaatg tcctacattc    26820
cagatttgta ttttccttttt agtttcctaa attatgcatc taacctcaat atttcctgta   26880
aactggaagt tgaatacaaa gacttgatta aattccagta caacattta tgcaagaaca    26940 ctgcttaagt gggccctcat acttcaaagg tttcacatca gaaggcacat ggtatctgat    27000
tatccagtat tagcaattct aagtgattac tgggttaagg tggtgacagc tgtattctac    27060
attgacgagt tctttctttc tcctctggta ccctcaagta atcagtagag tgacagagtg    27120
gcattaggta atagccaggt tccatcagct ttttacctta tggttttagc caaatgtatt    27180
gacaacccaa acccattgat gatccttgtc tgaatatttg ttgcaaaatg gttatatttc   27240
aaaattccaa tttttttttt ttttactttt tattacccag ccttcttctg tagctttcac   27300
tgatcaactg gggctatttg gttatcttaa aatacagttc ctagtctaat gaaaacaagt    27360
ttaattcatg acaacttttta tgtattactg accctgattt gggttttaa aattcctttg    27420 tatgacattt tagaaatata tttttatcac ttatttaata aatattggac cctttgctgt    27480
aggctgagaa acagagatgc acacaacatt gtctttgttt tcccaaggtt tacaatccag    27540
```

```
ttgaggtgag gggactaaac agaaaaatgt taaatatctt aggcagtttg tcatgtgatg    27600
ggtatgaatc actaattaac catgaaagga ggtaatgatc accagaatgc tttactaagg    27660
tcctgggtct taaggagga aatatgaagg gttggagggt gaagggtctt tgaaagaatt     27720
acagcaaagt gtctctggaa tgtgggtaat gaagagtaga gtagcttgtc taaagtgagg    27780
ctcagagagg ccaagaaacc tgccagtgtc acatggctaa taagtagaag atcttgtatt    27840
gaagctgaag agtcagactc aacattcatg ctgtttgcgt ataatacatg tcatgatctg    27900
tttcttagat atcaggctca atatttagat tttttttctg agttaaagat aagccatgga    27960
cgatttctta acaaaaggaa cttttatcaa gataaatttg gaatagttag tatgtaggga    28020
ataatggaga agagacatta aagtcacaaa cattcatttt agtttctttg aaaagaaggt    28080
tttgctcgtt tgtgcttcta atcacttaga tttaagcttt gtttcaacaa caatctgtg     28140 taactacata ttaatagtat aacatgtgag gccatgaagg ctaggactag aaggataga    28200 tgggagaaat gccctgaggg gaaaacatca ccaggactat aagcctgttt tccactgaga    28260
atattacaag attaggttag aatggaaagt cccgtagaag atagtagaat gttggtaagc    28320 atttaacct ggtcataaac aagactagga aacaagttta gattgatgaa aaagtatgaa     28380
aaatcttaag agaaattccc cttccctct cctttttaaa aattctttca ggccaaattt      28440
agtgttatga gaaaaactat atacatgcat gcaatacttt gttagtaaat atatgtaaag    28500
ataaatgttg taaaatataa aacactgtta gtattggact tgtaaaataa tccccaaaat    28560
tgaactctgg caaaaatatt cacagcagaa aaaaaaatc agtaaatgaa tgagttgctt     28620
gtgttttatc agcaagggcc atatagctta tgatgacaga actgttaata atcacttgtc    28680
cacaaaggtc tcttaggttg gagttcacac tcatatttaa acaactaggg cagattactt    28740
gaataaggac attagtaaat tgctcatgtt tccagggata ggggaaaggg gtaaaaggga    28800
gttgtgttgt tcagtgggta aagagtttca tttttgcaag atgaaaaagt tctgttgcct    28860
aacaatttgc atatagttga cactactgac ctgtacactt aaaaatagtg tacatgataa    28920
atttgatgtt gtatgttttt atcacaatta aagaacaaag caaaactgag ggaggactca    28980
atagatttga cagtaaggtg ttgaagacag cacttagtat gttaagtgat agttattagc    29040
ttttgtgtgt catttgtgt agtctacaga tttagggctc gtggcacacg ttctcactga     29100
taagtgagag ccgaacaatg tgaacacatg gacgtaggga gggaacaaca cacactgggc    29160
cctgtcgcgg ggtgggaacc ggggacagga gagtatcagg aaaaatagct aatgcacaca    29220
gagtgtaata cctaggtaat gggttgatag atgcagcaaa ccaccatgac acacatttat    29280
ctatgtaata aagctgcaca tcctgcatgt ataccctgga acttaaaaaa aaatattgaa    29340
gggtcatggt taacttgtat gtgtgccaat atgcatagta tatatacata tacaaatgca    29400
tatatgtaca catgcatatg tctaattttt catttgtaa ttaattttta gaccacacta     29460
aagttgctct tagtgatgat agggcttgtt tctttgtttc attgtggcta cttcttagca    29520
ccttctttag aaagcagtta ggagaagatc atttgaaggc caacgagtgt tgtgggttat    29580
tgttaagctg atttaacatt atctcccccc acaaccacgc ttgactagct tcacatttgg    29640
ccaggtgcag tggctcacgt ctgtaatcca gcactttggg aggctgaggt ggaagatcac    29700
aaggtcaaga gattgagacc atcctggcca acatagtgaa accctgtctc tactaaaaat    29760
acaaaaatta gctggttgtg gtggcgcacg cctgtcgtcc cagctactcg ggaggctgag    29820
gcaggagaat tgcttgaaca cgggaggtgg aggttgcagt gagccaagat tgcaccacag    29880
cactccagcc tgggcgacag agtgagactc tgtctcaaaa aaaaaaaaaa aaaaaaaaa    29940
```

```
gagaaagcaa acgtatttct tcttaaaaca gaataaataa atagtctgtc tctttctcct    30000
tctgttcaca tttgccccag tttcttctct tgaatcatga cagtttggaa aattgtctgg    30060
attgcttagt gccactgaat catgccatgg aaggattttg tatttcactt ttaaacttct    30120
ctgtgacagg agaagcactg cttcatggct tcttgcccaa ggattttaga tggacacagt    30180
gggtaataaa tggatgaatt tttgtttggg ttgaagaatc tctctgagaa gttgacacgt    30240
gggggcaatg gtttgtttct cttgtatttc tgaagttgca ataatcatg taagcagttc     30300
aaccaggagt ttacaccaaa cttttaatag gcgatatatc attattttt ttcccattgg     30360
tttggataac atccacttta actggcagtt agtcatactt agctatttt gttaaagcag     30420
gtgatttatt gttattttat atttatgaca tgattaataa gtgaatatgg aagattttac    30480
attgacttag gggatcaaag ttttcattat attaacacct ttaattgcca tgagttttct    30540
atttctagca tgcatatttt gtgttcattc aagtgaagaa acagtctttt gtgttctca     30600
ggtactgcat aagccgacca cagtataaga cttcttgtgg catctcttca ttaatttctt    30660
gttgaatttt cttatacagc acaatgggag ctggaaagta agtatgtcaa tttatcagta    30720
ccccaaaact ccaaagtaat ttgatgttgc tttttctata acagaaaaaa atttaagaat   30780
agatttttta taaatttaac aaaaccctgc tgtattttag tgtaagtctt ttagcttaaa    30840
atatatacat gtattatttt cagtgaaata aaaatgggct gggtacagtg gcccacactt    30900
gtaatgtcag cactttggaa ggccaaggcg ggagtattgc ttgaagccaa ggagtttgag    30960
accagcctgg gcaacaaagc aagaccccac ctctacaaag taaaaaaata aaacaacta    31020
gccaggcaca atggcatgta cttgtatttc tagtctctta ggagactgag gcaagaggat    31080
cacttgagcc caggagttta aggctgcagt gagctatgat cacgccactg cactccagcc    31140
tgggccacag agtgagaacc tgtctctaaa aaataaata aaataaata atgaaaaata     31200
ttactaatat tatttgcaaa tcagacaagc atattaacat tgagacaggc tgtatttgcg    31260
tatgactgga attgaaaaat gaaaggcaat gaatgtttct tttgtagcct ccacctatt     31320
acccaagaag aagctttaca tattctgggc tttcaacctc catttgaaga tattaggttt    31380
ggtcctttca cggggaatac aacacttatg aggtatgaag accctcttag aggcaatatc    31440
gtgtttctag ttttgcaaaa taataatgat gtagatgtgt gttgatagta aaccatgtat    31500
ccagctgctg ggcttcaacc tctcataggt ataccaactt gggctatgc ctgaatttct     31560
ttagaattgg aataatgcca tctttgttgt agaattgttg ccatgaacaa atcttcttgt    31620
tactttcagg tggtttagac aaattaatga ccacttccat gtaaaggat gctcttatgt     31680
tctatataag cctcatggga agaataaaac agcaggagaa actggtaggt aaacatatag    31740
aagatttaca tacacacata cacacatgca cacacacaca tacacacaca cggtttagag    31800
ttcgtctcaa agactgcctg tttagcttcc tgggacatta tgtaaaccct cagcacagtc    31860
tgttacttgc atgtaatctg tagggcactt tttaataagc agtttaatat tttacctctt    31920
ctaaccttt tatgtagaac ctttagaact ttaaggtata tcacaaacac tactctaaca    31980
cattgtattg tttgggtccg tggtgtgtgt gtgtgtttgt gtgtgtatgt atgtgcgtgt    32040
gtacgcgcac atgctagtaa aactctaagg aagcagcatg gagttagcag ttttcttcct    32100
aagaaggaat gtaaggattt gagaatattt gatgttagac ctgtgtggtg acatataatg    32160
gcaggaaaat agactgttga agtgacaaag ttctgctata aaatagtctt gtttataaca    32220
gaaatattaa tggagttgat ctcaaggatt attttagtta tgtgctaatt aaataatttg    32280
```

```
tactatttag caatttccat ttttaaaatt gttacaatct tttgactgtg taaatcagaa    32340
aattgtaata cattgttaaa gaaaaaatta ttctgacact tgttaatagg gtgagaagac    32400
tttattttaa acttgtgaaa ggcctattgt agtaggaatg agagatcagg ctcagctctg    32460
aatacagcaa agacaacaaa gacaactggg actttatagc caagggacac agcgaggggt    32520 ttggggtgg gatattacta agagggtcaa gggtatgggg attcttgcta aagcctaaca    32580
gacttcttgc taaaggcagg tcaagggctg agacatcagg agttggcagg ggacgtccgt    32640
aaggaacttg attagatatt aagggttgtg ggttctctct aaactgactt agcaggattc    32700
atgctaaaac tggacacaga agtctaaggt ccaggcctgt ttgagaagag gactcaagga    32760
ttaatcagga agagaattgt tatcaataga gggtatatgg tttaccaagg taaaagactg    32820
agcacaaagt cagatatatt tctgttgacc tatattgggt atatcaggtt ggttacttgg    32880
aggcaggctt ggagattaca tgttgctttc tacacatact agttttgtga ccttgaacaa    32940
gtcacttgct gagccttgat gtagaccttt tatctttcta tatttgtata gggtcagtgt    33000
gaggataaaa ggagacatac ttgtaatgta cttagcacgc tgtgttacag agtaaggact    33060
cagtaagtgc tagcatttat tcctactgac taaattctat gcattcacat ggggcctgtc    33120
tatccttctg gaaaacacag ctttaaatgc tgtgttgcta tttatttctg tttctagtga    33180
gactgtcacc acactactct cagtaagtga tcaggcaacg aaaaactaag aaaggatata    33240
ttatcctgtt tggtaatttt ctcttcagct gtgtctagtt tgcttttat actgcctatt    33300 gagtttgagt tttttaaaag aggttttcaa tcatttttat tctaaaatat gtagttcttt    33360
taaaaatctg cttttaaaaa taacctcatt ccttactcat attttcaaac cctttatttt    33420
tttaaatcta ttgaaacttt ttcctctgta tttggtgtaa tgtaggaaat gtgtatatat    33480
ctgattttgc tgtctcttgt ttcttctgga tcttatttga ggtgtcttcg tgtgccatga    33540
aaagaaaatg cataatttgg cattgtcttt tatagttctt gaatgtttac ttccacagga    33600
tgtgccaaac cttttctgg tccaaaagat ttttatggtc attctccagt tattagaagg    33660
tataataatg attctgtcag ttgtgttcat taaaagtttt ataaaatgtc tgccaatgac    33720
attttgcacc ctgtaaactg aatacatagc agttcagtga aagcaagtga gagggtaagg    33780
ggtgtcaagg cacagtaatt agcaacctga gctggcacca ccatgtggag ttcctgcccc    33840
tctctcagga tagcacatgt gtgacctggg acctttggat gtagggttgt atagtgtaga    33900
cagcatccac actcaatcca cagaataaat actagtaaag cttaatttct ttttaaaata    33960
tgagggtcac tataaataaa tgttctaata ttttgtttct gtgcccacaa aggggtcat    34020 cttgtataac cacctggatg tgtcggtact gaaaatcatt aacctagagg agcagtagtt    34080
ggcaaatgtt tttacataaa aggcttgata gtaaatattc ttggctttga gagacacatg    34140
gttctggggc agtcacagct gcttgatgca gctgcttgga tcttgaaggc agccatagac    34200
aacatgtaaa caaatggata tggtggtgtc ctgggaaaac cttactgatg gacctgaaat    34260
ttgaatatca cataattttc acatgtcaca aaatattatt tttcttttga acttttaaaa    34320
attttattat ttatttttta gagatgaggg tctcattccg tccactaggc tggaatgcag    34380
tggctgtgat catggcttac tgcagccttg aactcctagg ctcaagcgat cctttcccct    34440
tagcctccca agtagctagg actacaggtt catgccactg cacctggcta attttaatt    34500 taattaatta attaattttt tttttgagac ggagtctcgc tctgttgccc aggctggagt    34560
tcagtggcgc gatcttggct cactgcaagc tccacctgct gggttcacgc tattctcctg    34620
cctcagcctc ccgagtagct gggactacag gcgcccacca ccatgcccgg ctaatttttt    34680
```

```
gtattttttt tagtagagat ggggtttcac catgttagcc aggatggtct cgatctcctg    34740
accttgtgat ccgcccgcct cggcctccca aagtgctggg attacaggtg tgaaccactg    34800
tgcccagact aatttatttt tttaatttttt ttcaattaaa ttttttagaga tgggggctca    34860 ctatattgcc caggctagtc ttgaactcct ggccttaagt gatcctccta cctcggcctc    34920
ccaaagtgct gggattacag gcatgagcta ctgtgcctgg cccaattttc ttttgatttt    34980
taacaatgta aaaccatttt tagcttgctg cccatttcaa cacaggctgc agtctggaga    35040
ctggatttac ctgttggtgg gagtttgcca aaccctaacc tagaggatga agcctaaatt    35100
cctgagcatg gtgtttgagg gactggcttt cgaatatcct gcttcagcct acctcccctg    35160
gtgttcagcc atgctgggct cctcgatgtt tccctgttct tcacaagata caggtcatcc    35220
ttaggcctat gtgcctcact gatgggatgc cctgctgtgg agcatgtgga atgtgggatt    35280
tcatatcttt gtgattggtg gattcctatt tatttgtcca tcctggactt cagcgtaaca    35340
aatggatatg gtggtgtccc gtgaaaacct ggggggatgg ctttttcttc tgcttgccag    35400
gcaggattca atcccttcgt ctcctgggtt gtcacagcac catgtgtgcc tctggtagaa    35460 cttttgatttc attgcgaggt aattcttggt gcaccgtatg gtttcatgca gaaaaactag    35520
agttgccttt cttgaggatt aggccaagtt cttactcatt tgtgcatcac agtgcctgat    35580
acttaggtgc tcagtaggag ttaatttaat gaattcgcaa ttgaggatat gagtcaggag    35640
gaattcagga gattggggtt acgaaacttc taagagagaa ttttgttgtc cattccaaag    35700
ctggcattct tcctttgcaa gagctctctc ttgtgatgtg gaaggaaaa tgttttctct    35760 ttccctttct gtagctcatc tttccttctg gctcctacct gctctcccct ccccacactc    35820
ccagacacac actcacctgc acctgtgtgc tagatctgcc ctgctttcca tcagaaccca    35880
gtgcgtcctc cttctgtctt ctggagtctc tcagttgaca gtttttcgtg tgttcctaag    35940
gacaggaaat gagccaactc attgaatctg aagttttcaa ctttacatct tagcagtgcc    36000
ttgaacattg ccttttacat tataaatagt aagagattaa gattgtctca gaatcacttc    36060
ctaactgatt cataggqtgg ctttatatct cttttaatgg ggtgtggacc aaaatgcatg    36120
tctgggagta tagaaataat cactggaacg aatgtcatac ttacgtgtcg gatataatgg    36180
aaagctatta caatacagtt ctcagtcttg tgtcccaaga ctgcattatg agtaaggccc    36240
tgggagacac cagaacaagt ctcataattc cttttacttg ttttcttttt gcctgctgat    36300
tagaagagga cttcatttga gtagttaatg gcttttttcta ttaatatcag cagtatctag    36360
atggagtgag aggatagatg aagagatggg tcagtcaaag taaggaaat taagggaagc    36420 aggaagaccc agagaaatta gaataagaga gaaaatctat caaagaaact ctgggtatcg    36480
aggaaacatc agctatatac atttaatcaa attcccaaag taagaacata acttttttata   36540 attaatggaa tggaataaaa cactaaaagg gccatggaga gagttgactt aggaatcact    36600
attctggaat tttaaaagat ttttgatcaa ctgtcttgtc caactttaag attttatact    36660
ataattttgc tagaaattct catttgtaga tcttttgaat atctgtactt tatttattt     36720 attttccaat agtctggtac ctcccaagtt ctttgtgact tatttaaatg taatgatttg    36780
gtgcatgtgt taaccagttc ccttaataat ctaggatgtg tagcattggg tcccaatgac    36840
tttttttttt ttttaacct atttgtttaa atttcctcca gcatacatcc aaacttttca    36900
ttgaggaatg ggataaacta cctatttttcc ttaaatttgt tttctttttgt tagggggttg    36960 aggtgcttac tgtaatttga gtaagtttta atatattttt caagttttat tcctactttc    37020
```

```
aatttttttt ttccagaata ttcgactttt tactgctttt ctgtgtgcat ttcctgaagg    37080
ataattaatc tgcgtacgcc tcctggaata tttttgtctt tacctttgct aattggggga    37140
cccagttaag ccctgcttca tctctgatat gttccttggc cacctttagcc ctggattcct   37200 ctaaattcct ctagtactga tttttcacac ccatcatttt ccatttgcta tgtgctatgt    37260
tttattatgt ttcacctgtt caatgtgagt gtccagctcc ttgaccatag ggactgttct    37320
gagtagccct tacatgctag atatgatgcc cacgacatta cacgttaccc tatgaattct    37380
gatggtattc aggcggtagg gtggttcatg tgtaaagcag acgtctcttc cgttctctcc    37440
cattgtggaa gaaagagttg cagagatagg ctttctgatt tctctctggg atgttcactg    37500
gtgaaaacca ttgtcagtgg cgctatttgt ttaaaaacac ttttaaatct atcttctctt    37560
tgtgcttaaa ttgttttta aggaccacta agcctgtttt tcacaatggg ctttacgttt     37620
tcctggggac cacgctgttg tgattcaggg actccccggt gcttatgtcc agtgggctct   37680
tagtaactgt aaactaagca cactaatgga ataaagtga agtccaggga ttttgataag     37740
acttagctgt taatatcagt attttttttca gagatgtcac tagtcacaat gaaaatttat  37800
tctaggagtt gccaacatta ggtctctgtt cagataactt ccgagtatgg gttcacttag    37860
ccaccaacat ttgcaccagg caagtccaga ctcattttt taatcagcta gcttgaaaat     37920
tgcatttata ttcatgtatt tagtttttc tagtgggtat tgcagttcat aacttttgct    37980
taacagagaa gacccgtctc tggcctcatt cctgtataac tcacacatcg cttcaccatg    38040
attgttgtta ccagcttact gaagcacctc agtacatctc cggtggacaa tacattagta    38100
ttctgttttc ctcatgtact ggttttctcc aattaatatt agacacaaat aataaatctc   38160
ttgaacatgc agtgctaaca taccccttc ctctttagga gctgtttggt gcttgcttac    38220
agcataaact gcttagtgtc attccaagct gacacaaatt ggccttcccc tgctgtcctc   38280
catgtaccag ttgtatttaa gatgtcaggg gaagctggca tagtggctca cgcctgtaat    38340
cccagcaggt tgggaggccg aggtgggtgg attccttgag gccaggagtt tgagactatc   38400
ctggccaaca tagtgaaacc ttttctctac taagaataca aaaaattacc tgggcatggt    38460
ggcgtgcacc tgtaatccca gctacttggg aggctgaggc acgagaattg cttgaacccg    38520
ggaggtggag gttgcagtga gctgagattg tgccatgcac tccagcctgg gcatcttttt    38580
tttttttttt aaaataaaaa agatgtcagg ggaataagga ccttgcagag taatgttaga   38640
ttgctggatt acctatcaga gtttcagaag ctattcttgt ctttgaaggt gtaaaaatat    38700
actctataag ttcttatgga gttatctagc attcctctat agatgatcag ggtctacagg    38760
acaagctcat actaagcaaa ctcagaatgt cagaatgtta acagagtaac ttgaagtaag    38820
aaacataatc tcaaagggac cagaattctc ttattggctg ctcagaatac ctgctcttct    38880
ccatgcagca ggccagtgga ttcctgtagt ttttttctcc tttctctatg ccgtgcagat    38940
catggctctg catttggtgg tggttgcttt gttgcttaag tttcagattt taaagctata    39000
ctgaagtaca gactcaactt cattctgaat ttagcttccc tcagtaatac atttgtgtct    39060
tctcatacac agaattactt tcttggacaa ctaccttaat gtgttgaatg ctgtatttac   39120
tggctcggca cagtggctca cacctgtaat cccagcactt tgggaggctg agagggggcgg 39180 gacacttgat tttgggaatt tgagaccagc ctggccaaca tagtgaaacc ccgtctctac   39240
taaaaataca aaaattagct gggcgtggtg gtgagtgcat ggaatcccaa ttacttggga    39300
ggctgaggca tgaggattgt ttgaaccggg gaggtagagg ttgcagtgag ccagagatcat 39360 gccactgcac tccagcctcg gcgacagagc aaggccctgt ctcaaaaaat aaaataaaat    39420
```

```
aaaataaata attaaataaa tgctgtattt actatctttt atttcagagg gtgatctttt    39480
tcttattttg gcctgaaatt gttggattgt cccacagtag gctcctctat accatcctac    39540
cctgtattct ataaactaga tcacgggctg ttccctgagt atattccttt tccccagtgg    39600
ttttgttttc tcctaatgct ctttcctctg tctagattgt tgaaatcctg acacttcatt    39660
aagtttcatc ttgaatgcta cttcttcttg actcctcaaa cctgatgtgc tctttctcct    39720
ttgaattcta tgccccttt gtggcactat cttattccac cttatataaa agttacttgt    39780
tccatcttcc ctactaatgc acttgaggga ccgtgcatca ctccttggct ctcttctgcg    39840
gccgtggacc tgctgctctt agtggtcttc agctatttca gtggccagaa agtcgatcac    39900
tgaaactatg acttgcaagc tttcatctgc ttcatctatt tttaggattt ctagttttaa    39960
tgggctgttt atgaataaat aatttagctt cttctaggac atgccagtta atgaaacctc    40020
agttaatggc tttgagtact aagtgctggt gaaaagtcat ttcttatggt aatacttttg    40080
aaattgacca ctattatagt tatggcaaat gtccaggaa gagtgggcat aagaggttgt    40140
ggtggtacta ccagcctgtc tctgtagaga tgttatcttg tcacttggct tgtgaagact    40200
actcctctag cctccataag ttttgtgtaa agattaaagt gtgtgtagaa aaatctgggt    40260
tcttatcaca caacaaggaa agattaggct cacagatact ttgaagggtg aaggggaaca    40320
gaatttattg ggtgaaaagg aaaaaactca gcaaagcgag aagggttcct gctaacaggc    40380
ccccatctca cagattgaat cccaggttgc cacacaggga caggagaggc caaggtcctc    40440
ccctctgcaa acagcgggca cttcctgagg cccaaccca tcctcccagc acgcaggcca    40500
gctggagatt ctccaggaag ccgttttac ttggctgtct cattagtagg agaagtttgc    40560 attttagaa cttgattatt acctggagtt tattttatt catatacatc agtagttttt    40620
taagttggga tgtgtgtact gcatatatat tagaacttct atattttaac ctaattttaa    40680
attccaactt tttgtatatc ttttataaag acatattagt acagtggtat atgtatatac    40740
tttataaatg catgtgctaa cattgggcat gcttgttcag aattttaagt gacagctgtg    40800
tacaaccaga aaagttgaaa ccattgctga atacactagg taaatttcat agacaagtat    40860
gtgtgttatt agaaggtttt ggtaagcaag gacatatttt agttctttag tttgctaatg    40920
agcttacctg aatttcagtt taaagagtaa acagaatac atttattaac attttttgta    40980
cctatcaata gcttcttgtt tttccccagc agtgtcagtg tattccaagt aatgtctttt    41040
ctgtccttaa gcccttaacc ggtcctttgt gtaaagcatg gacactgctt tatgggcttt    41100
cagtttgtgt gtttgtttgt ttttaatagc ttcagggcc ctgtcaaagt taacccgtgg    41160
attgaaagat gaatcgctgg cttatatcta tcattgccaa aatcattatt tttgtccaat    41220
tggcttcgaa gcaaccctg ttaaagctaa taaagcattc aggtaagcat tgacgtgttt    41280
tagaaagtgc attttaagaa atattaaaaa atagatgggt gcggtagctc acgcctgtaa    41340
tcctagcact ttgggaggcc gaggtgggcg gatcacgagg tcagaagatc gagaccatcc    41400
tggctaacac ggtgaaaccc cgtctctact aaaaatacaa aaaaaaaaa aaaaaaaaa    41460 ttagccgggc gtggtggcag gcgcctgtag tcccagctac tcgggaggct gagggaggag    41520
aatggcgtga acccgggagg cagaacttgc aaaaaaaaa ttaaaaaaat taaaaaatat    41580
tcaaagtctg tgatattggg aggcttggcc atctgctttc ctgacatcaa gttagactat    41640 tcttaaaca ttatgactta ttcttctgca gaattgcatt tagttaattg tgctgttgaa    41700
aatatccatt tagatactgt tgttcagtca ttataggaaa agtcatttg aaaagtcact    41760
```

```
tgttttctc ttagagacag ggtctcactc tgtcatccag ctggagtgc aatggtgtaa    41820 ttataggtca ctgctgcctc aaactcctgg cctcaagcaa tccttctacc tcagcctcct    41880
gagtggctag aactacaggc atgcaccacc atgcccagct cataaaattt tttaatttgt    41940
gttttctata gagacggggt cttgctatgt tgtgcaggct ggtctcaaac tcctggcctc    42000
aagtggtcct tattcctggg cctcccaaag tgctgggatt acaggtgtga gccaccacac    42060
ccttcctgaa aagtaatttt tacatttatt ataaaacagt tgcaaaggat tttatagact    42120
atgtcacagt gcctcatcca acgtcccaca tgaacaatat attacagaat ctagtgtcaa    42180
gaagattgtc acaactgagt aaattaaaaa gcatcttctt ttcttaaagt gaagaatatg    42240
gaatttgtct gggttccccc tttgtcctga ttgcaaggaa gctctgagcc aattttatt    42300 tccaatgtca gaaactacat gactttcatg gttatatttc ttttttgcct aatctagagt    42360
ttctgtttta ttaactatat aactttactg gtaaacttgc atctttgtgg aagagatgat    42420
ccctaagaaa gagaaggtga ctaagtttta atggtttttt tcctgtttag ccacttttcc    42480
ttatgatggg ttgagataat accaggatgg ttgaaagcca agggagaagt atctagttaa    42540
gaattggtgg gtggggtgca gtggtgtaat cccagcattt tgggaggctg aggcaggcag    42600
attgcttgca cccaggagtt caagaccagc ctgggcaaca tagtgagacc ctgtctctta    42660
aaaaaataca aaagttagct gagtgtgttg gtatgcacct gtagtcccag ctacttggga    42720
ggctgagacg ggaggatcgc ctgagctgag aacatgccac tgcactccag cctgggcaac    42780
agagcgagat cctttctgta aaaaagaaa gaaagaaaga aagaattggt gaaaacacaa    42840
gccatgagta ctttgagcaa agggattggc ttggtcatgg gataggatg gttttttttt    42900 tttttttttt gagacaaggc cttgctgtgt tgcccagact ggagtgcagt ggtgagatca    42960
tagctcactg cagcctcgac ctcctgggct taagtgatcc tcccacctca gcctcctgag    43020
tagctggaac tacaggtaca caccaccata cttggctaat tttgagatgg ggtttcaggg    43080
tttcaccatg ttacccaggc tggtcttgaa ctcctgggct ccagtgatct gaccatgtca    43140
gtctcccaaa gtgcttggat tatagacgtg agccaccaca cccagccagg atgggttatt    43200
tggggctgga ggccatgtgg ctttggagtc ccactcaaag gcccctcggg tttggggaag    43260
agagggattc tgagacaggt tggaatgacc tgggagaacc aggaagctgg aagttgtgtt    43320
ttgtgaataa ggagcaagag ggaactctct tgttctctcc caatgctgaa atgctttatt    43380
catctttctg gaggtggaat ttcttgtaag tgaggtatac tgtatgtttc tttatgatt    43440 tcatcctgca gcttcacctt atttctgaca tttatcaaat ataaatcatg gttttaaacc    43500
aactttgtac cctttaaaag agagtccctc acttctgcct gtacctaaga atcatgtgag    43560
attttcttaa aaaactatat aaatccccag gctctactcc agacctattt gaattagaat    43620
gtccagggat gggtttagga catcagtgtg tttaaagact tcattgcttt agggtttcat    43680
ttttaggatg cgttttgaga tgtcttgaat tcatagtgaa aggagaagag tagtggaaaa    43740
atgcagatag cattccagga tttttttttc ctcctagaat tttagaggtg gtatattaaa    43800
acattttata gccctagatt ttgaatagag gattaaggct gaaattttaa tttgtgagtt    43860
ctctttaatg gcctgtagaa atttgccctc acctaagctc taatgtctgt tcttgatgaa    43920
tgaatgccag gttgaatac actctagtat gccttttatt aatatatatt tgaagcaata    43980
tactcaaggg agtaactatt aaacgtactg tgaatgtatt ttatatttag caggggacct    44040
ctctcaccac aggaagttga atattggatc ttaattggag aatcaagtag aaaacatcct    44100
gccattcact gtaaaaagta tgttaacttc cctttatttt ctttaattga ggtaacattt    44160
```

-continued

```
agatacagtg aaatgcacag atcttagttg tatataatta gtttgataaa tgaatgcacc    44220
tgtataatca ccacccaaac aggatatggt acacattcat tgccatggaa aatactctca    44280
ctctctactc ctatcaatct ccatagaaag cccctcttct gatttctgtc actacagatt    44340
tgctttgcct cttcttgaat tccatgtaaa gagaatcaga caatattatt tttgcatcaa    44400
tatcttaagt aacattttg agattcctcc attgtgtcat gtgtatcaag agtttattat     44460 tttttttattg ctgagtagta ttctgttgca taagcatgct gcaatttgtt ttccattttc   44520
ctgttgatgg gcatttggat tgctttgagg ttttggtctct tgtcaatgaa gctcttggga   44580
acattcatgt acaagccttg aaacaaatta tataaaaatt ttattaaaat ataattcaca    44640
taccataaag ttcactgcac ccaccatgcg cggtggctca tgcctgtaat cccagcactt    44700
tgggaggctg aggtgggagg atcgcttgag cccaggagtt caaggccaac ctgggcaaca    44760
tagtgagacc ctgtctctac aaaaaaatta aaaatgagg caagaggatt gcttgagcct     44820
aggagattga ggctgtaata agctgtgatc gtatcgctgc actctcatct gggtgacaga    44880
acgagatcct gcctcaaaaa aagggaaaaa agtgtacaat tccatagatt ttattatagt    44940
tacagggttc tgcaccaatc accactatat aattgcagaa cattttcatc actccagaaa    45000
gaaaccccat accccttggc agtcactccg tattccctga gccctggcaa ccactgatct    45060
accttctgtc tctagggatt tgcctattct tgtttgtttg tttgtttggt tttttaaga    45120 cagagtctct ttctgtcact taggtgggag tgcagtggtg tgatgtcagc tcactgaacc    45180
ttcatctccc aggttcaaga gattctcctg ccgtagcctc ctgagtagtt gggcttacag    45240
gcgcccacta tcacgcccag ctaattttg tgttttcgt agagacgggg tttcgccatg      45300
ttggccaggc tggtctcaaa ctactgatat caagtgatcc accctcctca gcctcccaaa    45360
gtgttgggat tacaggcgtg agccaccacg cctggctggg atttgcctgt tcttgacatt    45420
tcgtataaat ggtgtcatac agtatgtagc attttgtacc tggcttcttt cacttaatac    45480
agtgttttca atgtcatcca tgttttagca tggattagaa cttcattcct ttatatggcc    45540
aaatcatttc ctttgtatgg agaagtcact tttgttgtac aagtctttta gaggacatat    45600
gttttgttct cctggaagac acctaggact agaattgctg attcatagta tagatgtata    45660
tttaagaaac tgtgagaaaa ttctccaaag tggttgtaaa ccttctgatg aacagaagtt    45720
ctgattctaa ttaatcttaa ttaaatttat tttatcaatt ttcttctttt atatgttttg    45780
tgcctctata agaaattttt gcctaccccca cgacctcaaa gatgctttcc tgttttttc    45840 tagaagcttt atagatttta tgtttagatt tctgatccct ttctattatt gttttgagac    45900
agggtctctc tctatcaccc aggccagaga acagcggtgt gatcatggct cactaaagcc    45960
tcgacctcct gggttcaagt gatcctccca tctcagtctc ctgagtagct gagaccacag    46020
atgtgtgccc ccatgcccta ctaattttaa actttttttg tagagacaga gtcttgctgt    46080
gttgtccagg ctggtttcaa actcctggac tcaagtgatc ttacttcctt ggcctcccaa    46140
agggccggga ttacagatgt gagccaccat gcctggcctt aattaccttt tgtgtgtggt    46200
atgtggtaga gctcaacttt gattttttcc cccagtgttt atctagttat tctagcacta    46260 tttgttaca aagatttcc tttccgtatt taacttcttt ggtgcctctg ctgaaaactg       46320
tatgtgtggg ctgtttctgg accctgtcct actaatctgt ctgtccttt accgatgcca     46380 cactctcaat tgttgtttat actaaatcct gaaattagat agcacgaatt ctctgaatttt   46440 ttcttttct taaagattgt tttggctctt ctaggacctt ggcttttcca taaaaatttt     46500
```

```
agaatttgtc cttttaatta gagtttgtaa agattttgat gaggatagaa tctatagaat   46560
tcataatttt ggctgggcgc ggtggctcat gcttgtaatc ccagcgctta ggtgggagga   46620
tcacttcagc tcaggagttc gagaccagcc ttggcactat ggcgaaaccc catctctact   46680
aaaacgacaa aaattagcca ggcatggtgg catgtgcgtg tagtttcagc tactcgggag   46740
gctgaggggg gaggatcaac tgagcctggg aggtcgaggc tgcagtgagc tgagattgca   46800
ccactgcact cctccctaag tgataaggtg agaccctgtc tcataaagaa agaaagaatt   46860
catagtttag ttttggaaga attgacatca taacaacatg gactatatct ttacttaatt   46920
agagctttaa tttcaacttt ttaaaaaaat tttttcagta tggagtttta tgtcttttat   46980
taaacatttt ttctctatgt gttctattac actgctggtg ggaatgtaaa ttagtacaat   47040
cactatgaca aacagtatgg agattcctta aagaactaaa agtagatcta ccatttgatc   47100
cagcaatccc actactgagt atctgcccaa aggaaaataa gtcatatgaa aaacacacag   47160
gcacacacgt ttatagtggt acaattcgca gttgcaaaga tggagaatca acctaagtgc   47220
ccatcaacca atgagtggat aaagaaaatg tggtatgtat attaccacgg aatactactc   47280
agccataaaa aggaatgaaa tgatgtcttt tgcaacaact tgggtggagc cggaggccgt   47340
tattctaagt gaagtaactc aggaatggaa agccaaatat catatgtttt cactttaagt   47400
gggagctaag ctatgcggat gcaaaggcat aagaatgata taatggactt tggggactcc   47460
tgagggcagt ctgggaggcg ggtgagagat aaaagactac atattggatt cagtgtacac   47520
tgcttggatg atgggtgcac taaaatctca gaaatcacca ccgaagaact tattggtata   47580
accaaaaccc agctgtaccc caaaaacaat tgaagtaaaa cttaaaaaag atattgcaat   47640
aaaaaggttt tcctcagtgt gttatacttt ttgatgctat tgtaaattga ttttttttaaa   47700 atttcatttc ttcattattt gctggttgaa tacaaaaata caattgattt tcctatgtag   47760
accttgaatc ttccatcttt accaaatcct tttagttcta gtagttgttt tgtaattccc   47820
ttggattttc tgcacaattg tgttgtctcc taatagagac atattaactt tacattcttt   47880
taaaagtgga cttgactgta attgaaaagg aaatatagca tattgctgct ttagcatgca   47940
ggatgtcatc taacatgttg gtatttattt attctgtagg aagagtaacc aattgtacac   48000
tgaaaacctt ggcaacggtt ggataaacag aattgtcata aaactagaag ttattacagt   48060
ttagtagatg aaacaatgtt gagataagag aattactgcc aattattgct gtgataatat   48120
tgcagcaact tgctcatgaa aaattccatt gcaatgatac tttagaccta agaaaaattg   48180
tgctttatcc tttcttctta actatagatg ggcagatatt gttactgatc taaacactca   48240
aaatccagaa tacctggata tccggcactt agagagggga ctgcagtata gaaaacaaa   48300 gaaggtaaga agaacaccat tgtgtttgaa ggcatttccc agctgaccaa aatgtggtgt   48360
tttacttagc actctttagg ttgcaagtaa cagaaaccta tatttgatag aggagtgaaa   48420
attattttaa ggacacacgg ctgtctttaa aacccaaggg caaggggtat aacctggagt   48480
cataaaggaa tggtagatgg tagcaggtat tggaatgaca gcaagggcca agtagctggt   48540
agtctgcttc actcttttgg gggctatata ttgttcttag cttcctttt gtctgattac   48600 tttcttcgta agatcatcat ctttccattt atgtgtcgtt tttagatgaa cagtctagac   48660
tgagactgac ctgtcttggg ttcagttccg tagtcttagc ccagcttggg ccagattaac   48720
tgtggccttg tggcagagtc atgtgtacaa acaaggcttt gggagaggct ctcaggaaat   48780
gatatcttat tgatgcaatc ttactcatat aactatatga agaataggag agagaggaaa   48840
aggaatgatc ttggtgtttg aattaggcag atggggaagt tctctagtat gtgttgggag   48900
```

```
tgagtagtag agaggcatgg ggaggaaggt gttttggctc cggtgggcat tgttatattt   48960
tgtaaaggca gctgttagaa aaggtgcagg atgaggtgct ctgatgatgc ctggaaggaa   49020
agtaccattc tgaggccggt gaagtaaaaa aagaaagaag ggagttcata gggacctaca   49080
aattagtaca attaatttcc ctttattttc ttcagccaac atttttttct tctcaggttg   49140
ggggaaattt gcattgcatc atagcattcc agagacttaa ctggcaaaga tttggccttt   49200
ggaactttcc atttggaacc attagacaag aatcacaacc tccaacacat gcccagggaa   49260
ttgccaaatc tgagagtgaa gacaatattt ccaagaagca gcatgggcgt ctgggccggt   49320
cttctcagtgc tagtttccat caggactcgg catggaaaaa gatgtctagt atccatgaga   49380
gaaggaacag tggttaccag ggttacagtg attacgatgg gaatgattga ctatgcttgc   49440
tactgaacag ctggcattat atatgaaact gctatataca ggactgtata agacagtag    49500
aagattttag taagcctaca ttaaatagga gcagatcttg tggtataaaa ataaccttg    49560
tagttctcca gatactaagc ttgtatatga ttatggtggg tgatttcaga tatataagca   49620
gataagcaca gattattgtc ctttcaagtt aagagtatat aatctggaca gaaaatttca   49680
caaaattcaa taaaattaca actgttgtct aaataagtga aacacaaatt cacttaatag   49740
catcaagatt tgaaatactt aagcatgaag tgacttttat aatgactcga tccctagaca   49800
tttgttacag atagttttat gcctaagacc aagatgtaaa gtaccatctg cccttaaaaa   49860
aaattgggc tgtcaatttc tagttttcac tcatggttaa cacgcattta aaattatttc    49920
atgagtctag tagttctttg atttatagca ggatcttgct tgcctcattt gtttcctggt   49980
tatgttctta ggattctgac taagaggcaa aagagaaaag actcaagaaa ctgatcctgg   50040
agatcgagac catcctggct aacatggtga accccgtct ctactaaaca tacaaaaaat    50100
tagccgggtg tagtggtggg cacctgtagt cctagctact cgagaggctg aggcaggaga   50160
atggcgtgaa cccgggaggt ggagcttgca gtgagcggga atcgcgccac tgcactccag   50220
cctgggcgac aggcaagac tctgtctcaa aaaaaaaaa aaaaaaaag acggatcctt      50280
tttttttggtg caaatgggtg acttagtgca ttgattcaga tttttaaaat ttcttgatgt   50340
ggtttgtaat aatcaaatat tgacaagaac cttaggtctc gaaagacttt tataagtcta   50400
gatgacgttt gccttagggg taagtaaaa gaacaattgg caccttaagt ttctataccc    50460
aaggttatct gtgaaatgag atctcctgat atttgattgc tttctcagta tggagtcata   50520
tgttgataac agtactgaag atgcataaga aatgcccaag tcactcagag acaactacc    50580
catattccag actctgagct gtttccttt taaaaatcat atagacaatt agctgtttga    50640
agtgagtatt aaatatttca gaagtgtgaa tttcatgtat ttgagctcct ctagttgctg   50700
ttggttttc ttctgctgcc aacctgtgac tcacaaatga ctaggatctc ttgttcttta    50760
attttagggt cttgttccag gactcaaatc agtaacttgg tgattacaag gtgctgaatg   50820
tgttggtaac catatcgcaa tacacctcaa ggaaaaggtt cagatttta tttttaaaat    50880
attttcattt ttttcttgaa ttttatatcc gtttgttcac tcgtacatgc ctagcctaca   50940
gaagggata tatattatga aatggtcatt tttctgaaga gaatattttg cttgaaatgc    51000
aaaggactga aagagatttg taggttgttg attttgttac ttcatactgg aacttttaaa   51060
aagatttcat caaataaagt tttgttttct acttttaatt atatgaatgt ttttaaacct   51120
ttgttttagg tagaaggtac cattgtgtct ttgaagtaca tgataatttg tcaattctgc   51180
tcaactggta cattgtaaga aaccatcttg agcctttat aattaatgaa acaatatgca    51240
```

```
ttatgatgac tgtaatttta gatttctaat ttaataggaa atagaaaatt tgattctttt    51300
attagcttga accaaatgaa gttgtcatct ttgtaggtca aaaatggttg aatattagca    51360
atttcataca gttcaactga atatttcaga gaagacgtag gtaggaagaa ccaagaggaa    51420
aggagaaaaa tgcaaaataa aataagaaat taaaggatag ggagacacct agaaaaacag    51480
gatgagttat tcagactatt gaccataatc aattttttata aaagtcttga tctgttctaa    51540
gtttggcttc caagtttggc tttccagtta ttaagagcac aatgaggttt gagtttagtg    51600
agattatctt tcccgcagaa gctgtaagca agagttactg catacttctc ttagaagatt    51660
agtaaaattc ccttgatatt tgatttcttg gtcagctctt aggaatccta tagatacagt    51720
gaaagttcaa atactggctc tgcacttaca agctatatca cctatagtga tataggcaag    51780
ttaaggttaa tttttttttct gtgcctattt cctcattagt aaagtggggg taatagtatc    51840
tactttataa atgaatttga agaataagct aatacatgta gtgtttagaa cagtgctttg    51900
tagataggaa gtgctattta agagcttgct attattccaa aagatgtgaa ttttactatt    51960
cagagtcttt agagagagcc ctttagatag catcttaagg agctaattcc ttttaaatca    52020
catatgcacc ccttagttgc tgtttcttca aaagaatatt tcatattcaa gaatgttgct    52080 ttatttttttt gagacagagt ctcgctctat tgccaaggct ggagtgcagt ggtgctctct    52140
gcaacctccg cctcccgggt tcaagtggtt ctcctgcttc agcctcccga gtagctggga    52200
ttacaggcat gcaccaccat gcccggctaa ttttttgtatt tttagtagag actgggtttc    52260
accatgttgg ccagggtggt ctcgagctcc cggcctcaag tgatctgcct gcctcggcct    52320
cccaaagtgc tgggattaca ggcgtgagcc accatgccca gcctttgctt tggttttaaa    52380
agtacttaca atactcaaat gcctatgttg gctatttatt tttacccagc tcacaggcag    52440
aaaaaaaaaa gtttatttag atcaaattct gcagcaattc ctttccctac tgctattact    52500
gttaaagaac tgtgtgccat cattaggcca agttggtgca gcacccaaaa tacttgccaa    52560
cttgtcttct cccagactgg aggggctcag gcagctcttc taggatccat cacattctgc    52620
atctcaactt taccaataac actcccaccc ctcctgtacc agcgattcac tcaacaaact    52680
aaattataca ccattaccag gtcagttctt aaatagctca gcagcaacaa gaacaacaag    52740
atgttggtcg cattctaatt ttactggcag aaactgaggg tttcattggt gaagaaacct    52800
gcctaggatc acagtgtctt agtttctcag ggctaccata acaaaacacc acagacaggg    52860
tggcgtaaac aacagaaatt tgttttctca tggttctgga aactagaagt ccaggagcag    52920
gcaggtttgg tttcttctga ggcctgtctc cttcacctgc agagggccgc cttctcactg    52980
tgtcctcaca aggccttttcc tctgtgccta tcatccctgg agtctctccc tgtggcccaa    53040 tttcctctttt ctacaaagac accagtcaaa ttggatttag ggcctatcct aatggcctcg    53100
tttcaattta atcatttttta aacgctgtgt cttcagatag tcacattctg aggtactcag    53160
gcttccacag atgaattttg gaggacacaa ttcagaccat aacacaaggc aacatatggt    53220
tcagatgaga tctgaatgaa tgatcagcct aacctccaag cagattcttt cagcagactg    53280
caaggtgcac tggagagctt tagactagag gcttaagagg tcatttaggc aatatttaca    53340
gaactgctaa gtgccaggat tgggggatgt agcagtcacg aaaatcgttc ttcgtttcag    53400
taagtttaca gttttaccatg gggaagagac aaatactgaa caggcagtta tattactctc    53460
agtaaaataa caactgggaa cagtttctgg ggattacttt acatatggag gaaatgcaaa    53520
aaacactttg tcaggattat tcctgtagca aattagatgt gactaggtca accaaacatg    53580
gccactgtga accatcttat tgagcataga agtggttttg ctaaaaatgg atttctccac    53640
```

```
ggagcacggt ggctcatgtc tgtaactcca gcactttggg agactgaggc aggaggattg   53700
tttgagacca gtttgggcaa caaagcaaga ccctgtctca aaaaaaaaaa aatcagggcg   53760
tggtggtggg ggcctgtaat ctcaactact cgggaggctg aggcaagagc atcacttgag   53820
cctgagaggt ggaagttgca gtaagctgag actgcactac tgcactctag cctgggcgac   53880
agagtgagac cctgtcaaaa aaataaaaaa taaaaaaata aaaaaatca atttcccgta    53940 tacttctgtt ataagaagt cttaaaaaa ttgcctgctc ccttaagtca gccttttcac     54000
tgagtttaaa tttcgttcca atttgaacaa atatggatgc taatactatc ctttatagtt   54060
actagtgcta agtgcgttgc atgtaacacc ttgaatactt actgaagtct gcaaggttgg   54120
ttttatgccc tgattactga tggagacaca aattctgaac aactgtgact tcagggatgc   54180
taaacaccat agtgaggcac gatgcgggga tttgaatctt ggcctgaggg ttccagagct   54240
gtggcctttt ctggggttac tctgttaatt gatttctagt cctttctgat ctacaagccg   54300
cggcattata acttttagat gctgaagaaa actaaactat atgtcaagga ttaaggcttg   54360
tgaaccccca aaatttggga caggtctcag ttaatttaga agtttatttt tgccaacgtt   54420
aaggacgcgc agctgtgaca cagccccagg aagtccagat gacatgtgcc caaggtggtt   54480
ggggcacaga ttggttttat acattttagg gagacaggag acatcaatca acatatgtaa   54540
gtacactggt tccttccaga aaggtgggga caactcggaa gcaggaaggg cttctaggtc   54600
acaggtagat gagagacaaa aggctgcata cgagtttctg ataagccttt ccaaaggaga   54660
caatcagaat atgcatctat ctcagtgagc agaaggatga ctgactagaa tgggaggcag   54720
gttttgccct gagcagttcc cagcttgact tttccctttt gcttagtaat tttgggaccc    54780
taacattttc acaggcttta aattttatta ttctttagtt actacgtgct agcatataaa    54840
taaatagtac aaaaccaaga aggcatccac cttttggttg tctcttcacg tgtaaaacaa    54900
cactttgtgt taagtatctt cacacacggc ggcgcaaagg tagaaaccga tactaaaaaa    54960
gcgtgtagaa aatagttccc agcctgggca acacagggag acctcatttc tacaaaaata    55020
attcgccaag catagtggtg cgcacctgcg gtcccagcta cttgagaggc tgagatggga   55080
aagttgcttg agctcgggca gcaggagttc caggctgcag tgagctaaga atgcgccact   55140
ggactccagt atgggcgaca gcgtgagacc ctgtctcaaa caaaaacaaa agcccgttac   55200
tccaccaaga aggcgctttt gcacattgtt ttaatgctta acgccttcag gatgccagcg   55260
tgacggaagc aagtaaccac caaggcatca ccactggcgc taaacttctc acttccggag   55320
tgctgcaagc gcagaaaata tacgtcatgt gcggaggcgg agcttccgcc ctgcgcgtcg   55380
tattagacgg aaaccgagcg ggcccatttt tcatgggttt gcggacccac cagcgaaggc   55440
gggaggtgtc gcagggacat cttctggctg tttccgtcgc ctgcgtggcc cttgcacccc   55500
ggtcttccat tagcggcgca gacgtttggg cctaagcgct gggcgaggcg aggccctgcc   55560
cctccccgcc aacggccatt ctctggacct gtctttcttc cgggaggcgg tgacagctgc   55620
tgagacgtgt tgcagccaga gtctctccgc tttaatgcgc tcccattagt gccgtccccc   55680
actggaaaac cgtggcttct gtattatttg ccatctttgt tgtgtaggag cagggagggc   55740
ttcctcccgg ggtcctaggc ggcggtgcag tccgtcgtag aagaattaga gtagaagttg   55800
tcggggtccg ctcttaggac gcagccgcct catgggggtc caggggctct ggaagctgct   55860
ggagtgctcc gggcggcagg tcagcccega agcgctggaa gggaagatcc tggctgttgg   55920
tatccttaac gccgcgttgg gacttggggt gcagggattc ggggctggat tcctcgcggg   55980
```

```
gctctgcctt gggcacagtg gcatctgcag gatgatggtc ttgggtcggg gtcggggtcg    56040
ctatagaatc tctgtcacta ggttttctaa gtacagtcgt ccctcggtat ccccggggct    56100
ttggttccag cccctcctcc gtataccacg atgttcaagt tccttcaact cccttatata    56160
atggcgtggt atttgcatat aaactaccca cttccgtaat cttttaaatc gtttctagct    56220
tacttgtaat gccgaatgca atgtaagtga tctgtaaata gttgttatac tgtattttaa    56280 aatttttttgt agtttttatt ggtatgtttt atttatttat ttttttccat cgcaaatatt    56340
tttgatccgt ggtaggttga ttgcggaatc gggtgatgag gcgggccgcc ctgtctgctt    56400
tccccagctt tgcagtctta gcggcctgtg catcctggtt tgtcactttg tggcagtgct    56460
ttatgttcct ctctgcctta gttctctcat ctgcaaagta gaggtggtga tagtatctac    56520
acacaggatt ggaatgagga ataaagaaat tgcctacatg agagaagttt agtgcgatta    56580
atacagtaaa tcttaaagtt attatcctgt ccgggaggtc agtaaggaga gcagagtaga    56640
cttcgacgat tagttttgct tgagtcttgc cccatttatg tttcttagag aaggatagt    56700 gtggacaggt gttttaccca tttttttaaat tgactttta aggactattg tttctgtaca    56760
tgtttggctg gttttgtttg tcattggaat taaattcttt tttcattagc aaaacgtgat    56820
actgcttttg aaattttat cttttttcttt gttatgtagt catttttttt tttttttga    56880 gtatctattc tggctcagaa tctggtgata ccttacacca atttcctaaa tggggatcta    56940
tgagtctagg ggctcgtggg cttgtggaaa gagtcctgta aatgattgcg ggggattgg    57000 ggacgggaaa tggagtgcaa gagtgtgtgg gcgttcagca aaggaatccc tgactgtgga    57060
gccctaattc ttcagtaggt acaaaactta taaataaaac gacattgata agttttaaaa    57120
cataatgaga ttatcatttt ttgcaagtga ataatctttta aataaatctg taattgattt    57180
ttggcttaaa agtttttata cagggtactt tgaattgggg aaagccaaag gattttttgtt    57240 ttgttttgtt ttgttttttg ttttttagag cacatgcgct gttgctgccc tcaagctgtt    57300
gcttagtatc attgcagtct aaagatttttc tcagaaataa agggtaaagg ttagttttca    57360
gtgacaagaa cccttaaaac ttcagcaaag atttagatca ttttatgtag cagcccttgt    57420
gaagaattac taaagaggac tgtggccagg ctcagtggct tacgcctgtc atcccagcac    57480
tttgggaggt caaggcagga ggatcatttg agcccaggag ttcaagacca gcctgggcaa    57540
catagtgaac ccctgtctac acacagtcaa aaaattagct ggacgtggtg gcctgcacct    57600
ttggtcccag ctacacgaa ggctgaggca ggaagattgc ttgggcccag gcggtcaagg    57660
ctgcaatgag ccgtgttcat gtctgtctct gaataaaataa ataaaaagga ctgtgaaaga    57720
cattctagtc atgacaacct catatattta taataaactc gtttatgtca aaggagtata    57780
tctgattact tgttctacaa tcggttttgc tttatttcat tttcacggga attcagacac    57840
ctgaaattat ttagatttta ttgtattgtt tgttaatgac aaacttaccc gttattatac    57900 tagttttcata atttactctt gtatctctat actaaattgt ttggtctttta aaccatctat    57960 atagcttagt gtcttatttta tacagtctaa atgtctgtgt caaataatgc agaagtaagt    58020 taaactttttg tctcttatag attttaatgt ttgtaatatg cgtttaagtg tattagcaag    58080
atattaccat ctctttaggc tatgtatact aatggagatt tttaagtcac ctaactaaag    58140
aactaaagaa acttattttt tgtattgaaa tgttattggt ctttgggtct tataccgaaa    58200 gtgattttttg gctttgctgc agatttttaac ttttctgtcc gcagaaattt aattttgcgt    58260
atataaactt actgaaatta gacaagtcaa attatacaaa tattttcaga ttgtctcatt    58320
tttcatattt cttgtctaac aatttatgtg aatattttca ggtcgtctaa ttttacatat    58380
```

```
ttcatctcta agaattcaag ccaaaattct caaccctagc tgagaattgg cattacctgt    58440
agttaattga aaataaaaa ataaaagaag tcctacctca gtctctatga tttagaattt    58500
taggcccatg gggtttaata atccgtatgt ttcagaagct tcatatccta ttctaatgga    58560
tagcagggat gagagccact gatctgaaac tagatttcct cactgaagtt aaagtttaaa    58620
gtagtgggcc aagtagaaac taatttaatc ctatgtaata gtgagcttca tggcttttcc    58680
agactatact tgtagcaagc agaaacatcg atctaataca agacagatgc acatcaacac    58740
caagttctac ctctgagatg tatcttttat ccgatctctt ctcgtggtct ccaccactac    58800
tgtctgcgtt aacttgggct attgtaactc attttagaac tggtttcctt ataatctgtt    58860
cttcacatgt tcatcaaagt tatccttaaa tcatgttcta gaaacttccc agtggccgta    58920
tcacctcctg ccattccttt tgtcctgctg cactggcttc ctggagatag ggaccgtctc    58980
tgttttgttc atggctgaat tgtttggtgt atatccctag ggtcttggat atgcctggcc    59040
catggtattg ctaaatatta tagaaataag catagcagta gcttgctttc cactaggtat    59100
tttgttacat agtgttttgt aaattaattg ttgatggacc tacatttttt tttatgttag    59160
taaaagttag gcagtgtaca ttcatttaaa tactaaactg ttcaacttat ttaatagcag    59220
atatttattg tgtataagag tccctgtgaa agggagtgca gtgcacaaat tgcccgggca    59280
agccatggag cacacaggct gggttttttc cctgctagat tataaactcc ataggccaa    59340 tactgtgttt tgttcagtgc actggatatg ccagtgcata gaaaaaatgc tgccacataa    59400
taaaaacaga aataacgtga taggtggccc cttcaatgtt cttttcctat gttagaaatt    59460
tacctgcaaa tattagcatc agtccaggtt tctctctgtt tttttttttct tttttgttttt    59520 ttttgagaca gagtctccct ctgttacgca ggctcgagtg cagtggcgtg atcttggctc    59580
actgcaacct tcgcctccca ggttcaatcg attctcctgc ctcagcctta taggcacacg    59640
ccaccatgcc tggctaattt ttgtattttt agtagagaca ggatttcacc attttggcca    59700
ggatggtctc gatctcctga cctcaggtgg tctgcccgcc ttggcctccc aaagtgctgg    59760
gattacaagt gtgagctacc gcactcggcc tcaatatatt ttttaaatag gaatgtatac    59820
aaggaggatg tcttcatcta gactgaggag gggacccctg gactgagacc ttagagtagg    59880
agagaactag gcggagagag ggagaaactg tttcaggcag aggaagcagc atgtgagaag    59940
aacctggagg caggaaggag cttagtgatt tctgggtttg aggaaagccc agtagcagga    60000
agtgagcaga ggccagatca ttcaaggctt cctagaccag gagaagaagt tttagatagt    60060
atcttgaagg cagtgggaag cttgggaggg ttttcaccaa agatacgttg gtgaaatcta    60120 gtataacct tcaagataca ttagaagata gaattgatag acctggtaat agctataggt    60180
ggtgatgccc agcattctgg ctcaggtgaa tggcagggac attcactgag atgggggcat    60240
gagcagctga gtggagaaga catggagttc agttttgatc atgttaagtt tgaaatgtct    60300
atgaggtatg gggtagagac gtcatctggg ctctctgttc tggggtcagg agcgtgctct    60360
gggccagaca tatacatgga gtcagggcgt ggtgtatgtg gagggagtg gaggttgata    60420 gttcagacag gaggaaagaa gagggcctga gaaagatcac tgatgaagtg aatactttaa    60480
cagtgttaca ggagctggca aagagtctga gagcaggaaa accagcagag cgcggtgtca    60540
ctctttcttt tggacaaata taacattttt tgagaagcac tttttagaaa agtttaaaaa    60600
tataagaaaa cttcaagatg aaaatataag ttatctttag tctcagcaga cataatatct    60660
actttaatat tttggtatgt gaactagttt tttatattta acatatatac tgtatcagaa    60720
```

```
aatggagtta tactttatat ggttttatag cctgttttac tatctttaat aatatttaat    60780
gactatcttc cttatcacac atgctcctgc aacttccatt tttaagggct ttttggtatt    60840
ccagcaaata ggtctgccat aattagtttt tcttttttga gacggagtct tgctctgtca    60900
ccaggctgga gtgcagtggc gcgatctcgg ctcactgcaa cctctgcctc ctgggttcaa    60960
gcgattctcc tgcctcagcc tcctgagtag ctgggactac aggtgcgcac caccatgccc    61020
agccaatttt tgtattttta gtagagatgg ggtttcacca tgttggccag gatggtctcg    61080
atctcttgat ctcgtgatcc acctgcctcg gcctcccaaa gtgctgggat tacaggtgtg    61140
agccaccgcg cccggcctat gattagtttt ttaaaaagac ctgctggaaa acttttaagt    61200
tgatttttat attttcatta ttataaacaa gcattctgta ataactctc attatatatc     61260 catgatgatt ttctgaggat caatgtctgg aagtggtaaa atagactgca aagttttaaa    61320
aagttttttt cactatgaat tgtcaaattg tcctccagaa aatttgtgct aattcatgaa    61380
aattctttag caatcactta tttttttta aagaagcaat tctttgcaat gagacttctt     61440
aaaaggatat gtctgtcttt gtatgatttt aaaatgcagt atgtgaatag gggtaacaag    61500
agttcaacta aaagttaact gacttttaggt agatcccatg agagctaaat gttttttcaat   61560 tttaaatgaa tagtgataag tatttagtgt tcaacgtttg gataatatca gttattagga    61620
aattgaagtt gtgaggatga agagaaaaat cccggagttt tttccattaa caattctccc    61680
agatattagc atttggttaa accaagcact taaaggagtc cgggatcgcc atgggaactc    61740
aatagaaaat cctcatcttc tcactttgtt tcatcggctc tgcaaactct tattttttcg    61800
aattcgtcct attttttgtgt ttgatgggga tgctccacta ttgaagaaac agactttggt   61860
aagtgtcgta tagtttttag taagtgtcaa ataattttttt tctttctgca ttcttagaaa   61920
aattcacata aaatttttgt tttctcttta gaattttaga aacagactta ttttgacaca   61980
tacttaatta catctacttt tttatcttga acaattaatt tttctttaa aaagttttat    62040 gagagttcat catgggtaca atgataaaat ttaacttttta aataaaacta actactaaaa   62100
accttgctgt tgagagtttt ccccttcagag gatcttgtta ggtgttttat atttatttca   62160
aggatgcggc catcactcag aacactgtgg aaaccctctt ttgggaagtg cctccctgaa    62220
tctgagatca agtatcctcc gtgatagcaa gccttctttt aagggggaatt ggattttagg   62280 agtaagcaat gttatgtggt gccaagtggt gactaaagtg gattatctag gaaggaaatt   62340
gaccatgata tagaagagtc agaatgagtt gctgctttat tgttctggaa gtagttttaa    62400
aaaatgtttt tggaaggccg ggggcaggag gattgcttga gcccaagtcc agcctgggca   62460
acacagggag acccccatctc taaaaaaatg acataaaata atgtttaaac agtccaaatg   62520
acagcaccca tttggatata tgacttttat ttgttgaaaa taccaaagta atgaaatgat    62580
gactttgtaa tcataccaga tactctctaa atgaggatat aggataaaag taaggatata    62640
ggataaaaat aaaaagcatt tataaatgct gggggacctt tgttgcctca gtaagagtgt    62700
ctagtcttga atgttgcagt tttcagttac ccaaggcata ctgtaaatca ggtactttgt    62760
ggaaggatta gaaaggaaaa gagaatatct tggttatttt tatccgatat tcagccataa    62820
gcacagggac tatccatttg tcactacttg aacatttctt acaagatatt tctatacatt    62880
ttagaatttc tcatgatata taatcttgaa tattgagggg cagaattaca tgtaagtaat    62940
gcatgtttat aaaagcaat attagaaatt gttttggtg tcactgtgac attttataga     63000
ataaataaat aatttctttt gggaagcatt taagctttcc acttcttggg catattaaaa    63060
gacatttaaa agaaactgaa agtaaattaa gtttcccaaa tatattgtgt agtagcccat    63120
```

```
taagtaatag atggaaactc tgggtgtcct ttacgtagca gcaacctgaa gatatacact   63180
gatatggcaa ttaggaggaa atgctaaagc agccatagtc tgaaaactca gacaaaccaa   63240
attctctgga aaataaatca cagcaatgtt tctagtggtc taatatcctg aagtgagatc   63300
ttacatcctt tcttctcata ggtgaagaga aggcagagaa aggacttagc gtccagtgac   63360
tccaggaaaa cgacagagaa gcttctgaaa acatttttga aaagacaagc catcaaaact   63420
gccttcagaa gcaaaaggca agaggaaaat tatagtcgtg ttagagatga agttttaaaa   63480
aagtgatttt tgtcttgatt tcctgcgatt ctctttccct atctaatttt gactctcaac   63540
agaaaataga gagtgaaatg agacaagtag gctgccattt tgacctggta atttggagtt   63600
gtggcaattc tccgttctgt gagaatcaac tttgctaatg agaaaaaaaa gctgtcgtgt   63660
tgcgtcatgt acacttttta ctttgattat ggtcttcttg actctaggtg agcagccccg   63720
ccaaggttcc ttcctttctc tcggctgcat ttattttcca cagcagtggc ctgagagcag   63780
ccaggtcagg tccctgttca ccatcctgag cagggtctgc ataatctgtt taaagatttg   63840
tgtactttcc agagatgaag cactacccag tcttacccaa gttcgaagag aaaacgacct   63900
ctatgttttg cctcctttac aagaggaaga aaaacacagg taaatgttta actatttaag   63960
aatattattt tagtcattgc tacattcaga cacatttaaa ccttgatgtg ttatctacat   64020
gataaggcat gtgaacattt cttaatgcat ctgaaatagg catgctctat acctttcaga   64080
atatttttca aagactaaat ttttttattta ctattctttg tgttttggtg attcatgatt   64140
cttattcctc ttcattctaa agaacttctg ccagggctgt ggattctaaa ttctccaagg   64200
catgaatttt agttttgctt acactttgct tacacatgct gtctctagct gctttttcaat   64260 ccagtatggt ctctctcacc atgatgctaa aataccacaa cccatgacat tcttgttgct   64320
aaatctagca gacgctttgc acgtcttagt gtgctcgact tctctgcact aaacaccatg   64380
ccacactgcc ccgctccccc ggcatctctc tggcgctttc tgctcagcct ctctgtggac   64440
tcctcttcct ctgtctctct cttaatggtt ggtggtttct gtgtttgaag tgaaggtgga   64500
gaaccggaag cttggcagtt tgcctttgtc ccctgtcctt ccctccacct cttcctttcc   64560
caggagttcc caagagacaa cttagctttt gtatcagctc agttctattt gtctccattg   64620
ctaccactgt catttttcct ccaggttaca ttattagctt taaacttct ttctgtcttt   64680 gtctttgatc atacccttt tgtaatagtt cctcccacca agcccaatct ctgttttgtg   64740
ttatagtctg tttaaaatcc aaatctgata ttgtcatttc cttacttaaa cactttcta   64800 gcttctcctt ctcatttttt tctttctttt tttttgaga tggagtctct gttgcccaga   64860
ctggagtgca gtggcacaat ctcagctcac tgcaaccct gcctcctggg tttaagcgat   64920
tctcctgcct cagcctccgg agtagctggg attacaggca cgtgccacca cacctggcta   64980
attttttgta ttttttagtag agacgaggtt tcaccatgtt gtccaggctg gtctcgaact   65040
cctgacctca agtgatccac ctgcctcggc ctcccaaagt gctgggattg caggcgtgag   65100
ccaccacacg cagcttagct tctcatttct ttaggataaa actttaactc cttaattaca   65160
ctttccagtc ttatccctgc cttttcttcac atcatccaca ggcaggcttt cttttccttg   65220
tttctatatg gtcatacaac ttagttcttt tgcctggaac actcttctcc atgaaccttc   65280
ccgctcccta caactacact cattaattcg tggctaactc caaccagtgt aattgcagga   65340
gatcctggaa agcttttgtg actcctaaat tgggtgaggt gactccctat tgcatctcta   65400
gtgacctgcc cttcccttgt ggtggaagtt attagatccc actctaattg cttacttaca   65460
```

```
cgtgtccccc accagaccat gagaccagta gtggcacaga tcttgctgtt ttattcacca      65520
ctgtagcccg tataacgagc agagccttgc atacaagtat ttttgtaagg ggtccttaaa      65580
aatcatagat atcgtaaaag tatgtttgac tttcagttca gaagaggaag atgaaaaaga      65640
atggcaagaa agaatgaatc aaaaacaagc attacaggta tttagatcat ttttgaattc      65700
agaatgtatt ctgttatttg aaatgaatga catgaaaatg aatattaatg aggtatatca      65760
aactgtgaaa gttcctgata aaagtaaag acagatggct ttttggttgt gcatatatat       65820
gtgtacatgt atgtatttaa aacacactca cctacacacg tgtatatata tatatatgga      65880
atttgccatt atgcacatct atatattcaa aacaagctat ttttctttta caaccaacca      65940
accaatagta atatgtgctt acatagaaaa tatagaaaac atatcattca taaataactt      66000
gtaataacag tttgatatat tttcatccat tctttgcctg ccccatatag ttgaatatct      66060
gtgtgtgtat ttgtatatat gtatcaaatg tgcatgtgta catatatatg tgtacacata      66120
tgtgtgtatg ttctagttat ctgtcgctgt gtaacttagt ggttaaaaca tcatttgtta     66180
tcgtcatctg tctgggttcc aggggtagat gagctcagac aggcagttct ctctggggtc     66240
tcttgtgtag atgcagccag tctgtagctg gggctggagt gattaacgag gtttccttgc     66300
tgccatgggc ggtggttgat gctggctgtc agccagtctt ccatgcggcc agcaccagag     66360
cacctacttg tggcctctcc acgtggcctg ggcattttcc cagcatgatg actgtattcc     66420
cagtgtgggc atcccaagag aaagttctaa gcagaagccc tgttgccttt ctgacctagc     66480 tttgaagtt gtgcagcatc cttcccacta catcctgttc ctcagaagct agttactgcc      66540
ctatggaagg ggcagagagt tagacaagaa gaatgtccca cacatatttt catgaataac     66600 attttttacaa attgagatta tgctgtatat atacatttttt ttcataaaca tttttcaagt   66660
ttcttagtgt cacagatagc attttttgat tcccaaattc actgtttctt gtttgttcat    66720
atggttttgt tctatcaggt agaaactttt gagctaaaac ctcgagatcc ttcaggttgc     66780
ggaggtgctg tgctattaat gcagctagtg agagcaatct tagttaagac catgggcctc    66840
gtggtcaaaa agacctgcgt ttcagtccag gctccactgt tcactagctg tgtgatctta    66900
cacagattaa attctccaag gctttatttt tttttgtaaa acgaaattga tatcaatgcc    66960
ttcctgatgg gggtgatggg agcattagtg agggaaagca caggaaatgc tgagcgcagt    67020
gacaggtctg tcctacgtgt ttgctggttg gtacgtacac atgtaacata cagacatgca    67080
ggacatcagg ttgtattagc ttatcttttt tactaatgaa ggatttttaaa gtacttttgg  67140 taatgagtta aagttgagaa aagttttaca cttttccatg tcttctgtga atttctttta    67200
atttcatttc ttatgttata agcaaaataa aactaactta attatgggaa tgatatatat    67260
tgcttgaatt cctaaggcac attctgtctt gggttcttgc attttctgtt ctctcagcct    67320
gaaatgctct atcctcagtg aggctctttg atatcttcca agtccctgct cacacatcct    67380 cttttttagtg gggtcttctt tatctatcaa atagatcttt ttttccacgt tctgttcatg  67440
taatcactct catatcagat aaatctgctt tattttacca ttatcttgtt catttattta    67500
tttatttatt gtcttctctc ctctgctcct aagagcaggg accttatctg gcaccttatc     67560
cgatctcaca gtaccttagc acctagaaca gtgcctggtg ccttagaggt acctgctaag    67620 tattttttc ttttgaatga attaaagagt gaatggctac attccctaat ttgcctactc     67680
actttgttgc ctgtcacaga ttatatgcaa ctgtgtttag ccaattgttg attatgtaga    67740
actgtgttta ttatataaac ataatacata tccttaatgt tgaatagaac taagtgtatg    67800
aaatgtaaat ttcatggtgc tgtgatttta tctttacagg aagagttctt tcataatcct    67860
```

```
caagcgatag atattgagtc tgaggacttc agcagcctgc ccctgaagt aaagcatgaa  67920
atcttgactg atatgaaaga gttcaccaag cgcagaagaa cattatttga agcaatgcca  67980
gaggtgaaat atgcaacagt acattcatgc ttagaattaa gaacttcagc aaaactttt   68040
attagaaaga agagaaaatt gataagcaat acttacacga tatctcagtt aacagtaaac  68100
agcatttcta catctcagat tctaagaagc atcgtatatt tatacgtttg agcctataga  68160
catttactct aagaagtttt tcttgacttt tgacccgaga ctaggtcttt tttcctggtc  68220
tttgttctca cagcaccctg taatatcact tcatagttct tagttccaaa acacgcttat  68280
cttgctcacc tctgtatttt cagtgtctag ctcagtattt ttcacatggt atgtgtccag  68340
tagatgctta ctgactcaat tcttaggtta ggtcataaaa gttattgtaa cctataatat  68400
acattgtcta taaaaactaa tagtcatata gaatctaatc acaatggaaa ataagttct   68460
aaattgaaat tccaggtata tcttcctctg ctgcagccct agagatgcca ttggctctcc  68520
acattccctt gccctcttcc tggacagtgc gaatgggact tcttcacctt ggaacatctt  68580
gtagcttggc aggcccagaa agctagagtg gaggtggtat gtgcagttgg gtgctagcaa  68640
atgtgtctcc tgatcatgct gccattgata cttaattcat gttactattg atgactccct  68700
gtcttagttg ccagtgagtg agttcttttt ctctttctgt tgctgctacc tgttatttct  68760
accgtagttc tccattcacc cactatagga cagaatcgaa attttgcagc atcatcgacc  68820
ttagtgcata gatggagtgt ttttttattt tctacaattt ttgaatattg cttaaattga  68880
tagcagaaat atgaaaaagg aagggtaaat ttcttttctc atcactccct gttttttcca  68940
caaagaatgt gcagtagcac acactaaggt gcacagaagt gacattcttg ggtctttgga  69000
tatcaaagg acagaagtaa attgattttt atttcaggag aaaaatccag gctcagtctg  69060
tctatcaggc atttatttc ttgagtatga aggatctct ggctggcagt tgaggaagta  69120
gaatttggt tgtgtaaaca ataacaggaa gaaatgggag aaagagagac agtccctaat  69180
gatttactgt tctttatttt cttctgcaa ccatgaagtc tctggaagtg gtggactgta  69240
gggtggtgtg gagtagcagc ttactggatc tgtaattttg atagagatgt tctaagtcat  69300
ccatgttggg ccttttgtgtg atctgtatgt cgtgcaaatg taatattgat aatagtagtg  69360
atggtaggta ataatagcag tagtaataat cataatacca tagttccact ttactcacgg  69420
tttgcagttt tcagtgacct gtggtaaact gtggtctgaa aatattaaat ggaaactttc  69480
agaaataaac aattcataag tttttaagttg cacaccattc tgagtagagt gatgaaatct  69540
cacaccctcc tgctccatct tgcctggaac gtgaatcctc cctttgtcta gcatctccgt  69600
gctgtagatg cttcctgcct gttaatcact gagtagctgt cgcggtgatc agatcaactg  69660
tcgcgatatt gcagtgcttc tcctcaagtc actcttattt gacttaatga tggcacaaca  69720
gtgcaagagt atgatgctgg caatttgaat atgccaaaga gaagctgtaa agtgcctcct  69780
ttaaatgaaa aggtgaaagt tcttgaatta ataaggaaag aaaaaaatcg tattctggct  69840
gaggttgctt agatctgcat aaaaatgact tttctatctg tgatattgtg aagaagcgaa  69900
aagaaattgg tgctagtttt gctgccgtac cataaactgc aaaagtcatg acctcagcgt  69960
gtgataagtg ctcagttagg atggaaaagc cattacattt tggggtggaa gacatgaaga  70020
gaaacatgtt ctgattgatg acaatcaggt ttggtacttc tgcagtttca ggcatcctct  70080
gggggtcttg gaacataccc caaggatgag ggggctgtct actatgttaa tagaatcaat  70140
tgtagtaaat tgacatgctt ttgatcccag atctaccact tattagccct gtgactctag  70200
```

```
ggaggttacc taacctattt aagtcccaat ttcttcattt ataaaatgga ggtgatatct   70260
gtttcatagg atgattgtga gaataaaatg aggtattata tgtaaaagca cttagaaaaa   70320
tgccctccat gggaaatgcc ttataatgtt aagtattact gttaataact gtgattactg   70380
tgatttattg tgtcttttat gggataaggt tgtgcaggac acttcacttg catatttacc   70440
tacattctag aagattgtta agccataatc agatgtcata gtgactgcta tgcattacat   70500
gctcaataca tgtttattga ataatgatta aatcataaac agtattcatg atttttttt    70560 tttttttttt gaggggaagt ctcgctcttg tccctcaggc tggagtgcaa tggcacaatc   70620
tcggctcact gcaacctctg cctccccggt tcaagtgatt ctcctgcctc agtctcctgg   70680
gtagctggga ttacaggtgc ctgccatcac acccggctaa ttttgtatt tttagtagag    70740 acagggtttc accacgttgg ccaggctggt ctcgaactcc tgacctccgg tggtccaccc   70800
atctcggcct cccaaagtgc taggattaca ggcatgagcc accgcacctg ccatagtat    70860 tcatgatttt ttttgccca actctttcga agattatttt tttaaaagga agctgtagtt    70920
tttcttgtta ttcacctttt ataatatgaa actaccatca atgaaaaaag ccaattgttc   70980
tttgttccct gttggggaaa gggtggaaat atggtaatat tatctgtatt taatataaaa   71040
cagtaatttt gtttgtttat tttgcccttta ggagtctgat gactttttcac agtaccaact   71100 caaaggcttg cttaaaaaga actatctgaa ccagcatata gaacatgtcc aaaaggaaat   71160
gaatcagcaa cattcaggac acatccgaag gcagtatgaa gatgaagggg gctttctgaa   71220
ggaggtagag tcaaggagag tggtctctga agacacttca cattacatct tgataaaagg   71280
tatcaggcac catcatttat atatttacat taaaaaatca aagatatatc atgactctga   71340
attctataaa ctagcaccccc tggataatat taatgaaatt ctatttatgt aataactgta   71400
tactgctatt aatggattaa ctactatagt gccaaaccac tttaaaatta gctaatgaat   71460
taactcctag ttgccgatta aatgaaaatg tatatactta tttatgagaa ccagtgttct    71520
cttatccatc ttactagaag cgtattgtca cactgtaaaa ctgaatggtg agaagtgttt   71580
taattcttct taaggtattc aagctaagac agttgcagaa gtggattcag agtctcttcc   71640
ttcttccagc aaaatgcacg gcatgtcttt tgacgtgaag tcatctccat gtgaaaaact   71700
gaagacagag aaaagagcctg atgctacccc tccttctcca agaactttac tagctatgca   71760
agctgccctg ctgggaagta gctcagaaga ggagctggag agtgaaaatc gaaggcaggc   71820 ccgtggggagg aacgcacctg ctgctgtaga cgaaggctcc atatcacccc ggactctttc   71880
agccattaag agagctcttg acgatgacga agatgtaaaa gtgtgtgctg gggatgatgt   71940
gcagacggga gggccaggag cagaagaaat gcgtataaac agctccaccg agaacagtga   72000
tgaaggactt aaagtgagag atggaaaagg aataccgttt actgcaacac ttgcgtcatc   72060
tagtgtgaac tctgcagagg agcacgtagc cagcactaat gagggagag agcccacaga    72120 ctcagttcca aaagaacaaa tgtcacttgt tcacgtgggg actgaagcct ttccgataag   72180
tgatgagtct atgattaagg acagaaaaga tcggctgcct ctggagagtg cagtggttag   72240
acatagtgac gcacctgggc tcccgaatgg aagggaactg acaccggcat ctccaacttg   72300
tacaaattct gtgtcaaaga atgaaacaca tgctgaagtg cttgagcagc agaacgaact   72360
ttgcccatat gagagtaaat tcgattcttc tcttctttca agtgatgatg aaacaaaatg   72420
taaaccgaat tctgcttctg aagtcattgg ccctgtcagt ttgcaagaaa caagtagcat   72480
agtaagtgtc ccttcagagg cagtagataa tgtggaaaat gtggtgtcat ttaatgctaa   72540
agagcatgag aattttctgg aaaccatcca agaacagcag accactgaat ctgcaggcca   72600
```

```
ggatttaatt tccattccaa aggccgtgga accaatggaa attgactcgg aagaaagtga    72660
atctgatggt acgtgtctgt gcttttgtag aaatctggaa cggtaggatt tccctctgt    72720 aggaattcag atcggttta gtgtagtccc gttttaactt tttacagata aggaacgaga    72780
gacgtagaaa gaaagatgaa atgactttcc cagggagtca cagctggtca tggaatcttg    72840
accttccctg tgttgctctg cttttttgtta tcattttttaa aggcatgaag tgccctattt    72900
ggggaaggta aagttgagtt tccctctagt ttttaaaaac ttttttatttt gaaataatta    72960 tgaactttaa aaagttggaa gaatattata aaacactggt tccttcatcc agtacctcag    73020
tggctagcat gttaccacat tagcttagaa tttctcttgg tctctctgtg gccctctata    73080
tgtatatcat atatctccaa atctgtatac atatgtatac cattgatcct cattatttgt    73140
agattccata tttgcaaaat tgcctgatca ctaaaattta tttataactc caaaatcagt    73200
actcaccgca atgtctttgt ggtcatttgt ggacatttgc agagttgggg aaaagcttga    73260
gttgccacac tgtcccctgc tgaggttaag caaggtgaca ctctgcctgg ttcccgtgtt    73320
ctgagagaga tgaccagagg gtggggacag taggggatta tgcaatggag agagagcaag    73380
aagctccggc cccaggccag ttggaccaga tttgaatccc tattctggca cctgttagcg    73440
tggcagcttc acacaggtca ctaatttgtt tcttgaactt tgtttcttgt ttataaaata    73500
aatggaatct attaagatgg tggtttttta ggatttaaga taatatatat gaaatgtgtt    73560
catatatatg ttatatatgc atatgtgtgt atatgcacat agatatgttt aggagcaatg    73620
actcggtatt ggctaatta gtgttcacag agacttcata cgtgatggcc actttgaata    73680
agagaatcaa ccacacacac acacacacac acacacacac acacacacac aatttgttcc    73740
tggtatctgc tagttttctt cattcaaatg ttactatttc cctttttgtaa ttaataagta    73800 ttttgtggaa aaggaatttt tggagctata taaatatgct gttcctgaac aaacttccac    73860
ccacttgtta gcatccattg atgtttacct gaataatttg ttactacgtt ggttgccaaa    73920
tgatggtttt tctaactcca tcattcctta tatattatta cttgacatcc tcctatgagg    73980
aagatctttt ccttctcccc atttatttt attattttta atcagtgtag actcctgtat    74040
tcctatttag tgagttataa tccaatactg tcataattta cttttgttact caaattatca    74100 cagctttggc cattggggct ccttctaatg gctttcagca gttttttcat tatatttga    74160 gcttttcctt gctttctggc caagctgttt caggcatatg ttgtactttc tctgccctgg    74220
tcctggaacc agccatttca ccagggagct ctggttcctt tcagtggagc atggggttta    74280
gacaccacaa gctggatgtg agtgtgctta tggatcctga ggtataactg tctcaggcct    74340
tttcagcaac agtgccagga agtatattta tgtatacata tacatgcaca cacacatcta    74400
tatttatttc tatgtctatc tgtactaaaa tccatgagtt tatactgaca tctgcaattc    74460 catgggttc agtctagcct cctgcttctt tatagtttcc ctaacaatga gaaacattgc    74520
tccccttatc ctcaatacat ttacatctgc ttattctccc tggatatgta accatctccc    74580
cctcccactg gcctcctcct tggccctgct ctcttctttg cttcagctgt gtccttggtg    74640
ccagctccca gtccctgaga gcccctcct ctgttctgat tgtctcctta aacccagctg    74700
gacaggcctt gccagccctc tccacctaca gggaaggaag gcaaccatta aatatatttt    74760
aaggagaagg aaagacagta agacagtaag agaggagaga agggaagtgg aagaggaaga    74820
actatttctt agtcacagct ttattctgtg ctgtgtaaat agcataaaaa catactgagc    74880
aacttccatg attgtttata tactttgata atcctccttt ttgaattttt aaaacaatgt    74940
```

```
cagttaactt agaacatatt tatataaagc gaatatacaa atcttaagag agtttcctac    75000
tttcaaagac agtgccagtt tacctaattg aaaaggcttg ttttgaagtt acaggcattt    75060
gtgattacat ttatttatta ataacgctac tattacatgt attctgttat agtcatatct    75120
ttccttttta ggatgtagca tttttcaggt tcctccagaa agctcttgat gattgcagga    75180
tcattttaat gttttgattg tagatgaagt gacctttaa ttttggtaca ggaagtttca    75240
ttgaagtgca aagtgtgatt agtgatgagg aacttcaagc agaattccct gaaacttcca    75300
aacctccctc agaacaaggc gaagaggaac tggtaggaac tagggaggga aagcccctg     75360
ctgagtccga gagcctcctg agggacaact ctgagaggga cgacgtggat ggtgagccac    75420
aggaagctga aaagatgcg gaagattcgc tccatgaatg gcaagatatt aatttggtaa     75480
taccgtaaca ttgtgtttcg acttcttgct gaggaagcca ggttaagtag ttttgagtt     75540
ttaaggagtt ggtggatgag tatttagtag ctatttgcag tacatcttgt ggttgctgat    75600
ggcttcattt ttgtgtaggt tactggctgg atagactcc gtttccatg tggtttagtg      75660
atgaatctct aaagatatta cagagtcttg gttagacatc cagtggagta cttcctaagg    75720
agaaagagct tattggtaat ttcagtcaga ctaaatgcag gcttttgta aacaaaactc      75780
atttggatta ttaatataaa tctataaatg aaaaaacatt ttataggagg agttggaaac    75840
tctggagagc aacctcttag cacagcagaa ttcactgaaa gctcaaaaac agcagcaaga    75900
acggatcgct gctactgtca ccggacagat gttcctggaa agccaggtgg gtgcaggcag    75960
cttgggtttc ctttaccacc ttcttcagac ccctggggga atgcactgca tgaagggggt    76020
atgcactgtg cccctggtg ctcagggcct ggtgatgccg ttccctgggg gtcactgtgt     76080
gtccctaact ctgcaggaat gaatgcatta catgaagtgg taggcactgc tccccctgtg    76140
ctcagggcct ggcggtgccc ttccctgggc gtcactgtgt accctcact ctgcaggaac     76200
tcctgcgcct gttcggcatt ccctacatcc aggctcccat ggaagcagag gcgcagtgcg    76260
ccatcctgga cctgactgat cagacttccg gaaccatcac tgatgacagt gatatctggc    76320
tgtttggagc gcggcatgtc tatagaaact ttttaataa aaacaagttt gtagaatatt     76380
atcaatatgt ggactttcac aatcaattgg gtaagacttc agagtctttt tgattacttt    76440
ctgacattta ccttcagagt ttgtcctagg aagttttctt tccaaggaac tagtttgatg    76500
cattgatgga aattgcaggt ctatgcaaat ttttatga gtgatctttg cttatatag       76560
aggaatagga tttaaacat ttgaattaag gaattaaagt cctagtatgt ttaggtagtt     76620
aatcaactga cttagttaaa ctttgactag ttacccgaga tctccacagt gaacaaaagg    76680
tggtggagag gggaagcagg ccgcgcctgg gcctgtattc gggtttctgg cactgatctt    76740
cttctgttca tccagcaaat atatgtttgg tgactcctat atgccagttg ttcttaacaa    76800
gagggaagga acagagagta aaatagtagg agaaacagat gataagcaga tacataaatc    76860
ataatttgac agttggtggt aagtgccaaa tagaaaaata taacagtaaa ggagaggaga    76920
gagtgaactt caggcatcga gagtgcaggt gctgtttcag agagttgttg ggaaaggctt    76980
tactcgtgta acttcaaggc agggacctgc aggaaatagg aagcaagcac tgtagataga    77040
tacctcggga ctagtgagtg aaagggggctg aggcagaagc ttgtgggctg tgttctaggg   77100
aagcaaggag gccagtgtga gaggaggagg gaggaaatgg caaggttaa tcttagaaa      77160
taggaagaag ctgaaaccca ccagggtctg gtgtgctagg gtatgcaggc agattgaatg    77220
tggggtggga gaagaatgaa gtcgaggagg attccagata ctgagcagct ggtcgagtgg    77280
acctgccttc agtaagacaa ggagggagca cagtggagga ggagaaacga agtgttcagg    77340
```

-continued

```
tttggatatg ataaattggg gatgctcatt ggatacccag tggaggtgtt gagttgatag    77400
ttgaatatat gtgactgtgg ttcagagaga ctcaggctag atagctaact ttgggggtca    77460
gcgtatagag ggtatttaaa gctatgagaa tggatgaaac tttaaaaata ttaacagaat    77520
gccattgaat aaaataattt attttcaaat aataagatat ttttggtggt tggatataga    77580
tatagatata cacacgtaca tgatttatat aataaaatgt ttataaatgt catataagaa    77640
atcttgataa aaattaaaaa atattgttac tctttaggat tggaccggaa taagttaata    77700
aatttggctt atttgcttgg aagtgattat accgaaggaa taccaactgt gggttgtgta    77760
accgccatgg aaattctcaa tgaattccct gggcatggcc tggaacctct cctaaaattc    77820
tcgtaaggtc tttatttct taatttgga taattgtgta aatacccaaa taagcaaata    77880
gaactattat ttacagcatg aactgtcatg ctgtaacatg tgaacaatgg ttcactgaga    77940
aagcagcaga aagtattggt tgttttccat tttctagaga tgatgaaatc agagtcagtt    78000
cttagtggtg ctgggcttat cctagttcaa gggtacaaag ccagtcctgt ggatttcaca    78060
ggaatgtaga agttgccttt tcatccattg acatacttat agagcagcta tgatgtgtca    78120
gacactgtgc tggccctggg gaaaggagag atgagtaagg cataggccat accctcaagg    78180 actccccca tatacttgga ggtgatggag aagcaaagca aattgtactt gtctgtgtgt    78240
ttggtgtcct gagagaggtc agccaggaag cgacttggaa atataatgcc aggaatgtta    78300
catccagcac tcctgtcctg tttctcacca tgtgaatccc gtgacgtgtt cagtggtgaa    78360
gtcttgctcc atccagaacc cagagtcgtg ctatactcgg ggtacattta tcattttgaa    78420
gattctgaga tggtaggagt tatgagtatg tctgggaaag tagtttttc tttgtccttg    78480 atggcatctt tttaaaaaat tgaaatatag tcacatacca cagagttcac cgatttaaag    78540
tgtacagttc attggttttt agtgtattca caagattgtg gtggcatctt ttaaccgtca    78600
ctatgtcgtg agatgctgtt tggtggtggc tgatttaatg atccttgagt gttctctcca    78660
gttacatatc ctgtgtttga aagatgctag gatgctctga cctgaagagt cagtgactgg    78720
aatcactgaa atgaacggcg aaactgttgt agtgatcatg gtcttccagt catagcacac    78780
tcaccaatgt gttgtatttt atactttctt catttatctt tttctgattt tcttattgtt    78840
gaggaaattt atataccggg aatgagttat gaggtagaca tacgtcatgg taggtaaata    78900
acttgaaaac ctacaaataa ctttattata caaataaagt aaatacatca tagaaaatta    78960
taaatatgta ttaaaaagat gattacagtt tacaatttgt ttatgtaatt ttagacttca    79020
cacatatata tgcatataca ttgcatatat atgtatactc atttgagtgt gtgtatgatt    79080 tttttttataa gaatgggatg atgctatata ctttttattt tacctgtaac ccatttggta    79140
ttagaacaag acctattatc aacgatgata tagatttata tcgttttaa tggctacagg    79200 tagtatcttt ttgcgtctat cagggctagt ttaatcaagt gtcttttgtt atttctattt    79260
ttagaaaggt attaacagac attgatttga gtgtccttaa tcttcgggtt cttatctaat    79320
gattatttta gaataagtga aatagtatct gacttttcca tttggtttct tgataactat    79380
tgagagtgaa ttttttatgt tcatagacgg tttgtgtttc tgatttagtg aatgacctgt    79440
ttatgctgtt ccacttttct ttgttcagca gttttgctc gtttgttgcc tgctgaatca    79500
ttttcatatt tgagcagttt ctgcctttgg tcctccagct cgttgatgcc agataggagc    79560
agccttcgct ctgcctggct caggacattt aggatgaata cagagtaaag agcaggaagg    79620
atggtgggaa accagtaaaa tcagaatgtg gcctcacttt gttttctgtt ctcctcttct    79680
```

-continued

| | | | | |
|---|---|---|---|---|
| gagggcaccc | tggctggtga | atcattctta | gagtgggggct | gcattgggcc | tgcaggttga | 79740 |
| attgagctgt | agtcacattt | ggtttggact | acacggtgta | ttcttctctt | gagctttaat | 79800 |
| tttcaattgg | ctaccaacat | ttacctttgg | gagattttac | acaaaattat | ggattctgtt | 79860 |
| ggggggaaaaa | ggagagctga | aaatactggg | cctgaatttc | tggatagccc | caaaatagct | 79920 |
| ggcatggagc | aacagcagtt | cccctcccct | accccaaggc | cttggactgg | gcatgaatcc | 79980 |
| ttcagtttca | tcacagttgc | ctccactccc | ccagctcagc | tgattgacag | acaccttcct | 80040 |
| cctttcatct | ttatgtgaag | tgccaggccc | tcctgcttga | aggagtaacc | atagctttgg | 80100 |
| cttgatgagc | tcacaagtgc | actgattcta | actgccagtc | atgattacag | tttcaaaaac | 80160 |
| gaaaatctgc | aagtaaagta | gaggagaatt | atcggtattc | tctcagtgca | ctcctggaaa | 80220 |
| gaatgttgta | aaagtaatga | agaaaaatta | ttttttcctt | tttgcatttt | gttgttataa | 80280 |
| tactttgaag | accgcaatta | gtaatttcca | acgctagatg | gcactcctgc | atcggtgagg | 80340 |
| cggaccctgg | ccctgacagc | cggtctgagt | gggttcctaa | tgctgcacta | gcaagcttgt | 80400 |
| gaagcggggg | agcctgagct | gcgggcgttt | tttcaggttc | cattgagtac | atagattggt | 80460 |
| gaggattatg | ttagtaactt | tgatggcatt | tattttttcc | taattgtgta | aatgtttctg | 80520 |
| gtcagtcgtc | actgcattac | aaactacctt | cagccttagt | ggcttcacac | agcagtagtc | 80580 |
| actgattttg | ctcatgcctc | tgaagctcgc | tcaggcctgg | tggggtgtc | ttgtctctgt | 80640 |
| tccatgtcgg | ctaggacagc | tcagctgggc | taggacccct | taagatggct | cgcggggctg | 80700 |
| atgaggtggc | ttcggcctcg | gggcctgggt | ggacacttgg | tgagcttggc | ttcctcatag | 80760 |
| catgttggag | ccaagagcag | gaggtccagg | ggacaggaag | tggcgagggc | ctcccctagg | 80820 |
| cctggcacgg | cttgagtcac | actggtcagc | catggccgcc | ctgctcaaga | ggaggccaca | 80880 |
| gggaccccct | tcgtgatggg | aggagggtcc | aagagtgtgt | cgctgtcttt | atccggccga | 80940 |
| tttaggctta | gaatgaaaa | cattgaaaaa | tgaataaaat | ataaagaaga | aaatgaatgg | 81000 |
| ctgtgtgctc | acgtagaata | ttgcctagca | cacagcgaaa | taatagttgt | tagtgttatt | 81060 |
| tattttaagt | atctgtttac | ttttctcata | tatgtgttttt | ttccaaaact | ggaatcatac | 81120 |
| tttaagtaga | gttctattat | ctctgttttt | gtatatattt | atttgtttta | catacatatg | 81180 |
| tatttatata | tataaaaat | gttaaatttt | aaaaacagat | acatgtatct | gtttttacag | 81240 |
| atttttaaa | caaatttaac | attttcttgg | catatttaca | ttttattaaa | tattcttcga | 81300 |
| tccattattg | tatttgattt | gaggtaaata | atacagatac | attacttcca | ttttactgct | 81360 |
| gagaaagaga | cccagagaag | ttgtaacttc | tgtggtataa | ttatgagtgt | gggctctaga | 81420 |
| ggaagactgt | accaattcca | gctgtgaaat | cttgagccag | ttacttattt | ttgagttcag | 81480 |
| ttccctcctc | tgtgaggtga | gggtaacgat | agggcatggc | ttgtgtgatg | attgggcatg | 81540 |
| tgaaatattt | aacacagtgc | caagcacaga | ggaagacttc | cataaatgtt | tgccatcatt | 81600 |
| atacattgtg | gctaatagta | ctaaaattaa | taaaatattc | tatatagcat | acaatttgag | 81660 |
| ttagaacttg | agtttacatg | ttctaagttt | agttcttcat | ccatagtgta | tgaactataa | 81720 |
| tgtctcattg | ctgtgtaagt | aattgttttcc | tttattttac | agagaatggt | ggcatgaagc | 81780 |
| tcaaaaaaat | ccaaagataa | gacctaatcc | tcatgacacc | aaagtgaaaa | aaaaattacg | 81840 |
| gacattgcaa | ctcaccctg | gctttcctaa | cccagctgtt | gccgaggcct | acctcaaacc | 81900 |
| cgtggtggat | gactcgaagg | gatcctttct | gtggggaaa | cctgatctcg | acaaaattag | 81960 |
| agaatatcct | ttgcttctta | aaagagaagg | aaacaccttg | tcaaatatgt | gtttggttta | 82020 |
| aaacttatgg | aagagaaact | tggatcattt | ttttcttata | tcccgttaat | cccatttttct | 82080 |

```
taatatcccg ctctcctttt cactctttct tccctctcct cagttgttgt tttttgtttg    82140
tttgtttgtt ttaaaggaac agtgtatcac tctgtcaccc agcctggagt gcagtggtgc    82200
aatcatagct cactgcagcc accacttcct gggctcaagg aatcctcctg cctcagcctc    82260
ctaagtagca caagccactg catctggccc ctctccttag ttttaaagag ggtctttgtt    82320
tgaataagca gtgataagca ttcatagata taaccacata cttaaatatt attgattctg    82380
aaagaaggaa agatgactaa tcttgtcctt tttattactg gttgtccttt ccgtgtatat    82440
ttaagtaatc atttggatag atgtttcaaa acttgcacta gaattaatcc aactacgttt    82500
gattttttct cttaatgaaa taggcaagat atctgaaact tgttttatt ccagttaacc     82560
tttttcata gtcacaagtc tttgatgtcc taaagtgaga gctaaatatg ttttatttta    82620
tagaattgaa aagaacatag tgccagatga ttatgctgga gtcatttatt ttgttagtac    82680
tttcttttag cactctaatc tttataaata ggaaaatctt aggagataca gggaatggaa    82740
tcaagaatgg gttctttgga cctttttatt tgtcacttgt ttaaatatct ttcaaaatat    82800
ttataagtct taactgcatg catattttgt cagcggtatt tcggctggaa cagaacgaag    82860
acagatgaat ctctgttcc tgtattaaag caactcgatg cccagcaggt aatcatggtg      82920
gacccttctc ctaagttcag gatgaaggg aggctgtggt tgacagctgt taaagaccag     82980
ttaactctta ttttggggca tagagcagac attttgaaat taggataatt tagatgagag    83040
aatagaagaa aatagaaaaa gaaaagttag actttggctt cattttctat gatcactctt    83100
agggctgaac tttggagtcc tttcatattc atttttttct ttgaaaaaac cagtctaata    83160
actgatttca cactaaggtg tttctgatta aatacattac cccttgggat ttactttcat    83220
tttttaacga aaggaagtct tcaaagcaat tctgatcatt taagttttta taagtactaa    83280
tatttttaaa ttctataaac gaatcttgaa aggtagaagt tcagtcatta ttgtgtatca    83340
gtaggagagg tttttgtggg aaggagccct tttgtatgac ctttagttcc tctaggtacc    83400
tacttcttgc tttatctgtg agtatgttct gactcacaca aaacaagctt tcgcccacac    83460
tagaaacaac ccacaaaaca tacatacaaa taaaccactt agcagaaatg agaatgtagc    83520
ttttgtgata atatatttaa attaaaccca ttttcattag gcttggataa ttttgaaaaa    83580
catgaacaaa actaagacag catttctatg agtttctctt tgtttttggg atgactatct    83640
actggaaaca ttataaacca accaaaaagg aaagctattt gtcttagtgt ctggtgattt    83700
cttaatttca gataaatttt gttgtaatat ttatctcctt tttcattcta aaacttaatg    83760
tgtttatttt tccaaaatta gaaaatgaag aaaatgaatt aaaactactc attagttacc    83820
tcctctaata cagttgttaa catttaggtt aaaaaatttt cctgcattta tttgtggcca    83880
tactaaatgt aacttaatag atctaatcct ccccccaac ttattagcat attttcttct      83940
atgtattgtg tggttttctt aattccagat gactagatta tatttcatga aagatattta    84000
aataattagt tcagtttact tgttagacct ttaattttca agtttgttat agtaatgctg    84060
tgatgaacat taggcatata gctttaccca tatatttttt ttttgagacg gagtctcact    84120
ctgtctccca ggctggagtg cagtggtgag aactcggctc actgcaagct ccgcctcccg    84180
ggttcacgcc attctcctgc ctcagcctcc cgagtagctg ggactacagg cgcccgccac    84240
cacgcctggc taatgttttg tatttttttta gtagagacgg ggtttcaccg tgtaagccag    84300
aatggtctcg atctgacctc gtgatccacc cacctcggcc tcccagagtg ctggggttac    84360
aggcgtgagc caccatgccc ggccaaagaa tatcttctta aaagtgaatt tactgaataa    84420
```

```
aaggcatgaa tatttcttac agttgctaat atatactgtg aacttgcctc tcaaaggtat    84480
tgtatgatga taatgttttt aaaagaaaga tatagtagga cttagaaaca ggccccatga    84540
agtcgtgttg ctcctgagga agatgaaatg tttagctaca gaaaaatatt taacgctctt    84600
tgaatatctt aggaagagat ttctcatttg agatgtggac taaagactta gttgacagag    84660
atggtacaag tactgcttta ggtatgattt agaaagtgaa aattactgtc agtaattcac    84720
tgggagagaa ctgggttttg ggagataatg aattaatatt ctctgacata gtaatccaat    84780
gtgagtgatc aaggttgagc ttgttgattt ggtttagaaa cttgacttac ttgtctgatt    84840
tattattatt attcttttgt tattttttta gacacagctc cgaattgatt ccttcttttag   84900 attagcacaa caggagaaag aagatgctaa acgtattaag agccagagac taaacagagc    84960
tgtgacatgt atgctaagga aagagaaaga agcagcagcc agcgaaatag aagcagtttc    85020
tgttgccatg gagaaagaat ttgagctact tgataaggca aaaggaaaaa cccagaagag    85080
aggcataaca aataccttag aagagtcatc aagcctgaaa agaaagaggc tttcagattc    85140
taaaggaaag aatacatgcg gtggattttt ggggagacc tgcctctcag aatcatctga     85200
tggatcttca agtgaagatg ctgaaagttc atctttaatg aatgtacaaa ggagaacagc    85260
tgcgaaagag ccaaaaacca gtgcttcaga ttcgcagaac tcagtgaagg aagctcccgt    85320
gaagaatgga ggtgcgacca ccagcagctc tagtgatagt gatgacgatg gaggaaaga    85380 gaagatggtc ctcgtgaccg ccagatctgt gtttgggaag aaaagaagga aactaagacg    85440
tgcgagggga agaaaaagga aaacctaatt aaaaaatatg tatcctctat aattagttat    85500
gacagccatt tgtaatgaat tgtcgcaaa gacgtaataa aattaactgg tggcacggtc     85560
tttgtattta gtgtgtggtt cctaaaaaca aatgctaaat ctgacatttg tttttttaatg   85620 ttttactttt ctagtatttt ttagctgaat atttcaagta tcattggata ttatcttgta    85680
ttcacaggct ttgtcttttc atgttttcat tatcttaaca atgtctgatc cttcctggtc    85740
acatgttaaa aaagcgaaaa agatttctat tgatcagcac tcactctcaa taggctttcc   85800
ctctgacatt cagacgtagc tgagaagaaa tacgtgcatg tttctaattc cacaatagtg   85860
gcagttttac acaactgttt agccctgctg cccacggctt tgcatttcc ctcaggttcc    85920 acttaaaagc atagcaggag ggagcctcac tgctggaaca tatttcaata tgtttgctgt    85980
ggttttagca aacaattagg aaacctaaat ggggtgcatc attctacctg tgaacattaa    86040
gtgtatggga acctctgtac cgttatgttt ggcttttaaa ccagacttca cttattagaa    86100
gctgacttct gtgtaaatgg atttggaggc tggggctgg agttgaactg gtgtaggtgg     86160
gtcagcttta ggagtggcct gcaggggatg attgttgttg acacagtgtt tgttcagagt    86220
ggacaaagaa ggttatttta agactgctcc tgtggagacg tctcccaaga acaaccccca    86280
agctcctatt tgcttcgagt taagaatgat tggaggagag tactaccaat tactttgagc    86340
gtgggtcctc tgccttcaga gctaccttcc caagtctgtg tccttttggc atctttagta    86400
tttccatctt tcctgacttt ttccttcagc cttcaaattg aaaatcttca ccaatgaaaa    86460
caaaatccaa atagataatc tccagcagtc tttgaacgac tcctagatgt gttgtttttt    86520
aggctctcat ttatattgac ttggccagcc aaacttctcc agtacttgga ctacagcagc    86580
tgcttttctt tgcacactat ttttttcctaa tttcaaatac gtcttctgca tccatcattc    86640
ttctctagca gctccttcta aagtcaacaa tgatttccac ataaactcaa atcttttctt    86700
catgcttctt ttctctggag gtacttggag cagaacattt ttggaggcaa ggggagggga   86760
aaattaactt tttcgtgttt ttctcatttc tcagaattac ttgtcactgg gagttttctg    86820
```

-continued

| | | | | |
|---|---|---|---|---|
| catatatatt | tgcaggtaga | ataattgtct | tgctaacaaa | tttaatttga tgcctttaat | 86880 |
| agatatttac | atttgttttt | cactgcgtta | gctttgggaa | aggataagct actgtaacaa | 86940 |
| aagatgctca | tatacagtgg | tctgaataag | ctagaacatt | acttctctct tactcaacag | 87000 |
| tctggccagt | ctgagctggt | gaagcagttg | tgcaccatga | ggtcatgcag tcctgtgttc | 87060 |
| agccaacccc | tagggtgcta | tcttgcctga | gtggtctata | ctgggtgatt acttcatctg | 87120 |
| cattgcatcc | tgccagaagg | ggaaagaacc | aaagtccagg | gcaagcagaa ggggaaatgg | 87180 |
| atggtcagga | ccatgagaaa | cctgttctgt | aacactattt | atatgagagt ttgatattgt | 87240 |
| atcttctttt | tctcttaacc | ctgtgaccaa | gacataatgc | ttttacaagg ggagaaacac | 87300 |
| gtttagagac | attaaccagt | tttgccaaat | tcacccatgt | agtaggtaaa acttctcacc | 87360 |
| tgaaccaaaa | tcttctaact | caaaattcca | gggtgctatt | ttacctatga aagaggttgc | 87420 |
| ctgtttaaaa | taatcagcag | ctgaacaaat | tctttattat | tcacatcaag ttggtgtacc | 87480 |
| tagagcttat | ttaggatgat | gaccatcata | cgccttttcg | attatcttcc agctcattaa | 87540 |
| tattttgttt | agctttatct | atacttgctg | ttaaacccat | atattgagta ttttatttca | 87600 |
| ttgattgtta | ttttcagtt | ttatttgact | cttttttttt | ttcaatttga ctcattttta | 87660 |
| tagattccag | ttccctggtg | tacttcttgt | catctgtttt | tgagtatctt aatcacagtt | 87720 |
| actttaaagt | ctgtcgaata | actccaatat | ctaagtcacc | tatgagttta tttctattgt | 87780 |
| ctgtttcttg | gtatgcatgg | gtaaatttta | actgaatgtt | ggacagtcta tgggaaaaat | 87840 |
| tataggtacc | ctgtaccttc | ctctagagag | gattccagaa | tgtatttgga caggcagcag | 87900 |
| aggggaagat | cacctcagtg | cagccagcga | ggacaaagta | gattgaaggc tagtttgcag | 87960 |
| ttttttctgt | aagactccag | cttctagttt | cacccgtatt | ccaggaaagt cacttttccag | 88020 |
| gagtgccctg | atgtttcttc | ttttgcgctt | ggatctgctt | ttgccactga atgcttcaaa | 88080 |
| aattagccte | ttgccctaaa | cagcttaatc | agtcaattct | tcgactgaat agtcagcact | 88140 |
| aagcgtcagg | cttctctctc | cctttttttct | gggatcttgg | gcccacaaat ctgactgtct | 88200 |
| tggcagccac | actcttcttt | tgtctccaca | gttctgtgag | attgcctgat gctccgctgc | 88260 |
| tatccttaca | tgcggtcttc | tctttggctt | cctcaggaaa | cagcaatgcc tggaattctt | 88320 |
| ggctgccttg | acagctctct | gatactttat | aacagaggca | tgtttgtgtg gggtgtgtgt | 88380 |
| gtgtgtttaa | aaatctattt | ttctcattgt | taatagaagc | tgaggtttgc tataagctac | 88440 |
| ttacagctgg | aggcagaagt | ctgtatgtat | ttgttaaaca | gtcatgttgg ttaagatgct | 88500 |
| tgattgaggg | attctgcctc | ttaagagatc | taacagtgag | gattgcatga tctttcaaaa | 88560 |
| aaatccttaa | aaaagacaat | ggttttattt | cgtcatttat | tttgttttta aaaagccccc | 88620 |
| aaagaaagag | tatcctctgc | cccaagttaa | ctgcctatga | ataatagttc acattgctta | 88680 |
| ggattttgaa | cttccagaa | tgttttacc | tataatattc | accccacaaa tatatgttgt | 88740 |
| atgactttg | tatcattttt | aaaagacatt | tatattttt | tgagatagg tcttgctctg | 88800 |
| ctacccaggc | gggagtttgg | tggtgtgacc | acggctcact | gcagcctcca tttcctgggc | 88860 |
| tgagtggtcc | tcctgccttg | gtctcccaaa | ggctaaggca | ccctgccgat atatacttgt | 88920 |
| tctatagatg | atgaaaccaa | gaaacatact | aagtaaatgg | cttaaaatca caatctaatt | 88980 |
| ataggcagga | ataactaaaa | tcaggcttcc | caactcctag | ccctttccaa tacattaaag | 89040 |
| tgacctcgat | tcatctgtgt | atacattatg | gacctgtagt | cacactccta agtttaactt | 89100 |
| tccaatattg | ctttatctta | actctgtaac | tttctatcag | ggatctttcc agtggcatgg | 89160 |

-continued

```
gaaatgtgta tgtcctctga gaggcacaca tacatgcact tgggcaggtg cacagatgga   89220
tctatgttcg gagcctgccc attcagtctg aataaaaagg aatcatggta gtttgatttc   89280
tgggtgcaga gcaatgctac agacattcta gtatggttgt tggagtctaa agacagtgtt   89340
cccatgcaga taggtgacat gaaaaatatg tagcgttcat ttcctagaat gtcatagcca   89400
cggagtctta gaataactct tggcatccaa gttaaaagct ggatcacttc ctccaaatag   89460
tcttcactca cttccgggag tgggttgtat tcacctttag ctctgttcac gagacactcg   89520
tgggatattc ctagccttct gcccccttag ttacgggcat tgccgtctca ctgctgtata   89580
accagaggcg tgggagctgc agctgtcaga atcctaatcc cttctgcctg gactcgttac   89640
cagtggtagc gagtgtgtat agtagtaaac tgtgctgcga tgctagcctt tcagtcacta   89700
ccagaggtcc cagcagcaaa aacaaaaatt gtggatgata cattttaacc ttctagaaac   89760
tcagctaact ccttttaggta tgtccaggct ttccatttaa atatcagcct taaggcagac   89820
atgtctttct ttaatggaag agatctaaat tgggagcaaa acatgtgacc acttttgcta   89880
tcgttttagc tgtgtagcct caatgacata atttaacctt ggttttcctg atttgcaaac   89940
tgtagggaaa ataatgtctt ctaacttgct gaagtatgct gtaaagaaa atgtggtggc   90000 tgtaaaatgt gctttgggat tctcggaaga aaggagtgct atattaattc atggtactgc   90060
aattgttatt ttaccccaga ttgagaagta aaatatcaaa tcgttatttt ctaaagtttg   90120
aataactgtt aaatttattc agataatctg ctctattcaa gaggcataaa tagtttcttc   90180
agttttaaat atatcggctg tgatggtatg gactccttaa ggtagacgct gctcaaaaga   90240
ttatctggca atgaggctgt ttgacattgc ataggtgcta atgatgcatt gatggtaaca   90300
agtgaacttt caatgtttta atcgcctctt aaattttagg attgcagtct tactagtcaa   90360
tatgaagatg atgcctttct ttgttacaac tgaggtagtc tctggtgaag aatatgtttt   90420
ctttctgtag tagctttttta aaatttctga ctcagaagct tttgttctga ttttaatttg   90480
ttctagatag tgtttagatg gtctttctta agtcacgctt cgttaatata tgatatttta   90540
atataatttt gtctgctgta tttgaagtta agctttatta agaaactata aaagcactcc   90600
atacatattt tgaattatta ccatttgata ttttaatgta ttatctatct agttttcaag   90660
aaataatgaa gaaacatca atatatcacc taccatcatt tcattacttg atggattcag   90720
aagctcaaga aggtaagtca ttttatgttt atgtagctta ccaattctaa gaagacaaat   90780
aactaataga atataaagtg tcacctttgt agtattcatt aatgtcttaa atggagctga   90840
cacttttatc aatggcatat tatgtcttgg tttatatttg tgagcctgca acatcttga    90900 atcatgttta agtctattac tataccatga tcttgatgat atgttaaaga tacttttgac   90960
agattaaatt aaatatatag acttactaag catgtacagg ttttttgatc ttcaaataag   91020
gaatacattt ttttctcaag tgctgtacac taaatgtatg atgtgatttc taagcaaatt   91080
ttatttcaga taagaagctt gcaagaaaga taaaaatagt tttatgtgaa aactataagt   91140
ttttactggt ggttggatga aaggtgaatt taggctatac agacatctgt agcctgagtt   91200
tatggttcct ctaactattt attagaggca aatacataat gtaatttgac ctctggatgt   91260
aaagagatta agtttgaatt ctactatcag tgtggttatt tgaaattgaa ccatcatttt   91320
tatatagtct taagtatcaa gcgtgacttt gcatgggtta tgtaatataa ctgtccccat   91380
tgtcttgaga tcaaaagtac agacatacac tcttgacaga ctagaaaaat taccatatttt  91440 ttgtagagca gttgtaatac aaatctaaat atcttgattt cttttgttct ctccttatct   91500
gcacacactg tagatgtttt ctgaacacta tagttctggt ttttctgttt ttggccattc   91560
```

```
caggtggctt ctacctagga gaacacatct ttaggccaag aaagctgggt gtatgcccag    91620
tgttggcagc ctacctggct taaacacaaa tagttttacc aagcgattct tgcaaaccta    91680
accatttaag tcgatcactt agagaaccca gccatttaga tgatttgaat gaagacgcaa    91740
tttctgtatg gtttatgaat aaaattatat cattatcatt accattagta acaattcttg    91800
gtttcaactg tgtagaagat aatttggcaa attacaaagg aagtggaaga agttcaaggt    91860
aaggttgaga cggaactagc attacaatgt tttacaacac aaacaaacac actctgtaat    91920
catctatata gccaaatgaa gctttaaaaa tgtgttcaca cacacagagc taagggaatt    91980
aaggatgtgc ccttggagca gatcaggtgg catttagttg gaaagccatc accaagtaga    92040
ggaacactca gttctcaagt actgaaggat actgactttt cctgccctct tttatactta    92100
gaatcctgtg cttggaaagg atggagcaaa cccatagctc agtgctcata tttcaacact    92160
ggcatgaaga tccaagaact ataggatgtc acttatttat acacagatta aaattagggc    92220
tatggtgggt gctaaaaaat tcttctgtat gtgtttctaa ggctatattg taatctaagg    92280
tgtctaaaac cttacccaca ttaactattc taaatatcct atgttgcctg cctcatgcca    92340
gcagcctctc tccagctgtt agtacacgta gcaatctgtt atagaatagt agggtcaccg    92400
gaggacctgc agccttgggg cagattcatc cttgcccaag gctcagtgat tctggctctc    92460
aatgaccctc gagtctgtca cgtcagctgc ttacttgaca tcctacttac tacctcttgt    92520
cagtttaggg ccttcaagac atagatgcca aaatggggct aagcatgtaa gggatttact    92580
gggggaaatg tttgtggagg ataaggaaga aaacagaagt aggctagggg agccttcaga    92640
gcccaacatg ggtccagtgc ccgtgagagg agacagaaga cagattggat gggaagagtc    92700
tccaattgca acacaattct gagacagtct caggtgggct gatgaaaatc cctgagcagg    92760
agttgcccac tagaggagtg tcctatatgg aacaggaact ggctggcttg agtaggcagc    92820
ctcaggagga acatggtctc ccaggagcca caggtgcagc aatgggcagt gttgggcaac    92880
tctgctcctt gtggcaggtt ctcttaatct gagtggcaca ccagggtaat atgtatttaa    92940
aataattttc ctttacaggt ttgcccttcc acctatattt tcgatctcac tcaatgcaa     93000 catcactccc caggctaccc agaaacctgg aatcatcctg atttctcccc tttccttcac    93060
acccttcatc attacatctc attgatttta cattcctgat atgtttccct acgccttgtt    93120
ccatttccac catcacttac cttgattctt cattatctct gctcctgact gctgttaacc    93180
accttctaat tggctgtctc gctctgggcc aactcccttt cttaccctc tctagttctt     93240 ttcccacact gtaacctgca ctgcatgatc ttttaaaaat ccaaatcttg tcacatttgt    93300
cttctgcttg aaattcttca gtgcctcatt atttcttaca ggataaaatc aaggcttctt    93360
agtatggtgt aatgtgtttt accttgtgct actatcctca tttatcctat attctggttc    93420
tcagggtttc caaaattggt caggagactt tttgccagtg ggcttttgca catgtcattt    93480
cctgtatatg gcaggtcttc ccttctccta tttgacaaac tcataattag gaaggctcag    93540
ataattcttt cctgagctct ctgagaggtg gaactttcca ttttttgcatt gcctactgaa   93600 gtctctgtta tagcactttt actgaacctc tcttatatag cacttggtct gccttctaat    93660
tcatagtgcc caggtactta ataagtgagt gaatgaatga atgaatgaat tagctataac    93720
ataaccgtat tggctgactt aaatttgctc atgagtgatg atcttgtatt tctgatcata    93780
agtcagttga ctcccttcag gacctaatat aatgttctcc tcaaggcatc acattaaaaa    93840
ttttcaggag catcttcata aatctttgca gaattggatt aatgggtaat atggttttta    93900
```

```
taaacagtat tgcattaata tatatggaaa tttatgtaat tctaccactg ttttaagaaa   93960
cctatcaaac tacagtctga ggcaatatat ttaatatact agttggagta ctatagcaca   94020
tataattact aaagtgagaa taatttatta acacatttta aacatttac aagtaacatg    94080 aataattatc ttccagataa gactaataaa ttttctacat gttgaataaa aataactctt   94140
gaatatacca gtctacttca gatgtcttca aaactcagat ttgaacgtca agtttgaatg   94200
tcaattgtcc acccctaggg gaggcatacc accactttga aagcacacac gttcatactt   94260
ggctccttga cccaaggcct tcatttagac tcttgtcatt tttcatctag actgttccaa   94320
taatcttcta attagcttgt aaggtcacca gttcttcagc tcctgctgtc agatgtagtt   94380
cttaaatatc aaatctgatc atgtcaattc ctgttctaat aatctttatt agctcctcct   94440
caccttatag aacaaaggtc aatgttgcac ataaatttaa tcccaaccta cttcttcagg   94500
cttattttct atagttcccc tccatgcacc ttgtgtaata ttcattataa tccctaaaga   94560
cacaatccaa aatgccatga tcctgaatgt tgaaatcccc aaagaacaaa tgcccttaca   94620
gctaattgaa ttcccaaacc ataatgatag atttggaatt aggtgccatc aaaacttcta   94680
aaggtggatt tcaaggtgtt agcaacagtt tcttttttcca ttcagcccaa tacatttgcc   94740
ggaaaattca gatgaatgga ttgcctgtag aatatagtaa catggaaaac ttcagtttat   94800
aacgcattat ttgtctgcat tggcattcct tctagctgat gaaattctag gaggtcttaa   94860
tgagttaaag ctgaatttgc ctgatgaagc cagcaaagtt actgactcta aaataactat   94920
gtgcatggta ggataagaaa gcacacaatg atgttgctgt tcgatcacca gtattgtttc   94980
agccaaatct gtggtctgta tatgagtgca tgagcaaagg atttccatgt acccaaaaca   95040
acacagaagc atgacacaga gataggaaat ttaatagaaa atgctcatgt cagtgtgtat   95100
tgaataaaac tagaatttca aaaagagcag catcatgtag aaaatcaatg tgaatgtatt   95160
cttcaagaag agccatgtcc taaaagaaaa gaaacagtta ctcatctcca cgcaagactt   95220
cagaatacag ttaatgattg tggaagtcgg ccagctctta tgggctacct ccgtgcagtt   95280
gcccataatt tatccctgta atgcgctttt tcatatgttg aatttctctt ttagtttctt   95340
tgggaaggtt ttgttttttct ttttcctttt ttaaagtttt tttcctcacc atttaaaatc   95400
atcagcatta ttttttacaa ctcactatgg tatgctacgt gtttcatctt tacatttcca   95460
aaactagagg cataaattgt atgagctttt agagagttct aattgttttt atgcactttt   95520
tgttttttgc aaaattgact ccatggaagt gcattttaat aacactgacc ttgtgtgtaa   95580
gcattgtgca tatatatgta aaaaccttaa aacttcctca ataataaag ggatatcctt    95640 tttctgcatc tgcatttgtg aaagataaca ttttttcaata tctcagctct ttaggcaact   95700
gtatatgact gtatatgtgg tggtgaccca ttgttggtat ttaatttaa ttttttagc     95760 aagggggcgtc tcactatgtt gcccaggctg ggctctaacg atccttccac ctcagcttcc   95820
tgagtagcgg ggactacagg cgtgagccac tgcattcagc tccactgtag gtttggatct   95880
gtttcatcag aagacttagg ttgttcatca ggatatttca agtgaccaaa ctatataagt   95940 gatttctttta tgaatacaat ttctctgctc ataactgtta tgcctgtgta actgtgggta   96000
gcacacctga gtgcttatca ttgcaaaatt atgtatatac aatttttattg tataaagtag   96060 cccacaaagt gttctgttgt gttttatgt ttctaaactc ttttaaaaat gtaaatatgt     96120 tttaagaac ttttagaatt attttatca gaattatgta tttggggttt tgatctttca      96180
ggattcaaca ctgggattta tggcatcaga aactatcttt tgggattctg gcccaaacct    96240
ctagccttgt accctcgctc catagatctt ctaacagctc ctgggcttaa atatctcctc    96300
```

-continued

| | |
|---|---|
| ttttatgatg cttctcctga ttcaaccaac cagtggtgct tcccatagca ttttagaaag | 96360 |
| acctgtttta tagcatttat caaggtattg acatttgttc agttgtctgc cccttccgtg | 96420 |
| atctcagtag caaacttgta gtacaactaa tttaggttct ttattttcc acttgcatcc | 96480 |
| tgagcaacct caataaaagg tgcattttct ttcttttgta aacacaaagt gtagcattgt | 96540 |
| ttggtctact tgattagagt tacaacctct gtacattctt gaaactaaga agaccagcag | 96600 |
| acagagaata tctgtagaat cttctcagga attggtttca ataagggt ccaagacctt | 96660 |
| ggcattgctg aggttttcag aattctatct tttaagttaa gcctgtgact atttactaat | 96720 |
| ctgaaaatat ctttaacttc tttttttaa tctgtaggca tttctaagaa gcacatgaca | 96780 |
| ttcagctttg aatagaagat tcatttgaat gacagtttct ttcatttagt agagggatt | 96840 |
| ttactttaaa ttttgctgac aggttttcgt gacagccctc aaatggaagc ttgaattc | 96898 |

<210> SEQ ID NO 4
<211> LENGTH: 2129
<212> TYPE: DNA
<213> ORGANISM: Xenopus sp.
<220> FEATURE:
<221> NAME/KEY: misc_feature
<222> LOCATION: (74)..(74)
<223> OTHER INFORMATION: n = a, c, g, or t.
<220> FEATURE:
<221> NAME/KEY: misc_feature
<222> LOCATION: (292)..(294)
<223> OTHER INFORMATION: Translation initiation codon (ATG)
<220> FEATURE:
<221> NAME/KEY: misc_feature
<222> LOCATION: (1771)..(1773)
<223> OTHER INFORMATION: Translation termination codon (TGA)
<220> FEATURE:
<221> NAME/KEY: misc_feature
<222> LOCATION: (1810)..(1884)
<223> OTHER INFORMATION: Repeat
<220> FEATURE:
<221> NAME/KEY: misc_feature
<222> LOCATION: (1888)..(1962)
<223> OTHER INFORMATION: Repeat

<400> SEQUENCE: 4

| | |
|---|---|
| gaagaagagg agaatggtag gacggagcca gcagctttat gacaaaatag gttgaaaatt | 60 |
| gttgattgag gcanccgctg tgggatgtgc aaagattgta agctgttgtg agtggcagag | 120 |
| atctctggcc ccatttggat ccccgtacct atgtttgtta cgtaattgtt ttactggcga | 180 |
| acaaggtctc agttaaagga tgaagctcat tcggtgagac ttttattgac caaaacatag | 240 |
| tcaatatttt tgttgtgatt tgcaccgaac tgcattgttc atcttcattc aatgcctaac | 300 |
| atagaagcgg acagagttac aagcgttccc gaaaataacg actgcaaatc caagagtcag | 360 |
| cctctgagga ataatctcca tgaaactgta aaatcctaca gtatacaagg tgctgccaca | 420 |
| gcaaatatcg agcctcctgc agaaagacct tatccctggg gatgtcctgt gacacacaca | 480 |
| aaggaaaagt tctataccat ctgcgcagac tacgcctttt tgaatcaagc aacatctctt | 540 |
| tgcaaatcgt ctagttctgt ctgcagctca agctcgagg acaaatctgc tctgagcaat | 600 |
| acaataaatt acattgatct tcagaccagc gaatcagatt ctgtatacaa cgaggatgca | 660 |
| agcttggagt ctttatctag caatcttggt acacgtccgc ttgcctggga aattgataaa | 720 |
| tcagacttca gcacaatgac ttccaagtta aaagatcag gtgtaaaaaa acaaacacct | 780 |
| aagaagaaac ctgacaggaa ggcaaaacca ttaagggact gtcctcaaca cttaatcctg | 840 |
| gatgatgtta aacagcggaa agttctagac ctcagacgat ggtattgtat cagtcgaccc | 900 |

```
cagtacaaga cctcgtgtgg catttcttct ctggtatcat gctggaactt tctttacagt    960
actctgggag caggaagcct cccaccaatt actcaagagg aagctttaca tattttgggc   1020
tttcaaccac cctttgaaga gattaggttt ggtccttta ctgggaacac aactttgatg    1080
agatggttca gacaaatcaa tgatcatttc catgtaaaag gatgctccta tgttctgtat   1140
aagccgcatg gcaagaacaa gacagcagga gaaactgctg ttggggcact atcaaagtta   1200
acacaagggt taaagaaga ctcaacagcc tacgtctatc attgtcagaa tcattatttt    1260
tgcccaattg gttttgaggc aacccctgtg aaggcatcca agcatacag gggccaactt    1320
ttcccgcatg aagtggagta ctggatttta attggtgagc caagcagaaa acaccctaca   1380
attcactgca aaaagtgggc agatattgtt actgacttaa atactcaaaa tccagaatat   1440
tttgatatta gacacactga agaggcctt cagtacagga aaacaaaaaa ggttggagga    1500
aaccttcact gccttctggc atttcagaga ctcagctggc aaagatttgg tccatggccc   1560
ttacagcttg gaacccttag gccagaaccc cagccacccg tacaaggaag aagaatccct   1620
aaatctgaaa gtgaggataa tgtctccaag aaacagcatg ggcgtctggg gaggtcattt   1680
agtgctggat ttcagcaaga gcttgcatgg aaaagaatgt gtaatatacg tgaacgcagg   1740
ggcagtggct cacctgaaag tgatacggac tgagaaggaa atgattaaat tatacaaagt   1800
cagtgttact tgtagttttg ggttcatggc actacgatta aactaaacat tagtcatata   1860
atgctggaca tggttggcag acattatttg tagttttggg ttcatggcac taccattaag   1920
ctaaacatta gtcatataat gctggacatg gttggtagac atctatagtg ctctcccatt   1980
aatcataaaa cctttgcaaa cttttacaa tcatttatga acttattgct caaatgccat    2040
tcctgatcta cagtatactg ggtattgtat actgccatgt caggagtatt ttcattaatt   2100
aataaaattg gagtttaaaa tcaaaaaaa                                     2129
```

<210> SEQ ID NO 5
<211> LENGTH: 493
<212> TYPE: PRT
<213> ORGANISM: Xenopus sp.

<400> SEQUENCE: 5

```
Met Pro Asn Ile Glu Ala Asp Arg Val Thr Ser Val Pro Glu Asn Asn
1               5                   10                  15

Asp Cys Lys Ser Lys Ser Gln Pro Leu Arg Asn Asn Leu His Glu Thr
            20                  25                  30

Val Lys Ser Tyr Ser Ile Gln Gly Ala Ala Thr Ala Asn Ile Glu Pro
        35                  40                  45

Pro Ala Glu Arg Pro Tyr Pro Trp Gly Cys Pro Val Thr His Thr Lys
    50                  55                  60

Glu Lys Phe Tyr Thr Ile Cys Ala Asp Tyr Ala Phe Leu Asn Gln Ala
65                  70                  75                  80

Thr Ser Leu Cys Lys Ser Ser Ser Val Cys Ser Ser Ser Glu
                85                  90                  95

Asp Lys Ser Ala Leu Ser Asn Thr Ile Asn Tyr Ile Asp Leu Gln Thr
            100                 105                 110

Ser Glu Ser Asp Ser Val Tyr Asn Glu Asp Ala Ser Leu Glu Ser Leu
        115                 120                 125

Ser Ser Asn Leu Gly Thr Arg Pro Leu Ala Trp Glu Ile Asp Lys Ser
    130                 135                 140

Asp Phe Ser Thr Met Thr Ser Lys Leu Lys Arg Ser Gly Val Lys Lys
145                 150                 155                 160
```

```
Gln Thr Pro Lys Lys Pro Asp Arg Lys Ala Lys Pro Leu Arg Asp
                165                 170                 175
Cys Pro Gln His Leu Ile Leu Asp Asp Val Lys Gln Arg Lys Val Leu
            180                 185                 190
Asp Leu Arg Arg Trp Tyr Cys Ile Ser Arg Pro Gln Tyr Lys Thr Ser
        195                 200                 205
Cys Gly Ile Ser Ser Leu Val Ser Cys Trp Asn Phe Leu Tyr Ser Thr
210                 215                 220
Leu Gly Ala Gly Ser Leu Pro Pro Ile Thr Gln Glu Glu Ala Leu His
225                 230                 235                 240
Ile Leu Gly Phe Gln Pro Pro Phe Glu Glu Ile Arg Phe Gly Pro Phe
                245                 250                 255
Thr Gly Asn Thr Thr Leu Met Arg Trp Phe Arg Gln Ile Asn Asp His
            260                 265                 270
Phe His Val Lys Gly Cys Ser Tyr Val Leu Tyr Lys Pro His Gly Lys
        275                 280                 285
Asn Lys Thr Ala Gly Glu Thr Ala Val Gly Ala Leu Ser Lys Leu Thr
290                 295                 300
Gln Gly Leu Lys Glu Asp Ser Thr Ala Tyr Val Tyr His Cys Gln Asn
305                 310                 315                 320
His Tyr Phe Cys Pro Ile Gly Phe Glu Ala Thr Pro Val Lys Ala Ser
                325                 330                 335
Lys Ala Tyr Arg Gly Gln Leu Phe Pro His Glu Val Glu Tyr Trp Ile
            340                 345                 350
Leu Ile Gly Glu Pro Ser Arg Lys His Pro Thr Ile His Cys Lys Lys
        355                 360                 365
Trp Ala Asp Ile Val Thr Asp Leu Asn Thr Gln Asn Pro Glu Tyr Phe
        370                 375                 380
Asp Ile Arg His Thr Glu Arg Gly Leu Gln Tyr Arg Lys Thr Lys Lys
385                 390                 395                 400
Val Gly Gly Asn Leu His Cys Leu Leu Ala Phe Gln Arg Leu Ser Trp
                405                 410                 415
Gln Arg Phe Gly Pro Trp Pro Leu Gln Leu Gly Thr Leu Arg Pro Glu
            420                 425                 430
Pro Gln Pro Pro Val Gln Gly Arg Arg Ile Pro Lys Ser Glu Ser Glu
        435                 440                 445
Asp Asn Val Ser Lys Lys Gln His Gly Arg Leu Gly Arg Ser Phe Ser
450                 455                 460
Ala Gly Phe Gln Gln Glu Leu Ala Trp Lys Arg Met Cys Asn Ile Arg
465                 470                 475                 480
Glu Arg Arg Gly Ser Gly Ser Pro Glu Ser Asp Thr Asp
                485                 490

<210> SEQ ID NO 6
<211> LENGTH: 2841
<212> TYPE: DNA
<213> ORGANISM: Gallus sp.
<220> FEATURE:
<221> NAME/KEY: misc_feature
<222> LOCATION: (235)..(237)
<223> OTHER INFORMATION: Translation initiation codon (ATG)
<220> FEATURE:
<221> NAME/KEY: misc_feature
<222> LOCATION: (1750)..(1752)
<223> OTHER INFORMATION: Translation termination codon (TAG)

<400> SEQUENCE: 6
```

-continued

```
ggacactgac atggactgaa ggagtagaaa gcaggtgagc gctcgtcgtg gcttctcccc      60
cccctgcgtc gcgcactgcg tctgtttccg gcgcgggcac attccccgct ccgccgcggg     120
cccgcgcagg tacctcacct tgcagtaaca atggaggcag cgatgcaaac tatgtggtaa     180
ttaaaaataa gcaaaaccat tcctcgcagt acaagacgct tccaatatta ttcaatgcct     240
cacatctcag aagatgaaaa ggagaatggt tctggaaaca atggaaacac tgaaaagaaa     300
cctgggaaag aatcctcaga agcttctctt cgtgatccta taaagtcgta ctgcatctca     360
gatgcctcca ctgtgtcttt ggtgtccagg ggagatggac attacccatg ggatgtcct      420
gtgactcaca cacgagagaa attttatacc atttgctcag actatgcttt tttaaacaga     480
gtaacatcta tttgtaaaag cccaagtgct tcagttaacg cctgcctgtc aggcagtgct     540
gccttaaacg ttgaaaataa cacacctagc ttactgggca ttcaaactgg tgcttcggag     600
ataatctaca gtgaagatgc taacttggaa accttgtctg gcagccttgg aaagcttcca     660
ctggcatggg aaattgacaa atcagaattc aacagcgtga ctgcgaatca taaaaacaaa     720
gcaggcaaca tgaagaaaca agtggcaaag aaaaagtcct cagacaaaaa aagcaaacag     780
tacaaggagt gtcctcagct gtctgctctt gaagatgtga aggagaggaa agtgttggac     840
ctccgaagat ggtactgtat tagccgacct cagtacaaga cttcttgtgg aatttcttca     900
ttagtgtctt gctggaattt cttatatagt acgctgggag ctggcagttt accacctatt     960
actcaagaag aagctttgca tatattgggt tttcaacccc catttgagga gatcaggttt    1020
ggtcccttca ctgaaaatac gactttaatg agatggttta ggcaaataaa tgatcacttc    1080
catatcaagg gttgctcata tgttctgtat aaacctcatg gaaagaacaa gacagctgga    1140
gaaactgctg tgggggccct tgcaaagcta cacgtggac tgaaagatga atcaatggcc     1200
tacatctacc attgccaaaa ccattatttt tgcccaattg gatttgaagc aactccagta    1260
aaagctagta aagcgtatag aggtcgtgtt ttgcagcaag aagtagaata ctggatctta    1320
attggagagc cgagcagaaa acatccaacg atacactgta aaggtggaca agatattgtc    1380
actgacctaa acacccaaaa tccagagtac ctagatattc ggcacctaga gagggactg     1440
cagcatcgga aaacaaagaa ggttggagga atcttcatt gcatcatcgc cttcagaga     1500
cttaactggc aaagatttgg tccttggaat attccatttg gaagtgtcag acaggataaa    1560
caatcccaaa cacaaggaca aggtattgcc aaatctgaga gtgaagacaa tatctctaaa    1620
aaacaacatg gacgactggg tcgatctttc agtgctggtt ccatcaaga atctacatgg     1680
aaaaagtcta gtcttcgtga gaggaggaac agcgggtatc agagctataa tgattatgat    1740
ggagatgatt agaattaact ttaggtaata gagtttatat atcaaagtta gttttaatca    1800
acacagaata ggggtttatt agtcctagga tacatgtgaa tagaaaatat ggcataagat    1860
acagctttgt aatccttaaa tcaattatga attatatggt tgcagtggat aaaagagcag    1920
attgaaatta gccaatgtaa taaacagatt tcattgaaaa tacttgatat tcagaagcat    1980
gaaaatgtat tatatgactt tataaaaagg gttatactgc atatggtgta aggataaaag    2040
taaacatttg ccttcctttt tagcactcca ttttgttaag gctgctgata tccagtgaga    2100
agaaagaaat tgaataggtt agaaaaccct gtcagattaa caaaattgaa tgtatattct    2160
caatctagtt gtcagtagaa ttctgtgagt cagataatcc tgttttgtag gtagatccca    2220
gttattttc ccatagctag atacctgttt taaactgaga agaattgctg gtggcaagga     2280
aggtttgaag atggacattt actgcttttg ctctgtggat atggtagcag attttctatc    2340
```

-continued

```
ctgtgagctc tggtgagcag tgactgcata acacaggctt gtgaaaatca tttttataaa      2400
gctgcattta acctgagccc aatgaactgg ctgaacagtg tgttctgctg gcaattcttt      2460
tccttgttca gtctcaaaac tcctgttgtt tttgtgctgc tctcttgatt ttgtatgaag      2520
gtgatgcaag tgccgacaac tgctggcagc ccttatgata tacctctatg ccagcaaaca      2580
atccaagtct tttcaggtgt ccatgtgcag ttttttttttt ttcctttctg gtttattcag     2640
ttgtttgccc aaatgcatct cgacagttgt aactttgtgt gcgaatgtcc acacctgctc      2700
aaggattttt ttttttttac ataaaacaat ttgtcatgta atgcagggtt tttgtaggtt      2760
gatgctgttg ttaaccaaaa atggagggag acttttggac tttcgttcat tcaataaaat      2820
ttgttttatt taaaaaaaaa a                                                2841
```

<210> SEQ ID NO 7
<211> LENGTH: 3038
<212> TYPE: DNA
<213> ORGANISM: Gallus sp.
<220> FEATURE:
<221> NAME/KEY: misc_feature
<222> LOCATION: (235)..(237)
<223> OTHER INFORMATION: Translation initiation codon (ATG)
<220> FEATURE:
<221> NAME/KEY: misc_feature
<222> LOCATION: (1281)..(1352)
<223> OTHER INFORMATION: Sequence of alternative splicing
<220> FEATURE:
<221> NAME/KEY: misc_feature
<222> LOCATION: (1822)..(1824)
<223> OTHER INFORMATION: Translation termination codon (TAG)
<220> FEATURE:
<221> NAME/KEY: misc_feature
<222> LOCATION: (1982)..(2106)
<223> OTHER INFORMATION: Sequence of alternative splicing

<400> SEQUENCE: 7

```
ggacactgac atggactgaa ggagtagaaa gcaggtgagc gctcgtcgtg gcttctcccc        60
cccctgcgtc gcgcactgcg tctgtttccg gcgcgggcac attccccgct ccgccgcggg       120
cccgcgcagg tacctcacct tgcagtaaca atggaggcag cgatgcaaac tatgtggtaa       180
ttaaaaataa gcaaaaccat tcctcgcagt acaagacgct tccaatatta ttcaatgcct       240
cacatctcag aagatgaaaa ggagaatggt tctggaaaca atggaaacac tgaaaagaaa       300
cctgggaaag aatcctcaga agcttctctt cgtgatccta taaagtcgta ctgcatctca       360
gatgcctcca ctgtgtcttt ggtgtccagg ggagatggac attacccatg gggatgtcct       420
gtgactcaca cacgagagaa attttatacc atttgctcag actatgcttt tttaaacaga       480
gtaacatcta tttgtaaaag cccaagtgct tcagttaacg cctgcctgtc aggcagtgct       540
gccttaaacg ttggaaataa cacacctagc ttactgggca ttcaaactgg tgcttcggag       600
ataatctaca gtgaagatgc taacttggaa accttgtctg gcagccttgg aaagcttcca       660
ctggcatggg aaattgacaa atcagaattc aacagcgtga ctgcgaatca taaaaacaaa       720
gcaggcaaca tgaagaaaca agtggcaaag aaaaagtcct cagacaaaaa agcaaacag       780 tacaaggagt gtcctcagct gtctgctctt gaagatgtga aggagaggaa agtgttggac       840
ctccgaagat ggtactgtat tagccgacct cagtacaaga cttcttgtgg aatttcttca       900
ttagtgtctt gctggaattt cttatatagt acgctgggag ctggcagttt accacctatt       960
actcaagaag aagctttgca tatattgggt tttcaacccc catttgagga gatcaggttt      1020
ggtcccttca ctggaaatac gactttaatg agatggttta ggcaaataaa tgatcacttc      1080
catatcaagg gttgctcata tgttctgtat aaacctcatg gaaagaacaa gacagctgga      1140
```

-continued

```
gaaactgctg tgggggccct tgcaaagcta acacgtggac tgaaagatga atcaatggcc    1200
tacatctacc attgccaaaa ccattatttt tgcccaattg gatttgaagc aactccagta    1260
aaagctagta aagcgtatag gttgctggat ttggactcgg gagacctggg ttcggttccc    1320
agttcaaccg cagacttcca ttgtgatttt agaggtcgtg ttttgcagca agaagtagaa    1380
tactggatct taattggaga gccgagcaga aacatccaa cgatacactg taaaaggtgg     1440
acagatattg tcactgacct aaacacccaa atccagagt acctagatat tcggcaccta    1500
gagagaggac tgcagcatcg gaaaacaaag aaggttggag gaaatcttca ttgcatcatc    1560
gcctttcaga gacttaactg gcaaagattt ggtccttgga atattccatt tggaagtgtc    1620
agacaggata acaatccca aacacaagga caaggtattg ccaaatctga gagtgaagac     1680
aatatctcta aaaacaaca tggacgactg ggtcgatctt tcagtgctgg tttccatcaa     1740
gaatctacat ggaaaaagtc tagtcttcgt gagaggagga acagcgggta tcagagctat    1800
aatgattatg atggagatga ttagaattaa ctttaggtaa tagagtttat atatcaaagt    1860
tagttttaat caacacagaa tagggggttta ttagtcctag gatacatgtg aatagaaaat   1920
atggcataag atacagcttt gtaatcctta aatcaattat gaattatatg gttgcagtgg    1980
atgcatctg atacatgaac tgacagataa gcacagatta ttgtactttt gtaatcaaaa     2040
gcagatatga cagctaaatc aatcacttat tttgaagtta ctatactata tcctgatctg    2100
tgagaataaa agagcagatt gaaattagcc aatgtaataa acagatttca ttgaaaatac    2160
ttgatattca gaagcatgaa aatgtattat atgactttat aaaaagggtt atactgcata    2220
tggtgtaagg ataaaagtaa acatttgcct tcctttttag cactccattt tgttaaggct    2280
gctgatatcc agtgagaaga aagaaattga ataggttaga aaaccttgtc agattaacaa    2340
aattgaatgt atattctcaa tctagttgtc agtagaattc tgtgagtcag ataatcctgt    2400
tttgtaggta gatcccagtt attttttccca tagctagata cctgttttaa actgagaaga   2460
attgctggtg gcaaggaagg tttgaagatg gacatttact gcttttgctc tgtggatatg    2520
gtagcagatt ttctatcctg tgagctctgg tgagcagtga ctgcataaca caggcttgtg    2580
aaaatcattt ttataaagct gcatttaacc tgagcccaat gaactggctg aacagtgtgt    2640
tctgctggca attcttttcc ttgttcagtc tcaaaactcc tgttgttttt gtgctgctct    2700
cttgattttg tatgaaggtg atgcaagtgc cgacaactgc tggcagccct tatgatatac    2760
ctctatgcca gcaaacaatc caagtctttt caggtgtcca tgtgcagttt ttttttttc     2820
ctttctggtt tattcagttg tttgcccaaa tgcatctcga cagttgtaac tttgtgtgcg    2880
aatgtccaca cctgctcaag gatttttttt tttttacata aaacaatttg tcatgtaatg    2940
cagggttttt gtaggttgat gctgttgtta accaaaaatg gagggagact tttggacttt    3000
cgttcattca ataaaatttg tttatttaa aaaaaaaa                             3038
```

<210> SEQ ID NO 8
<211> LENGTH: 505
<212> TYPE: PRT
<213> ORGANISM: Gallus sp.

<400> SEQUENCE: 8

```
Met Pro His Ile Ser Glu Asp Glu Lys Glu Asn Gly Ser Gly Asn Asn
1               5                   10                  15

Gly Asn Thr Glu Lys Lys Pro Gly Lys Glu Ser Ser Glu Ala Ser Leu
            20                  25                  30
```

-continued

```
Arg Asp Pro Ile Lys Ser Tyr Cys Ile Ser Asp Ala Ser Thr Val Ser
        35                  40                  45

Leu Val Ser Arg Gly Asp Gly His Tyr Pro Trp Gly Cys Pro Val Thr
 50                  55                  60

His Thr Arg Glu Lys Phe Tyr Thr Ile Cys Ser Asp Tyr Ala Phe Leu
 65                  70                  75                  80

Asn Arg Val Thr Ser Ile Cys Lys Ser Pro Ser Ala Ser Val Asn Ala
                 85                  90                  95

Cys Leu Ser Gly Ser Ala Ala Leu Asn Val Gly Asn Asn Thr Pro Ser
                100                 105                 110

Leu Leu Gly Ile Gln Thr Gly Ala Ser Glu Ile Ile Tyr Ser Glu Asp
            115                 120                 125

Ala Asn Leu Glu Thr Leu Ser Gly Ser Leu Gly Lys Leu Pro Leu Ala
130                 135                 140

Trp Glu Ile Asp Lys Ser Glu Phe Asn Ser Val Thr Ala Asn His Lys
145                 150                 155                 160

Asn Lys Ala Gly Asn Met Lys Lys Gln Val Ala Lys Lys Ser Ser
                165                 170                 175

Asp Lys Lys Ser Lys Gln Tyr Lys Glu Cys Pro Gln Leu Ser Ala Leu
            180                 185                 190

Glu Asp Val Lys Glu Arg Lys Val Leu Asp Leu Arg Arg Trp Tyr Cys
            195                 200                 205

Ile Ser Arg Pro Gln Tyr Lys Thr Ser Cys Gly Ile Ser Ser Leu Val
            210                 215                 220

Ser Cys Trp Asn Phe Leu Tyr Ser Thr Leu Gly Ala Gly Ser Leu Pro
225                 230                 235                 240

Pro Ile Thr Gln Glu Glu Ala Leu His Ile Leu Gly Phe Gln Pro Pro
                245                 250                 255

Phe Glu Glu Ile Arg Phe Gly Pro Phe Thr Gly Asn Thr Thr Leu Met
            260                 265                 270

Arg Trp Phe Arg Gln Ile Asn Asp His Phe His Ile Lys Gly Cys Ser
        275                 280                 285

Tyr Val Leu Tyr Lys Pro His Gly Lys Asn Lys Thr Ala Gly Glu Thr
    290                 295                 300

Ala Val Gly Ala Leu Ala Lys Leu Thr Arg Gly Leu Lys Asp Glu Ser
305                 310                 315                 320

Met Ala Tyr Ile Tyr His Cys Gln Asn His Tyr Phe Cys Pro Ile Gly
                325                 330                 335

Phe Glu Ala Thr Pro Val Lys Ala Ser Lys Ala Tyr Arg Gly Arg Val
            340                 345                 350

Leu Gln Gln Glu Val Glu Tyr Trp Ile Leu Ile Gly Glu Pro Ser Arg
        355                 360                 365

Lys His Pro Thr Ile His Cys Lys Arg Trp Thr Asp Ile Val Thr Asp
    370                 375                 380

Leu Asn Thr Gln Asn Pro Glu Tyr Leu Asp Ile Arg His Leu Glu Arg
385                 390                 395                 400

Gly Leu Gln His Arg Lys Thr Lys Lys Val Gly Gly Asn Leu His Cys
                405                 410                 415

Ile Ile Ala Phe Gln Arg Leu Asn Trp Gln Arg Phe Gly Pro Trp Asn
            420                 425                 430

Ile Pro Phe Gly Ser Val Arg Gln Asp Lys Gln Ser Gln Thr Gln Gly
        435                 440                 445

Gln Gly Ile Ala Lys Ser Glu Ser Glu Asp Asn Ile Ser Lys Lys Gln
```

```
                450                 455                 460
His Gly Arg Leu Gly Arg Ser Phe Ser Ala Gly Phe His Gln Glu Ser
465                 470                 475                 480

Thr Trp Lys Lys Ser Ser Leu Arg Glu Arg Arg Asn Ser Gly Tyr Gln
                485                 490                 495

Ser Tyr Asn Asp Tyr Asp Gly Asp
                500             505

<210> SEQ ID NO 9
<211> LENGTH: 529
<212> TYPE: PRT
<213> ORGANISM: Gallus sp.

<400> SEQUENCE: 9

Met Pro His Ile Ser Glu Asp Glu Lys Glu Asn Gly Ser Gly Asn Asn
1               5                   10                  15

Gly Asn Thr Glu Lys Lys Pro Gly Lys Glu Ser Ser Glu Ala Ser Leu
                20                  25                  30

Arg Asp Pro Ile Lys Ser Tyr Cys Ile Ser Asp Ala Ser Thr Val Ser
            35                  40                  45

Leu Val Ser Arg Gly Asp Gly His Tyr Pro Trp Gly Cys Pro Val Thr
    50                  55                  60

His Thr Arg Glu Lys Phe Tyr Thr Ile Cys Ser Asp Tyr Ala Phe Leu
65                  70                  75                  80

Asn Arg Val Thr Ser Ile Cys Lys Ser Pro Ser Ala Ser Val Asn Ala
                85                  90                  95

Cys Leu Ser Gly Ser Ala Ala Leu Asn Val Gly Asn Asn Thr Pro Ser
            100                 105                 110

Leu Leu Gly Ile Gln Thr Gly Ala Ser Glu Ile Ile Tyr Ser Glu Asp
        115                 120                 125

Ala Asn Leu Glu Thr Leu Ser Gly Ser Leu Gly Lys Leu Pro Leu Ala
130                 135                 140

Trp Glu Ile Asp Lys Ser Glu Phe Asn Ser Val Thr Ala Asn His Lys
145                 150                 155                 160

Asn Lys Ala Gly Asn Met Lys Lys Gln Val Ala Lys Lys Ser Ser
                165                 170                 175

Asp Lys Lys Ser Lys Gln Tyr Lys Glu Cys Pro Gln Leu Ser Ala Leu
            180                 185                 190

Glu Asp Val Lys Glu Arg Lys Val Leu Asp Leu Arg Arg Trp Tyr Cys
        195                 200                 205

Ile Ser Arg Pro Gln Tyr Lys Thr Ser Cys Gly Ile Ser Ser Leu Val
    210                 215                 220

Ser Cys Trp Asn Phe Leu Tyr Ser Thr Leu Gly Ala Gly Ser Leu Pro
225                 230                 235                 240

Pro Ile Thr Gln Glu Glu Ala Leu His Ile Leu Gly Phe Gln Pro Pro
                245                 250                 255

Phe Glu Glu Ile Arg Phe Gly Pro Phe Thr Gly Asn Thr Thr Leu Met
            260                 265                 270

Arg Trp Phe Arg Gln Ile Asn Asp His Phe His Ile Lys Gly Cys Ser
        275                 280                 285

Tyr Val Leu Tyr Lys Pro His Gly Lys Asn Lys Thr Ala Gly Glu Thr
    290                 295                 300

Ala Val Gly Ala Leu Ala Lys Leu Thr Arg Gly Leu Lys Asp Glu Ser
305                 310                 315                 320
```

-continued

```
Met Ala Tyr Ile Tyr His Cys Gln Asn His Tyr Phe Cys Pro Ile Gly
            325                 330                 335

Phe Glu Ala Thr Pro Val Lys Ala Ser Lys Ala Tyr Arg Leu Leu Asp
            340                 345                 350

Leu Asp Ser Gly Asp Leu Gly Ser Val Pro Ser Ser Thr Ala Asp Phe
            355                 360                 365

His Cys Asp Phe Arg Gly Arg Val Leu Gln Gln Glu Val Tyr Trp
            370                 375                 380

Ile Leu Ile Gly Glu Pro Ser Arg Lys His Pro Thr Ile His Cys Lys
385                 390                 395                 400

Arg Trp Thr Asp Ile Val Thr Asp Leu Asn Thr Gln Asn Pro Glu Tyr
                405                 410                 415

Leu Asp Ile Arg His Leu Glu Arg Gly Leu Gln His Arg Lys Thr Lys
            420                 425                 430

Lys Val Gly Gly Asn Leu His Cys Ile Ile Ala Phe Gln Arg Leu Asn
            435                 440                 445

Trp Gln Arg Phe Gly Pro Trp Asn Ile Pro Phe Gly Ser Val Arg Gln
            450                 455                 460

Asp Lys Gln Ser Gln Thr Gln Gly Gln Gly Ile Ala Lys Ser Glu Ser
465                 470                 475                 480

Glu Asp Asn Ile Ser Lys Lys Gln His Gly Arg Leu Gly Arg Ser Phe
                485                 490                 495

Ser Ala Gly Phe His Gln Glu Ser Thr Trp Lys Lys Ser Ser Leu Arg
            500                 505                 510

Glu Arg Arg Asn Ser Gly Tyr Gln Ser Tyr Asn Asp Tyr Asp Gly Asp
            515                 520                 525

Asp
```

<210> SEQ ID NO 10
<211> LENGTH: 1946
<212> TYPE: DNA
<213> ORGANISM: Danio rerio
<220> FEATURE:
<221> NAME/KEY: misc_feature
<222> LOCATION: (165)..(167)
<223> OTHER INFORMATION: Translation initiation codon (ATG)
<220> FEATURE:
<221> NAME/KEY: misc_feature
<222> LOCATION: (1671)..(1673)
<223> OTHER INFORMATION: Translation termination codon (TAA)

<400> SEQUENCE: 10

```
cgttgaaaca gctaggcagt cagagaggtc gcgcagcgca ttttatataa aatattcttg      60
ctgaacttgc gagtcggtgg attattttgg gactgagtca tcatatctgc ggtacacctg     120
acctgttggt tattctctta accatcatcc cagttctcca ttcaatgcct aacactgtgg     180
aaagtgaagg cgccaaggta tccgctagta cagatcagga ggccccatca cgggccccgg     240
gacgagagga tgaacgtgag cgcagcttcc tgagccccat gatgcgagat gctctgcggg     300
tacgacgggc ctccagcgca gagctccagc ttcatggac gtgccctgta acccactcca     360
gggagaagtt ctacaccgtc tgctcggact atgccctgct caaccgagct cgaccagtta     420
tcacatccga agatgcatca cagaccaatc ctgacagcgg gacatcatta gccaagagca     480
acacagcaac atcttctcag agtcactcag ggggaataag cgtatcttta gatgggaact     540
gtgatatgga ggttgtgtcc tccagcaaca agcctgtgct ggcctgggag attgacacct     600
cagatttcga tgccgtttta acccggaaag ccagaacaag taatttgaag aaattcaaca     660
```

-continued

```
ctaagaaaat gaaatcatct gacaggccaa gcagaaacct gcaagatgtc ccgccacaag    720
cctctctaga tgaaatcaaa cagagaaaag tgctggacct ccgtagatgg tactgcatca    780
gccgaccaca gtataaaaca tcatgtggaa tctcttcact tgtttcttgc tggaactttc    840
tctacagtac tctcggagca ggcagtctcc cacctatttc tcaagaagaa gctctgcata    900
tacttggatt tcagcctccg tttgaagata tcaaatttgg accatttact ggcaatgcca    960
ctttaatgag atggttcaga caaatcaatg ataattttcg tgttcggggt tgctcatata   1020
ttctgtacaa gcctcatggg aagcacaaga cagcaggaga gacagccgag ggggcgctca   1080
tgaagcttac acagggtctt aaagacgaat ccatggccta catttatcac tgtcagaatc   1140
actacttctg tcctgtgggc tatgaagcta ctccactgaa agcagccaaa gcatacaggg   1200
gaccactgcc tcttaatgag atggagcact ggattctcat tggtgaacca agccggaaac   1260
atcctgcaat ccactgtaaa aaatgggcag acatcgtgac ggacctaaat actcagaacc   1320
cagaatactt agacattcgc catattgaga gaggcataca gtatcgcaaa accaagaagg   1380
ttggaggcaa tctgcattgc atcatggcct tccagagagt gaactggcaa aaattgggac   1440
catgggcgct gaatctggaa aacctgaggc atgatctcca tcatcaggct ccagaacaca   1500
gaggccaagc ttcaacagag gacagttctg aggagcgaac ggtgaaacgc ctgggtaggt   1560
ctctcagcac ggggaacaag cctgaaaatg cctggaagcg tttgtccaac acagccgagt   1620
acaggcacag aggctctcca gacagtgacc tggatgaaga catcactgac taaatatgaa   1680
gggccaggtg ggtttcgaca cttttattca agattattaa ccttccaggt tattagctat   1740
agttaaaggt tacaatccgg tatgaggttg tgatgtaaga gttagtgctc agactggtaa   1800
acttaaaaat ggaagtttga cgccaataag aatatgggaa agagctcttg tggaggacat   1860
ctgtgtaata ctgacagcaa tgtgaattaa gttacactgg ctttggtgat gtgccgataa   1920
ataaaggttt aaaatactaa aaaaaa                                        1946
```

<210> SEQ ID NO 11
<211> LENGTH: 502
<212> TYPE: PRT
<213> ORGANISM: Danio rerio

<400> SEQUENCE: 11

```
Met Pro Asn Thr Val Glu Ser Glu Gly Ala Lys Val Ser Ala Ser Thr
1               5                   10                  15

Asp Gln Glu Ala Pro Ser Arg Ala Pro Gly Arg Glu Asp Glu Arg Glu
            20                  25                  30

Arg Ser Phe Leu Ser Pro Met Met Arg Asp Ala Leu Arg Val Arg Arg
        35                  40                  45

Ala Ser Ser Ala Glu Leu Gln Leu Pro Trp Thr Cys Pro Val Thr His
    50                  55                  60

Ser Arg Glu Lys Phe Tyr Thr Val Cys Ser Asp Tyr Ala Leu Leu Asn
65                  70                  75                  80

Arg Ala Arg Pro Val Ile Thr Ser Glu Asp Ala Ser Gln Thr Asn Pro
                85                  90                  95

Asp Ser Gly Thr Ser Leu Ala Lys Ser Asn Thr Ala Thr Ser Ser Gln
            100                 105                 110

Ser His Ser Gly Gly Ile Ser Val Ser Leu Asp Gly Asn Cys Asp Met
        115                 120                 125

Glu Val Val Ser Ser Ser Asn Lys Pro Val Leu Ala Trp Glu Ile Asp
    130                 135                 140
```

-continued

```
Thr Ser Asp Phe Asp Ala Val Leu Thr Arg Lys Ala Arg Thr Ser Asn
145                 150                 155                 160

Leu Lys Lys Phe Asn Thr Lys Lys Met Lys Ser Ser Asp Arg Pro Ser
                165                 170                 175

Arg Asn Leu Gln Asp Val Pro Pro Gln Ala Ser Leu Asp Glu Ile Lys
            180                 185                 190

Gln Arg Lys Val Leu Asp Leu Arg Arg Trp Tyr Cys Ile Ser Arg Pro
        195                 200                 205

Gln Tyr Lys Thr Ser Cys Gly Ile Ser Ser Leu Val Ser Cys Trp Asn
    210                 215                 220

Phe Leu Tyr Ser Thr Leu Gly Ala Gly Ser Leu Pro Pro Ile Ser Gln
225                 230                 235                 240

Glu Glu Ala Leu His Ile Leu Gly Phe Gln Pro Pro Phe Glu Asp Ile
                245                 250                 255

Lys Phe Gly Pro Phe Thr Gly Asn Ala Thr Leu Met Arg Trp Phe Arg
                260                 265                 270

Gln Ile Asn Asp Asn Phe Arg Val Arg Gly Cys Ser Tyr Ile Leu Tyr
            275                 280                 285

Lys Pro His Gly Lys His Lys Thr Ala Gly Glu Thr Ala Glu Gly Ala
        290                 295                 300

Leu Met Lys Leu Thr Gln Gly Leu Lys Asp Glu Ser Met Ala Tyr Ile
305                 310                 315                 320

Tyr His Cys Gln Asn His Tyr Phe Cys Pro Val Gly Tyr Glu Ala Thr
                325                 330                 335

Pro Leu Lys Ala Ala Lys Ala Tyr Arg Gly Pro Leu Pro Leu Asn Glu
                340                 345                 350

Met Glu His Trp Ile Leu Ile Gly Glu Pro Ser Arg Lys His Pro Ala
            355                 360                 365

Ile His Cys Lys Lys Trp Ala Asp Ile Val Thr Asp Leu Asn Thr Gln
        370                 375                 380

Asn Pro Glu Tyr Leu Asp Ile Arg His Ile Glu Arg Gly Ile Gln Tyr
385                 390                 395                 400

Arg Lys Thr Lys Lys Val Gly Gly Asn Leu His Cys Ile Met Ala Phe
                405                 410                 415

Gln Arg Val Asn Trp Gln Lys Leu Gly Pro Trp Ala Leu Asn Leu Glu
            420                 425                 430

Asn Leu Arg His Asp Leu His His Gln Ala Pro Glu His Arg Gly Gln
        435                 440                 445

Ala Ser Thr Glu Asp Ser Ser Glu Glu Arg Thr Val Lys Arg Leu Gly
    450                 455                 460

Arg Ser Leu Ser Thr Gly Asn Lys Pro Glu Asn Ala Trp Lys Arg Leu
465                 470                 475                 480

Ser Asn Thr Ala Glu Tyr Arg His Arg Gly Ser Pro Asp Ser Asp Leu
                485                 490                 495

Asp Glu Asp Ile Thr Asp
            500

<210> SEQ ID NO 12
<211> LENGTH: 2062
<212> TYPE: DNA
<213> ORGANISM: Strongylocentrotus purpuratus
<220> FEATURE:
<221> NAME/KEY: misc_feature
<222> LOCATION: (164)..(166)
<223> OTHER INFORMATION: translation initiation codon (ATG)
```

<400> SEQUENCE: 12

```
gcagtttgtg tgtgattctc aatctcattg tgcgcattat aggcctatag ctttcgggaa      60
aacagacaga ttagtgcttt gcaaaccttg catacattga ggcaaccaga aagttgggct     120
caactttcag ataacctttg acctttcctg ggcctgaggt ataatgggta actggccttc     180
agttctctct ggtgagggaa gtgaggacag cagcgcgag agcaacaacg aaagcaacaa      240
ccaggaaacc agtgatcagg aaaacacaag acatcatctc tgtggctcag aggagagcta     300
cttctccgag gaggaactcc ttcccattgt ctaccctgat gatgatgatg atgctgctgc     360
tcgtgatgac gtgttgggag acttcttgtc cgttaaagaa gatggagagt ttacaactga     420
cgaggttgat gggtctcgat atgacctagc acccgagtat taccccacct ctcttcatga     480
agacgtcact gcgagattct cagatcttgc ctcacctgta gatcgcaaag aaagcagcta     540
cagcagcact gacgactatg atgacaatga cagtgatgat gaggaggagg aggaggatga     600
ccactattac caaagaagga ggaatgataa atattcccta tgaaggaag acgatgatga      660
taatgagctc tccagcattc cactgccacc tccctcatca ctgtatgaag ttgcatcagc     720
tgagcagatg caagggtca cagcttacct gaatgctgac cgacctgaca cactccaaga     780
aaccatcgtc ccttttgaga gtcgtgcaga agagtgcagt gcccctgaga gggtggttgc     840
atgggagata gacgtcagcg acatgacggg atccaagaag actaagaaga gaccacccaa     900
taaactttca aaggcaaaat caaggaaaag ttcatcgaaa ggtagcatgg atagtgccta     960
tatcccgcca actgtatcaa caacacctga gctcctagca cagagaaagt gcttggacca    1020
aaagagatgg ttttgtgtga gtagaccccca gtacagcaag tcatgtggcc tatcgtcctt    1080
ggtttcttgc tggaactacc tgttcagtac cctaggaggg ggcaccatgc cccccatcac    1140
ccaggagcaa gccccttaacg tcctgggggtt ccaaccaccc ttcggtgaga tccgttttgg    1200
gccttttcaca gggaatgcca ccctcatgag gtggttcaag cagctgaatg atcactacag    1260
agtgagagga aaggcatact tccagtacaa accccatggc aggagtagaa cagtgggaag    1320
aacatctgcc caaggtttac atctgttacg acaaggggttg aaggatccta acatggcttt    1380
catataccac tgccataacc actacttctg ccccattgga tacgaagatg tgcctctgaa    1440
ggctgtagat gcatacaggg atcctttaaa ccttgatgag gtagagacat ggatactgat    1500
cggtgatcct agtagaaagc aaccaggaat ccactgtttc aaatgggaag acatcagcac    1560
agatctgaac tgccagaacc ctgactatct caacatccgc aagctacggc ttggagtgca    1620
gcagaggagg acaaagagaa ccggtggcaa cttgcactgc atcatggcct tctgtcgcag    1680
tgcaggcttt ctcaccagac caaccaagag caagaaagag ggtgcaatga aggacacttc    1740
tagtaacagc aagagtagga agtctggctc cgttcggatg tcaggacgta aggttggcga    1800
gagtaagagt gagggggatgg tggggcgtcc agctccagga gggagtgtgc catgtctgca    1860
gactggcaaa gcgacagta gcgatatcat cgagcacttt gcttttgaga ctgtgagttg    1920
cgaccatagc agtgagggcc gaagctgtag atcagaagtt gttaaaaaga ctaaaagtga    1980
atctcaggtt ggcagacgaa gggcaaaggc atctgttgta aagcaggagg ataaggagat    2040
cagagtgaag agttctgagg ca                                              2062
```

<210> SEQ ID NO 13
<211> LENGTH: 633
<212> TYPE: PRT
<213> ORGANISM: Strongylocentrotus purpuratus

<400> SEQUENCE: 13

-continued

```
Met Gly Asn Trp Pro Ser Val Leu Ser Gly Glu Gly Ser Glu Asp Ser
1               5                   10                  15

Ser Ser Glu Ser Asn Asn Glu Ser Asn Gln Glu Thr Ser Asp Gln
            20                  25                  30

Glu Asn Thr Arg His His Leu Cys Gly Ser Glu Glu Ser Tyr Phe Ser
            35                  40                  45

Glu Glu Glu Leu Leu Pro Ile Val Tyr Pro Asp Asp Asp Asp Ala
    50                  55                  60

Ala Ala Arg Asp Asp Val Leu Gly Asp Phe Leu Ser Val Lys Glu Asp
65                  70                  75                  80

Gly Glu Phe Thr Thr Asp Glu Val Asp Gly Ser Arg Tyr Asp Leu Ala
                85                  90                  95

Pro Glu Tyr Tyr Pro Thr Ser Leu His Glu Asp Val Thr Ala Arg Phe
                100                 105                 110

Ser Asp Leu Ala Ser Pro Val Asp Arg Lys Glu Ser Ser Tyr Ser Ser
            115                 120                 125

Thr Asp Asp Tyr Asp Asp Asn Asp Ser Asp Asp Glu Glu Glu Glu Glu
    130                 135                 140

Asp Asp His Tyr Tyr Gln Arg Arg Arg Asn Asp Lys Tyr Ser Leu Met
145                 150                 155                 160

Lys Glu Asp Asp Asp Asn Glu Leu Ser Ser Ile Pro Leu Pro Pro
                165                 170                 175

Pro Ser Ser Leu Tyr Glu Val Ala Ser Ala Glu Gln Met Gln Gly Val
            180                 185                 190

Thr Ala Tyr Leu Asn Ala Asp Arg Pro Asp Thr Leu Gln Glu Thr Ile
                195                 200                 205

Val Pro Phe Glu Ser Arg Ala Glu Glu Cys Ser Ala Pro Glu Arg Val
    210                 215                 220

Val Ala Trp Glu Ile Asp Val Ser Asp Met Thr Gly Ser Lys Lys Thr
225                 230                 235                 240

Lys Lys Arg Pro Pro Asn Lys Leu Ser Lys Ala Lys Ser Arg Lys Ser
                245                 250                 255

Ser Ser Lys Gly Ser Met Asp Ser Ala Tyr Ile Pro Pro Thr Val Ser
            260                 265                 270

Thr Thr Pro Glu Leu Leu Ala Gln Arg Lys Cys Leu Asp Gln Lys Arg
    275                 280                 285

Trp Phe Cys Val Ser Arg Pro Gln Tyr Ser Lys Ser Cys Gly Leu Ser
    290                 295                 300

Ser Leu Val Ser Cys Trp Asn Tyr Leu Phe Ser Thr Leu Gly Gly
305                 310                 315                 320

Thr Met Pro Pro Ile Thr Gln Glu Gln Ala Leu Asn Val Leu Gly Phe
                325                 330                 335

Gln Pro Pro Phe Gly Glu Ile Arg Phe Gly Pro Phe Thr Gly Asn Ala
            340                 345                 350

Thr Leu Met Arg Trp Phe Lys Gln Leu Asn Asp His Tyr Arg Val Arg
    355                 360                 365

Gly Arg Ala Tyr Phe Gln Tyr Lys Pro His Gly Arg Ser Arg Thr Val
370                 375                 380

Gly Arg Thr Ser Ala Gln Gly Leu His Leu Leu Arg Gln Gly Leu Lys
385                 390                 395                 400

Asp Pro Asn Met Ala Phe Ile Tyr His Cys His Asn His Tyr Phe Cys
                405                 410                 415
```

-continued

```
Pro Ile Gly Tyr Glu Asp Val Pro Leu Lys Ala Val Asp Ala Tyr Arg
            420                 425                 430

Asp Pro Leu Asn Leu Asp Glu Val Glu Thr Trp Ile Leu Ile Gly Asp
        435                 440                 445

Pro Ser Arg Lys Gln Pro Gly Ile His Cys Phe Lys Trp Glu Asp Ile
    450                 455                 460

Ser Thr Asp Leu Asn Cys Gln Asn Pro Asp Tyr Leu Asn Ile Arg Lys
465                 470                 475                 480

Leu Arg Leu Gly Val Gln Gln Arg Arg Thr Lys Arg Thr Gly Gly Asn
                485                 490                 495

Leu His Cys Ile Met Ala Phe Cys Arg Ser Ala Gly Phe Leu Thr Arg
            500                 505                 510

Pro Thr Lys Ser Lys Lys Glu Gly Ala Met Lys Asp Thr Ser Ser Asn
        515                 520                 525

Ser Lys Ser Arg Lys Ser Gly Ser Val Arg Met Ser Gly Arg Lys Val
    530                 535                 540

Gly Glu Ser Lys Ser Glu Gly Met Val Gly Arg Pro Ala Pro Gly Gly
545                 550                 555                 560

Ser Val Pro Cys Leu Gln Thr Gly Lys Ala Asp Ser Ser Asp Ile Ile
                565                 570                 575

Glu His Phe Ala Phe Glu Thr Val Ser Cys Asp His Ser Ser Glu Gly
            580                 585                 590

Arg Ser Cys Arg Ser Glu Val Val Lys Lys Thr Lys Ser Glu Ser Gln
        595                 600                 605

Val Gly Arg Arg Arg Ala Lys Ala Ser Val Val Lys Gln Glu Asp Lys
    610                 615                 620

Glu Ile Arg Val Lys Ser Ser Glu Ala
625                 630
```

<210> SEQ ID NO 14
<211> LENGTH: 2031
<212> TYPE: DNA
<213> ORGANISM: Giardia lamblia
<220> FEATURE:
<221> NAME/KEY: misc_feature
<222> LOCATION: (230)..(232)
<223> OTHER INFORMATION: Translation initiation codon (ATG)
<220> FEATURE:
<221> NAME/KEY: misc_feature
<222> LOCATION: (1040)..(1042)
<223> OTHER INFORMATION: Translation termination codon (TAG)

<400> SEQUENCE: 14
gcacatcttg caggtcaaaa cgaacacccc ctccttcgat atcctctcag accctacact    60
ctcaattgtg ttacagaccg ggcatgggaa gaacttgcta cggccggctt tcttaggggg   120
cgccgccctt gtcctcttct tctttcccat cctcctgtcc tctttttgtg actgtttgtg   180
actagacgcc gtttctaaca aaattgccaa gcatgtatgc aaaattaaaa tggaaagata   240
ccccagacaa cggttagacg acggcaggtg gcagtgcgtg gcagcgcagt acagatactc   300
ctgcgccatc tcatgccttg tgagcatatt caatcatctc ttcaacagag acatgaccct   360
ggacgagtgt attgctattc tctttccaga cctgaaagaa gacccacgac actatgattt   420
tggacctcag gcttctaaca gtgctgttca aagctggttc aagaccctct gcatgcacta   480
tggcctttct ggcacctctt gcacgatata caaggagcag gcagaacga gaactgcgtg   540 tagcaagcaa gaggcactta agaatatcat cactgctttg aatacgccaa gatgtgcgtt   600
actgtatcac tgcttgaacc attactgcat aatcgtaggc tatataataa gtccatctac   660

-continued

```
gcctaataga ccaagtaatc attgcgtctt cagcggggat gatggatgca ccctcaagct      720
cctgtgtgca gacggcacag aagccgagga cgtggacgat agtaatattt ggttaatagt      780
ggcagactgt gggaaaggaa ctgctcccct taggtcactg acctgggaat ttgtacataa      840
agatatatct acccgacctc cgtatgcata taacgctagg tgccctgaga gaggactgct      900
aaggaaaaca gaatcaaagg gatatatacc agttgagata gactcagtgc ttgttaacag      960
cacgggagta tccacctgtg ttagatctgg tggcgtcatc aagggatcgt cgcactgcat     1020
cattggattt gttagtgact agagccccgt ttattactcc cggacgaaag tataactatt     1080
aacaccacaa gcacaacgat agctccagta gagcagagcc gaagcacttg aggcagcgag     1140
gcctccaaat acccacatag aacgtcacag atgatagctg tccatgtcgc aattgacaag     1200
gttaacggga aggttgaaac aggcgagggc gtccatctgg tacgttgtac tttggttgtt     1260
gaatattgaa ctgttgtaag tgttgatttg ctgggtatat ctattgctta tgtaccgaaa     1320
aagggcattg caaacgtcat atattgcatc tatctgatga cacagaccc  cagttttttg     1380 aagatttgca agtcttcttt gtggtggggc attcatatat gaataagagc agacttctcc     1440
gcaggcaaag gacatggact gaatggcatg ctcgtaacca gttaggtcca gtgctttggt     1500
tcgtgcatag tatttaaaga ccttctgaag aaggatggtt tgaaataggg tcgtcctgtc     1560
cacacagtcc aggcagttta tccgcggata gcacttctga acaaagtcag gaagagcaac     1620
tccgacatca ccgctaggaa ctagaactgt gcttgtggct atgtcatctg ctaactggtg     1680
atactctgtg ttgctgtgtc tacgtatgtt gtagttcatc aacttaacgt tgagggagtt     1740
cttgcggcga gaatcagcag ttttctcat  agactcggta agaacgccg  tcagagccgc     1800 tcatcggcgg tctcaaggct tttcttttca ctggcagcaa tggagtcatc caaaagatcg     1860
acttcatttt tgaggaggtt gacgataagt atctctgcgt ctgcagtcac taagttaccc     1920
aatagaaggc ttatatgcct ttgcaagaga ctactaaact gagcgaggcc ctgctcttca     1980
tgagccccat ctgggaagcg tatggcagga gtgaacttgt aagtaaaaaa a              2031
```

<210> SEQ ID NO 15
<211> LENGTH: 270
<212> TYPE: PRT
<213> ORGANISM: Giardia lamblia

<400> SEQUENCE: 15

```
Met Glu Arg Tyr Pro Arg Gln Arg Leu Asp Asp Gly Arg Trp Gln Cys
1               5                   10                  15

Val Ala Ala Gln Tyr Arg Tyr Ser Cys Ala Ile Ser Cys Leu Val Ser
                20                  25                  30

Ile Phe Asn His Leu Phe Asn Arg Asp Met Thr Leu Asp Glu Cys Ile
            35                  40                  45

Ala Ile Leu Phe Pro Asp Leu Lys Glu Asp Pro Arg His Tyr Asp Phe
        50                  55                  60

Gly Pro Gln Ala Ser Asn Ser Ala Val Gln Ser Trp Phe Lys Thr Leu
65                  70                  75                  80

Cys Met His Tyr Gly Leu Ser Gly Thr Ser Cys Thr Ile Tyr Lys Glu
                85                  90                  95

Gln Gly Arg Thr Arg Thr Ala Cys Ser Lys Gln Glu Ala Leu Lys Asn
                100                 105                 110

Ile Ile Thr Ala Leu Asn Thr Pro Arg Cys Ala Leu Leu Tyr His Cys
            115                 120                 125
```

```
Leu Asn His Tyr Cys Ile Ile Val Gly Tyr Ile Ile Ser Pro Ser Thr
    130                 135                 140

Pro Asn Arg Pro Ser Asn His Cys Val Phe Ser Gly Asp Asp Gly Cys
145                 150                 155                 160

Thr Leu Lys Leu Leu Cys Ala Asp Gly Thr Glu Ala Glu Asp Val Asp
                165                 170                 175

Asp Ser Asn Ile Trp Leu Ile Val Ala Asp Cys Gly Lys Gly Thr Ala
                180                 185                 190

Pro Leu Arg Ser Leu Thr Trp Glu Phe Val His Lys Asp Ile Ser Thr
                195                 200                 205

Arg Pro Pro Tyr Ala Tyr Asn Ala Arg Cys Pro Glu Arg Gly Leu Leu
    210                 215                 220

Arg Lys Thr Glu Ser Lys Gly Tyr Ile Pro Val Glu Ile Asp Ser Val
225                 230                 235                 240

Leu Val Asn Ser Thr Gly Val Ser Thr Cys Val Arg Ser Gly Gly Val
                245                 250                 255

Ile Lys Gly Ser Ser His Cys Ile Ile Gly Phe Val Ser Asp
                260                 265                 270

<210> SEQ ID NO 16
<211> LENGTH: 196
<212> TYPE: DNA
<213> ORGANISM: Branchiostoma floridae

<400> SEQUENCE: 16
tgatttgtgg ttccggcaga tcaatgatca tttccatgta aaaggatgct cctatgttct     60
gtataagccg catggcaaga acaagacagc aggagaaact gctgttgggg cactatcaga    120
gttaacacaa gggttaaaag aagacccaac agcctacgtc tatcattgcc agaaccacta    180
cttctgcccc aatccc                                                    196

<210> SEQ ID NO 17
<211> LENGTH: 65
<212> TYPE: PRT
<213> ORGANISM: Branchiostoma floridae

<400> SEQUENCE: 17

Asp Leu Trp Phe Arg Gln Ile Asn Asp His Phe His Val Lys Gly Cys
  1               5                  10                  15

Ser Tyr Val Leu Tyr Lys Pro His Gly Lys Asn Lys Thr Ala Gly Glu
                 20                  25                  30

Thr Ala Val Gly Ala Leu Ser Glu Leu Thr Gln Gly Leu Lys Glu Asp
             35                  40                  45

Pro Thr Ala Tyr Val Tyr His Cys Gln Asn His Tyr Phe Cys Pro Asn
     50                  55                  60

Pro
 65

<210> SEQ ID NO 18
<211> LENGTH: 382
<212> TYPE: DNA
<213> ORGANISM: Mus musculus
<220> FEATURE:
<221> NAME/KEY: 5'UTR
<222> LOCATION: (1)..(382)
<223> OTHER INFORMATION: Exon A - untranslated

<400> SEQUENCE: 18
ccccaactac tttcgtccct tccctccgtc cctcactctc cctcctcctt tctccccccc     60
```

```
taccttcctt tctacttctt ttttcaactt tggagcacgg ctttctggca accttaaata      120
ctacagttgc gcaactagca tgtctggagt cacagcaaag atttcccaac ttatattttg      180
ttcaaggtat ccaccgcaaa tggcaggtat atagtaaacg ctgaaaggga ggctaggtgt      240
tatcaatgat acccagtcac tcggtgctat tcttgtgcgc tcaatgggac gaaagattct      300
gggccttggg taggagactt ggagatgcaa gatctggtgt tgccttccag caccagagtt      360
ccgggaccca acaggaacag ag                                              382
```

<210> SEQ ID NO 19
<211> LENGTH: 42
<212> TYPE: DNA
<213> ORGANISM: Mus musculus
<220> FEATURE:
<221> NAME/KEY: 5'UTR
<222> LOCATION: (1)..(42)
<223> OTHER INFORMATION: Exon B - untranslated

<400> SEQUENCE: 19

```
ccctggaagg atctgggtcg agctgagtct ctgaggagag at                         42
```

<210> SEQ ID NO 20
<211> LENGTH: 311
<212> TYPE: DNA
<213> ORGANISM: Mus musculus
<220> FEATURE:
<221> NAME/KEY: 5'UTR
<222> LOCATION: (1)..(311)
<223> OTHER INFORMATION: Exon C - untranslated

<400> SEQUENCE: 20

```
ttttcttccg gctgggagtg agggagcagg ccgggaggag gttacaaggc tttagatctg       60
gtcttggcca gtggggacta gggacgcctg gcactgggtt ggccaccgca ggacagtagt      120
gggaacccgg cacagtagcg ctgcagcagt tgcacttgca acatccctgc tctcccggtt      180
ctcctccacc tgcacctttg tcaccttcag gtgcttcgga gcctcaaaga gggggcagtg      240
ggaagtctcc tggctcctca gagtctgaac tccagagggc atcatgtgct gcatgaatct      300
catactcaca g                                                          311
```

<210> SEQ ID NO 21
<211> LENGTH: 601
<212> TYPE: DNA
<213> ORGANISM: Mus musculus
<220> FEATURE:
<221> NAME/KEY: 5'UTR
<222> LOCATION: (1)..(125)
<223> OTHER INFORMATION: Exon 1 - untranslated
<220> FEATURE:
<221> NAME/KEY: misc_feature
<222> LOCATION: (126)..(128)
<223> OTHER INFORMATION: Translation initiation codon (ATG)

<400> SEQUENCE: 21

```
gatcccattt gtcagctctc aagccttttt agaatcctgt gaacatttgc caaagttgct       60
tttttttttt ttaaagagag ggttgcggct tcttcctagg aacagagaca tctgcatttg      120
ctctcatgcc taacgccact gaagctggaa aagccactga tcctggacat ggtgagcaca      180
catctgagaa caagtcacca gaagagggtc tacaaggtgc tgtaccatct ttctacacaa      240
gtgcctcaga agcacccata gcgcccagag gagatgggca ttatccatcg agttgtccag      300
tgactcacac tcgagagaaa atttatgcga tctgctcaga ttatgccttc ctcaaccagg      360
```

| caacatcagt ctacaaaact cctagcctaa cccgctctgc ttgcctccct gataacacct | 420 |
| ctctttctgc tggaaatact acaagatata ttggaatttc aactagtaca tcagaaataa | 480 |
| tctataatga aggaaaataa cttggaaaac ttgtccactg gcatgggcaa gctacctctt | 540 |
| gcatgggaga ttgataaatc tgaatttgat ggggtgacta caaatttgat acataagtca | 600 |
| g | 601 |

<210> SEQ ID NO 22
<211> LENGTH: 912
<212> TYPE: DNA
<213> ORGANISM: Mus musculus
<220> FEATURE:
<221> NAME/KEY: misc_feature
<222> LOCATION: (1)..(912)
<223> OTHER INFORMATION: Alternative BIVM 5' end clone (6359)
<220> FEATURE:
<221> NAME/KEY: misc_feature
<222> LOCATION: (1)..(210)
<223> OTHER INFORMATION: Alternatively spliced exon A
<220> FEATURE:
<221> NAME/KEY: misc_feature
<222> LOCATION: (211)..(311)
<223> OTHER INFORMATION: Alternatively spliced exon C
<220> FEATURE:
<221> NAME/KEY: misc_feature
<222> LOCATION: (312)..(912)
<223> OTHER INFORMATION: Exon 1
<220> FEATURE:
<221> NAME/KEY: misc_feature
<222> LOCATION: (437)..(439)
<223> OTHER INFORMATION: Translation initiation codon

<400> SEQUENCE: 22

| atattttgtt caaggtatcc accgcaaatg gcaggtatat agtaaacgct gaaagggagg | 60 |
| ctaggtgtta tcaatgatac ccagtcactc ggtgctattc ttgtgcgctc aatgggacga | 120 |
| aagattctgg gccttgggta ggagacttgg agatgcaaga tctggtgttg ccttccagca | 180 |
| ccagagttcc gggacccaac aggaacagag gtgcttcgga gcctcaaaga gggggcagtg | 240 |
| ggaagtctcc tggctcctca gagtctgaac tccagagggc atcatgtgct gcatgaatct | 300 |
| catactcaca ggatcccatt tgtcagctct caagcctttt tagaatcctg tgaacatttg | 360 |
| ccaaagttgc tttttttttt tttaaagaga gggttgcggc ttcttcctag aacagagac | 420 |
| atctgcattt gctctcatgc ctaacgccac tgaagctgga aaagccactg atcctggaca | 480 |
| tggtgagcac acatctgaga acaagtcacc agaagagggt ctacaaggtg ctgtaccatc | 540 |
| tttctacaca agtgcctcag aagcacccat agcgcccaga ggagatgggc attatccatc | 600 |
| gagttgtcca gtgactcaca ctcgagagaa aatttatgcg atctgctcag attatgcctt | 660 |
| cctcaaccag gcaacatcag tctacaaaac tcctagccta acccgctctg cttgcctccc | 720 |
| tgataacacc tctctttctg ctggaaatac tacaagatat attggaattt caactagtac | 780 |
| atcagaaata atctataatg aaggaaaata acttggaaaa cttgtccact ggcatgggca | 840 |
| agctacctct tgcatgggag attgataaat ctgaatttga tggggtgact acaaatttga | 900 |
| tacataagtc ag | 912 |

<210> SEQ ID NO 23
<211> LENGTH: 912
<212> TYPE: DNA
<213> ORGANISM: Mus musculus
<220> FEATURE:
<221> NAME/KEY: misc_feature
<222> LOCATION: (1)..(912)
<223> OTHER INFORMATION: Alternative BIVM 5' end clone (6358)

```
<220> FEATURE:
<221> NAME/KEY: misc_feature
<222> LOCATION: (1)..(311)
<223> OTHER INFORMATION: Exon C
<220> FEATURE:
<221> NAME/KEY: misc_feature
<222> LOCATION: (312)..(912)
<223> OTHER INFORMATION: Exon 1
<220> FEATURE:
<221> NAME/KEY: misc_feature
<222> LOCATION: (437)..(439)
<223> OTHER INFORMATION: Translation initiation codon

<400> SEQUENCE: 23
ttttcttccg gctgggagtg agggagcagg ccggggaggag gttacaaggc tttagatctg      60
gtcttggcca gtggggacta gggacgcctg gcactgggtt ggccaccgca ggacagtagt     120
gggaacccgg cacagtagcg ctgcagcagt tgcacttgca acatccctgc tctcccggtt     180
ctcctccacc tgcaccttg tcaccttcag gtgcttcgga gcctcaaaga ggggggcagtg     240
ggaagtctcc tggctcctca gagtctgaac tccagagggc atcatgtgct gcatgaatct     300
catactcaca ggatcccatt tgtcagctct caagcctttt tagaatcctg tgaacatttg     360
ccaaagttgc tttttttttt tttaaagaga gggttgcggc ttcttcctag gaacagagac     420
atctgcattt gctctcatgc ctaacgccac tgaagctgga aaagccactg atcctggaca     480
tggtgagcac acatctgaga acaagtcacc agaagagggt ctacaaggtg ctgtaccatc     540
tttctacaca agtgcctcag aagcacccat agcgcccaga ggagatgggc attatccatc     600
gagttgtcca gtgactcaca ctcgagagaa aattatgcg atctgctcag attatgcctt     660
cctcaaccag gcaacatcag tctacaaaac tcctagccta acccgctctg cttgcctccc     720
tgataacacc tctcttctg ctggaaatac tacaagatat attggaattt caactagtac     780
atcagaaata atctataatg aaggaaaata acttggaaaa cttgtccact ggcatgggca     840
agctacctct tgcatgggag attgataaat ctgaatttga tggggtgact acaaatttga     900
tacataagtc ag                                                          912

<210> SEQ ID NO 24
<211> LENGTH: 888
<212> TYPE: DNA
<213> ORGANISM: Mus musculus
<220> FEATURE:
<221> NAME/KEY: misc_feature
<222> LOCATION: (1)..(888)
<223> OTHER INFORMATION: Alternative BIVM 5' end clone (6356)
<220> FEATURE:
<221> NAME/KEY: misc_feature
<222> LOCATION: (1)..(186)
<223> OTHER INFORMATION: Alternatively spliced exon A
<220> FEATURE:
<221> NAME/KEY: misc_feature
<222> LOCATION: (187)..(287)
<223> OTHER INFORMATION: Alternatively spliced exon C
<220> FEATURE:
<221> NAME/KEY: misc_feature
<222> LOCATION: (288)..(888)
<223> OTHER INFORMATION: Exon 1
<220> FEATURE:
<221> NAME/KEY: misc_feature
<222> LOCATION: (413)..(415)
<223> OTHER INFORMATION: Translation initiation codon (ATG)

<400> SEQUENCE: 24
ccccaactac tttcgtccct tccctccgtc cctcactctc cctcctcctt tctccccccc      60
taccttcctt tctacttctt ttttcaactt tggagcacgg ctttctggca accttaaata     120
```

```
ctacagttgc gcaactagca tgtctggagt cacagcaaag atttcccaac ttatattttg      180
ttcaaggtgc ttcggagcct caaagagggg gcagtgggaa gtctcctggc tcctcagagt      240
ctgaactcca gagggcatca tgtgctgcat gaatctcata ctcacaggat cccatttgtc      300
agctctcaag cctttttaga atcctgtgaa catttgccaa agttgctttt tttttttta      360 aagagagggt tgcggcttct tcctaggaac agagacatct gcatttgctc tcatgcctaa      420
cgccactgaa gctggaaaag ccactgatcc tggacatggt gagcacacat ctgagaacaa      480
gtcaccagaa gagggtctac aaggtgctgt accatctttc tacacaagtg cctcagaagc      540
acccatagcg cccagaggag atgggcatta tccatcgagt tgtccagtga ctcacactcg      600
agagaaaatt tatgcgatct gctcagatta tgccttcctc aaccaggcaa catcagtcta      660
caaaactcct agcctaaccc gctctgcttg cctccctgat aacacctctc tttctgctgg      720
aaatactaca agatatattg gaatttcaac tagtacatca gaaataatct ataatgaagg      780
aaaataactt ggaaaacttg tccactggca tgggcaagct acctcttgca tgggagattg      840
ataaatctga atttgatggg gtgactacaa atttgataca taagtcag                  888
```

<210> SEQ ID NO 25
<211> LENGTH: 668
<212> TYPE: DNA
<213> ORGANISM: Mus musculus
<220> FEATURE:
<221> NAME/KEY: misc_feature
<222> LOCATION: (1)..(668)
<223> OTHER INFORMATION: Alternative BIVM 5' end clone (cDNA)
<220> FEATURE:
<221> NAME/KEY: misc_feature
<222> LOCATION: (1)..(42)
<223> OTHER INFORMATION: Exon B
<220> FEATURE:
<221> NAME/KEY: misc_feature
<222> LOCATION: (43)..(143)
<223> OTHER INFORMATION: Alternatively spliced Exon C
<220> FEATURE:
<221> NAME/KEY: misc_feature
<222> LOCATION: (144)..(668)
<223> OTHER INFORMATION: Alternatively spliced Exon 1
<220> FEATURE:
<221> NAME/KEY: misc_feature
<222> LOCATION: (193)..(193)
<223> OTHER INFORMATION: Translation initiation codon (ATG)

<400> SEQUENCE: 25

```
ccctggaagg atctgggtcg agctgagtct ctgaggagag atgtgcttcg gagcctcaaa      60
gagggggcag tgggaagtct cctggctcct cagagtctga actccagagg gcatcatgtg     120
ctgcatgaat ctcatactca cagagagggt tgcggcttct tcctaggaac agagacatct     180
gcatttgctc tcatgcctaa cgccactgaa gctggaaaag ccactgatcc tggacatggt     240
gagcacacat ctgagaacaa gtcaccagaa gagggtctac aaggtgctgt accatctttc     300
tacacaagtg cctcagaagc acccatagcg cccagaggag atgggcatta tccatcgagt     360
tgtccagtga ctcacactcg agagaaaatt tatgcgatct gctcagatta tgccttcctc     420
aaccaggcaa catcagtcta caaaactcct agcctaaccc gctctgcttg cctccctgat     480
aacacctctc tttctgctgg aaatactaca agatatattg gaatttcaac tagtacatca     540
gaaataatct ataatgaagg aaaataactt ggaaaacttg tccactggca tgggcaagct     600
acctcttgca tgggagattg ataaatctga atttgatggg gtgactacaa atttgataca     660
taagtcag                                                               668
```

```
<210> SEQ ID NO 26
<211> LENGTH: 3312
<212> TYPE: DNA
<213> ORGANISM: Mus musculus
<220> FEATURE:
<221> NAME/KEY: misc_feature
<222> LOCATION: (1)..(209)
<223> OTHER INFORMATION: Exon A
<220> FEATURE:
<221> NAME/KEY: misc_feature
<222> LOCATION: (210)..(309)
<223> OTHER INFORMATION: Exon C
<220> FEATURE:
<221> NAME/KEY: misc_feature
<222> LOCATION: (310)..(911)
<223> OTHER INFORMATION: Exon 1
<220> FEATURE:
<221> NAME/KEY: misc_feature
<222> LOCATION: (437)..(439)
<223> OTHER INFORMATION: Translation initiation codon
<220> FEATURE:
<221> NAME/KEY: misc_feature
<222> LOCATION: (912)..(1038)
<223> OTHER INFORMATION: Exon 2
<220> FEATURE:
<221> NAME/KEY: misc_feature
<222> LOCATION: (1039)..(1134)
<223> OTHER INFORMATION: Exon 3
<220> FEATURE:
<221> NAME/KEY: misc_feature
<222> LOCATION: (1135)..(1239)
<223> OTHER INFORMATION: Exon 4
<220> FEATURE:
<221> NAME/KEY: misc_feature
<222> LOCATION: (1240)..(1334)
<223> OTHER INFORMATION: Exon 5
<220> FEATURE:
<221> NAME/KEY: misc_feature
<222> LOCATION: (1335)..(1467)
<223> OTHER INFORMATION: Exon 6
<220> FEATURE:
<221> NAME/KEY: misc_feature
<222> LOCATION: (1468)..(1554)
<223> OTHER INFORMATION: Exon 7
<220> FEATURE:
<221> NAME/KEY: misc_feature
<222> LOCATION: (1555)..(1651)
<223> OTHER INFORMATION: Exon 8
<220> FEATURE:
<221> NAME/KEY: misc_feature
<222> LOCATION: (1652)..(3312)
<223> OTHER INFORMATION: Exon 9
<220> FEATURE:
<221> NAME/KEY: misc_feature
<222> LOCATION: (1943)..(1945)
<223> OTHER INFORMATION: Translation termination codon (TGA)

<400> SEQUENCE: 26
atattttgtt caaggtatcc accgcaaatg gcaggtatat agtaaacgct gaaagggagg      60
ctaggtgtta tcaatgatac ccagtcactc ggtgctattc ttgtgcgctc aatgggacga     120
aagattctgg gccttgggta ggagacttga ggatgcagat ctggtgttgc cttccagcac     180
cagagttccg ggacccaaca ggaacagagg tgcttcggag cctcaaagag gggcagtggg     240
aagtctcctg gctcctcaga gtctgaactc cagagggcat catgtgctgc atgaatctca     300
tactcacagg atcccatttg tcagctctca agccttttta gaatcctgtg aacatttgcc     360
aaagttgctt ttttttttt tttaaagaga gggttgcggc ttcttcctag gaacagagac     420
atctgcattt gctctcatgc ctaacgccac tgaagctgga aaagccactg atcctggaca     480
tggtgagcac acatctgaga acaagtcacc agaagagggt ctacaaggtg ctgtaccatc     540
tttctataca agtgcctcag aagcacccat agcgcccaga ggagatgggc attatccatc     600
```

-continued

| | | | | | |
|---|---|---|---|---|---|
| gagttgtcca | gtgactcaca | ctcgagagaa | aatttatgcg | atctgctcag | attatgcctt | 660 |
| cctcaaccag | gcaacatcag | tctacaaaac | tcctagccta | acccgctctg | cttgcctccc | 720 |
| tgataacacc | tctctttctg | ctggaaatac | tacaagatat | attggaattt | caactagtac | 780 |
| atcagaaata | atctataatg | aagaaaataa | cttggaaaac | ttgtccactg | gcatgggcaa | 840 |
| gctacctctt | gcatgggaga | ttgataaatc | tgaatttgat | ggggtgacta | caaatttgat | 900 |
| acataagtca | ggcaatgtaa | agaaacaatt | ttccaagaag | aaaacgtcgg | ataaaaaagg | 960 |
| gcggcatcag | agggagtgtc | tccactattc | tcctcttgat | gatgttaaac | aacgcaaagt | 1020 |
| gttagacctt | aggcgatggt | actgcataag | ccgaccacag | tacaagactt | catgtggtat | 1080 |
| ctcctcattg | atttcttgtt | ggaatttctt | atacagcata | atgggagctg | gaatctccc | 1140 |
| acctattacc | caagaagagg | cattacatat | tttgggcttc | caaccccat | ttgaagatat | 1200 |
| taggtttggc | cctttcactg | gaaatacaac | actcatgaga | tggtttagac | aaattaatga | 1260 |
| ccactttcat | gtgaaaggat | gctcttatgt | tctatataag | ccccatggga | agaacaaaac | 1320 |
| agctggagaa | actgctccag | gggccttatc | aaagttgacc | cgaggattga | agatgagtc | 1380 |
| actggcttat | atctatcatt | gccaaaatca | ctatttctgt | ccaattggct | ttgaagcaac | 1440 |
| ccctgtgaaa | gctaataaag | cattcagcag | ggggcccctc | tcttcacaag | aagtagaata | 1500 |
| ctggattta | attggagagt | caagtagaaa | acatcctgcc | attcactgta | aaagatgggc | 1560 |
| agatattgtc | actgatctaa | acactcaaaa | tccagaattc | ttagatatcc | gacatctaga | 1620 |
| gaggggctg | cagttccgga | aaataaagaa | ggttggagga | aatttgcatt | gcatcatagc | 1680 |
| attccagaga | ctcagttggc | agagatttgg | cttttggaac | tttccatttg | gaaccattac | 1740 |
| acaagaatca | caacatccca | cacatgtccc | gggaattgcc | aaatctgaga | gtgaggacaa | 1800 |
| tatctctaag | aagcagcatg | ggcgcctggg | caggtccttc | agtgcgagtt | tccatcagga | 1860 |
| ctcggcatgg | aagaacatgt | ctagcatcca | cgagaggagg | aacagtggct | accacagctt | 1920 |
| tagagattat | aatggcaatg | actgaccatg | ccaaaactta | gccactggtg | ttacccacac | 1980 |
| agctgttatg | tacaggactg | cattaggaca | tcagctggtt | ttattaagtc | tgtcaatagg | 2040 |
| aacagatttt | gtggtacaaa | acacaccctg | tagttctcta | gtaaaaaagc | ctacatagga | 2100 |
| ttactatggt | tggcttcaaa | tatacaggca | ggtaagcaca | gaaccccgcc | cttctaaagt | 2160 |
| taaaagtaga | taagcaatct | ggacaaaggg | tttcacaaaa | tccaatacaa | tcaaaacggc | 2220 |
| ttcaaagcaa | aaacacaaat | gcatttaatt | tgaaaagcat | cgaaacttga | actacttaag | 2280 |
| catgaagcga | cttattgata | cttgatccct | agcatttatt | acaacacttt | aattcctaag | 2340 |
| gcatcatctg | tccttaaaaa | atgggggcag | tcaaggtcta | gtttttgctc | atggttaaaa | 2400 |
| ctaatttaaa | attatctttc | tagtctagtt | gttctttcag | tgctaacagt | atccacctcc | 2460 |
| catcgttgct | ttcctgaata | actctcagga | ttctccaaaa | agcagcagaa | actactccag | 2520 |
| gaactgacct | tttctctagg | tgcagatagg | tgacttaggt | cattgatcct | gatactcttg | 2580 |
| acttggcacg | tggttgtgaa | atagctacaa | gaagaatata | ggtctggagc | gaagtctgat | 2640 |
| gttctagaac | aaaccttgtt | tcagggatat | agttagagag | cacttggcat | ccaaagtttc | 2700 |
| cttatccacg | gtaacatgtg | ctgtgagatg | tcacatttga | cttgtctctt | aatggagtca | 2760 |
| tgtgttaaca | acagcactga | tgtcatgttg | gcaatgtcca | gctcactctg | aggaagactt | 2820 |
| tgtattttca | actctgagcc | gtttcctttt | gtgaaacctc | caagcaatta | ggtgttggaa | 2880 |
| gtgtgagtta | catattctgg | aagtgtgagt | tcaatacttg | agctcctctt | tagcggctct | 2940 |
| tgttttcctt | ttgctgccaa | ggtgtgactc | atagccgtct | atgatgctgc | tctttcacgt | 3000 |

-continued

```
cgtaggttta ttccaggatt caaatcagta acttggtgat tacaaggtgc tgagtatgtt    3060
ggaaccattg caatacacct caaagggagg tgtcggattt tgacttttta aaaaaattt    3120 tcatttttct cttgaatttc atatccatct atccactcat atatgtttag cctacagaat    3180
tacaaactag tcctgtttct gaagaggttc tttagcttga aatgtaaagg actgaaagat    3240
ttgtaggtgt tcttttgtta cttcacactg gaactttgaa aatgttttca tcaaataaag    3300
ttttgttttc ta    3312
```

<210> SEQ ID NO 27
<211> LENGTH: 502
<212> TYPE: PRT
<213> ORGANISM: Mus musculus

<400> SEQUENCE: 27

```
Met Pro Asn Ala Thr Glu Ala Gly Lys Ala Thr Asp Pro Gly His Gly
1               5                   10                  15

Glu His Thr Ser Glu Asn Lys Ser Pro Glu Glu Gly Leu Gln Gly Ala
                20                  25                  30

Val Pro Ser Phe Tyr Thr Ser Ala Ser Glu Ala Pro Ile Ala Pro Arg
            35                  40                  45

Gly Asp Gly His Tyr Pro Ser Ser Cys Pro Val Thr His Thr Arg Glu
        50                  55                  60

Lys Ile Tyr Ala Ile Cys Ser Asp Tyr Ala Phe Leu Asn Gln Ala Thr
65                  70                  75                  80

Ser Val Tyr Lys Thr Pro Ser Leu Thr Arg Ser Ala Cys Leu Pro Asp
                85                  90                  95

Asn Thr Ser Leu Ser Ala Gly Asn Thr Thr Arg Tyr Ile Gly Ile Ser
            100                 105                 110

Thr Ser Thr Ser Glu Ile Ile Tyr Asn Glu Glu Asn Asn Leu Glu Asn
        115                 120                 125

Leu Ser Thr Gly Met Gly Lys Leu Pro Leu Ala Trp Glu Ile Asp Lys
    130                 135                 140

Ser Glu Phe Asp Gly Val Thr Thr Asn Leu Ile His Lys Ser Gly Asn
145                 150                 155                 160

Val Lys Lys Gln Phe Ser Lys Lys Thr Ser Asp Lys Lys Gly Arg
                165                 170                 175

His Gln Arg Glu Cys Leu His Tyr Ser Pro Leu Asp Val Lys Gln
            180                 185                 190

Arg Lys Val Leu Asp Leu Arg Arg Trp Tyr Cys Ile Ser Arg Pro Gln
        195                 200                 205

Tyr Lys Thr Ser Cys Gly Ile Ser Ser Leu Ile Ser Cys Trp Asn Phe
    210                 215                 220

Leu Tyr Ser Ile Met Gly Ala Gly Asn Leu Pro Pro Ile Thr Gln Glu
225                 230                 235                 240

Glu Ala Leu His Ile Leu Gly Phe Gln Pro Phe Glu Asp Ile Arg
                245                 250                 255

Phe Gly Pro Phe Thr Gly Asn Thr Thr Leu Met Arg Trp Phe Arg Gln
            260                 265                 270

Ile Asn Asp His Phe His Val Lys Gly Cys Ser Tyr Val Leu Tyr Lys
        275                 280                 285

Pro His Gly Lys Asn Lys Thr Ala Gly Glu Thr Ala Pro Gly Ala Leu
    290                 295                 300

Ser Lys Leu Thr Arg Gly Leu Lys Asp Glu Ser Leu Ala Tyr Ile Tyr
```

```
                305                 310                 315                 320
            His Cys Gln Asn His Tyr Phe Cys Pro Ile Gly Phe Glu Ala Thr Pro
                            325                 330                 335
            Val Lys Ala Asn Lys Ala Phe Ser Arg Gly Pro Leu Ser Ser Gln Glu
                            340                 345                 350
            Val Glu Tyr Trp Ile Leu Ile Gly Glu Ser Ser Arg Lys His Pro Ala
                            355                 360                 365
            Ile His Cys Lys Arg Trp Ala Asp Ile Val Thr Asp Leu Asn Thr Gln
                370                 375                 380
            Asn Pro Glu Phe Leu Asp Ile Arg His Leu Glu Arg Gly Leu Gln Phe
            385                 390                 395                 400
            Arg Lys Ile Lys Lys Val Gly Gly Asn Leu His Cys Ile Ile Ala Phe
                            405                 410                 415
            Gln Arg Leu Ser Trp Gln Arg Phe Gly Phe Trp Asn Phe Pro Phe Gly
                            420                 425                 430
            Thr Ile Thr Gln Glu Ser Gln His Pro Thr His Val Pro Gly Ile Ala
                            435                 440                 445
            Lys Ser Glu Ser Glu Asp Asn Ile Ser Lys Lys Gln His Gly Arg Leu
                450                 455                 460
            Gly Arg Ser Phe Ser Ala Ser Phe His Gln Asp Ser Ala Trp Lys Asn
            465                 470                 475                 480
            Met Ser Ser Ile His Glu Arg Arg Asn Ser Gly Tyr His Ser Phe Arg
                            485                 490                 495
            Asp Tyr Asn Gly Asn Asp
                            500

<210> SEQ ID NO 28
<211> LENGTH: 34562
<212> TYPE: DNA
<213> ORGANISM: Mus musculus
<220> FEATURE:
<221> NAME/KEY: misc_feature
<222> LOCATION: (349)..(554)
<223> OTHER INFORMATION: KDEL exon
<220> FEATURE:
<221> NAME/KEY: misc_feature
<222> LOCATION: (1630)..(2075)
<223> OTHER INFORMATION: KDEL exon
<220> FEATURE:
<221> NAME/KEY: misc_feature
<222> LOCATION: (2300)..(2681)
<223> OTHER INFORMATION: Exon A
<220> FEATURE:
<221> NAME/KEY: misc_feature
<222> LOCATION: (2794)..(2835)
<223> OTHER INFORMATION: Exon B
<220> FEATURE:
<221> NAME/KEY: misc_feature
<222> LOCATION: (3269)..(3579)
<223> OTHER INFORMATION: Exon C
<220> FEATURE:
<221> NAME/KEY: misc_feature
<222> LOCATION: (9571)..(10171)
<223> OTHER INFORMATION: Exon 1
<220> FEATURE:
<221> NAME/KEY: misc_feature
<222> LOCATION: (9696)..(9698)
<223> OTHER INFORMATION: Translation initiation codon (ATG)
<220> FEATURE:
<221> NAME/KEY: misc_feature
<222> LOCATION: (10945)..(11071)
<223> OTHER INFORMATION: Exon 2
<220> FEATURE:
<221> NAME/KEY: misc_feature
<222> LOCATION: (12030)..(12125)
<223> OTHER INFORMATION: Exon 3
```

```
<220> FEATURE:
<221> NAME/KEY: misc_feature
<222> LOCATION: (12562)..(12666)
<223> OTHER INFORMATION: Exon 4
<220> FEATURE:
<221> NAME/KEY: misc_feature
<222> LOCATION: (12885)..(12979)
<223> OTHER INFORMATION: Exon 5
<220> FEATURE:
<221> NAME/KEY: misc_feature
<222> LOCATION: (16786)..(16962)
<223> OTHER INFORMATION: n = a, c, g, or t; length of "nnnnnnnnnn"
      nucleotides is undetermined.
<220> FEATURE:
<221> NAME/KEY: misc_feature
<222> LOCATION: (20099)..(20231)
<223> OTHER INFORMATION: Exon 6
<220> FEATURE:
<221> NAME/KEY: misc_feature
<222> LOCATION: (21686)..(21772)
<223> OTHER INFORMATION: Exon 7
<220> FEATURE:
<221> NAME/KEY: misc_feature
<222> LOCATION: (24881)..(24977)
<223> OTHER INFORMATION: Exon 8
<220> FEATURE:
<221> NAME/KEY: misc_feature
<222> LOCATION: (25952)..(27613)
<223> OTHER INFORMATION: Exon 9
<220> FEATURE:
<221> NAME/KEY: misc_feature
<222> LOCATION: (26243)..(26245)
<223> OTHER INFORMATION: Translation termination codon (TGA)

<400> SEQUENCE: 28
ccagacttgg tcctttgcaa gtgcttttca ctgccgagcc atctctctag cttttttttt      60 ttttttttt ctctctagct ttttaagttg attattctca caggtgtgtc ctcaaggagc      120
aacttttcta gtaatgtttc ttggtcttta gtgaattata atccccatgt aaataatcaa      180
tatctctctt ttgccaagtt gcctaattta gttttcaatt agaaaaacat ctagttttt       240 tttccattta gtgaaaaaag tatgctaagt ttttgataga attcttattg atggaatgac      300
atgccttttt gtatacaaat cctaccataa attttgttt caaaataccct cttaaaacat       360 aaggagactc ggcaacatgt tgcccatggt gtttaacctc tatcttcaga tttctgtagc      420
tggcatacat tctgtatctt actatgaagg aaccgtcctt tcgatctaaa acctggacac      480
caactctcgt gaactgctca tcgggtgctg agatttta ac ctggaacacc ttttcacctg      540
gagaagatgt aaacctgtta tggaaaacaa tgagagatga gggttattt taagatcaaa       600 tgcacgctac ttattctctt taatgtgtaa aggttggacc ttctgcttta tcctgatttt      660
aagatattgt tgttcgatta ctctcttagg cttttaggac cagaaccaat atgatagaac      720
aaagataaaa aagaaaacaa taataacata aaataatttc attagatagt tgccaggaga      780
taacacttaa gactagcaat ctatttagca taccaaatag agcactatca gtgtactatt      840
attaattcat aaccaacaca gctggcaatt tgtcatttgt aacatgttta cttcaaggga      900
tgaccttatt tgaaaaattg ttcttaatgg cttaaaatac aatccagtac tgtgggcta       960 gggagatagc tgaatggttt agagcattta ccattatgta aaagacttag ttcagttcct     1020
agtatccatt gtccttaagg ctcacaacta tctgcagttt cagctcaagg agattcaagg     1080
ccctcttctg gcttcctcca gcacttgggt gtgagtatac accctaccca catcatgtaa     1140 ttaaatatt actactaata aaagtctaac aaatatacca gtactctaaa ttatgtttag      1200
ttatggggga aatcaaaata actggtcatc atgttagtaa cacaagtgtt ttggactgaa     1260
tattcctgca ttttgaatgc atttagtttc tagtgtttag ttttcccatt taaaaataac     1320
```

-continued

```
ggagatttgt ttagcctcaa ttcccatcta aacagccaag aagagagctg ttattttagc      1380
aatattattt acactataca tatttcagaa ttattaagtc acagagaaaa gttgattttg      1440
aaggaaaagt ctattataac cagatgtaga cagcactcga gaattctgga atgtaaatgg      1500
acagcagtaa agacgagtcg gggcatataa agatgaagga caaaaccaaa ataaacaaca      1560
ggaacaaaaa cccctcgagt tattttaaac cgcgatctca aatagttgag gagtcatttc      1620
tccacttact gttcccctga ggtatccacc gcccgaatgt acgaaatagc gggcaggaag      1680
gaccacgtgt gcttttagcc cgggtcccat atttcgctct tctctgggct cagctcctct      1740
ctccgccggt ctgggcaagt gctggcacag tccccagaaa aaggcaggaa agcagcgaaa      1800
tgctgaacat ttacaagacc gagtcttgga agatccacga ataaatgcaa acgtgctaag      1860
tggacggagc tagcctgggt aggtaggagg acggtggtca gtcctagcag cagtcaaagt      1920
ccctaaagtg tcgcttgacg tgcggggtcc gccgtgggac tatgctgtgc caagaatgt       1980 cacaacccga gcggtggcat gtccaggaga aggatgccac acgttctgct gaacctggtt      2040
aagaaccgca ggctccactt tctccggaca atgacaaact tgtgttactc ttgccactag      2100
agcatcactt tgggaacgaa tccgtcgcaa gttctagcca aggtgagagg agaaggattg      2160
gcctgcgctg tgaccagtct tagtaaagtc ttctgctagt ggatgagtgg gtcagagtgg      2220
aaaacgcgtc ccgggcccct tagcttcctg ggatatgtag tccgccatag gactagcgga      2280
aatcctgcca ggagttcacc cccaactact ttcgtccctt ccctccgtcc ctcactctcc      2340
ctcctccttt ctccccccct accttccttt ctacttcttt tttcaacttt ggagcacggc      2400
tttctggcaa ccttaaatac tacagttgcg caactagcat gtctggagtc acagcaaaga      2460
tttcccaact tatattttgt tcaaggtatc caccgcaaat ggcaggtata tagtaaacgc      2520
tgaaagggag gctaggtgtt atcaatgata cccagtcact cggtgctatt cttgtgcgct      2580
caatgggacg aaagattctg ggccttgggt aggagacttg gagatgcaag atctggtgtt      2640
gccttccagc accagagttc cgggacccaa caggaacaga ggtattcccc agcggagggc      2700
ctagcccagg cactgcggtg cgctccgcct tccgtagcg ccgtcactgc ctcgttgcag       2760 acaacccca cccccacccc caccccgccg cgccctggga aggatctggg tcgagctgag       2820
tctctgagga gagatgtaag ggatagaaat caccagaaga aagctcggcc tgagggggt       2880 gcatccgtgg gtatccctgt actctcttca ggagcgggtc ttcccvtgcg ctagcggatc      2940
ccaggcaccc ggcctgcagt ggccatcctc tctttgcacc ctcgcttctc ggccagtgag      3000
gtcaagagga gtagcaggct ttgtcctcct ccacgggta agggcgtgg aaaacataga        3060 cggcctggtt gtgagcccaa gcaaggggga ttcttttcc cctgccccc cccccgct          3120 attgttatta ttggtgatat aatcattcat cgcggcctcc cctcccagct ctcaggctgt      3180
cactgtctgc gtgccaccag cctctccagt ccctagcgcg taggaagcgg ccccccttcag    3240 gcctgcgcgc tcccctcct ggcgagcctt ttcttccggc tgggagtgag ggagcaggcc      3300
gggaggaggt tacaaggctt tagatctggt cttggccagt ggggactagg gacgcctggc      3360
actgggttgg ccaccgcagg acagtagtgg gaacccggca cagtagcgct gcagcagttg      3420
cacttgcaac atccctgctc tcccggttct cctccacctg caccttttgtc accttcaggt    3480 gcttcggagc ctcaaagagg gggcagtggg aagtctcctg gctcctcaga gtctgaactc      3540
cagagggcat catgtgctgc atgaatctca tactcacagg taggcctccc aggtctggtc      3600
tggtagtcta ggcaagggcg ctgatagaaa agggggggcgg tgggggcacc tggctgctgt    3660
```

-continued

```
cttagcagct cttatcaatc ctcagcaaaa cacttttctg ggtctcagtt gctttctatg   3720
cagaatattg attatactgt ttgtgatatg tggaaggctt tactgagatt ttattggatg   3780
tctagctctc tactgaatgt gatacttcag catgtagaca cgaaaggcac ataaatggaa   3840
aagaataaac tcaggcaatc gatatcggtt ttgcaaacag tatgtttatt tgacagaatt   3900
gttcattcca aagactttca taagtcattc ctctagtgcc gtcctagaag cttgggttt    3960 atattgctta tgagatactg tgaataaatt gagtggtatt ccgcaagtcc taatatgtta   4020
atcaaaacga gggagaacaa tttcaataat gcctagtgca ttgtagacac ctaaaaatgt   4080
ttgttagacc tggcttctac aagactaggc ctggagatgc aatttcagga aaactagact   4140
ttcaggagtt aaccatttgt gtacacacac acacacacac acacacacac acacacattt   4200
agaaagctta atcatattct agaagaaaa gttcctcact atggataggg tatctggcct    4260
agttagaaca gcaaaaaaaa aaaaaaaaat tcttcagaaa gtgacatttg agtataactt   4320
tgaaagatgg atgagaatga ataattagta agggctaca ggaagacaac attcagaaaa    4380
ccaaaaagta atgtggaagg acagaagaag gtatgtaggg taaggagttg atcttttgct   4440
tcaatagctg agggccttag gcagaaaatt tctatgagga tatatatgta gcagacttta   4500
ctctttgatg tctatgcagg gatcagacta gaaagaacag ctcaaagggt gggtggcatg   4560
aagttataag cataaagata aaagcagata taaacccag atagctgcag atacagtgct    4620
ggacaatcaa tcagccttca taactccgtt ttccctgaga ctaccattgc atcttactag   4680
aataatctat gcctgtaatg gtcttgtttc cagtagttgt ggctttcttc attctaagaa   4740
agcaggctct gagtgaagtc ctaaggatac catagcagaa gcccttcaga gtttaactac   4800
aaagggtgga gatgcagatc agtcacggga tgcaaagaag tagagtgcca gcatgggttc   4860
tgggtcattc tttttcattt tctgtgaata tcttctgata tttcataatt ttctacaata   4920
tactttgtgt catcaaacct ataaatatat gtattttcag agatattcac ataaaacagt   4980
ggttcaaatg aggaaatgtt gatatctttc attttcagtg acaactatgt aaaatcttca   5040
ggtagatggc aggtttgttt gtttttttt aagataaaat gagagcaaag agattatttt   5100
tattcagtga ccattgctta aagcatacaa tccaaaacca gatggttgca tgttttataa   5160
atcaagtgtt ttactcttaa cagcttcatc tcctagcaat ttccattgta ttttttcatt   5220
cataaatgaa cctgtttccc ttggcaatgt tatttggtta gctttggtta tttgagctag   5280
ggtcttgccc ggtgtgtact gggctagatc agaagtagct gtgtagttta gtctagagta   5340
gatcttgcag cagctctctt gtatctgcat cttgagtctt ggaattacag aaatgggcta   5400
ccacgttcta ttttgaccat actttttttt ctttccatat gttccaaatg agcataaaac   5460
catcaaactc tggtacattg tactagtccc ataggcaaaa ttatattcaa ggtgagcgag   5520
gcagtgatgg caaggtgagg ttaatgtcgg gttgtgatct acaaaaggta gagcctgggg   5580
tgcctgggat gtactgaatc aagctttccc actgccccag ctgaccatct gttgtttcct   5640
atcgttccac acccaaccac agacacatta taccctcta ccacacagct tttaaagaag    5700
aacgtgagca tcagacagag gaagtgggca atggagaagt ggagaaactc agtgctcaga   5760
ggaaaggaag cagtgtggtc tgcaagcctc atgcactgta catcctttga gtcttcttcc   5820
actgtcacca tcacacgca cacagaatga ggacaaagga gagagctcag acactacttg    5880
tacacacact aagacctttt taccaaacag tatttgaaag gaaagcactg cagatgccag   5940 cttttggtgat aatgtacttg catcctgtga gccactgtta actgaagatg agaaaaaagc   6000
ggacgggaag ttgtgagaag gtgcatctca taaggggagc tcactctgca cagataggag   6060
```

```
ttccttccta ggactgtttc cccttagatt ccataatggt gaaagtgcct tcacccttc    6120 cattcagaag atactggaga ttccggttta tcatcacatc tgttcgttag agactcagac    6180
aggcttgtgc cattcaattc tttttataatg gttattaaac aaatcataat ctgtgattat    6240
tttcatttct gatgaggaga gagattaata atggatgggt ttagtctctc atgcactgcg    6300
cggtcactgg agcctggaaa ggcagatctc gccctgcatt tggtggttgg tgaaggtgat    6360
ttgaactgtg gaagcctggc tctagaggtt tcagagaaga attttaatat gtagccataa    6420 tatttttggtg aagaatgtgg ctgctttttt gcccttgtct gaagagtcta ccggaggcta    6480
aggtgaagag atttagatta attcctttgt taaaggaaat ctcaagacat cctgatataa    6540
attctgttga gtggttacta aacttctctc ttacaaagac tgtttaatg aaaagaagca    6600 agctgagaaa ggaataatat aaaatatatg gttgcagtat taaaaggggc accaggaagt    6660
gaaatggagc tgaatcctgt gttcatggat attaaattga attaatgggg tggtgacttt    6720
gaggcaagag tccatccagc taaatttagg tccaggcatg gtagtataca agcctttaat    6780
cccaggagtc aaggcaagca ggtctctgag tttaaggcca gcctaggaca gagcaagttc    6840
taggtgaaga aaatcttaag tgcaggcatg gtggcatata cctttaatt caggagacat    6900 ctctgagttc aaaatcaatc tacagaacaa gttccaggac agccaagctt aggaagtgaa    6960
ggagttggaa acaaaaagc tggtaataga atatgggggg aggggggaa ggggccatg    7020 ttctaatccc agcatgcagc agaactcagc agctttgacc atgtggctct ggctttagag    7080
tccagaatag aagggactac tggaacaatt gatgctcgtt agctggagct aagacattag    7140
tgatgattaa gaagagaccg gtatcactga ggtgtaatct ggcgttttct gagagcacaa    7200
agaagctgtg ttccagagat agccaatgtt gtccctcgtg ctgcagctgg acttggtagt    7260
gtgtaagaac cacccaagtt gtactggttt tgaaggtatg gaggagtcat ggagagcagc    7320
cgaggctgct gtgagaggcc atgggaagcc actggtgaag gtgcagcatt agttgtagtt    7380
gatggcccag gactgaaggg gccatgcaaa gaagttgagg cttgactcca tgaagagagc    7440
ctacgagagg ctattggtga atcctagttg cagtggaaga ccccagggta ttggagatgc    7500
cactaccatg gggatgatca ccaagaacag cagcagcagt ggagtagagt caaccagagc    7560
ctagagtgct acagagagca gagctggaga tatgacccaa gcccctttgaa ggagtccaga    7620 agatcatgtg tggatcccag acattggaaa gagaagctgt aatgttgaag tggccttgga    7680
taccctaaga tgttcgagat tgcagagctg tggaatacct gtcaaggaaa gctgctaaca    7740
gggagtggaa tcacccagga gaaaaaacct tgttgcagtc agtaaagatg aaaagggagt    7800
agagatatga agacagcttt gacatagaca tggagatgaa gagtttggat tttgcccagc    7860
tggtgtcctg tcttgttttg gggattacag ttaagtgatt ggatgaatgt cagaagagac    7920
tttgaccttt ggacttttaa cattgttgag actgctgtag actatgggga ctttggaagt    7980
tggagtaagt gtagtttttt attatgctgt atttaggtat ggccctatag actcatatgt    8040
ttgaacgagc ctatgggtcc atggagtaga atgtagtggt ttgagtattc ctagctcagg    8100
gagtggcact attaggaggt gtggtcttgt tggagtaact ttgtcactgt gggtgtgggc    8160
tttaataccc tagtcctagt tgcctagaag ccagtcttct cctagcagct ttcagatgaa    8220
tatgtagaac tctcagcttc tcctgcacca tgcctgcctg gatgctgcca tgctcttgcc    8280
ttgatcataa tgcattgaaa cttggaacct gtaagccagc ctcatttaaa tgtcatcttt    8340
ttaacagttt cctttgttat ggtgtctgtt cgcagcagta aaaccctaag taagacacac    8400
```

```
gctataaatc actcattaca atgtataatg tacaaaaagc tcatcttgtt gaacctttca   8460
tcccaaggca actgctaagg tgtattgtag acttgtccct cctggaggtc ctgggctgtt   8520
aggggaccag ctcctttgtg attggcatgt ttccaaagtc cattcacgtt gtatcatgac   8580
cagtagttct ttttattgca aagtagaatt ttaccaaatg catgtggcac ttttatccat   8640
aattcagttg ctaggctttg ggttgtttcc acttttttgcc attcatgggc atggtttaat   8700
gttttctgta tgtatctaga acagcaattt ccatattaca tgggaagtgt tgaaatgtat   8760
gaaaactgct ctgtaaccct atatcatttt atatccttga aagcagctta tgaaggatct   8820
gattcgccac acattttcta atgctctttg ttatcgatgt cttttttttt ttttttttaa   8880
agatagggtt tctctgtgta gccctggctg tcctggaact cactctgtag accaggctgg   8940
cctcgaactc agagatctgc ctgcctctgc ttcccgagtg ctggtattaa aggcatgtgt   9000
caccactgcc cggctttatg tctttttatt atagacatct tggtgggtat gagttggcaa   9060
accattgagg ttcggattgt gtttccatag caacttatga tgaggaactt cttttcatgc   9120
aatcattgtt catctctgta gcatctttac agatgtgact tcccctttta actaggttat   9180
gtatattttc tccttataat ttgttttaaa ctaattttg tgtgtatgtg tttatgtgta    9240
tatgtggtgt gtgttttcct gcctctcttt acccagagct ggcattatgg tttacacagc   9300
ttcttattga tctattgttt aatgtgggtg ctggagatcc agttcagatc ctcatatttg   9360
catgacaccc ccttaaccaa ctaagccata ttccccatcc gcaagctcat ctttaatgta   9420
agatagatgg ttagtaatca taactcagga tgtatggtca taaaatcaat atgcattgag   9480
tgcaggtata tgaatcatac aataatgttt attgccattc atcatgcctg ctggatagtc   9540
aatcagtctt tcttctctgt cttttcttag gatcccattt gtcagctctc aagcctttt    9600 agaatcctgt gaacatttgc caaagttgct ttttttttt ttaaagagag ggttgcggct    9660
tcttcctagg aacagagaca tctgcatttg ctctcatgcc taacgccact gaagctggaa   9720
aagccactga tcctggacat ggtgagcaca catctgagaa caagtcacca aagagggtc    9780 tacaaggtgc tgtaccatct ttctacacaa gtgcctcaga agcacccata gcgcccagag   9840
gagatgggca ttatccatcg agttgtccag tgactcacac tcgagagaaa atttatgcga   9900
tctgctcaga ttatgccttc ctcaaccagg caacatcagt ctacaaaact cctagcctaa   9960
cccgctctgc ttgcctccct gataacacct ctctttctgc tggaaatact acaagatata  10020
ttggaatttc aactagtaca tcagaaataa tctataatga aggaaaataa cttggaaaac  10080
ttgtccactg gcatgggcaa gctacctctt gcatgggaga ttgataaatc tgaatttgat  10140
ggggtgacta caaatttgat acataagtca ggtaagaagg agctatgaag tttacaggta  10200
acaacaatca gaaacgaatg ctatctattg ctaagtcttc caatgaaatg ttttttgttg   10260
ctaagccagc agcatcattg ccatcttatc tgtcattgca gttttttggtt ttgttttgtt  10320 tctttcgtaa gtaaccctag atatggttag tctctgactg tgttgcccat ggaaacttct  10380
aatatcatat gtgcatttga gcagctttga aaatcaaaaa gaacaaaata taagtattaa  10440
agataataca gtagcttcaa aaaggctact gacataacta gaatattacc attatcttac  10500
agttttgcag agatgtgata atattttcta attcaggagg tattaagaca ttttttgtttt  10560 gaaaaaattt gagttaaaaa agaacattca ttttgatcaa agtcttgatt ttatttaaag  10620
ctacaattat gtggctctct tttctaaacc atattctaaa gtccatttta tttctcatgt  10680 tatttttaacc cgctctaaga gtctagctct ggacttggat acaatcttga taggaatacc  10740
gtttctgatg gttcaaattg ttttaaattc tcttcctgct ttctctctag agaagagtag  10800
```

```
tattctagaa agcacaggta ttactttgag acatttgcag ataccatttt cagaatgcat    10860
ggccagtcct ctaattctgt tgtaacttct ggcacgggtt ttactttatc tgaacatttc    10920
ttgtattact tctttgttct gtaggcaatg taaagaaaca attttccaag aagaaaacgt    10980
cagataaaaa agggcggcat cagagggagt gtctccatta ttctcctctt gatgatgtta    11040
aacaacgcaa agtgttagac cttaggcgat ggtatgtggc catgtcagtt tttacttttt    11100
ccaatcttaa aaatatgtaa tttgacatta attttcctga gtataggtta ataaattata    11160
ttaactataa acactgttag ttccaaaatt atgtctagat actttaggta tatctccgat    11220
tttggaagta gtctagttta gctcagcctg gctgtcagtc tcattcagtg atccctctta    11280
atgttaagcc acattggctg acacttaaag tcggaatagt cattcacctg gttgttcttt    11340
gtgactaatt ctataggcag tgatggtagc ttacagctat tttaattatt gccataccta    11400
gtaaaatgaa caatatttcc tgtatgtata ctttcagact aaattgacac tttcctttct    11460
agattgttct aaaagttcat catatgcgtg cttgtttgtc atggcccgtg agtttcaatt    11520
tagagtttcc agctttcttt ctttgtctcc gtctctccct ggaggatttg tgttttcctt    11580
ttaggtcccc agtgacagtt ctgttctggg gatttctgcc caggggttca tgggatgtgc    11640
ttagcctgag gagaatctct gaatctcttg acaaaggag agcggtttgc tttgcttctc    11700
cagtatttca gaagctgcag aggatgcctg gcccactcaa atgagaattc acatagacat    11760
ttgagtcgtt gccatcaaaa tttcttggtt tgaataagac atactttagt aggttgctgg    11820
ccataatgta gctcatcttg ataaaacatg attttatgc tcatgcattt tttatgtgtt    11880
taataggtag gggatacttt aaacaaaaaa tgagttacac tgcattgaag tttgtattat    11940
ggtcacgttt taaatcaccc ataaactata tatttctgtt ctgcatgttt tgtattcatt    12000
cgagtgaaga atactgtttg atttcccagg tactgcataa gccgaccaca gtacaagact    12060
tcatgtggta tctcctcatt gatttcttgt tggaatttct tatacagcat aatgggagct    12120
gggaagtaag tatgccagtt tactgctgac accaaactcc atctttgaaa gtagtgtcaa    12180
ggaaactgag tatagtgatg cacacctta atcccagcac tcgggaggca gagtgaggca    12240
gatcactgtg agttggaaat cagactggtc tacagaatag attctaggac atctagggct    12300
acatagagac cctgtctaat tttaaggtac ctgtgtttata atggaaagtc tctgagagtt    12360
gactttgtac aaactgagaa aaattgtgtg tattgttaca agcctttcag gttaaaatat    12420
ttgcatgtat tcttttcaat aaaataaatg aaaaatattg ctaaaatgtt tctaagctaa    12480
gcctatatat tactaacact ggggcatatt ttatttgcat atgactggaa ctgtgaaatg    12540
aaaggaatgt ttcttttata gtctcccacc tattacccaa gaagaggcat tacatatttt    12600
gggcttccaa cccccatttg aagatattag gtttggccct ttcactggaa atacaacact    12660
catgaggtac ggagctgcca cttagggatt acatacgcct tcctttaatt ctgtgaagtg    12720
ataactatgt agtgtttggg gacggtacaa gatagacttt gctgctgggt cgcaggctcc    12780
ctaagatatg ccatgtgtgg gctgtgcttg ggtttctgtg caattaggac agtagcctgt    12840
gttatgaaac tattgctatg agcaaatctt cttcttaatt tcacatggtt tagacaaatt    12900
aatgaccact ttcatgtgaa aggatgctct tatgttctat ataagcccca tgggaagaac    12960
aaaacagctg gagaaactgg taggtgaaaa tacacacaaa cacacaaaca cacacacaca    13020
cacacacaca cacacacaca cacacacaca caccccaaac tttcaggttg agtacatcgc    13080
agaaattggc cacgttgttt cctgggatat caaattaact cttaatagtc tgatgttttc    13140
```

```
atacctcttt aagaggaaaa tcatgatagt aatatataga gcactttcaa tattcaattc    13200
cattttcacc cctttctgat attttctatg taaatgttac aaatttaaag cattgtctat    13260
aaacactgtc tcttaacaca ttgttttgtc tgggtttagg acttgttata tttgcggtgc    13320
gcatgttgtt tgtgcgtgtg tccaccttct acgcaaaaac cttgaattta cagtttattt    13380
taaaacagag tgagagcact tgaggacatg tgatgttgga ctggcatcaa gtgaatacac    13440
agaacagcag agtaacaaac tgggaagtga caacactctg ttggttttaa catactcatt    13500
aatgaagttg aatttaagga ttatttgtta tctattagtt gaattatttg tattgtttaa    13560
tgatttcact tataaatggt cacaataaac tttgaaattt atggagcagg ctgctgtaag    13620
gtcctgctgt taaagaagaa acttttcgga ctatcctgga aacgggagac tttatctaag    13680
gttgttacag tggggtgttg tgataaggat taaagattaa cctcggcttc aaaggtgata    13740
aaggtggctg taaaggcaga tggataattg atgcgaaaga atacagggta ttgagaaact    13800
ataggtagta atgcaaattt aacaacattc tcaaagtata aaaatataaa acaattaata    13860
aaatgtagta aaacaacaaa agggctcctg agtgttagct taggattagt attcagaaat    13920
tttatgattt ttttttttga tcaattgtgc tgtccagtat gttttggagc ataatttgtt    13980
agagatttta gtgtatggat ctttagaaca acagtacttg gtttactttc aaatggtcct    14040
ggttcgtaca attctccctg agttatttat aaaatgagtg gaaggatatg aatgctgtta    14100
tccagtttcc taacggacta ggatatgcta ggctgcttgg caccgacagg cacactctga    14160
tttcgtttac ctctgtttaa acatccttca acatatgcac agtctttttac ttatagaatg    14220 gaataaagtg ttttccttta caaggtttaa aatgacatat atgcatgtgt ttatttcatg    14280
tgtgatcaaa ggacagcctg agggatttgg ttctctcctt tcaccatttg ggccctgggg    14340
atcaagcttg ggcaagaggg taccgttact tccaaagcca tcttcctaag cccctcccct    14400
tttatctctc tttttatgca aaggcaagat ggtagtttct tcagatttct tcaaatacag    14460
tttaatgaca tcttttacca attgtggtct ccccaacccc cttccacctc cacagcctgg    14520
caccatttct gaaatgtccc tggacagtct agccccagga tcctattatc tcatgtactt    14580
ctatccattg gccccagaat cctattagct catgtactac ttactatcca ttggcctctg    14640
tcaggtgggg tttgggatgg actatcatga cttttatctt tttaatgtaa atgtcttgct    14700
cagtgcccat agtcaccatc tgaagtagcg ctttgatgct tgattctgt gtatgataca    14760 catcagcgat agttacactc aggtcggcag agcactgata ttctgcttcc tgtcctcatt    14820
ttgtccatac tctctcttat agaagagctg ccaagaggag ctttcttcaa tggtttcgga    14880
tcttcaatgg ttaaaaccat ggccagctgg tattgcttat ttagtaacta ctcggaaact    14940
tccctcccca cccccaccc cccttttgagg tagatctgat tttcacagtg tgctttcagt    15000
gttcttggta cttgcacaac ctggatttag taactcaggt tcttgaatgg cagtgccatg    15060
gccctcaata gtcactgtaa atgaagcagc tcatagagtt taaaaaaaca aacaaacctg    15120
tgcacatctc aggtgtacag cacactggta ctgttttcct catctccagt gcttttcgag    15180
ttcatattga gccgtttct ttaacctgca gtgtggttat gccccttttcc acctcgggag    15240 ctctcgaggt ttgcgtacag accaagcttc atagtgttga tagcatgtgg agccaacatc    15300
aactggactc atgtgcctgc tgtatttaaa aggtatcaaa tggataggg ccttgcagga    15360 caatgccatg ttgcttgact acttaccata gttccagaat cttcccttga cttttcaatgt    15420 ataaagatgt gctctcagtt ctctaaggct cttctgcaga aggactggtt aatactaaac    15480
catcttgaag aatgtacggt gctgacagtg tattggagtg agagctataa tgccaaaggt    15540
```

```
ggccgaaccc attgacagct caagttgtcc actcctttca actctgaacc taattcttat    15600
cgcttttcc acatccatcc tgtctgtttg ctgtacagct gtggaggtag tggctttgtg     15660
acttggcttt taggtttcct ctgttattgg gtgaactata ctctgaacct cgtttctctt    15720
agcaacacat ttgtcttctt atcacagatc atttcctttg gtaactgcct tctgagtaat    15780
gctgcattgt cttttatttt agaaggtgat cttttctctg attttgtcct gaaattgtgg    15840
aggctttctc tgttttactc tacattctta cctagtgtct tgatgtatgt tcccctgtgg    15900
atttgcctct ccttatactc cttcctctgt ctagattgct aaaaccctcg ctcctcatta    15960
agttccatct tgaatgccat ccttcttga ttcctctgat ttctataccc atttgtgatg    16020
ccttaacatt agctctttca tctttcacgc tagagcttgt cttgcttcca tatggtatct    16080
gacagagtta ctaggtactc atgagttaaa tcaaaatctc catttaatct aaactagctg    16140
ctttcaaaat actgtccctg gatgcatcac ctgataactt gttaacaatg caaattctta    16200
gttcccaacc acagacctat aaggccagcc actcagactg ggctctagta agactttatt    16260
gaagtcttaa caacgagatg gtatgtagcc tctttaccag gagtttgatt ttgcattgag    16320
agaagatgca gtcattttct aattgtgttc agatgaaacc tgaggattcc ttttaaaggc    16380
ctgaaaggga ggtgatagaa gagaactgtg cacacactta ttttagctac agcagctctg    16440
ctttaagaat aagtttgctg atcttgaaaa catatgaaga atgttatgta ccttggagaa    16500
acaagagcaa acatcccatt actagaaatc atgtgtatag atgttatata tcgtatttaa    16560
caatgctaga agcattactt catagaagaa aacccatgtc atggcatttg gaaaactagg    16620
acatggtaaa agagtgtttg cagcagacaa aattatgtga ttgccaagga gggcagactt    16680
tgttatccat ttcatctgcc tctagaatcc ttacttctcc tcccctatgt gattgccaag    16740
gagggcagac tttgttatcc atttcatctg cctctagaat ccttannnnn nnnnnnnnnn    16800
nnnnnnnnnn nnnnnnnnnn nnnnnnnnnn nnnnnnnnnn nnnnnnnnnn nnnnnnnnnn    16860
nnnnnnnnnn nnnnnnnnnn nnnnnnnnnn nnnnnnnnnn nnnnnnnnnn nnnnnnnnnn    16920
nnnnnnnnnn nnnnnnnnnn nnnnnnnnnn nnnnnnnnnn nncatgatgt gattcaggct    16980
agcctgaact tgtctatggc cttacatctc tgttttttta aaatttaatt taattttttaa    17040
tttgttttt ccactccata ttccattcct ctybbyyycc cccacccca tccaccctct     17100
gactgctcca catcccacac ctcctcccca ctccaccctg tctccatgtg ggtactccta    17160
ccccccaccc cacctgatct ttaaactccc tggggccgcc agtctcttga ggttaggtgc    17220
atcatcttaa aattaattta atttttaatt tgttttttcc actccatatt ccattcctct    17280
cgcccccccc cccatccac cctctgactg ctccacatcc cacacctcct ccccactcca    17340
ccctgtctcc atgtgggtac tctaccccc caccccacct gatctttaaa ctccctgggg    17400
cctccagtct cttgagggtt aggtgcatca tttctgaatg tacacagacg gaagtcctct    17460
actgtatgtg tgttgggggc cgcatatcag atggtgtgtg ctgtctgttt ggtggtccag    17520
tgtttgagag atctcggagg tccacattaa ttgagactgc tggtcctcct acaggatcac    17580
ccttctcctc agcttctttt agccttctct aattcaacca cagggtcagc tgcttctgtc    17640
cattgattgg gtgcaaatat ctgcatctga ctctttcagc tgcttgttgg atctttcaga    17700
gggcagtcat gatagatccc tttttgtgag cgctccatag cctcagtaat agtgtcagac    17760
cttgggacct ccccttgagc tggatccac tttgggcctg tctttggacc ttgtttggat     17820
caggctctct ccatttccat ccctgtaatt ctttcagaca ggaacaatta tctgtcagag    17880
```

```
atgtgactgt ggggtggaac cccatccctc acttgatgtc ctgtcttcct gctggaggtg    17940
ggctctatac gttccctctt cctactgtca gccttacatc tctgaatgag ttcaatcttg    18000
cctgatccta aaaggtctag cctgattaat acttgggaga aagagtgaga ttctgtcttc    18060
aagagtcaat tactggaact tacactgtat tcagtggtag agcttgcctg acataactaa    18120
aggctttgag tacaagtatt attgcaaaac agtattttca gttatctgag aaagcttctc    18180
attgattaat ttaaatttaa agagatttca ggagttttc tatggcaatg gtggtaatag    18240
tcatctttta caatgttttc atctacagag tacagttaac tgaatccacc atctggaatc    18300
tatttacagt catgctcttt tatggaaatt aaagactgtt ctgaatttat tcctaaaaat    18360
tctttatcta aactgccaag gtggggtca gttttaaga tgtgaaggaa tacaactcaa    18420
tcctggggag tagctagtca tgactggtct ttgtgaagta gagattttag tagagaggac    18480
tccctgtctg tgctgatcta cctggaagtg aaagcttatg tggaatgcct tgatggaact    18540
tcagagtaga gaccagacac attaacttat gcataggcag agctcccacc cccaaaccct    18600
tgtgaggcag tcaggttgcc tctgtggagc tgctgcacac actgactagc agatctcaat    18660
ggtcatcagc tatttcagtg gtcagaaaat cgatcgctgt gaacatacca tgcaggcttt    18720
cagcttgctt tttttagggt tcccagtttt aatggactac ttgttaatga ataatttaag    18780
ttcttccagg aatggaagtt aatgaaatct cagttaatgg ctttgagtac tgagtgctga    18840
taaaattgtg tctcttacgc taatactttg gaaatcattt gacagctatt acaatgatgg    18900
gcaacagatg aggagaaaca gttgtgtaac tccagcccga ctgcagagct gatgcctttg    18960
atgtgtgtga tgcaggtgta gaaagacaat tttcttagtg tttctattgc tgtgatgaaa    19020
accatgacca aagcaactta gggaggcatt tggctggtgt gtcctgaatc ccagtccatt    19080
gagcaaagtc aaagcaggaa ctcgacaggg taggaacctg gaggcaggac ctgatgtaga    19140
gaccatagag aaatgctgct tactggcctg ctccacatgg gttgctcaga ctactttta    19200 atggaatcca gaaccagtag cccagagatg gcactgccca caatgggctg agtcctccca    19260
catcaattac taattaagga aatgctctac aggctcccct acagccaaat cttatgaaag    19320
tattttctaa atcaatgttt cctcctttca aatgactgta gcttgtggga gttgacacaa    19380
aaatgagcca atataatgat aatatttgtt atgtggcagg tgtgagtgtt attgtgtggc    19440
aggtacactc aagtgcatgc atgtgtgtgt gtgtgtacga gtgtgtgtgt gtatgcatgc    19500
acaccattgt tgaggtttgt tgttatttaa ggtttgtgtt tattcatatg cattaataaa    19560
ctttaagttg gatgtagatg ttggatgtta tttaaggttt atgtttattc atatgcatta    19620
ataaacttta agttggatgt agatccagac attagaatgt ctataattta acctaattta    19680
aggttctttt gttaattctt ttgtagactt agtttatatg tgagcgttta tagacacatg    19740
tttcacttgg gcatgcttat tcagacgctg gtagtgaggg atgcccacag cagaaaagct    19800
aagacggtga ttgtgcaatt actgggtttt acacaatcat tgaatatctt agacaacttg    19860
gtatattctt agaaagttct gataagcaag acatttgtt ttactactga gtttatctaa    19920
aactaaaagt aaattaattc atgttttgc ccacattggt agcgtctcat tcattccctc    19980
gatggaactc agaatttcag tgtattccaa attctgtctt ttagtcctta actagtcctc    20040
tgcattaaat gtggacatcg ctttgtgttc ctcaggttgt ctggttttgt ctttgtagct    20100
ccaggggcct tatcaaagtt gacccgagga ttgaaagatg agtcactggc ttatatctat    20160
cattgccaaa atcactattt ctgtccaatt ggctttgaag caacccctgt gaaagccaat    20220
aaagcattca ggtaagcatt ccatacttga taaaggcaca gcactaggaa aatttgatat    20280
```

```
acaaagtaat tttgggaatt aaacaaattc tagtctctta gaaattggga agcatggtaa    20340
tgtgttttat tcaaaccaag tgtgcatatg ttttgcagga ctgattgcac ttcagagctg    20400
ttgctcagtc attgtaagaa aaagccatct gatgtaccac ttttatgatt agtatacaca    20460
gatgcagggg ccttcccatg ttattccctg tgtcctctcc gttgccatac atgtccttgt    20520
gtcaagagtc ctacaactaa gtacattaag aagcacctte tatgctcata gtgaagaact    20580
aaggaattgt taggattttt ctccaaggga gctcaggacc agtttcatct ctaatcttct    20640
tggttatatt tgcctcttgc ttttcttaat ccagtttctg tcttttttgaa caacgtgctt    20700
ttacacacac ataaacttgg gtctctttga aggagatgct tatgtgctga gaggttgccg    20760
agtttgaatg ttattctctt taccaagttc ctcataaggg acctgaaaac agaggttagg    20820
tttaagaaca ggtggcgtga ctgtcttacc ccgctgctct gctggttgat gcacccttgg    20880
attgctgaga ttggtgatta gggaggatga aaagattggg aggctcttgg aagttatctc    20940
ttaggtgaag gcccagattc tggctgaaga acaggcttgg cctttaggac tggagggttt    21000
ttatgtactg gaggtcatgg atccctggag tcccactcaa aggtccttgg atgtggtgcc    21060
taggggaacc tggaacagag gagcagaagt tggaggactt aggaggctgg atactacttg    21120
tgtagaagga gcaagagtaa cactgctttc tctccaactg ctgatgtgct cggttcactt    21180
tctggagtga ggggcacttt tgcacttctt tgatggctcc aacctctgcc tttaccttcc    21240
ttcaggtacc tatcaaatgt aaaacatgcg ttgacttcta ctgctctgct cctttaatag    21300
ttaggcttcc ccagtgaatg cctgtgccta tgaaccatct gattttttt cttaaaaatt    21360
atgtaaatct ccaggctcct ctccagactt gaattagagt ttctggggat gggaccgaaa    21420
cattgtgtgt ttaaaatcat catcatctcc tctgatccaa gggggtgata tgttaaaatg    21480
cttataaccc tagattttga atatggaagt aataaagctc aaacctaatt caaggatttc    21540
tagaatggga ccaaacctaa gtgctcatat ccatcctaga ttaacaaagc catctttgag    21600
tatcagtgta ttttagttca aacagcattc tctggggag tgaatgccat ttatcaagct    21660
gattgtgaac gtattttctt tttagcaggg ggcccctctc ttcacaagaa gtagaatact    21720
ggattttaat tggagagtca agtagaaaac accctgccat tcactgtaaa aggtatgttt    21780
tagtagcctt tatgttttct ttaattggta atagttccgt caccgaaaga acagatcaaa    21840
attgtgtaac tagatgcatg tagataaatg tgcacacttg tgtggtctgt actctgtaca    21900
gtcttgccac agaaagttct gcattctact tctctccaat ctcacagcta accggttatg    21960
tttcccatta ccacagaagt catttttcttc tctctctctc tctctctctc tctgctttcc    22020
catataagta acatattaag aactttttct ctaaaaataa ttagaattgg ttcatttctg    22080
ctaaaagtcc tgatgcatac ttgattaaaa taaaatcttc aggactggtg tggtggctta    22140
ccaggtacag gtgcttgcat gcagtcccga tgatctgagt tagattccag gagtcaacat    22200
ggtagaatga cagaaccaat agttctcttc caaactccag acatacagaa tggcatgtgc    22260
atgcatgcgc ctgtctgtcc tccctccctc cctgttagtc tctttctctc ccctactctg    22320
tttcccaca cctgctgaga gctcctggcc cagagagggt agagacaggg catagagtag    22380
gactctggtg tggcttttaaa gactgcagat ctccagacag tctagctctc taactgtact    22440
aaaatgctgg agataccttc tgaagtccta caagctttct tgctaattct gagagtaaaa    22500
agctgttggc ttaggtgatt gacacctgta gcctgcagtg ggggattagg taaagtggcc    22560
ttttcctatc tcagcaggaa ctgcacagct ctaactttca gcctgctagt agaagtccca    22620
```

```
ggaagaaaaa gggactcttt gaaaagtgtt tatagcattt attactaagt tgtaaaaagt    22680
tacccatgaa agctatctag gagaatgggg ggtagcagga agatcctaag tggggcaggg    22740
aataattttc cctttggatc aataaacttc tattgaacca ggagacaaga ataatgcttg    22800
cagaaggaaa aactttacat aagcaaatat gcataaatgc acatgaattc atatgcagat    22860
tcacacatac acattatac atatccattc aaaccagtta gatccagctt gcattcattc    22920
ccacaattac acacacacac acacacacac acacacacac acacacacac acacagatcc    22980
atacttacat atgcatttga aacaaaagac caagcaccag tccagaaaga actcacttat    23040
tctggatgaa aaatgagctc caatctttat tgcataggga gagaaaaggc ttctaccatt    23100
tgaatgccaa atgaattaaa ctcatgtttg taagaagaaa gctttattcc ttttaatagt    23160
actaagcttg ccttaagagt agacctgttc tgttgcatgc taagaagcct gcctgcttct    23220
tctgctctct cttaagtttt gtttatatct gactaaaaaa tgttttgtct aaaaagattc    23280
tcctcagttc agttatgact cttctctttg acctcagctc tgaaacacct ttcaggatac    23340
atggctacac gattaaaagt tcaccacaag tttacacaaa ttcaaatcat aactagaata    23400
ggaagtttac gacagagaat gtttacatgt atatccatta ggagtaatta tctggctaac    23460
catttgccac ctgtcacagc tccacaggtt cactggaagt taaaaactgt aactgtgaag    23520
gtttgtatag atttaccctg tcaaaatgtt atcttctctc ctaccaccta taataaattg    23580
ttagttccct ttttatgacc gtagttaatg gttgtagaaa gtctggttac tatctagctg    23640
gcgacacaat ggaagactgg cagagttctc attgcagttt tgacaatcag aagagaccta    23700
atagcacttc cactataaaa gagcttagta aatactgata taattttagg aattcttata    23760
gggtcatcat taagaattaa gaagtcattt atttgtctat atagcattac tacaagacag    23820
tacatctttg tagatcggca gaaagctact caaaagggtg ggctaatatc tagtgattgt    23880
tgtatatgtt taataataac aggagaaata tattaatagc aggaatcttt cctaaaatga    23940 ttttccctg ggccttgcct atgggatcaa atctgtcatg gattacaatc cgaggcagac    24000
cgtctcagga agatcacctg ctagttatta gcttgtccta tgatggctcc tgacacacac    24060
ccttgctctt tttcactatt gcctgtgcat acacacagac tgacacaatc tgaggattca    24120
tggtgtagtt aagggagtac tgacatcata atgacatgga ctcttacaag ctaacatcaa    24180
ggactctatc accacatact cagaacttta atttccttta gcactgattt tgattttca    24240 aaaaaaact cataatgtcc tttaaatgat ttttcctatt gtaaattaat ttaaaaattt    24300
cattttatgt tattgctggt aatataaaga aaaagaactc cccgatttta ctatatagac    24360
cttgattttc acatctttgc caaatttact tattatttgt ataaaatgtg ctttgatttt    24420
tctccacaag catttatta gtatattgtt tattagtaat tctgacagaa tgtggcacat    24480
agtggcacac tggtaaatga agcaaaagga tcctgtaaac caaggggttc aaggccagct    24540
tatacaacat acaaaaccat accccattgc tgccccccc ataagaaaat aaattaacga    24600
gtataacaga aagtgtagta tgccactgct ttagcctgcc aggtattatc tggtatgttg    24660
acatataaga ataggaccag ttataaactg agaacattga cagtaattgg ataatcataa    24720
ctgtcactta cacacaaaaa agaagctttt aaagtctagt tgatggaaca atgctgacct    24780
aagagaaaaa tcaccaatta ttgtggcagc ttgctcatgg aaaaagctta ctaaagtggt    24840
actttgaacc tgaagaaaac tgtccttttt cttactatag atgggcagat attgtcactg    24900
atctaaacac tcaaaatcca gaattcttag atatccgaca tctagagagg gggctgcagt    24960
tccggaaaac aaagaaggta agaatactat tacattggaa gtaacttgtc gaatgaccag    25020
```

```
attgcaatat tttattaata atcttgtctt ggtaaataac agaaaccaag ttcaaactac   25080
cttagtcagg aaagtaagat tattttaagg attcaggcta actttaagct tccagctaag   25140
gatagtcata aggaaatgac acacagcact gcagtaatgg tagaatggct tatgtaggct   25200
gtgctgtact aagtgctttta tctgaatgta aatttcttga gcaataactt tcaactttt   25260 attctcaggt gtagattgag acttaacatg ccttggttga gctccatagt cttggcctaa   25320
gttgggtaaa ttatggtcac aagacagagc caggtgttca agcatgacta cagaaagaag   25380 cttttcagaaa cagatatagt atagattgag taggcaagct tttgctataa atgaagctgg   25440
gagtggtagc acatgcttgt aatctcagct cttaggcgag aggattttca tgctatctta   25500
aactattgag attattatct caaaagtctt gtgtaaacat acacacacac acacacacac   25560
acacacacac acacacacac acatgcgtgc gtgtgcacgt gggagggaat aagataggat   25620
tttagtagaa tggaggagag gagactacac acacagcaaa ggaaaagcat gattttaatt   25680
tgtgagtcag gaatatgtgg atatgactat gccgactcta ggctgtggag gggcatatgg   25740
gacacagtgc tctggtccct aagggctttta ttataatgta aaggcaggtg ttgggaaagg   25800
tgagtatgtt aaagtgttct gataaagcag agtagtagtg ttttcagaca tgtggaagaa   25860
taccaccatc acctcaaggg agtcaataag agccctaaaa acttacaaac ttatttctc    25920 tttattgtct tcatcttttt tcccttctca ggttggagga aatttgcatt gcatcatagc   25980
attccagaga ctcagttggc agagatttgg cttttggaac tttccatttg gaaccattac   26040
acaagaatca caacatccca cacatgtccc gggaattgcc aaatctgaga gtgaggacaa   26100
tatctctaag aagcagcatg ggcgcctggg caggtccttc agtgcgagtt tccatcagga   26160
ctcggcatgg aagaacatgt ctagcatcca cgagaggagg aacagtggct accacagctt   26220
tagagattat aatggcaatg actgaccatg ccaaaactta gccactggtg ttacccacac   26280
agctgttatg tacaggactg cattaggaca tcagctggtt ttattaagtc tgtcaatagg   26340
aacagatttt gtggtacaaa acacaccctg tagttctcta gtaaaaaagc ctacatagga   26400
ttactatggt tggcttcaaa tatacaggca ggtaagcaca gaaccccgcc cttctaaagt   26460
taaaagtaga taagcaatct ggacaaaggg tttcacaaaa tccaatacaa tcaaaacggc   26520
ttcaaagcaa aaacacaaat gcatttaatt tgaaaagcat cgaaacttga actacttaag   26580
catgaagcga cttattgata cttgatccct agcatttatt acaacacttt aattcctaag   26640
gcatcatctg tccttaaaaa atggggggcag tcaaggtcta gttttttgctc atggttaaaa   26700 ctaatttaaa attatctttc tagtctagtt gttcttttcag tgctaacagt atccacctcc   26760
catcgttgct ttcctgaata actctcagga ttctccaaaa agcagcagaa actactccag   26820
aaactgacct tttctctagg tgcagatagg tgacttaggt cattgatcct gatactcttg   26880
acttggcacg tggttgtgaa atagctacaa gaagaatata ggtctggagc gaagtctgat   26940
gttctagaac aaaccttgtt tcagggatat agttagagag cacttggcat ccaaagtttc   27000
cttatccacg gtaacatgtg ctgtgagatg tcacatttga cttgtctctt aatggagtca   27060
tgtgttaaca acagcactga tgtcatgttg gcaatgtcca gctcactctg aggaagactt   27120 tgtatttttca actctgagcc gtttccttttt gtgaaacctc caagcaatta ggtgttggaa   27180
gtgtgagtta catattctgg aagtgtgagt tcaatacttg agctcctctt tagcggctct   27240
tgttttcctt ttgctgccaa ggtgtgactc atagccgtct atgatgctgc tctttcacgt   27300
cgtaggttta ttccaggatt caaatcagta acttggtgat tacaaggtgc tgagtatgtt   27360
```

```
ggaaccattg caatacacct caaagggagg tgtcggattt tgactttta aaaaaaattt    27420
tcattttct cttgaatttc atatccatct atccactcat atatgtttag cctacagaat    27480
tacaaactag tcctgtttct gaagaggttc tttagcttga aatgtaaagg actgaaagat    27540
ttgtaggtgt tgctttgtt acttcacact ggaactttga aaatgttttc atcaaataaa    27600
gttttgtttt ctactttaa tcctatgaat tttaatgtct atgtttaagt tagcgtgtat    27660
tcttgtaact gtgtgaagca gatgataatt tgctaattcc atgtaatcag tgttataaga    27720
aacatcttac aattttata atcaccggaa caatgtgaaa agccaataac ttccattcca    27780
tgcttgctac ttttcaagta cttgagcact gattctctaa tccttcacaa cgtgatttag    27840
gaattttctt atattaatta aaaaaaaaag gttggaattt tgtggttca ggcatatttt    27900
caatataaac tgctttaat agttcaattg agtatttcaa agcaataggt ttgaagagct    27960
aagaggaaag aatacaaatg caaataaga tgtaaacctt aagaacaaag tgacagctgg    28020
gaaaataaga tgagtttatt tcctgtacac taatcatatg ctttattgaa atcactgaca    28080
gacatctgac cacttaaaac ttaagcttac agattaaag atgacttaga gcacagaatg    28140
tttgaattca gtgggagttt ttttttttt ttttttttt tttttcaggg tatgtaggta    28200
agaggtcctg caaagtccct tttgaaaact agtaatattc ctatttgatt tgttagtcaa    28260
cctgtcttag aaattgtcat agatcttcta aggaaggata ctgattggct cagaagttac    28320
aagttgtctc acctgtgaga ttatgtcctc tttggtagtg atgtggaaga acggttacgc    28380
taatgagcat ggtatttata atagtagttg aaaagctatt taaatgcttg ctataattat    28440
tattttgaaa atgtgttctt aattgattag tctgttatca gcatggcaac ctgcaggcag    28500
gcatggcact ggagaaggag ctgagagtcc tacatcctga tcggaaggca gccaggagag    28560
gacagtcttc cacaggcatc caggaagaag gttcttttcc acacgaggag gagcttgaga    28620
ataggacctc aaagctcacc cctggtgatg aacttcctct gacaagggca cacctcctaa    28680
gagtaccact tcccatgggc caagtatttt gaaaccacca catttataga acctgttaat    28740
cctttatgca ctactacagt tacaggggta tatcccatca tagaaaagcag gtatagcaac    28800
tgaagtgttt ctcaagttgc tttgttacag ccatggagtg agcctaggca accactccag    28860
aacctatggc attatttaac tcagtttcac tcttagcatt tctaccctgc caatcttca    28920
cttaaaaaa aaaataaaga caaacaaaa gccctgatct ctatgccatc actttctagg    28980
tgctttcata ggaaaatcag aacagcaccc cagctgttgg tggtagtgac gtgtgccagc    29040
taaaactgag gtttgcattg gtggagcatc ttgcctacgt ttatagagat tcttagtttg    29100
ctagagcttt cataataaag tactcaggtt gcttaaaaac aagtttgttt ttgtttcgtt    29160
tttttttcc ctcacagtta catagaccaa gacaaggtct ggcacatttg gtttcttatc    29220
ttttggactt gaagctggtc acccttttg tcctcccatg gcctttcctg tatttgtggg    29280
catactttat gatgttccca ctccttctta ttagtataac cgttatactg gattagaggc    29340
caccctgata gtctctctgt atatcaatgg tgaggtagaa atcacatcca tggacttaga    29400
cgtatcttca tgtttgtgat ctattactga ccatgactct gtcagacaca gaaatggttt    29460
tgttaagttc tggttcatgt gcccttaggt gcctaatggc cttattgttt tgacaatcat    29520
tttctaaaaa tcactttgaa tacaggcaca ttgtgcagta cttatattca acacgtgaat    29580
tttgaattct acatggatac tgacctgaat acatagtaat tccgcggtcc agccaagatc    29640
tgaactatca tctgcatgac ctctactcca aatattttcc acaggatgca aaatgtcctg    29700
gggagcatca gacctgagac ttgagaggtc acttaagcaa cattgacgaa ctcccgctat    29760
```

```
gcactactaa ggaagggtg taacactcat caagattgat accagtttca acatgtttac    29820
agtctactgc tggaagtgat aaaaattaaa caggcaatta aattgccttc agtaaaatac    29880
gactttacta aaatgcaaaa gtccgtaatt ttacacattg agggaatgct aaactgtaaa    29940
ccacctgttt ggacatagat acgttttttgc taaaatttga cttctgatag acttcagctg    30000
taaatgaatt tttttcccca gaaattatct acttctatcc cttccttttt ttttttttttc    30060 ttagacaagg ccatgtgagt cttgagcttg tgatattcct gcccatctcc cagatatttg    30120
tgccaccatg tcgggctatc tattgtttct tatcaatctt tttactgggt ttgaataatt    30180
acaataccgt ccatcaaaat tgagccattg tatgctaagt gctttgccca tattcactct    30240
gctcggtaaa agattgttct tttgtactgc ttacagatga cggagaagaa attctgaaga    30300
aacgtaatct ccacagagct aactctatag taaggcctca aagggctgca ttcgatttag    30360
aatgtgcata tcgtgtcttt tcctggctct actctgcccc aagtcatttt tcccaattgt    30420
ggaactcaaa gtttcagatg ctggaggaaa ttcaaagtta agcactgcgt tgtactgcca    30480
tccagttact gcacgttgtg aaaatatttg ccttcaccaa agtcaagatg ctcatctttc    30540
cgttcttttc ttgtcgaacc caatacttgg cgccaaatcg gcaaagctgg ggaggcaatg    30600
gggagactga tactgaaaat gcacaaagga gacctcactc cattaagaaa gccaatatgt    30660
gcaaacactt tttgcgccta acagtcagcc gaacagaggc acagattcaa aaccgaatcg    30720
ccacacacac tgacttcggg agtgctcggg cgtgggattt acgtgtcaag tgtcaacgcg    30780
ggaatcccaa ccctcgcgtt cacttggaag ccaagaggtt tcatcgtttg gtcagcggga    30840
gaaatcactc gcgaccggag gaaggctcgg cgctggcgtc accggtgctg cttctcagta    30900
cttttaggcg tgccagtact ggggctgaaa cctttctgct cctcccacca catttaaatt    30960
ccgctgttct ttcgggagac cgggtccgct ccggaagtgc gtcagcgccg tgttcctcct    31020
tcaagccctg gtgacagcgg gttccaggcg gagagcggtg ggctctgcgt gagttggtgg    31080
cgctgcgtgc tggtgcgggg cgcgtccttt atcctaacgg gaaacaaagg ccccgcgagc    31140
ccggccgaga gagagcgcct gcgccatggg agtgcagggg ctgtggaagc tgctggagtg    31200
ctcgggccac cgggtcagcc cggaggcgct ggagggcaag gtgctggccg tgggtatcct    31260
tcaaggcggc tccggagcgc cggatgagcg cctgctcggc gactgggctt cgtccgggac    31320
ttggtgctgg gggtcgattg ggtgtctgtc tatctagagt gcaggcctgc gctccttagg    31380
ccggcccatt ttgtgccccc tatgctttag ttctcacagc agagtggcta cagagttgtc    31440
gcggagaata aggagattta aatgataaaa tttggtatag cgtcaggctc cgtagtactg    31500
tacatctgag aagtcattct gtcagagtag agggggggaa aaaaagaag agttccgaac    31560 cctcccaccc tccttttga atagttacct cttgtttgtt ggaataaaaa aagttcatac    31620
ggtgtatagt gaattagttt cctccagctt ctgtgatggg tgtgtgcatt ttagttttgt    31680
gtcattggag ttttgttttt ctcccacttt gaaaatgtga taccaatttt gaagttttgt    31740
ttacgtttat ctgttccacg gcccgtttca cagtgcctct tttatcttag aaggtacttt    31800
tacatagttt tcttaatgaa aactagaaat tcctgtaaat agttgctgaa tgtgcgtaca    31860
tgcctggacg tgtgtccgta ggtggtggca tgccatgcca ttctgtaaac tatgtcagtt    31920
cttcacgatg tgcccagctt ataattaatg gagaacttgc agttttgaaa aatcacattt    31980
tatgccaaat acatcaatga caaaaattaa aaatttgtct tacaagtctt tgcacagggt    32040 accataaaacc ctagtggttt ctcggcgtca ctgctgttta aggatttctt cattatttat    32100
```

```
gatggaagaa caatttttag tgaggggtt cttaaattct catcaaaggg ttttagtagt    32160
ggtagagcac tttcttagta tgtatgataa accagagttc cattcacatc tttgtgagaa    32220
agtattgctg acaacaccat caaggagtta cgttattttc tcttccagcc cttataaaca    32280
attaggaagt taagcatcct agcattcagg gttgtcaaat gaaaagtaat ccatgtagat    32340
tattcataaa tggctgtgtt ccatttgggg tgtgaagtta tgtttatgag gttattaagc    32400
tcttctgaaa taatggatcg tttaaagaaa atcgtgaggg attttgccta cactcacatg    32460
taatctggtt acttctgtaa tttaattttc tgtgtttcat catgagaatt ctgatatctg    32520
aaatttaggt gttagaaatt tattcggttt gctaataaat aaatcatcca caattatctc    32580
aggtttgtaa tttacatact tttccaaata aactgtttgg gttttagacc atgtgaatag    32640
ctgagtgtat tatttaaaca gtttatgtct gtgtcaaaaa aatgttagga aataacagat    32700 tagttttttcc tcattattga ccttaacatc tgttagtgca ttggcagtat taagcagata    32760
gtaccctcac tggacacatg aacaacatgg attaacttag tctccagtca cctaattcca    32820
ggactaagga aaattcccat ttattttcag atgttattgg ttctttgagt ttaaattcta    32880
aagcaagttt tgactttgcc tttgcttcat tctttaattc ttctaaccct tgaggagttt    32940
agttttgcca catttgtgtt gaagcttgac taatcaaact gtgtaaattc tttcagccta    33000
tctgatttta tctgtttttt tttttgtttt ttgttttttg tttttttta actaagagtt    33060 tcatgttgga actctcggcc ttccatgaga agtggtaagc tgtggttaat ttaaatgtga    33120
aaaggaatta tttcagtgtg atttagtgtt ttaggaacat ggggtttaat cttttctcag    33180
aagctgtagg ccctagactc atatatatga gttaagaggt atcttaactc tgaaattgag    33240
ttttctcaat tctaaagtca aaagtgattg attgtataga cacttttgat ggcagtgtag    33300
caagcagaaa tggaccaagt atgagtagct gtccagagta gaactgagac tgcagaaggc    33360
ttgctctaag ctggatcctg gacctgatca ctcatgtctg agacctacca tcactatcat    33420
ctcctttcat gtgggctgct ggaacattct tttttttttt ttttgttat atggatttc    33480 atacttcttc tttcttgtat tagatatttt ctttatatac atttcaaatg ctatcctgaa    33540
agttccctat accctcccct actgctgtaa cattcttaaa actactctcc ttgcagttga    33600
tttttacatg tctcctaagg cccgaagtca ttctggaaac tgctcagatg tgtatattgt    33660
atatcagctt ccatacccaa gtgccccacc cctgcgccca ccacagggaa ctgtgtagac    33720
gtggctctgc cctaggcgtt tgtatttgct gcgtctcgtc tcccttctgt aactagagtg    33780
ctaaactcat aactactctc ctgacctatt atttcttggc acttaatgtg tcaattcttt    33840
taggatatgt gcatctcaga catagggtg catttgtctt gctcacaaat acaatgttta    33900
atgtatctcc gtagggtctt ggatttactt ttacatggga gctctttaac atataggat    33960 ggagatacac acacacacac acacacacac acacacacac acatattgtc    34020
aacttggcat ggcatgagag tcatcaagag tcaattgaga aaattccttt ggaagaccaa    34080
gcaagactat agggcttttc ctaattagcc attaatggga gagggcccag ccaattgtgg    34140
atggtgccac ccctgggctt gtgtcctggg ttctataagc aggcaagctg agtaagccat    34200
gaggagcaag cagctaagca gctcctgtac ccaagttcct gctctcttgg agtcgctgcc    34260 ttgatttttcc tcagtgatgg actgtgatgt ggatgtgtaa gccaaataaa ctccccagtt    34320
tgcttttggt tatggtgttt tatcatagca agtagaaatc ctaagatatt ggcttaaaac    34380
acaaaataca ctagcaactt ttgcagtagt aaatgaataa ctgtacatta attttttattt    34440 atttattttc ccttaatttt tttattattt aaatgcattt tatacatcaa ccatattaat    34500
```

```
aatattgagt atttttataa tacataaaaa tgttcaactt ttatattcat atcctttcag    34560
ac                                                                  34562
```

<210> SEQ ID NO 29
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon A1 splice donor sequence

<400> SEQUENCE: 29
cggccccagg gtaac                                                    15

<210> SEQ ID NO 30
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon A2 splice donor sequence

<400> SEQUENCE: 30
tgtgatccag gtccg                                                    15

<210> SEQ ID NO 31
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon A3 splice donor sequence

<400> SEQUENCE: 31
caggccagag gtacc                                                    15

<210> SEQ ID NO 32
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon B splice acceptor sequence

<400> SEQUENCE: 32
ttccctaaag gaatc                                                    15

<210> SEQ ID NO 33
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon B splice donor sequence

<400> SEQUENCE: 33
tttctgtcag gtgat                                                    15

<210> SEQ ID NO 34
<211> LENGTH: 15
<212> TYPE: DNA

```
<213> ORGANISM: Homo sapiens
<220> FEATURE:
<221> NAME/KEY: misc_feature
<222> LOCATION: (1)..(15)
<223> OTHER INFORMATION: BIVM Exon 1 splice acceptor sequence

<400> SEQUENCE: 34
ttcctcttag gagct                                                          15

<210> SEQ ID NO 35
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 1 splice donor sequence

<400> SEQUENCE: 35
cacaaatcag gtaag                                                          15

<210> SEQ ID NO 36
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 2 splice acceptor sequence

<400> SEQUENCE: 36
tgtattctag gcaat                                                          15

<210> SEQ ID NO 37
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 2 splice donor sequence

<400> SEQUENCE: 37
tcagacgatg gtgat                                                          15

<210> SEQ ID NO 38
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 3 splice acceptor sequence

<400> SEQUENCE: 38
gtgttctcag gtact                                                          15

<210> SEQ ID NO 39
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 3 splice donor sequence

<400> SEQUENCE: 39
gagctggaaa gtaag                                                          15
```

```
<210> SEQ ID NO 40
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 4 splice acceptor sequence

<400> SEQUENCE: 40
tcttttgtag ccttc                                                    15

<210> SEQ ID NO 41
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 4 splice donor sequence

<400> SEQUENCE: 41
cacttatgag gtatg                                                    15

<210> SEQ ID NO 42
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 5 splice acceptor sequence

<400> SEQUENCE: 42
ttactttcag gtggt                                                    15

<210> SEQ ID NO 43
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 5 splice donor sequence

<400> SEQUENCE: 43
ggagaaactg gtagg                                                    15

<210> SEQ ID NO 44
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 6 splice acceptor sequence

<400> SEQUENCE: 44 ttttaatag cttca                                                     15

<210> SEQ ID NO 45
<211> LENGTH: 15
<212> TYPE: DNA
<213> ORGANISM: Homo sapiens
<220> FEATURE:
<221> NAME/KEY: misc_feature
<222> LOCATION: (1)..(15)
```

<223> OTHER INFORMATION: BIVM Exon 6 splice donor sequence

<400> SEQUENCE: 45
aagcattcag gtaag                                                     15

<210> SEQ ID NO 46
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 7 splice acceptor sequence

<400> SEQUENCE: 46
ttatatttag caggg                                                     15

<210> SEQ ID NO 47
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 7 splice donor sequence

<400> SEQUENCE: 47
actgtaaaaa gtatg                                                     15

<210> SEQ ID NO 48
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 8 splice acceptor sequence

<400> SEQUENCE: 48
ttaactatag atggg                                                     15

<210> SEQ ID NO 49
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 8 splice donor sequence

<400> SEQUENCE: 49
aacaaagaag gtaag                                                     15

<210> SEQ ID NO 50
<211> LENGTH: 15
<212> TYPE: DNA
<213> ORGANISM: Homo sapiens
<220> FEATURE:
<221> NAME/KEY: misc_feature
<222> LOCATION: (1)..(15)
<223> OTHER INFORMATION: BIVM Exon 9 splice acceptor sequence

<400> SEQUENCE: 50
ttcttctcag gttgg                                                     15

<210> SEQ ID NO 51
<211> LENGTH: 30

```
<212> TYPE: DNA
<213> ORGANISM: Artificial Sequence
<220> FEATURE:
<223> OTHER INFORMATION: HSMAP5 primer

<400> SEQUENCE: 51
ccatgcctct ctactactca ctcccaacac                              30

<210> SEQ ID NO 52
<211> LENGTH: 30
<212> TYPE: DNA
<213> ORGANISM: Artificial Sequence
<220> FEATURE:
<223> OTHER INFORMATION: HSMAP6 primer

<400> SEQUENCE: 52
ggtaagaaga acaccattgt gtttgaaggc                              30

<210> SEQ ID NO 53
<211> LENGTH: 30
<212> TYPE: DNA
<213> ORGANISM: Artificial Sequence
<220> FEATURE:
<223> OTHER INFORMATION: zfbivmMAPF1 primer

<400> SEQUENCE: 53
caatgcctaa cactgtggaa agtgaaggcg                              30

<210> SEQ ID NO 54
<211> LENGTH: 29
<212> TYPE: DNA
<213> ORGANISM: Artificial Sequence
<220> FEATURE:
<223> OTHER INFORMATION: zfbivmMAPR1 primer

<400> SEQUENCE: 54
gataactgtc gagctcggtt gagcagggc                               29

<210> SEQ ID NO 55
<211> LENGTH: 8
<212> TYPE: PRT
<213> ORGANISM: Artificial Sequence
<220> FEATURE:
<223> OTHER INFORMATION: M1 amino acid motif
<220> FEATURE:
<221> NAME/KEY: MISC_FEATURE
<222> LOCATION: (2)..(7)
<223> OTHER INFORMATION: Xaa = any amino acid

<400> SEQUENCE: 55

Gly Xaa Xaa Xaa Xaa Xaa Xaa Cys
 1               5

<210> SEQ ID NO 56
<211> LENGTH: 4
<212> TYPE: PRT
<213> ORGANISM: Artificial Sequence
<220> FEATURE:
<223> OTHER INFORMATION: M2 amino acid motif
<220> FEATURE:
<221> NAME/KEY: MISC_FEATURE
<222> LOCATION: (2)..(2)
<223> OTHER INFORMATION: Xaa = Tyr or Phe
<220> FEATURE:
<221> NAME/KEY: MISC_FEATURE
<222> LOCATION: (4)..(4)
<223> OTHER INFORMATION: Xaa = Gln or His

<400> SEQUENCE: 56
```

Trp Xaa Arg Xaa
1

<210> SEQ ID NO 57
<211> LENGTH: 3
<212> TYPE: PRT
<213> ORGANISM: Artificial Sequence
<220> FEATURE:
<223> OTHER INFORMATION: M3a amino acid motif

<400> SEQUENCE: 57

Tyr Phe Cys
1

<210> SEQ ID NO 58
<211> LENGTH: 3
<212> TYPE: PRT
<213> ORGANISM: Artificial Sequence
<220> FEATURE:
<223> OTHER INFORMATION: M3b amino acid motif

<400> SEQUENCE: 58

Tyr His Cys
1

<210> SEQ ID NO 59
<211> LENGTH: 5
<212> TYPE: PRT
<213> ORGANISM: Artificial Sequence
<220> FEATURE:
<223> OTHER INFORMATION: BIVM N-terminus region of homology
<220> FEATURE:
<221> NAME/KEY: MISC_FEATURE
<222> LOCATION: (3)..(3)
<223> OTHER INFORMATION: Xaa = Val or Cys

<400> SEQUENCE: 59

Arg Lys Xaa Leu Asp
1               5

<210> SEQ ID NO 60
<211> LENGTH: 6
<212> TYPE: PRT
<213> ORGANISM: Artificial Sequence
<220> FEATURE:
<223> OTHER INFORMATION: BIVM C-terminus region of homology

<400> SEQUENCE: 60

Gly Gly Asn Leu His Cys
1               5

<210> SEQ ID NO 61
<211> LENGTH: 9
<212> TYPE: PRT
<213> ORGANISM: Artificial Sequence
<220> FEATURE:
<223> OTHER INFORMATION: BIVM amino acid motif 1

<400> SEQUENCE: 61

Gly Asn Thr Thr Leu Met Trp Arg Phe
1               5

```
<210> SEQ ID NO 62
<211> LENGTH: 9
<212> TYPE: PRT
<213> ORGANISM: Artificial Sequence
<220> FEATURE:
<223> OTHER INFORMATION: BIVM amino acid motif 2

<400> SEQUENCE: 62

Tyr Phe Cys Pro Ile Gly Phe Glu Ala
1               5

<210> SEQ ID NO 63
<211> LENGTH: 9
<212> TYPE: PRT
<213> ORGANISM: Artificial Sequence
<220> FEATURE:
<223> OTHER INFORMATION: BIVM amino acid motif 3

<400> SEQUENCE: 63

Trp Phe Arg Gln Ile Asn Asp His Phe
1               5

<210> SEQ ID NO 64
<211> LENGTH: 10
<212> TYPE: PRT
<213> ORGANISM: Artificial Sequence
<220> FEATURE:
<223> OTHER INFORMATION: BIVM amino acid motif 4

<400> SEQUENCE: 64

Tyr Arg His Gln Asn His Tyr Phe Cys Pro
1               5                   10
```

BIVM (BASIC, IMMUNOGLOBULIN-LIKE VARIABLE MOTIF-CONTAINING) GENE, TRANSCRIPTIONAL PRODUCTS, AND USES THEREOF

CROSS REFERENCE TO RELATED APPLICATION

The application claims priority to U.S. Provisional Application Ser. No. 60/373,146, filed Apr. 16, 2002, which is hereby incorporated by reference in its entirety, including all figures, nucleic acid sequences, amino acid sequences, and tables.

The subject invention was made with government support under a research project supported by the National Institutes of Health Grant No. AI23338. The government may have certain rights in this invention.

BACKGROUND OF INVENTION

Considerable uncertainty remains with regards to the total number of human genes. Initial interpretations of genomic sequences resulted in estimates that placed the numbers of genes in man in the range of 30,000 to 40,000 (Lander, E. S., et al. [2001] "Initial Sequencing and Analysis of the Human Genome," *Nature*, 409:860–921; Ventner, J. C., et al. [2001] "The Sequence of the Human Genome," *Science*, 291:1304–51). Subsequent re-examination of the sequence data suggests the number of genes in the human genome is likely to be between 65,000 and 75,000 (Wright, F. A., et al. [2001] "A Draft Annotation and Overview of the Human Genome," *Genome Biology* 2:1.1–1.39). Predictions of 35,000 to 120,000 genes have been projected on the basis of EST sequences (Ewing, B., et al. [2000] "Analysis of Expressed Sequence Tags Indicates 35,000 Human Genes," *Nature Genet.* 25:232–234; Liang, F., et al. [2000], "Gene Index Analysis of the Human Genome Estimates Approximately 120,000 Genes," *Nature Genet.* 25:239–240). New genes continue to be recognized through inspection of genomic sequences as well as through a variety of different biochemical, immunological and other directed approaches.

The immunoglobulin superfamily (IgSF) represents a particularly large and extensively diversified family of genes (Barclay, A. N., et al. [1997] *The Leucocyte Antigen Facts-Book*, Academic Press, San Diego). Each IgSF member encodes at least one Ig that consists of ~100 amino acid residues that are arranged in two β sheets, which are comprised of anti-parallel β strands that are linked by an intrachain disulfide. Although the majority of genes in the IgSF function in the immune response, other IgSF genes are involved with cell-adhesion or growth factor recognition. IgSF domains are the most abundant domain type found in leukocyte membrane proteins.

In the course of an electronic EST database search for novel human genes encoding Ig domains, we identified an anonymous EST (IMAGE 785450; GenBank AA449273) (Hawke, N. A., et al. [1999] "Expanding Our Understanding of Immunoglobulin, T-cell Antigen Receptor, and Novel Immune-Type Receptor Genes: a Subset of the Immunoglobulin Gene Superfamily," *Immunogenetics* 50:124–133) and cloned the corresponding full-length cDNA. The predicted structure of the protein encoded by this gene, which is termed BIVM (basic, immunoglobulin-like variable motif-containing), includes short peptide motifs characteristic of an Ig variable (V) region, one of the subtypes of Ig domains. However, it lacks significant sequence identity to any group of proteins heretofore described.

We have determined the sequence of BIVM cDNA in species representative of critical points in phylogeny, examined the intracellular distribution of a recombinant form of BIVM, characterized its expression patterns in various tissues at different times in development, and defined other features of the gene that further emphasize its unique character. In addition, we have identified a BIVM-like gene in the protozoan parasite, *Giardia lamblia*.

BRIEF SUMMARY

The subject invention provides polynucleotide sequences, designated BIVM, and transcriptional/translational products obtained from the polynucleotide sequences of the invention (SEQ ID Nos:1–28). The subject invention also provides methods of detecting the presence of BIVM nucleic acids, transcriptional products, or polypeptides in samples suspected of containing BIVM genes. These methods are also useful for the detection of BIVM orthologs. Other embodiments provide polypeptide and/or nucleic acid vaccines for the induction of an immune response. Kits for detecting the presence of BIVM genes, orthologs thereof, BIVM polypeptides, or BIVM transcriptional products obtained from the polynucleotide sequences are also provided.

BRIEF DESCRIPTION OF THE TABLES AND DRAWINGS

The file of this patent contains at least one drawing executed in color. Copies of this patent with color drawings will be provided by the Patent and Trademark Office upon request and payment of the necessary fee.

Table I. Exon-intron organization of human BIVM. Three alternative splice donors in the 5' untranslated region are designated $A_1$, $A_2$, and $A_3$. Nucleotide positions are relative to FIG. 1, intron length and splice donor/acceptor sequences are shown. Coding sequence is in upper case.

FIG. 1. Human BIVM The nucleotide sequence (SEQ ID NO: 1) and predicted amino acid translation product (SEQ ID NO: 2) of a human BIVM transcript. Translational start and stop codons are in reverse text. RNA splice junctions are underlined (see Table I). Nucleotides at 5' ends, defined by analyses of RACE products, are boxed. Nucleotide numbering is on the right; amino acid numbering is on the left. The M1 ($GX_6C$), M2 (WFRQ), M3a and M3b (YFC and YHC) motifs are shaded. The Alu sequence in the 3' untranslated region is in lower case.

FIG. 2. Predicted genomic organization of human BIVM. BIVM consists of nine coding exons (exons 1–9) and two 5' untranslated region exons (A and B). Alternative splice donor sites are present within exon A (see Table I); transcripts have been identified that include exon A, but not exon B. The CpG island is denoted by a solid bar, the Alu sequence is denoted by a hatched bar, and the location of the sequence-tagged site (STS) marker, WI-5740, is indicated (see also FIG. 1A).

Figure 3B:
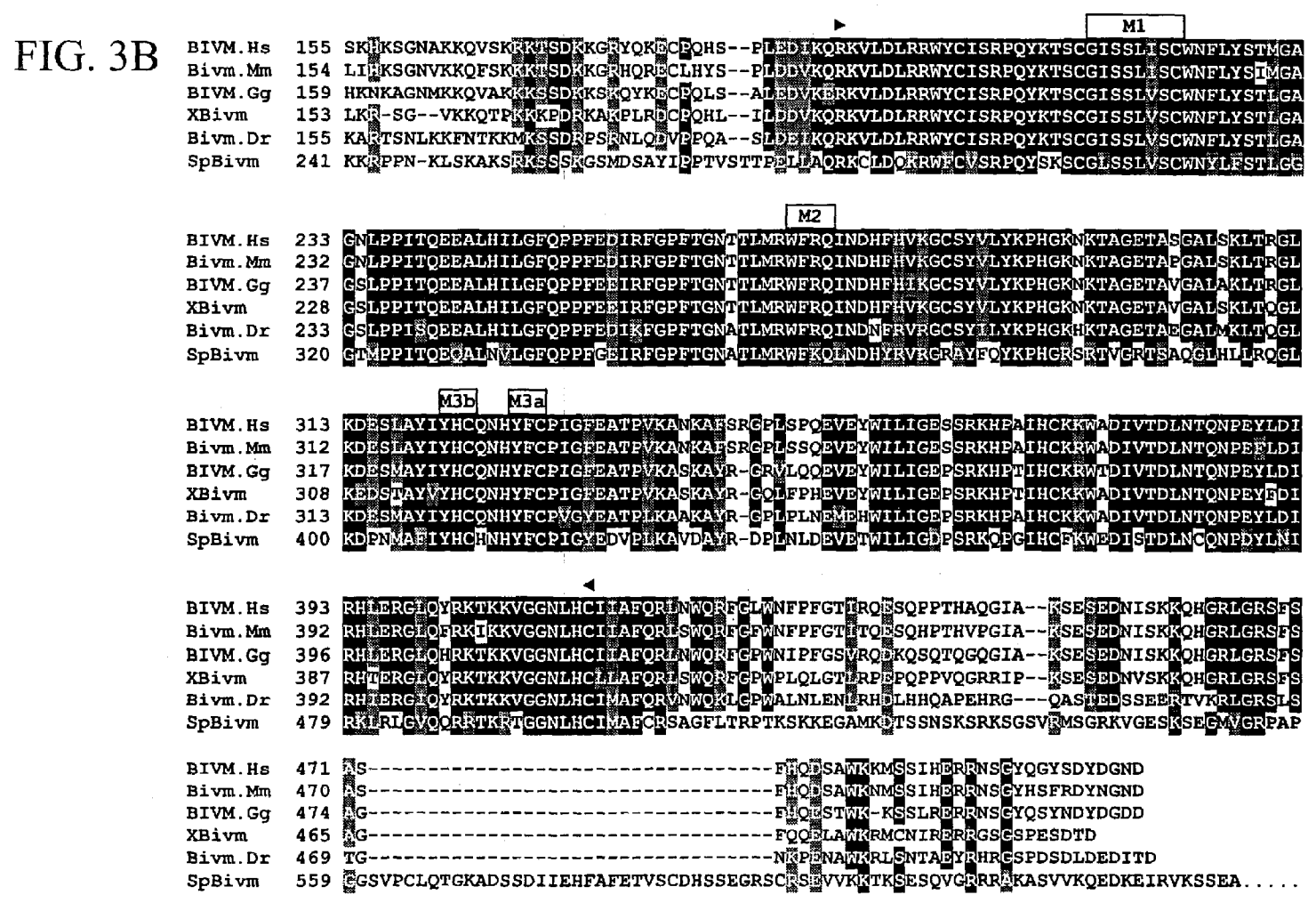

FIG. 3. BIVM is well conserved among deuterostomes. ClustalW alignment of the human BIVM peptide sequence (BIVM.Hs; (SEQ ID NO: 2)) with orthologous sequences from mouse (BIVM.Mm (SEQ ID NO: 27)), chicken (BIVM.Gg: (SEQ ID NO: 8)) *Xenopus* (XBIVM; (SEQ ID NO: 5)), zebrafish (BIVM.Dr: (SEQ ID NO: 11)), and sea urchin (SpBIVM: (SEQ ID NO: 13)). The sea urchin sequence lacks a stop codon and therefore is predicted to encode a longer polypeptide (indicated by . . . ). The M1, M2, M3a and M3b motifs are indicated. The highly conserved domain within BIVM is indicated with arrowheads.

Identical residues are shown in reverse text (black), similarities are shaded (gray). Gaps introduced to maintain/maximize alignment are indicated with (-).

Figure 4:
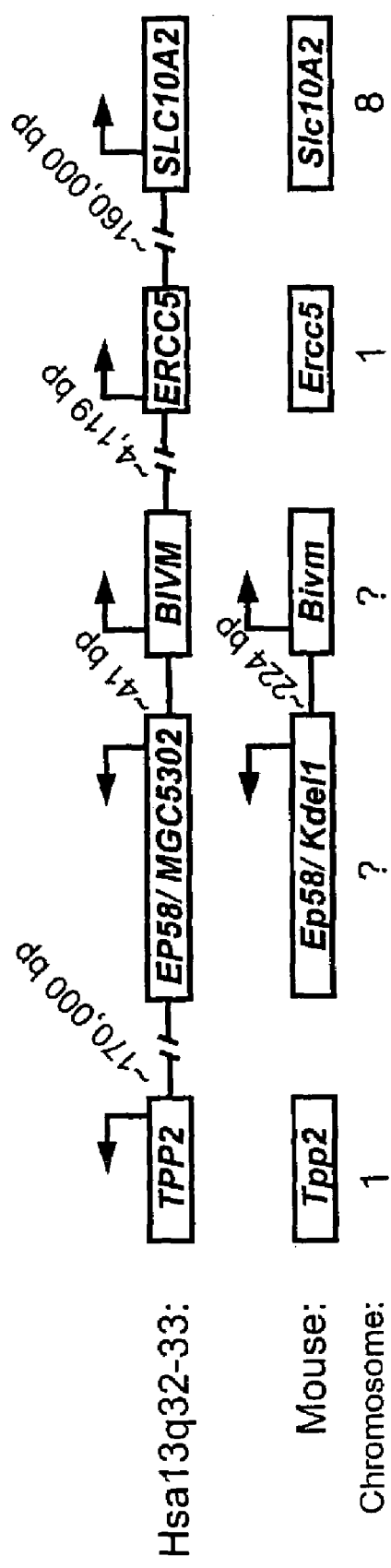

FIG. 4. Syntenic relationship between the human BIVM region and the mouse genome. The relative locations of human BIVM and flanking genes on chromosome 13q32–33; known corresponding chromosomal map positions are indicated for mouse. Transcription direction is indicated with arrows. Approximate distances between genes (if known) are indicated.

FIG. 5. Expression of BIVM. RNA blots of BIVM expression from (A) human tissues and cell lines, (B) mouse embryos and somatic tissues, (C) Xenopus embryos and kidney, and (D) sea urchin embryos. Approximately 2 µg of polyA+ RNA/track was analyzed in human and mouse; ~10 µg of total RNA/track was analyzed in Xenopus and sea urchin. Actin is used as a loading control with human and mouse blots; 18S ribosomal RNA is used as a loading control with Xenopus and sea urchin blots. Real time PCR analysis of BIVM expression in (E), developing zebrafish embryos and adult tissues, and in (F) chicken bursa at various stages of embryonic development. The quantity of BIVM (designated on the left) is relative and normalized (see Methods). Note that the level of zebrafish BIVM expression in the 0 hpf embryo is approximately 10 times the level detected at 6 hpf. Time points in the analysis of bursa are days of embryonic life (e.g. E12) and chicken embryonic fibroblasts (CEFs) were included as a control. Days post coitus=dpc, stage=st., hour post fertilization=hpf, days post fertilization=dpf and intestine=intest.

FIG. 6. BIVM localizes to the nucleus and the cytoplasm. (A) Western analysis of whole cell lysates from pIRES2-EGFP (EGFP), pBIVM-N2/EGFP (N2/EGFP) and pBIVM-K1/EGFP (K1/EGFP) transfected Cos-7 cells. Recombinant BIVM is detected with an anti-V5 antibody. EGFP is shown as a transfection and loading control. Note that only a single protein corresponding to the 5' ATG is generated from the endogenous transcript (pBIVM-N2); protein synthesis is increased by modification of the translational start site (pBIVMK1). Size standards are indicated. (B) Western analysis of nuclear and cytoplasmic fractions from pBIVM-K1/EGFP transfected Cos-7 cells. OCT-1 (Pombo, A., et al. [1998] "Regional and Temporal Specialization in the Nucleus: A Transcriptionally-Active Nuclear Domain Rich in PTF, Oct1 and PIKA Antigens Associated with Specific Chromosomes Early in the Cell Cycle," EMBO J. 1768) and HSP90 (Perdew, G. H., et al. [1991] "Evidence that the 90-kDa Heatshock Protein (HSP90) Exists in Cytosol in Heteromeric Complexes Containing HSP70 and Three Other Proteins with Mr 63,000, 56,000, and 50,000," J Biol Chem 6708) are nuclear and cytoplasmic markers, respectively. (C–J) Immunocytochemical localization of BIVM. Cos7 cells transiently transfected with pBIVM-K1 were analyzed by conventional fluorescent microscopy. Recombinant BIVM (green), actin s(red), nuclei (blue), and overlayered images are shown. Note that levels of nuclear BIVM vary (compare C to G).

FIG. 7. Giardia BVIM-like sequence. (A) The nucleotide sequence (SEQ ID NO: 14) and predicted amino acid translation product (SEQ ID NO: 15) of a Giardia lamblia BIVM-like (BIVML) transcript. Translational start and stop codons are in reverse text. Numbering is as in FIG. 1. Grey shading indicates conserved motifs. A sequence resembling predicted giardial initiator regions is boxed. A classic giardial polyadenylation signal sequence is underlined. (B) Alignment of the predicted BIVML protein (SEQ ID NO: 15) with the C-terminal region of human BIVM (SEQ ID NO: 2). Labeling is as in FIG. 3. (C) RNA blot (10 µg/track) probed for BIVML in vegetative-stage (veg) and 21 hr encysting Giardia. Calmodulin is shown as loading control.

FIG. 8. RT-PCR analysis of extracts from BIVM expressing and non-expressing human cell lines indicated that EP58/MGC5302 was expressed in all cell lines that express BIVM but not in a BIVM non-expressing cell line.

Figure 9:
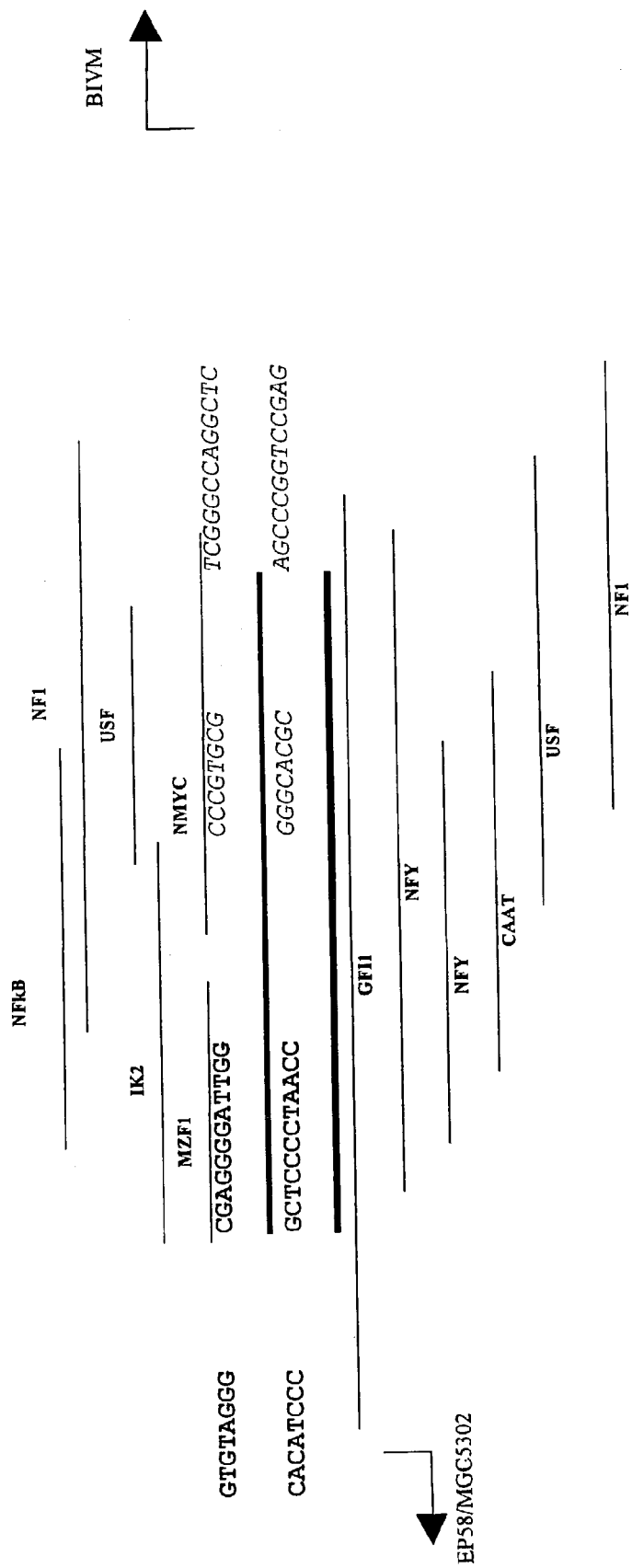

FIG. 9. Potential binding sites contained in the 41 bp region separating the BIVM and EP58/MGC5302 genes revealed sites for cell type specific factors such as the myeloid zinc finger-1 (MZF-1), the hematopoietic-expressed Ikaros-2 (IK2) factor, and the ubiquitously expressed transcription factors NF1, USF, NFκB, and NMYC.

FIG. 10. Detection of bands representing NFκB-specific binding constitutively present in nuclear extracts.

Figure 11:
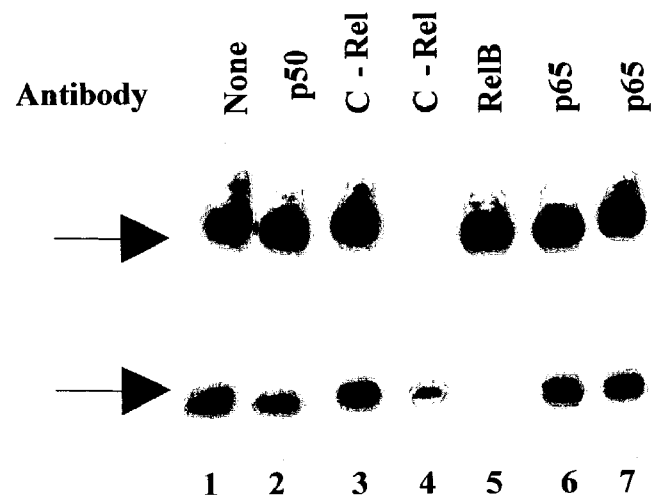

FIG. 11. Binding of the 41 bp intergenic region by NFκB complexes containing c-Rel and RelB factors, which are constitutively present in the nuclear extracts from the BIVM expressing K562 cell line.

Figure 12:
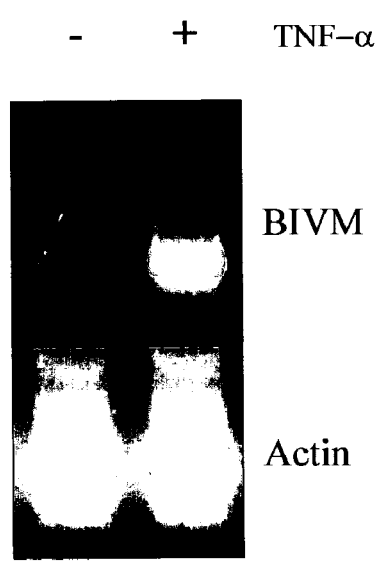

FIG. 12. TNF-α activated NFκB increases the expression of BIVM in the BIVM-expressing HeLa cell line (DNS). A cell line devoid of basal BIVM expression, the Raji Burkitt's lymphoma line, is induced to express BIVM by TNF-α.

Figure 13A:
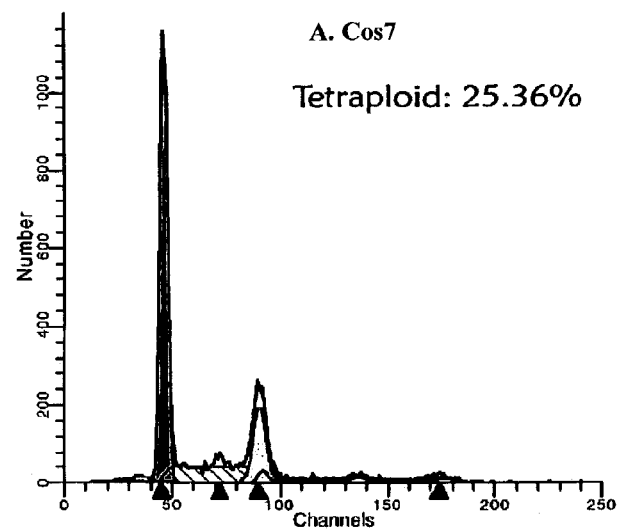
Figure 13B:
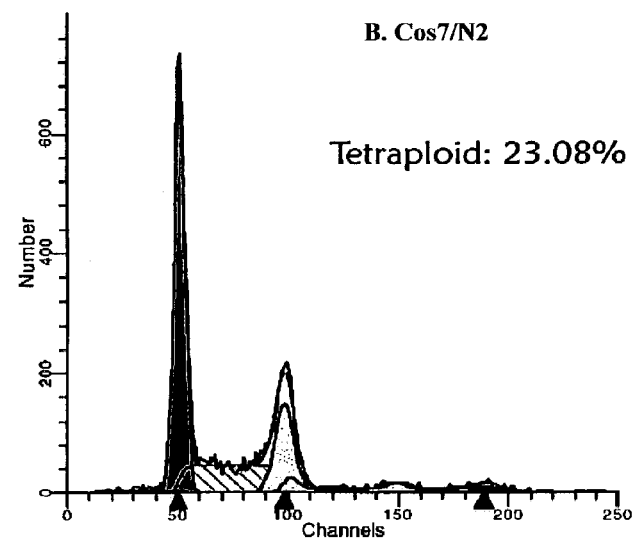
Figure 13C:
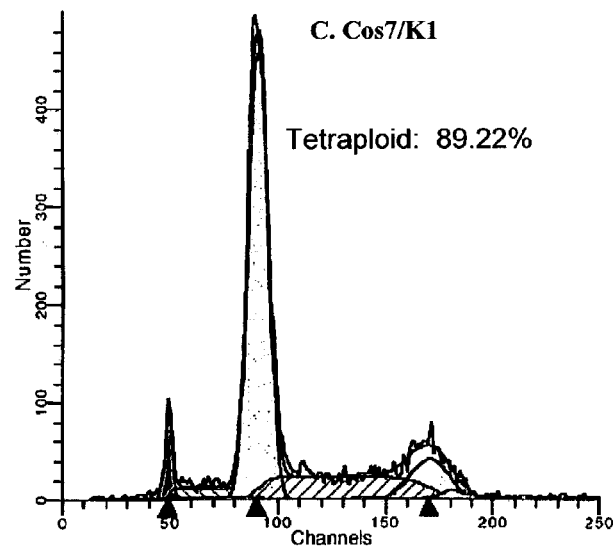

FIG. 13. Flow cytometer analyses of cells stained with propidium iodide.

BRIEF DESCRIPTION OF THE SEQUENCES

SEQ ID NO: 1—human BIVM cDNA
SEQ ID NO: 2—human BIVM amino acid sequence
SEQ ID NO: 3—human BIVM gemonic sequence with upstream partial sequence of MGC5302 gene and downstream partial sequence of ERCC5 gene
SEQ ID NO: 4—Xenopus BIVM open reading frame
SEQ ID NO: 5—Xenopus BIVM amino acid sequence
SEQ ID NO: 6—Chicken BIVM open reading frame
SEQ ID NO: 7—Alternatively spliced chicken BIVM open reading frame
SEQ ID NO: 8—Chicken BIVM amino acid sequence
SEQ ID NO: 9—Alternatively splice chicken BIVM amino acid sequence
SEQ ID NO: 10—Zebrafish BIVM open reading frame
SEQ ID NO: 11—Zebrafish BIVM amino acid sequence
SEQ ID NO: 12—Sea urchin BIVM partial coding sequence
SEQ ID NO: 13—Sea urchin BIVM partial amino acid sequence
SEQ ID NO: 14—Giardia BIVM-like open reading frame
SEQ ID NO: 15—Giardia BIVM-like amino acid sequence
SEQ ID NO: 16—Lancelet BIVM partial coding sequence
SEQ ID NO: 17—Lancelet BIVM partial amino acid sequence
SEQ ID NO: 18—Mouse BIVM exon A nucleotide sequence
SEQ ID NO: 19—Mouse BIVM exon B nucleotide sequence
SEQ ID NO: 20—Mouse BIVM exon C nucleotide sequence
SEQ ID NO: 21—Mouse BIVM exon 1 nucleotide sequence
SEQ ID NO: 22—Alternative mouse BIVM 5' end clone (6359)
SEQ ID NO: 23—Alternative mouse BIVM 5' end clone (6358)

SEQ ID NO: 24—Alternative mouse BIVM 5' end clone (6356)
SEQ ID NO: 25—Alternative mouse BIVM 5' end clone (cDNA)
SEQ ID NO: 26—Mouse BIVM cDNA with clone 6359 5' end
SEQ ID NO: 27—Mouse BIVM amino acid sequence
SEQ ID NO: 28—Mouse BIVM genomic sequence with upstream partial sequence of KDEL gene
SEQ ID NO: 29—Human BIVM exon $A^1$ splice donor sequence
SEQ ID NO: 30—Human BIVM exon $A^2$ splice donor sequence
SEQ ID NO: 31—Human BIVM exon $A^3$ splice donor sequence
SEQ ID NO: 32—Human BIVM exon B splice acceptor sequence
SEQ ID NO: 33—Human BIVM exon B splice donor sequence
SEQ ID NO: 34—Human BIVM exon 1 splice acceptor sequence
SEQ ID NO: 35—Human BIVM exon 1 splice donor sequence
SEQ ID NO: 36—Human BIVM exon 2 splice acceptor sequence
SEQ ID NO: 37—Human BIVM exon 2 splice donor sequence
SEQ ID NO: 38—Human BIVM exon 3 splice acceptor sequence
SEQ ID NO: 39—Human BIVM exon 3 splice donor sequence
SEQ ID NO: 40—Human BIVM exon 4 splice acceptor sequence
SEQ ID NO: 41—Human BIVM exon 4 splice donor sequence
SEQ ID NO: 42—Human BIVM exon 5 splice acceptor sequence
SEQ ID NO: 43—Human BIVM exon 5 splice donor sequence
SEQ ID NO: 44—Human BIVM exon 6 splice acceptor sequence
SEQ ID NO: 45—Human BIVM exon 6 splice donor sequence
SEQ ID NO: 46—Human BIVM exon 7 splice acceptor sequence
SEQ ID NO: 47—Human BIVM exon 7 splice donor sequence
SEQ ID NO: 48—Human BIVM exon 8 splice acceptor sequence
SEQ ID NO: 49—Human BIVM exon 8 splice donor sequence
SEQ ID NO: 50—Human BIVM exon 9 splice acceptor sequence
SEQ ID NO: 51—HSMAP5 primer
SEQ ID NO: 52—HSMAP6 primer
SEQ ID NO: 53—xfbivmMAPF1 primer
SEQ ID NO: 54—xfbivmMAPR1 primer
SEQ ID NO: 55—M1 amino acid motif
SEQ ID NO: 56—M2 amino acid motif
SEQ ID NO: 57—M3a amino acid motif
SEQ ID NO: 58—M3b amino acid motif
SEQ ID NO: 59—BIVM N-terminus region of homology
SEQ ID NO: 60—BIVM C-terminus region of homology
SEQ ID NO: 61—BIVM amino acid motif 1
SEQ ID NO: 62—BIVM amino acid motif 2
SEQ ID NO: 63—BIVM amino acid motif 3
SEQ ID NO: 64—BIVM amino acid motif 4

DETAILED DESCRIPTION OF THE INVENTION

The subject invention provides isolated and/or purified nucleotide sequences comprising: a) a polynucleotide sequence, or fragment thereof, or a polynucleotide encoding an amino acid sequence, or fragment of said amino acid sequence, of a sequence selected from the group consisting of SEQ ID NOs: 1–64 (or the complements of said polynucleotide sequences or fragments thereof); b) a polynucleotide sequence, or fragment thereof, comprising a sequence having at least about 20% to 99.99% identity to a polynucleotide selected from the group consisting of SEQ ID NOs: 1–28; c) a polynucleotide sequence encoding a polypeptide comprising a sequence selected from the group consisting of SEQ ID NOs: 2, 5, 7, 8, 9, 11, 13, 15, 17, or 27; d) splice variants of SEQ ID NOs: 1–3 or 6–9; or e) a polynucleotide sequence encoding a polypeptide fragment of SEQ ID NOs: 2, 5, 7, 8, 9, 11, 13, 15, 17, or 27, wherein said fragment has substantially the same biological or serologic activity as the native (or intact) polypeptide.

Nucleotide, polynucleotide, or nucleic acid sequence(s) are understood to mean, according to the present invention, either a double-stranded DNA, a single-stranded DNA, or products of transcription of the said DNAs (e.g., RNA molecules). It should also be understood that the present invention does not relate to the genomic nucleotide sequences encoding BIVM in their natural/native environment or natural/native state. The nucleic acid, polynucleotide, or nucleotide sequences of the invention have been isolated, purified (or partially purified), by separation methods including, but not limited to, ion-exchange chromatography, molecular size exclusion chromatography, affinity chromatography, or by genetic engineering methods such as amplification, cloning, or subcloning.

Optionally, the polynucleotide sequences of the instant invention can also contain one or more polynucleotides encoding heterologous polypeptide sequences (e.g., tags that facilitate purification of the polypeptides of the invention (see, for example, U.S. Pat. No. 6,342,362, hereby incorporated by reference in its entirety; Altendorf et al. [1999-WWW, 2000] "Structure and Function of the $F_0$ Complex of the ATP Synthase from *Escherichia Coli*," *J. of Experimental Biology* 203:19–28, The Co. of Biologists, Ltd., G.B.; Baneyx [1999] "Recombinant Protein Expression in *Escherichia coli*," Biotechnology 10:411–21, Elsevier Science Ltd.; Eihauer et al. [2001] "The FLAG™ Peptide, a Versatile Fusion Tag for the Purification of Recombinant Proteins," *J. Biochem Biophys Methods* 49:455–65; Jones et al. [1995] *J. Chromatography* 707:3–22; Jones et al. [1995] "Current Trends in Molecular Recognition and Bioseparation," *J. of Chromatography A.* 707:3–22, Elsevier Science B. V.; Margolin [2000] "Green Fluorescent Protein as a Reporter for Macromolecular Localization in Bacterial Cells," *Methods* 20:62–72, Academic Press; Puig et al. [2001] "The Tandem Affinity Purification (TAP) Method: A General Procedure of Protein Complex Purification," *Methods* 24:218–29, Academic Press; Sassenfeld [1990] "Engineering Proteins for Purification," TibTech 8:88–93; Sheibani [1999] "Prokaryotic Gene Fusion Expression Systems and Their Use in Structural and Functional Studies of Proteins," *Prep. Biochem. & Biotechnol.* 29(1):77–90, Marcel Dekker, Inc.; Skerra et al. [1999] "Applications of a Peptide Ligand for Streptavidin: the Strep-tag", *Biomolecular Engineering* 16:79–86, Elsevier Science, B. V.; Smith [1998] "Cookbook for Eukaryotic Protein Expression: Yeast, Insect, and Plant Expression Systems," The Scientist 12(22):20; Smyth et al. [2000] "Eukaryotic Expression and Purification of Recombinant Extracellular Matrix Proteins Carrying the Strep II Tag", *Methods in Molecular Biology* 139:49–57; Unger [1997] "Show Me the Money: Prokaryotic Expression Vectors and Purification Systems," *The Scientist* 11(17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or In Vitrogen (San Diego, Calif.).

TABLE 1

Splice variants of BIVM(SEQ ID NOs:29–50)

| Seq ID No. | Exon | Splice Donor | Splice Acceptor | Position | Intron (bp) |
|---|---|---|---|---|---|
| 29 | A$^1$ | CGGCCCCAGGgtaac | — | 1–415 | — |
| 30 | A$^2$ | TGTGATCCAGgtccg | — | 1–365 | — |
| 31 | A$^3$ | CAGGCCAGAGgtacc | — | 1–473 | — |
| 33/32 | B | TTTCTGTCAGgtgat | ttccctaaagGAATC | 474–557 | 5785 |
| 35/34 | 1 | CACAAATCAGgtaag | ttcctcttagGAGCT | 558–1157 | 1754 |
| 37/36 | 2 | TCAGACGATGgtgat | tgtattctagGCAAT | 1158–1284 | 8682 |
| 39/38 | 3 | GAGCTGGAAAgtaag | gtgttctcagGTACT | 1285–1380 | 4481 |
| 41/40 | 4 | CACTTATGAGgtatg | tcttttgtagCCTTC | 1381–1485 | 609 |
| 43/42 | 5 | GGAGAAACTGgtagg | ttactttcagGTGGT | 1486–1580 | 216 |
| 45/44 | 6 | AAGCATTCAGgtaag | tttttaatagCTTCA | 1581–1713 | 9405 |
| 49/48 | 7 | AACAAAGAAGgtaag | ttaactatagATGGG | 1714–1800 | 2768 |
| 50 | 8 | — | ttcttctcagGTTGG | 1801–1897 | 4089 |
| 50 | 9 | — | ttcttctcagGTTGG | 1898–3029 | 832 |

Other aspects of the invention provide vectors containing one or more of the polynucleotides of the invention. The vectors can be vaccine, replication, or amplification vectors. In some embodiments of this aspect of the invention, the polynucleotides are operably associated with regulatory elements capable of causing the expression of the polynucleotide sequences. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations of the aforementioned vector sources, such as those derived from plasmid and bacteriophage genetic elements (e.g., cosmids and phagemids).

As indicated above, vectors of this invention can also comprise elements necessary to provide for the expression and/or the secretion of a polypeptide encoded by the nucleotide sequences of the invention in a given host cell. The vector can contain one or more elements selected from the group consisting of a promoter, signals for initiation of translation, signals for termination of translation, and appropriate regions for regulation of transcription. In certain embodiments, the vectors can be stably maintained in the host cell and can, optionally, contain signal sequences directing the secretion of translated protein. Other embodiments provide vectors that are not stable in transformed host cells. Vectors can integrate into the host genome or be autonomously-replicating vectors.

In a specific embodiment, a vector comprises a promoter operably linked to a protein or peptide-encoding nucleic acid sequence, one or more origins of replication, and, optionally, one or more selectable markers (e.g., an antibiotic resistance gene). Non-limiting exemplary vectors for the expression of the polypeptides of the invention include pBr-type vectors, pET-type plasmid vectors (Promega), pBAD plasmid vectors (Invitrogen) or those provided in the examples below. Furthermore, vectors according to the invention are useful for transforming host cells for the cloning or expression of the nucleotide sequences of the invention.

Promoters which may be used to control expression include, but are not limited to, the CMV promoter, the SV40 early promoter region (Bernoist and Chambon [1981] *Nature* 290:304–310), the promoter contained in the 3' long terminal repeat of Rous sarcoma virus (Yamamoto, et al. [1980] *Cell* 22:787–797), the herpes thymidine kinase promoter (Wagner et al. [1981] *Proc. Natl. Acad. Sci. USA* 78:1441–1445), the regulatory sequences of the metallothionein gene (Brinster et al. [1982] *Nature* 296:39–42); prokaryotic vectors containing promoters such as the β-lactamase promoter (Villa-Kamaroff, et al. [1978] *Proc. Natl. Acad. Sci. USA* 75:3727–3731), or the tac promoter (DeBoer, et al. [1983] *Proc. Natl. Acad. Sci. USA* 80:21–25); see also, "Useful Proteins from Recombinant Bacteria" in *Scientific American,* 1980, 242:74–94; plant expression vectors comprising the nopaline synthetase promoter region (Herrera-Estrella et al. [1983] *Nature* 303:209–213) or the cauliflower mosaic virus 35S RNA promoter (Gardner, et al. [1981] *Nucl. Acids Res.* 9:2871), and the promoter of the photosynthetic enzyme ribulose biphosphate carboxylase (Herrera-Estrella et al. [1984] *Nature* 310:115–120); promoter elements from yeast or fungi such as the Gal 4 promoter, the ADC (alcohol dehydrogenase) promoter, PGK (phosphoglycerol kinase) promoter, and/or the alkaline phosphatase promoter.

The subject invention also provides for "homologous" or "modified" nucleotide sequences. Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to the invention provide for a "modified nucleotide sequence". Likewise, substitutions, deletions, or additions of nucleic acid to the polynucleotides of the invention provide for "homologous" or "modified" nucleotide sequences. In various embodiments, "homologous" or "modified" nucleic acid sequences have substantially the same biological or serological activity as the native (naturally occurring) BIVM polypeptides. A "homologous" or "modified" nucleotide sequence will also be understood to mean a splice variant of the polynucleotides of the instant invention (see Table I) or any nucleotide sequence encoding a "modified polypeptide" as defined below.

A homologous nucleotide sequence, for the purposes of the present invention, encompasses a nucleotide sequence having a percentage identity with the bases of the nucleotide sequences of between at least (or at least about) 20.00% to 99.99% or higher. The aforementioned range of percent identity is to be taken as including, and providing written description and support for, any fractional percentage, in intervals of 0.01%, between 20.00% and 99.99% or higher. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman [1988] *Proc. Natl. Acad. Sci. USA* 85(8):2444–2448; Altschul et al. [1990] *J. Mol. Biol.* 215 (3):403–410; Thompson et *Nucleic Acids Res.* 22(2):4673–4680; Higgins et al. [1996] *Methods Enzymol.* 266:383–402; Altschul et al. [1990] *J. Mol. Biol.* 215(3): 403–410; Altschul et al. [1993] *Nature Genetics* 3:266–272).

The subject invention also provides nucleotide sequences complementary to any of the polynucleotide sequences disclosed herein. Thus, the invention is understood to include any DNA whose nucleotides are complementary to those of the sequence of the invention, and whose orientation is reversed (e.g., an antisense sequence).

The present invention further provides fragments of the polynucleotide sequences provided herein. Representative fragments of the polynucleotide sequences according to the invention will be understood to mean any nucleotide fragment having at least 8 or 9 successive nucleotides, preferably at least 12 successive nucleotides, and still more preferably at least 15 or at least 20 successive nucleotides of the sequence from which it is derived. In other embodiments, fragments contain from one nucleotide less than the full length polynucleotide sequence to fragments comprising up to, and including 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or 255 consecutive nucleotides of a particular sequence disclosed herein. Yet other embodiments provide fragments (or detection probes) comprising nucleotides 1446 to 1697 or 1447 to 1698 of FIG. 1 (SEQ ID NO:1). It is to be understood that such fragments refer only to portions of the disclosed polynucleotide sequences that are not listed in a publicly available database or prior art references.

Among these representative fragments, those capable of hybridizing under stringent conditions with a nucleotide sequence according to the invention are preferred. Conditions of high or intermediate stringency are provided infra and are chosen to allow for hybridization between two complementary DNA fragments. Hybridization conditions for a polynucleotide of about 300 bases in size will be adapted by persons skilled in the art for larger- or smaller-sized oligonucleotides, according to methods well known in the art (see, for example, Sambrook et al. [1989]).

The subject invention also provides detection probes (e.g., fragments of the disclosed polynucleotide sequences) for hybridization with a target sequence or an amplicon generated from the target sequence. Such a detection probe will advantageously have as sequence a sequence of at least 9, 12, 15, 20, 25, 30, 35, 40, 45, 50, 55, 60, 65, 70, 75, 80, 85, 90, 95, or 100 nucleotides. Alternatively, detection probes can comprise 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or 255 consecutive nucleotides of the disclosed nucleic acids. The detection probes can also be used as labeled probe or primer in the subject invention. Labeled probes or primers are labeled with a radioactive compound or with another type of label. Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications.

The nucleotide sequences according to the invention may also be used in analytical systems, such as DNA chips. DNA chips and their uses are well known in the art and (see for example, U.S. Pat. Nos. 5,561,071; 5,753,439; 6,214,545; Schena et al. [1996] *BioEssays* 18:427–431; Bianchi et al. [1997] *Clin. Diagn. Virol.* 8:199–208; each of which is hereby incorporated by reference in their entireties) and/or are provided by commercial vendors such as Affymetrix, Inc. (Santa Clara, Calif.).

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak [1987] *DNA Probes*, Stockton Press, New York, N.Y., pp. 169–170.

By way of example, hybridization of immobilized DNA on Southern blots with $^{32}$P-labeled gene-specific probes can be performed by standard methods (Maniatis et al. [1982] *Molecular Cloning: A Laboratory Manual*, Cold Spring Harbor Laboratory, New York). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20–25° C. below the melting temperature (Tm) of the DNA hybrid in 6×SSPE, 5× Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266–285).

$T_m$=81.5° C.+16.6 Log[Na+]+0.41(% G+C)−0.61(% formamide)−600/length of duplex in base pairs.

Washes are typically carried out as follows:
(1) twice at room temperature for 15 minutes in 1×SSPE, 0.1% SDS (low stringency wash);
(2) once at $T_m$−20° C. for 15 minutes in 0.2×SSPE, 0.1% SDS (moderate stringency wash).

For oligonucleotide probes, hybridization can be carried out overnight at 10–20° C. below the melting temperature ($T_m$) of the hybrid in 6×SSPE, 5× Denhardt's solution, 0.1% SDS, 0.1 mg/ml denatured DNA. $T_m$ for oligonucleotide probes can be determined by the following formula:

$T_m$ (° C.)=2(number T/A base pairs)+4(number G/C base pairs) (Suggs et al. [1981] *ICN-UCLA Symp. Dev. Biol. Using Purified Genes*, D. D. Brown [ed.], Academic Press, New York, 23:683–693).

Washes can be carried out as follows:
(1) twice at room temperature for 15 minutes 1×SSPE, 0.1% SDS (low stringency wash;
2) once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:
Low: 1 or 2×SSPE, room temperature
Low: 1 or 2×SSPE, 42° C.
Moderate: 0.2× or 1×SSPE, 65° C.
High: 0.1×SSPE, 65° C.

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5–20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography.

Other conditions of high stringency which may be used are well known in the art (see, for example, Sambrook et al. [1989] *Molecular Cloning, A Laboratory Manual, Second Edition*, Cold Spring Harbor Press, N.Y., pp. 9.47–9.57; and Ausubel et al. [1989] *Current Protocols in Molecular Biology*, Green Publishing Associates and Wiley Interscience, N.Y., each incorporated herein in its entirety).

A further non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art (see, for example, Sambrook et al. [1989] *Molecular Cloning, A Laboratory Manual, Second Edition*, Cold Spring Harbor Press, N.Y., pp. 9.47–9.57; and Ausubel et al. [1989] *Current Protocols in Molecular Biology*, Green Publishing Associates and Wiley Interscience, N.Y., each of which is incorporated herein in its entirety).

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual*, Cold Spring Harbor Laboratory, New York; Wei et al. [1983] *J. Biol. Chem.* 258:13006–13512. The nucleic acid sequences of the subject invention can also be used as molecular weight markers in nucleic acid analysis procedures.

The invention also provides host cells transformed by a polynucleotide according to the invention and the production of BIVM (or BIVM ortholog) polypeptides by the transformed host cells. In some embodiments, transformed cells comprise an expression vector containing BIVM, or BIVM ortholog, polynucleotide sequences. Other embodiments provide for host cells transformed with nucleic acids. Yet other embodiments provide transformed cells comprising an expression vector containing fragments of BIVM, or BIVM ortholog, polynucleotide sequences. Transformed host cells according to the invention are cultured under conditions allowing the replication and/or the expression of the nucleotide sequences of the invention. Expressed polypeptides are recovered from culture media and purified, for further use, according to methods known in the art.

The host cell may be chosen from eukaryotic or prokaryotic systems, for example bacterial cells (Gram negative or Gram positive), yeast cells, animal cells, plant cells, and/or insect cells using baculovirus vectors. In some embodiments, the host cell for expression of the polypeptides include, and are not limited to, those taught in U.S. Pat. Nos. 6,319,691; 6,277,375; 5,643,570; 5,565,335; Unger [1997] *The Scientist* 11(17):20; or Smith [1998] *The Scientist*

12(22):20, each of which is incorporated by reference in its entirety, including all references cited within each respective patent or reference. Other exemplary, and non-limiting, host cells include *Staphylococcus* spp., *Enterococcus* spp., *E. coli*, and *Bacillus subtilis*; fungal cells, such as *Streptomyces* spp., *Aspergillus* spp., *S. cerevisiae, Schizosaccharomyces pombe, Pichia pastoris, Hansela polymorpha, Kluveromyces lactis*, and *Yarrowia lipolytica*; insect cells such as *Drosophila* S2 and *Spodoptera* Sf9 cells; animal cells such as CHO, COS, HeLa, C127, 3T3, BHK, 293 and Bowes melanoma cells; and plant cells. A great variety of expression systems can be used to produce the polypeptides of the invention and polynucleotides can be modified according to methods known in the art to provide optimal codon usage for expression in a particular expression system.

Furthermore, a host cell strain may be chosen that modulates the expression of the inserted sequences, modifies the gene product, and/or processes the gene product in the specific fashion. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product whereas expression in yeast will produce a glycosylated product. Expression in mammalian cells can be used to provide "native" glycosylation of a heterologous protein. Furthermore, different vector/host expression systems may effect processing reactions to different extents.

Nucleic acids and/or vectors can be introduced into host cells by well-known methods, such as, calcium phosphate transfection, DEAE-dextran mediated transfection, transfection, microinjection, cationic lipid-mediated transfection, electroporation, transduction, scrape loading, ballistic introduction and infection (see, for example, Sambrook et al. [1989] *Molecular Cloning: A Laboratory Manual*, $2^{nd}$ Ed., Cold Spring Harbor Laboratory Press, Cold Spring Harbor, N.Y.).

The subject invention also provides for the expression of a polypeptide, derivative, or a variant (e.g., a splice variant) encoded by a polynucleotide sequence disclosed herein. Alternatively, the invention provides for the expression of a polypeptide fragment obtained from a polypeptide, derivative, or a variant encoded by a polynucleotide fragment derived from the polynucleotide sequences disclosed herein. In either embodiment, the disclosed sequences can be regulated by a second nucleic acid sequence so that the polypeptide or fragment is expressed in a host transformed with a recombinant DNA molecule according to the subject invention. For example, expression of a protein or peptide may be controlled by any promoter/enhancer element known in the art.

The subject invention also provides nucleic acid based methods for the identification of the presence of the BIVM gene, or orthologs thereof, in a sample. These methods can utilize the nucleic acids of the subject invention and are well known to those skilled in the art (see, for example, Sambrook et al. [1989] or Abbaszadega [2001] "Advanced Detection of Viruses and Protozoan Parasites in Water," *Reviews in Biology and Biotechnology*, 1(2):21–26). Among the techniques useful in such methods are enzymatic gene amplification (or PCR), Southern blots, Northern blots, or other techniques utilizing nucleic acid hybridization for the identification of polynucleotide sequences in a sample. Thus, the subject invention can provide nucleic acid based methodologies for the identification of *G. lamblia* in environmental or biological samples and provides sensitive assays for the diagnosis of *G. lamblia* infections. Alternatively, the nucleic acids can be used to screen individuals for cancers, tumors, or malignancies associated with dysregulation of the BIVM gene or its transcriptional products.

The subject invention also provides polypeptides encoded by nucleotide sequences of the invention. The subject invention also provides fragments of at least 5 amino acids of a polypeptide encoded by the polynucleotides of the instant invention. In some embodiments, the polypeptide fragments are reactive with antibodies found in the serum of an individual infected with *G. lamblia*.

In the context of the instant invention, the terms polypeptide, peptide and protein are used interchangeably. Likewise, the terms variant and homologous are also used interchangeably. It should be understood that the invention does not relate to the polypeptides in natural form or native environment. Peptides and polypeptides according to the invention have been isolated or obtained by purification from natural sources (or their native environment), chemically synthesized, or obtained from host cells prepared by genetic manipulation (e.g., the polypeptides, or fragments thereof, are recombinantly produced by host cells). Polypeptides according to the instant invention may also contain non-natural amino acids, as will be described below.

"Variant" or "homologous" polypeptides will be understood to designate the polypeptides containing, in relation to the native polypeptide, modifications such as deletion, addition, or substitution of at least one amino acid, truncation, extension, or the addition of chimeric heterologous polypeptides. Optionally, "variant" or "homologous" polypeptides can contain a mutation or post-translational modifications. Among the "variant" or "homologous" polypeptides, those whose amino acid sequence exhibits 20.00% to 99.99% (inclusive) identity to the native polypeptide sequence are preferred. The aforementioned range of percent identity is to be taken as including, and providing written description and support for, any fractional percentage, in intervals of 0.01%, between 50.00% and, up to, including 99.99%. These percentages are purely statistical and differences between two polypeptide sequences can be distributed randomly and over the entire sequence length.

"Variant" or "homologous" polypeptide sequences exhibiting a percentage identity with the polypeptides of the present invention can, alternatively, have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 91, 82, 83, 84, 85, 86, 87, 88, 89, 90, 91, 92, 93, 94, 95, 96, 97, 98, or 99 percent identity with the polypeptide sequences of the instant invention. The expression equivalent amino acid is intended here to designate any amino acid capable of being substituted for one of the amino acids in the basic structure without, however, essentially modifying the biological activities of the corresponding peptides and as provided below.

By way of example, amino acid substitutions can be carried out without resulting in a substantial modification of the biological activity of the corresponding modified polypeptides; for example, the replacement of leucine with valine or isoleucine; aspartic acid with glutamic acid; glutamine with asparagine; arginine with lysine; and the reverse substitutions can be performed without substantial modification of the biological activity of the polypeptides.

In other embodiments, homologous polypeptides according to the subject invention also include various splice variants identified within the BIVM coding sequence (see Table I).

The subject invention also provides biologically active fragments of a polypeptide according to the invention and includes those peptides capable of eliciting an immune response. In one embodiment, an immune response directed against *G. lamblia* is provided. The immune response can provide components (either antibodies or components of the cellular immune response (e.g., B-cells, helper, cytotoxic, and/or suppressor T-cells)) reactive with the biologically active fragment of a polypeptide, the intact, full length, unmodified polypeptide disclosed herein, or both the biologically active fragment of a polypeptide and the intact, full length, unmodified polypeptides disclosed herein. Biologically active fragments according to the invention comprise from five (5) amino acids to one amino acid less than the full length of any polypeptide sequence provided herein. Alternatively, fragments comprising 5, 6, 7, 8, 9, 10, 11, 12, 13, 14, 15, 16, 17, 18, 19, 20, 21, 22, 23, 24, 25, 30, 35, 40,45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, or 255 consecutive amino acids of a disclosed polypeptide sequence are provided herein.

Fragments, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be equally well prepared by chemical synthesis or using hosts transformed with an expression vector containing nucleic acids encoding polypeptide fragments according to the invention. The transformed host cells contain a nucleic acid and are cultured according to well-known methods; thus, the invention allows for the expression of these fragments, under the control of appropriate elements for regulation and/or expression of the polypeptide fragments.

Modified polypeptides according to the invention are understood to designate a polypeptide obtained by variation in the splicing of transcriptional products of the BIVM gene, genetic recombination, or by chemical synthesis as described below. Modified polypeptides contain at least one modification in relation to the normal polypeptide sequence. These modifications can include the addition, substitution, deletion of amino acids contained within the polypeptides of the invention.

In order to extend the life of the polypeptides of the invention, it may be advantageous to use non-natural amino acids, for example in the D form, or alternatively amino acid analogs, such as sulfur-containing forms of amino acids. Alternative means for increasing the life of polypeptides can also be used in the practice of the instant invention. For example, polypeptides of the invention, and fragments thereof, can be recombinantly modified to include elements that increase the plasma, or serum half-life of the polypeptides of the invention. These elements include, and are not limited to, antibody constant regions (see for example, U.S. Pat. No. 5,565,335, hereby incorporated by reference in its entirety, including all references cited therein), or other elements such as those disclosed in U.S. Pat. Nos. 6,319,691; 6,277,375; or 5,643,570, each of which is incorporated by reference in its entirety, including all references cited within each respective patent. Alternatively, the polynucleotides and genes of the instant invention can be recombinantly fused to elements that are useful in the preparation of immunogenic constructs for the purposes of vaccine formulation or elements useful for the isolation of the polypeptides of the invention.

The polypeptides, fragments, and immunogenic fragments of the invention may further contain linkers that facilitate the attachment of the fragments to a carrier molecule for the stimulation of an immune response or diagnostic purposes. The linkers can also be used to attach fragments according to the invention to solid support matrices for use in affinity purification protocols. In this aspect of the invention, the linkers specifically exclude, and are not to be considered anticipated, where the fragment is a subsequence of another peptide, polypeptide, or protein as identified in a search of protein sequence databases as indicated in the preceding paragraph. In other words, the non-identical portions of the other peptide, polypeptide, of protein is not considered to be a "linker" in this aspect of the invention. Non-limiting examples of "linkers" suitable for the practice of the invention include chemical linkers (such as those sold by Pierce, Rockford, Ill.), peptides which allow for the connection of the immunogenic fragment to a carrier molecule (see, for example, linkers disclosed in U.S. Pat. Nos. 6,121,424; 5,843,464; 5,750,352; and 5,990,275, hereby incorporated by reference in their entirety). In various embodiments, the linkers can be up to 50 amino acids in length, up to 40 amino acids in length, up to 30 amino acids in length, up to 20 amino acids in length, up to 10 amino acids in length, or up to 5 amino acids in length.

In other specific embodiments, the polypeptides, peptides, derivatives, or analogs thereof may be expressed as a fusion, or chimeric protein product (comprising the protein, fragment, analog, or derivative joined via a peptide bond to a heterologous protein sequence (e.g., a different protein)). Such a chimeric product can be made by ligating the appropriate nucleic acid sequences encoding the desired amino acid sequences to each other by methods known in the art, in the proper coding frame, and expressing the chimeric product by methods commonly known in the art (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli," J. of Experimental Biology* 203:19–28, The Co. of Biologists, Ltd., G.B.; Baneyx [1999] "Recombinant Protein Expression in *Escherichia coli," Biotechnology* 10:411–21, Elsevier Science Ltd.; Eihauer et al. [2001] "The FLAG™ Peptide, a Versatile Fusion Tag for the Purification of Recombinant Proteins," *J. Biochem Biophys Methods* 49:455–65; Jones et al. [1995] *J. Chromatography* 707:3–22; Jones et al. [1995] "Current Trends in Molecular Recognition and Bioseparation," *J. Chromatography A.* 707:3–22, Elsevier Science B. V.; Margolin [2000] "Green Fluorescent Protein as a Reporter for Macromolecular Localization in Bacterial Cells," *Methods* 20:62–72, Academic Press; Puig et al. [2001] "The Tandem Affinity Purification (TAP) Method: A General Procedure of Protein Complex Purification," *Methods* 24:218–29, Academic Press; Sassenfeld [1990] "Engineering Proteins for Purification," *TibTech* 8:88–93; Sheibani [1999] "Prokaryotic Gene Fusion Expression Systems and Their Use in Structural and Functional Studies of Proteins," *Prep. Biochem. & Biotechnol.* 29(1):77–90, Marcel Dekker, Inc.; Skerra et al. [1999] "Applications of a Peptide Ligand for Streptavidin: The Strep-tag", *Biomolecular Engineering*

16:79–86, Elsevier Science, B. V.; Smith [1998] "Cookbook for Eukaryotic Protein Expression: Yeast, Insect, and Plant Expression Systems," *The Scientist* 12(22):20; Smyth et al. [2000] "Eukaryotic Expression and Purification of Recombinant Extracellular Matrix Proteins Carrying the Strep II Tag", *Methods in Molecular Biology*, 139:49–57; Unger [1997] "Show Me the Money: Prokaryotic Expression Vectors and Purification Systems," *The Scientist* 11(17):20, each of which is hereby incorporated by reference in their entireties). Alternatively, such a chimeric product may be made by protein synthetic techniques, e.g., by use of a peptide synthesizer.

Another embodiment of the subject invention provides for the use of polypeptides encoded by the polynucleotides of the subject invention for the induction of an immune response or protective immunity in a subject to which the polypeptides are administered. In this aspect of the invention, compositions containing polypeptide are administered to a subject in amounts sufficient to induce an immune response, and/or induce protective immunity. The composition administered to the subject may, optionally, contain an adjuvant and may be delivered to the subject in any manner known in the art for the delivery of immunogen to a subject. Compositions may be formulated in any carriers, including for example, carriers described in E. W. Martin's *Remington's Pharmaceutical Science*, Mack Publishing Company, Easton, Pa.

The expression of the BIVM gene or BIVM gene product (e.g., DNA, RNA, or polypeptide) is dysregulated in a variety of cancers, tumors, and/or malignancies. Non-limiting examples of such cancers, tumors, and/or malignancies include prostate cancer, breast cancer, melanoma, chronic myelogenous leukemia, cervical cancer, adenocarcinomas, lymphoblastic leukemia, colorectal cancer, and lung carcinoma. Accordingly, the present invention provides a method for screening, or aiding in the diagnosis of, an individual suspected of having a malignancy or cancer. The subject invention provides methods comprising the steps of determining the amount of BIVM in a biological sample obtained from said individual and comparing the measured amount of BIVM to the amount of BIVM found in the normal population. The presence of a significantly increased amount of BIVM is associated with an indication of a malignancy or cancer. BIVM gene product can be detected by well-known methodologies including, and not limited to, Western blots, enzyme linked immunoassays (ELISAs), radioimmunoassays (RIAs), Northern blots, Southern blots, PCR-based assays, or other assays for the quantification of gene product known to the skilled artisan. This information, in conjunction with other information available to the skilled practitioner, assists in making a diagnosis.

The terms "comprising", "consisting of" and "consisting essentially of" are defined according to their standard meaning and may be substituted for one another throughout the instant application in order to attach the specific meaning associated with each term.

Following examples illustrate procedures for practicing the invention. These examples should not be construed as limiting. All percentages are by weight and all solvent mixture proportions are by volume unless otherwise noted.

EXAMPLE 1

Identification of BIVM

Human BIVM was identified originally as an EST (IMAGE #785450; GenBank AA449273) that encodes the two short motifs WFRQ (motif 2 [M2]) and YFC (motif 3a [M3a]), which correspond to framework region 2 (FR2) and FR3 of an Ig V domain, respectively (Barclay, A. N., et al. [1997] *The Leucocyte Antigen FactsBook*, Academic Press, San Diego). The W in M2 and C in M3a correspond to $W^{41}$ and $C^{104}$ of the IMGT numbering system. Complete sequencing of this EST, overlapping ESTs (IMAGE #2184889, GenBank AI538125; IMAGE 136117, GenBank R33273; IMAGE 1060823, GenBank AA568610; and IMAGE 785450, GenBank AA449273) and RACE strategies were used to resolve the complete mRNA sequence.

Human BIVM mRNA is 3857 nucleotides and encodes a 503 amino acid protein (FIG. 1). No proteins with significant identities (E<0.01) to BIVM have been identified using BLAST analyses. Searches of current motif databases (BLOCKS, PRINTS, Conserved Domain Database, Domain Architecture Retrieval Tool, Simple Modular Architecture Research Tool) also failed to identify any additional significant motifs within the BIVM protein.

In addition to the shared M2 and M3a motifs, a second V domain FR3 motif, YHC (M3b), is located several residues amino terminal of M3a. Furthermore, a putative FR1 motif (M1), encoding the conserved V domain residues $G^{16}$ and $C^{23}$ (IMGT amino acid numbering), was identified by visual inspection of BIVM peptide sequences (FIG. 1).

The 42 amino acids between M1 and M2 in BIVM are inconsistent with the sequence relationship in a V region in which the corresponding motifs would be separated by no more than 12 residues. This increased distance between $C^{23}$ and $C^{104}$ of M1 and M3a (or M3b), which normally form a disulfide bridge and stabilize the Ig domain architecture, strongly suggests that BIVM is not a member of the IgSF. Since these peptide motifs are extremely short, it could be argued that their presence in BIVM may be a random occurrence. However, it should be emphasized that in the original search of the EST database, only 17 sequences were identified that encode W(Y/F)R(Q/H) and YFC that are correctly spaced and maintain an open reading frame. Of these 17 sequences, 16 were TCR cDNAs (encoding WYRQ) and one was BIVM (encoding WFRQ) (Hawke, N. A., et al. [1999] "Expanding Our Understanding of Immunoglobulin, T-cell Antigen Receptor, and Novel Immune-Type Receptor Genes: a Subset of the Immunoglobulin Gene Superfamily," *Immunogenetics* 50:124–133).

EXAMPLE 2

Genomic Organization of BIVM

GeneBridge 4 radiation hybrid panel mapping (Gyapay, G., et al. [1996] "A Radiation Hybrid Map of the Human Genome," *Hum Mol Genet* 5:339–346) localized BIVM on chromosome 13q32–33 (data not shown). Examination of the publicly available Human Genome Project database revealed the exon-intron structure of BIVM. A 5' truncated BIVM sequence (hypothetical protein FLJ20159) was initially placed on the publicly available human genome map at 13q14–q21. The 5' untranslated region of BIVM consists of two separate exons (designated exons A and B), followed by the coding region consisting of nine exons; the exon/intron boundaries are indicated in Table I.

Inspection of genomic sequence localizes BIVM between ERCC5 and "hypothetical protein" MGC5302, a human ortholog of the gene encoding the mouse protein Kdel1/EP58 (Kimata, Y., et al. [2000] "Identification of a Novel Mammalian Endoplasmicreticulum-Resident KDEL Protein Using an EST Database Motif Search," *Gene* 261:321–327).

A CpG island is located in the 5' untranslated region of BIVM; the 3' untranslated region contains an Alu sequence (FIGS. 1 and 2). The Alu polyA sequence in the 3' untranslated region leads to the spurious production of 3' truncated cDNAs including many that are represented as ESTs.

Multiple 5' untranslated region splice variants were observed in analysis of 5' RACE products. Specifically, exon A has at least 3 splice donor sequences and exon B, which has a poor splice acceptor sequence, can be absent from the mature transcript (FIGS. 1 and 2; Table I). In addition, it is likely that multiple transcriptional start sites are present (FIG. 1).

EXAMPLE 3

BIVM is Highly Conserved within Deuterostome Species

BIVM orthologs were identified in: mouse, chicken, Xenopus and zebrafish in order to address its potential phylogenetic conservation, as well as to define conserved motifs potentially relevant to function. In addition, a partial sequence for a BIVM ortholog was identified in sea urchin. The identity of the human BIVM protein to these orthologs ranges from 35–87% overall and is consistent with the phylogenetic relationships of the species considered (FIG. 3; see below). The C-terminal region of BIVM shares the highest degree of interspecific sequence identity. The N-terminus of this peptide domain is RK(V/C)LD and the C-terminus is GGNLHC. This region includes all of the V domain motifs, and is 220 amino acids in human (indicated by arrowheads in FIG. 3).

The corresponding domains in mouse, chicken, Xenopus, zebrafish and sea urchin are 97%, 91%, 91%, 87% and 64% identical to the human domain, respectively. In addition, BIVM ESTs have been identified from an ascidian, sea squirt (*Halocynthia roretzi*) (e.g., GenBank AV385966), and a BIVM cDNA fragment has been isolated from a protochordate (cephalochordate), lancelet (*Branchiostoma floridae*), using an RT-PCR strategy (Yoder and Litman, GenBank AF411393). Their sequences within this domain are highly conserved.

EXAMPLE 4

Close Physical Linkage of BIVM and EP58/MGC5302

Human BIVM maps between EP58/MGC5302 and ERCC5 on 13q. The human EP58 EST (that extends most 5'), places the transcriptional start sites of EP58 and BIVM only 41 bp apart. We identified a mouse BIVM genomic clone (from a ë FixII library), which also encodes the 5' end of Ep58/Kdel1 (FIG. 4). The mapping position of Ep58/Kdel1 and BIVM in mouse has not yet been determined. The tight physical linkage of the EP58 to BIVM (41 bp in human and 224 bp in mouse) is consistent with a shared regulatory control system that functions in opposite directions (FIG. 4). Notably, both Ep58 and BIVM appear to be ubiquitously expressed (FIG. 5) (Kimata, Y., et al. [2000] "Identification of a Novel Mammalian Endoplasmicreticulum-Resident KDEL Protein Using an EST Database Motif Search," *Gene* 261:321–327). Finally, zebrafish BIVM has been mapped to linkage group 6 (LG6); however, its linkage relationship to kdel1 is unknown.

EXAMPLE 5

Expression of Human BIVM

The human BIVM transcript is ~3.8 kb and appears to be expressed ubiquitously; the highest relative levels of expression are in spleen, ovary, small intestine, colon, peripheral leukocytes and liver (FIG. 5A). Additional RNA dot blot analyses indicate expression of BIVM in human testes, ovary, aorta, appendix, trachea, pituitary gland, bladder, uterus, spinal cord, salivary gland, stomach, mammary gland and bone marrow as well as in several fetal tissues (data not shown). Notably, BIVM expression was not detected in fetal spleen, adult thymus and certain cancer cell lines (e.g., promyelocytic leukemia, HL-60, and Burkitt's lymphoma Raji) while significant expression was evident in other lines (e.g., HeLa, S3, and colorectal adenocarcinoma, SW480).

EXAMPLE 6

Expression of BIVM in Other Species

The predominant mouse BIVM transcript also is 3.8 kb (FIG. 5B), of which ~3.3 kb have been sequenced. Comparisons of 5' mouse BIVM RACE products indicate that the 5' untranslated region undergoes alternative RNA splicing, which, like in the human gene, does not affect the coding sequences. The highest levels of expression of mouse BIVM are in heart, brain, liver and kidney (FIG. 5B).

A major difference between the expression of human and mouse BIVM is observed in the spleen, in which expression is high in the human but appears to be minimal in the mouse. In the developing mouse embryo, BIVM expression is detected at a uniform level after gastrulation (FIG. 5B). An ~2.1 kb XBIVM cDNA was identified in *Xenopus* that is consistent with the length of the predominant transcript observed in RNA blotting (FIG. 5C). The broad, diffuse nature of the principal hybridizing band could reflect sequence heterogeneity. The nature of the larger transcript (~4.4 kb) is unknown. Northern blot analysis of sea urchin RNA detects two SpBIVM transcripts of ~7.4 and 8 kb (FIG. 5D), which are notably longer than the human and mouse forms. The additional sequence in these transcripts might be a result of additional 5' or 3' untranslated regions and/or could reflect polyadenylation effects. Extended 3' untranslated regions are encountered frequently with sea urchin mRNA.

Figure 5F:
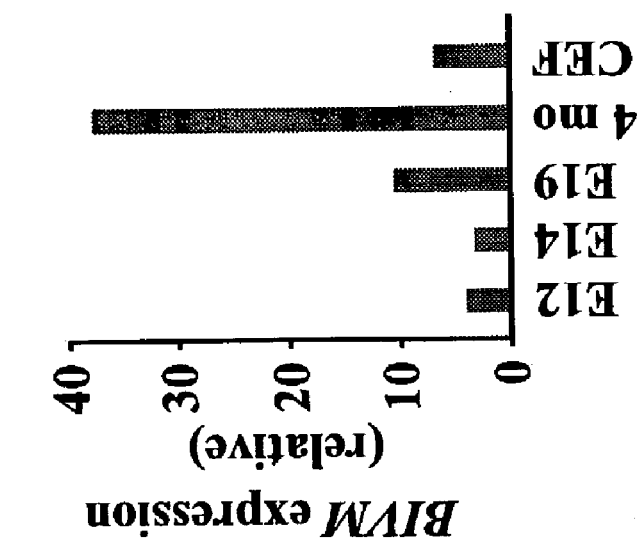
Figure 5E:
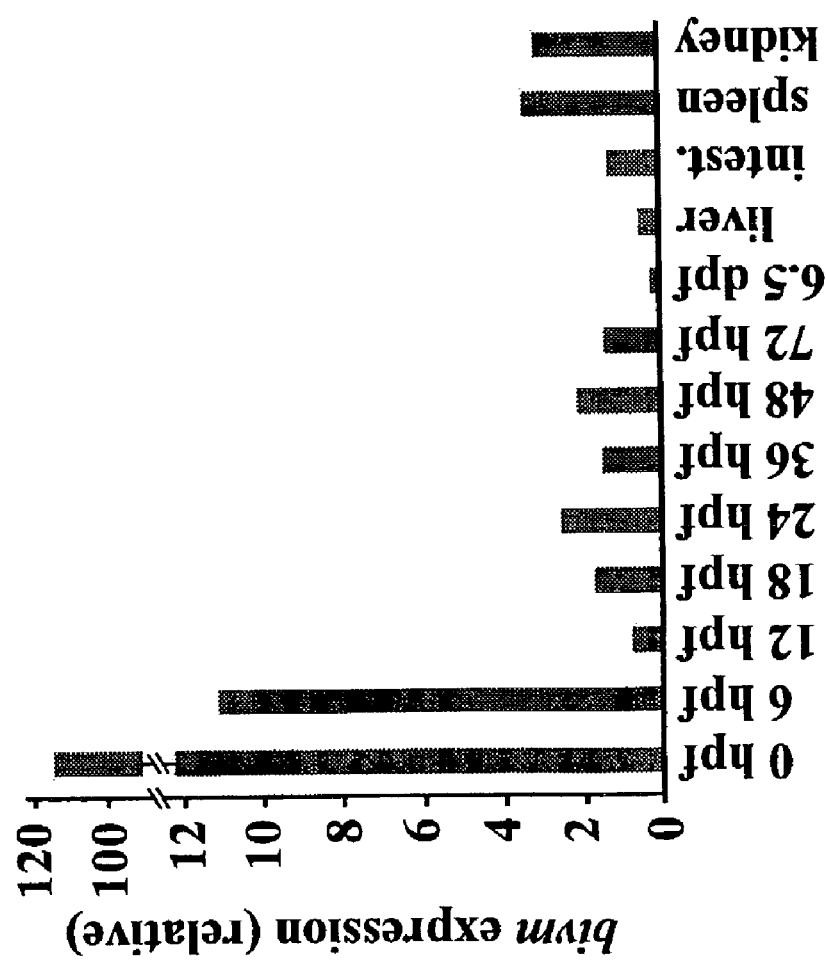

Real-time PCR was used to analyze BIVM expression levels throughout development in zebrafish (FIG. 5E). As observed in *Xenopus* and sea urchin, there is a large maternal store of BIVM transcript in the 1-cell embryo (0 hpf in zebrafish) which appears to be quickly lost after the initial cellular division(s). In zebrafish, the level of BIVM expression drops by ~90% within the first 6 hours of life (midgastrula stage) and is comparatively undetectable by 12 hpf (post-gastrula stage). Although comparable stages of development were not examined in mouse (see above), it is likely that this early embryonic regulation of BIVM expression will be conserved.

We noted BIVM expression in chicken bursa, which serves as the primary site of B lymphocyte differentiation. BIVM expression in chicken bursa decreases slightly between embryonic day 12 and day 14, increases significantly at day 19, and is the highest in the 4 month old chicken bursa, in which levels are 6-fold greater than observed in embryonic fibroblasts (CEFs; FIG. 5F). Expression of BIVM in other tissues in chicken has not been characterized.

EXAMPLE 7

BIVM Encodes a Nuclear/Cytoplasmic Protein

Figure 6A:
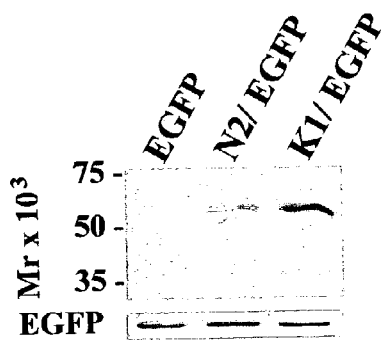
Figure 6B:
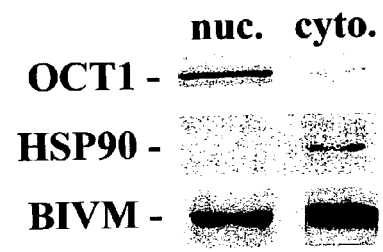
Figures 6C, 6D, 6E, 6F:
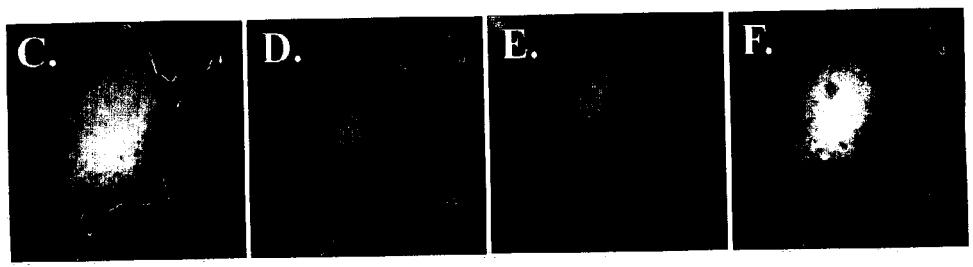
Figures 6G, 6H, 6I, 6J:
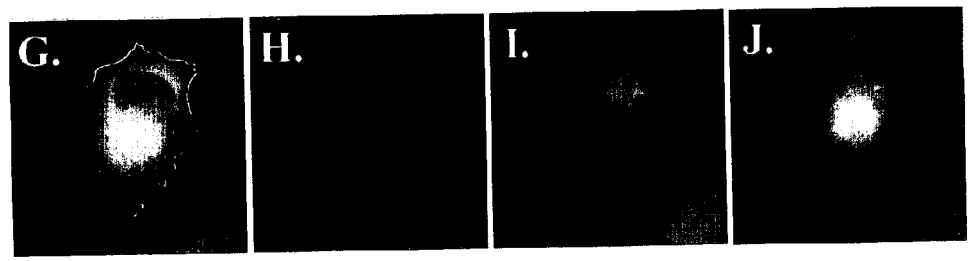

The relatively high predicted pI of BIVM (9.1) suggests that it may bind other proteins and/or DNA (or other nucleic acids). The levels of BIVM produced from the native pBIVM-N2 construct and modified pBIVM-K1 construct (see Methods) were compared in whole cells lysates from transiently transfected Cos7 cells. BIVM levels are higher in cells transfected with the modified pBIVM-K1 (FIG. 6A), which was used in all subsequent transfection experiments. It should be noted that the size of this recombinant protein (with C-terminal epitope tags) is ~61 KDa, whereas the native protein (without post-translational modifications) is predicted to be ~57 kDa. The observation that a single protein is generated from this transcript argues that translation does not begin at a more 3' ATG as suggested by the "hypothetical protein" FLJ20159 GenBank entries (which are predicted to encode a ~27 kDa protein). Western analysis using antibodies that recognize the V5 peptide sequence indicate that the epitope-tagged BIVM is present both in cytoplasmic and nuclear fractions (FIG. 6B). These results were confirmed by direct immunohistochemical localization of BIVM in the cytoplasm and nucleus (FIG. 6C-J). Variation in the relative amounts of BIVM in the nucleus was observed in individual cells. Thus, it is possible that the BIVM protein enters and exits the nucleus in a regulated or cell-cycle-dependent manner.

EXAMPLE 8

*Giardia* may have Acquired a BIVM Ortholog by Horizontal Gene Transfer

Figure 7C:
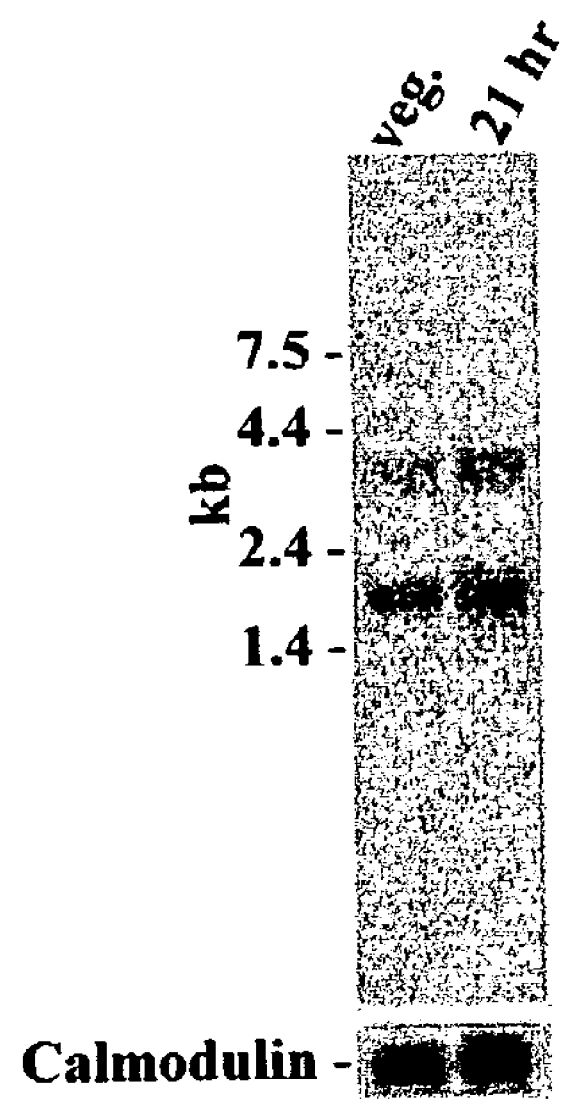

A tBLASTn search identified a BIVM-like gene (named BIVML) in the genome of the primitive protozoan parasite, *Giardia lamblia* (McArthur, A. G., et al. [2000] "The *Giardia* Genome Project Database," *FEMS Microbiol Lett* 189:271–273). The 2045 nucleotide BIVML cDNA is predicted to encode a 270 amino acid protein (predicted MW ~30 kDa; Pi=7.56) with no predicted signal peptide, membrane spanning regions or nuclear localization signal- thus, it is likely to be cytosolic. BIVML contains 17 cysteine residues (6.2%) throughout the protein (FIG. 7A). Known giardial proteins that are secreted to the trophozite surface or the cyst wall are also highly cysteine rich. This sequence is 22–25% identical and 46–49% similar to the carboxyl-terminal region of all deuterostome BIVM peptides described here, correlates directly with the conserved domain described above, and includes the M2 and M3b motifs (FIG. 7B). Northern analysis detects an ~2.0 kb BIVML transcript as well as a larger transcript of unknown identity in both vegetatively growing and encysting cells (FIG. 7C).

BIVML is unusual in having long untranslated regions consistent with the size of the transcript. The 5' and 3' untranslated regions were determined by RACE and are 229 nucleotides and 983 nucleotides, respectively (FIG. 7A). most transcripts of giardial chromosomal genes characterized to date have very short (<20 nucleotides) untranslated regions, although exceptions are being noted.

The identification of a BIVM ortholog in such an early branching eukaryote was unexpected since tBLASTn searches of the currently available *S. cerevisiae* and *Drosophila* as well as *S. pombe* and *C. elegans* genome databases failed to identify any sequences exhibiting significant identity to BIVM. Furthermore, it has not been possible to identify BIVM-like sequences in the complete genomes of *Campylobacter jejuni* (Parkhill, J., et al. [2000] "Complete DNA Sequence of a Serogroup A Strain of *Neisseria Meningitidis* Z2491," *Nature* 404:502–506), *Mycobacterium leprae* (Cole, S. T., et al. [2001] "Massive Gene Decay in the Leprosy Bacillus," Nature 409:1007–11), *Mycobacterium tuberculosis* (Cole, S. T., et al. [1998] "Deciphering the Biology of *Mycobacterium* Tuberculosis from the Complete Genome Sequence," *Nature* 393:537–544), or *Neisseria menigitidis* (Parkhill, J., et al. [2000] "The Genome Sequence of the Food-Borne Pathogen *Campylobacter Jejuni* Reveals Hypervariable Sequences," *Nature* 403:665–668). In DNA hybridization studies, a *Giardia* BIVML probe failed to cross-hybridize to *Trichomonas foetus, Trichomonas vaginalis* or *Entamoeba histolytica* genomic DNA (data not shown).

The identification of a BIVM-like gene in the *Giardia* genome, but not in other similar proteostome genomes, taken together with the fact that *Giardia* is parasitic, suggests that BIVML may have been acquired via horizontal gene transfer from a higher eukaryotic host.

EXAMPLE 9

Physical Linkage of Human and Mouse BIVM to the EP58/MGC5302-EP58/Kdel1 Gene The transcriptional start site of the human EP58/MGC5302 sequence (GenBank XM_015844) is only 41 bp from that of BIVM; BIVM and EP58 genes are in a head-to-head orientation, in opposite transcriptional orientation. The mouse EP58/Kdel1 and BIVM genes share the same physical orientation separated by 224 bp. This exceedingly tight physical linkage and close spacing of BIVM and EP58 suggests that common regulatory elements located in or near the intergenic region potentially control the expression of both genes. RT-PCR analysis of extracts from BIVM expressing and non-expressing human cell lines indicated that EP58/MGC5302 was expressed in all cell lines that express BIVM but not in the BIVM non-expressing cell line, Raji (FIG. 8). Based on these results, it is possible that these genes are co-regulated and that the transacting factors associated with the 41 bp intergenic region linking these genes control their expression.

EXAMPLE 10

DNA Binding Activity on the BIVM-EP58/MGC5302 41 bp Intergenic Region

A MatInspector V2.2 search for potential binding sites contained in the 41 bp region separating the BIVM and EP58/MGC5302 genes revealed sites for cell type specific factors such as the myeloid zinc finger-1 (MZF-1), the hematopoietic-expressed Ikaros-2 (IK2) factor, and the ubiquitously expressed transcription factors NF1, USF, NFκB, and NMYC (FIG. 9). Nearly identical sites also were predicted for the mouse 224 bp Bivm-Kdel1 intergenic region. MZF-1 and IK2 are expressed in the K562 human erythroleukemia cell line and IK2 is expressed in the Raji Burkitt's lymphoma cell line. Based on this information, electrophoretic mobility shift assays (EMSAs) were performed to compare protein binding to the 41 bp region in nuclear extracts from BIVM expressing and non-expressing cells (FIG. 10).

MZF-1 and IK2-specific binding would be expected to produce unique bands in the K562 and Raji nuclear extracts that are not observed in nuclear extracts from non-lymphoid cell lines. In addition, an NFκB consensus sequence was used as probe and competitor (Santa Cruz Biotechnology) to detect bands representing NFκB-specific binding that may be constitutively present in the nuclear extracts (FIG. 10). Significant DNA binding activity was observed with the 41 bp BIVM-specific probe in all extracts assayed, producing 1 minor band and two major bands (FIG. 10; Lanes 4–10), one of which was competed by the addition of cold NFκB-specific probe, indicating that NFκB complexes may be present (FIG. 10; Lane 3). One major band was detected with the NFκB consensus probe in the nuclear extracts from BIVM expressing lines (FIG. 10; Lanes 13–17) that was competed by the BIVM-specific probe (FIG. 10; Lane 11). An additional complex also was observed bound to the NFκB-specific probe in the extracts from a BIVM non-expressing line (FIG. 10; Lane 18). Together these results show that the 41 bp BIVM-EP58/MGC5302 intergenic region supports DNA binding activity and that the bound complexes include factors that also bind the NFκB consensus probe. Similar DNA binding activity was observed in the BIVM non-expressing Raji cell line as in the BIVM expressing cells and may result from constitutive nuclear NFκB factors and suggests either that additional flanking regions function in BIVM gene regulation or that protein co-factors or other mechanisms, such as methylation-dependent promoter silencing, could play a role in BIVM expression. The presence of a CpG island 5' of the BIVM gene, together with the lack of both BIVM and EP58/MGC5302 expression in the Raji cell lines, supports the latter hypothesis.

EXAMPLE 11

Regulation of BIVM Expression by TNF-α or Other Inducing Agents

As described above, the 41 bp intergenic region contains putative sites for ubiquitous transacting factors and an NFκB site that appears to be bound by NFκB complexes containing c-Rel and RelB factors, which are constitutively present in the nuclear extracts from the BIVM expressing K562 cell line (FIG. 11). NFκB comprises a large family of transcription factors, most of which are sequestered in the cytoplasm through inhibitor binding. Activation of the cell by various agents, such as the proinflammatory cytokine TNF-α, leads to phosphorylation-induced degradation of the inhibitor and nuclear translocation of additional NFκB transacting factors. Although constitutive factors may drive basal BIVM expression, TNF-α activated NFκB increases the expression of BIVM in the BIVM-expressing HeLa cell line (DNS). Furthermore, a cell line devoid of basal BIVM expression, the Raji Burkitt's lymphoma line, is induced to express BIVM by TNF-α (FIG. 12). The specific TNF-α activated factors associated with the BIVM promoter can be defined using antibody shift assays.

EXAMPLE 12

Characteristics of Recombinant BIVM Protein

The BIVM encoded protein has a high proportion of lysine and arginine residues and a predicted isoelectric point (pI) of 9.1. The net positive charge under physiological conditions suggests that BIVM may interact with other proteins and/or DNA. Western blot analysis and cytoimmunofluorescence studies utilizing transfected, epitope-tagged BIVM expression constructs revealed that BIVM is present in both cytoplasmic and nuclear fractions. Variation in the relative amounts of nuclear recombinant BIVM was observed in individual cells and may reflect regulated or cell cycle-dependent BIVM nuclear import/export. The Cos7 cells that have been transformed stably with BIVM exhibit a decreased cell doubling time compared to untransformed Cos7 cells, suggesting the potential role for BIVM in cell cycle regulation. Furthermore, preliminary studies of Cos7 BIVM stable transformants stained with a nuclear stain (DAPI) reveal a high proportion of cells containing multiple nuclei compared to untransformed cells. Flow cytometer analyses of these cells stained with propidium iodide indicate that ~90% of the cells contain tetraploid or greater DNA content, consistent with the presence of multiple nuclei (FIG. 13; Panel 3). This phenomenon was not observed in a G418-resistant, BIVM-revertant cell line, which has lost expression of recombinant BIVM and exhibits both a nuclear morphology and a diploid DNA content similar to that of the untransformed parental line (FIG. 13; Panels 1 & 2).

EXAMPLE 13

Identification of BIVM Protein Binding Partners

The high proportion of lysine and arginine residues and the net charge of the protein (pI 9.1) suggest that BIVM may interact with proteins and/or DNA (or other nucleosides). Specifically, protein-protein interactions are being assayed using the BacterioMatch two hybrid system (Stratagene). This system provides a rapid, selective approach to identify BIVM-specific protein interactions in vivo. Mouse Bivm has been utilized initially as we can take advantage of mouse cDNA libraries that are commercially available for this system (Stratagene) and because the results obtained can be used to complement concurrent BIVM knock out mice studies now underway in our laboratory. Although it is possible that BIVM may function differently in human and mouse, the 87% sequence conservation between human and mouse BIVM protein, strong synteny in BIVM flanking genes, and the tight physical linkage observed between the BIVM and EP58 genes, is consistent with functional equivalence.

EXAMPLE 14

Materials and Methods

EXAMPLE 14A

General Methods

RNA was isolated with RNAzol B (Teltest, Friendswood, Tex.) or Trizol (Gibco BRL, Rockville, Md.). Mouse genomic DNA (ë FixII) and liver cDNA (ë ZAPII) libraries were screened using standard procedures (Strong, S. J., et al. [1999] "A Novel Multigene Family Encodes Diversified Variable Regions," *Proc Natl Acad Sci USA* 96:15080–15085). DNA sequencing and the analysis of DNA sequences were carried out as described previously (Rast, J. P. et al. [1994] "T Cell Receptor Gene Homologs are Present in the Most Primitive Jawed Vertebrates," *Proc. Natl. Acad. Sci. USA* 91:9248–9252). Alignments were constructed using ClustalW 1.8. Identity relationships were examined using BLAST and ALIGN software. Rapid amplification of cDNA ends (RACE) utilized a standard protocol (Mertineit, C., et al. [1998] "Sex-Specific Exons Control DNA Methyltransferase in Mammalian Germ Cells," *Development* 125:889–897) or the GeneRacer kit (Invitrogen, Carlsbad, Calif.). The RNA sources for RACE were: human HeLa cells, mouse liver, chicken bursa, *Xenopus laevis* liver, zebrafish (*Danio rerio*) liver, 15 hpf sea urchin (*Strongylocentotus purpuratus*) embryos, and vegetative-stage *Giardia lamblia*.

EXAMPLE 14B

Genomic Mapping

Human BIVM was mapped using HSMAP5 (CCATGC-CTCTCTACTACTCACTCCCAACAC) and HSMAP6 (GGTAAGAAGAACACCATTGTGTTTGAAGGC) intronic primers (which correspond to sequence between exon 8 and 9) and the GeneBridge 4 radiation hybrid (RH) panel (Gyapay, G., et al. [1996] "A Radiation Hybrid Map of the Human Genome," *Hum Mol Genet* 5:339–346) (Research Genetics, Huntsville, Ala.). Zebrafish BIVM (see below) was mapped using the zfBIVMMAPF1 (CAATGC-CTAACACTGTGGAAAGTGAAGGCG) and zfBIVM-MAPR1 (GATAACTGTCGAGCTCGGTTGAGCAGGGC) primers and the T51 RH panel (Glusman, G., et al. [1996] "Sequence Analysis in the Olfactory Receptor Gene Cluster on Human Chromosome 17: Recombinatorial Events Affecting Receptor Diversity," *Genomics* 37:147–160) (Research Genetics). Additional gene mapping data were derived from the Human-Mouse Homology Map and the Mouse Genome Informatics Database (Blake, J. A., et al. and Mouse Genome Database Group [2001] "The Mouse Genome Database(MGD): Integration Nexus for the Laboratory Mouse," *Nucleic Acids Res* 29:91–94).

EXAMPLE 14C

Identification of BIVM Orthologs

Mouse BIVM Partial sequence of the mouse BIVM gene was obtained by screening a mouse genomic library with a human BIVM cDNA probe. A mouse BIVM cDNA was recovered by screening a liver cDNA library with a probe corresponding to mouse exon 6.

Chicken BIVM tBLASTn searches using the human BIVM sequence identified a chicken (*Gallus gallus*) bursal EST (GenBank AJ399198) encoding an avian ortholog (BIVM). RACE strategies identified a complete open reading frame cDNA. A single RNA-splicing variant, which encodes an additional 23 amino acids, also has been sequenced (GenBank AF411388; data not shown).

*Xenopus* XBIVM Partial *Xenopus laevis* XBIVM sequence was identified as an oocyte EST (GenBank BF047666) using tBLASTn searches with the human BIVM sequence. RACE strategies resolved a complete open reading frame cDNA.

Zebrafish BIVM Touchdown PCR (Don, R. H., et al. [1991] "'Touchdown' PCR to Circumvent Spurious Priming During Gene Amplification," *Nucleic Acids Res* 19:4008) and nested degenerate primers, designed with CODE-HOP software (Rose, T. M., et al. [1998] "Consensus-Degenerate Hybrid Oligonucleotide Primers for Amplification of Distantly Related Sequences," *Nucleic Acids Res* 26:1628–35), were used to amplify BIVM cDNA fragments from zebrafish liver. Primers for the primary PCR were designed to amplify the coding sequence between the amino acid motifs GNT-TLMWRF and YFCPIGFEA; primers for the nested PCR were designed to amplify the sequence between motifs WFRQINDHF and YRHQNHYFCP. PCR products of the expected size were gel purified, cloned and sequenced. Full-length clones were derived by RACE.

Sea urchin SpBIVM A fragment of the sea urchin SpBIVM cDNA was recovered from 20 hpf embryo cDNA using nested PCR as described for zebrafish. RACE strategies identified a 1,899 nucleotide coding region that corresponds to the complete open reading frame of BIVM from other species; as of yet it has not been possible to identify a stop codon.

*Giardia lamblia* BIVM-like The *Giardia lamblia* BIVML sequence was initially identified with a tBLASTn search of the High Throughput Genomic (HTGS) database with the human BIVM sequence. BIVML is encoded in four overlapping genomic clones (clone KJ1556, GenBank #AC049185; clone MJ4898, GenBank AC083097; clone EJ2770, GenBank #AC038625; and clone K10613, GenBank #AC046875). RACE was used to identify the complete, 2,045 nucleotide cDNA.

EXAMPLE 14D

Transient Transfections

The coding region of human BIVM was cloned into pcDNA3.1/V5-His TOPO (Invitrogen) in order to generate pBIVM-N2, which encodes a BIVM-V5 fusion protein (the V5 epitope is at the C terminus). A similar construct, pBIVM-K1, was generated in which the translational start sequence was modified in order to increase protein synthesis, as described in Kozak, M. [1996], "Interpreting cDNA Sequences: Some Insights from Studies on Translation," *Mamm. Genome* 7:563–574. Both of these constructs were then subcloned into pIRES2-EGFP (Clontech, Palo Alto, Calif.) to create pBIVM-N2/EGFP and pBIVM-K1/EGFP, which produced recombinant BIVM and EGFP from the same plasmid. Cos7 cells (~60% confluent) were transiently transfected with expression constructs using the GENE-JAMMER™ transfection reagent according to manufacturer's instructions (Stratagene, La Jolla, Calif.).

EXAMPLE 14E

Western Blots

Whole cell lysates were prepared from transfected cells in the presence of 1× Protease Inhibitor Cocktail Set III (Calbiochem, San Diego, Calif.) essentially as recommended by Santa Cruz Biotechnology. Nuclear and cytoplasmic extracts were prepared from transfected cells essentially as described in Yu, C. L., et al. [1995] "Enhanced DNA-Binding Activity of a Stat3-Related Protein in Cells Transformed by the Src Onco Protein," *Science* 269:81–83. Protein concentrations were determined using Protein Assay Reagent (Bio-Rad, Hercules, Calif.). Whole cell, nuclear, and cytoplasmic extracts were separated by SDS-polyacrylamide gel electrophoresis (10% polyacrylamide), transferred to Immobilon P filters (Millipore, Bedford, Mass.) and blocked prior to incubation with mouse anti-V5 monoclonal antibody (Invitrogen), anti-OCT1 polyclonal antibody (Santa Cruz) or anti-HSP90 monoclonal antibody (StressGen Biotechnologies Corp, Victoria, BC, Canada). Following incubation with alkaline phosphatase-conjugated secondary antibodies, reactive proteins were detected using Western Blue Stabilizer Substrate (Promega, Madison, Wis.).

EXAMPLE 14F

Immunohistochemistry

Transfected Cos7 cells were fixed for 15 minutes with 3% paraformaldehyde, permeabilized in 1% Triton-X 100, incubated with primary antibodies, washed and incubated with secondary antibodies and 2 µg/ml Hoechst 33258. Primary antibodies included a mouse anti-V5 monoclonal antibody and an anti-actin polyclonal antibody (ICN Pharmaceuticals, Inc., Costa Mesa, Calif.) that were detected with a Cy2-conjugated, anti-mouse antibody (Jackson Immuno Research Laboratories, West Grove, Pa.) and a Cy3-conjugated, anti-rabbit antibody (Sigma, St. Louis, Mo.), respectively.

EXAMPLE 14G

RNA Blots

Multiple Tissue Northern (MTN™) blots (human and mouse) were obtained from Clontech. In addition, 10 µg of *Xenopus*, sea urchin and *Giardia lamblia* total RNA were subjected to electrophoresis through 1.2% agarose, 2.2 M formaldehyde gels and transfer to nylon membranes (Zetaprobe™-GT; BioRad). RNA blots were hybridized with radiolabeled probes in Expresshyb ™ (Clontech). The *Giardia* RNA blot was hybridized with single strand-specific probes as described in Knodler, L. A., et al. [1999] "Developmental Gene Regulation in *Giardia Lamblia*: First Evidence for an Encystation-Specific Promoter and Differential 5' mRNA Processing," *Mol Microbiol* 2:327–340. Blots were stripped and reprobed with actin, 18S rRNA or *Calmodulin* probes.

EXAMPLE 14H

Quantitative PCR

Real time PCR analysis detected BIVM expression from chicken bursa and zebrafish embryos and tissues using a GeneAmp 5700 Sequence Detection System (PE Biosystems, Foster City, Calif.) with SYBR Green detection. Each PCR series was done in triplicate. The relative expression levels were determined for each transcript from plasmid standards that were included in each experiment and normalized to the expression of SI17 rRNA (chicken bursa) or S26 rRNA (zebrafish) levels.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An isolated or recombinant polynucleotide:
   a) comprising SEQ ID NO: 1;
   b) comprising a polynucleotide sequence complementary to a polynucleotide sequence comprising SEQ ID NO: 1;
   c) comprising a fragment of SEQ ID NO: 1 that spans i) nucleotides 1446 to 1697, or ii) nucleotides 1446 to 1698;
   d) comprising a polynucleotide encoding a polypeptide comprising the amino acid sequence of SEQ ID NO: 2;
   e) comprising a vector comprising a polynucleotide sequence as set forth in 1a), 1b), 1c), or 1d);
   f) comprising a promoter operably linked to a polynucleotide sequence as set forth in 1a), 1b), 1c), or 1d);
   g) comprising a polynucleotide as set forth in 1a), 1b), 1c), or 1d) and a detectable label; or
   h) comprising a polynucleotide as set forth in 1a) 1b), 1c), or 1d) and a heterologous polynucleotide sequence encoding a heterologous polypeptide sequence.

2. A composition comprising culture media and a transformed host cell comprising a polynucleotide sequence according to claim 1.

3. The composition according to claim 2, wherein said host cell is selected from the group consisting of Gram negative bacterial cells, Gram positive bacterial cells, yeast cells, animal cells, plant cells, and insect cells.

4. A method of detecting the presence of the BIVM gene comprising:
   a) contacting a sample suspected of containing the BIVM gene with a polynucleotide according to claim 1 under conditions that allow for the formation of a hybrid comprising the BIVM gene and a polynucleotide according to claim 1; and
   b) detecting the formation of said hybrid, wherein the formation of a hybrid is indicative of the presence or differential expression of the BIVM gene in said sample and the absence of the formation of a hybrid is indicative of a sample lacking said BIVM gene.

5. The method according to claim 4, wherein said sample is a biological or environmental sample.

6. The method according to claim 4, wherein said method is selected from the group consisting of Southern blots, Northern blots, enzymatic gene amplification and methods utilizing DNA chips.

7. The isolated or recombinant polynucleotide according to claim 1, wherein said polynucleotide comprises the polynucleotide sequence of SEQ ID NO; 1.

8. The isolated or recombinant polynucleotide according to claim 1, wherein said polynucleotide comprises a polynucleotide sequence complementary to the polynucleotide sequence of SEQ ID NO: 1.

9. The isolated or recombinant polynucleotide according to claim 1, wherein said polynucleotide comprises a fragment of SEQ ID NO: 1 that spans i) nucleotides 1446 to 1697, or ii) nucleotides 1446 to 1698.

10. The isolated or recombinant polynucleotide according to claim 1, wherein said polynucleotide encodes a polypeptide comprising the amino acid sequence of SEQ ID NO:2.

11. The isolated or recombinant polynucleotide according to claim 1, wherein said polynucleotide comprises a vector comprising a polynucleotide sequence as set forth in claim 1a), 1b), 1c), or 1d).

12. The isolated or recombinant polynucleotide according to claim 1, wherein said polynucleotide comprises a promoter operably linked to a polynucleotide sequence as set forth in claim 1a), 1b), 1c), or 1d).

13. The isolated or recombinant polynucleotide according to claim 1, wherein said polynucleotide as set forth in claim 1a), 1b), 1c), or 1d) further comprises a detectable label.

14. The isolated or recombinant polynucleotide according to claim 1, wherein said polynucleotide as set forth in 1a), 1b), 1c), or 1d) further comprises a heterologous polynucleotide sequence encoding a heterologous polypeptide sequence.

15. The polynucleotide according to claim 10, wherein said polynucleotide comprises nucleotides 680 through 2188 of SEQ ID NO1.

UNITED STATES PATENT AND TRADEMARK OFFICE
CERTIFICATE OF CORRECTION

| | |
|---|---|
| PATENT NO. | : 7,038,030 B2 |
| APPLICATION NO. | : 10/417476 |
| DATED | : May 2, 2006 |
| INVENTOR(S) | : Gary W. Litman et al. |

It is certified that error appears in the above-identified patent and that said Letters Patent is hereby corrected as shown below:

Column 9,
Line 53, "Thompson et *Nucleic*" should read --Thompson *et al.* [1994] *nucleic*--.

Column 21,
Line 42, "signal- thus" should read --signal; thus--.

Column 28,
Line 12, "SI17 rRNA" should read --S17 rRNA--.

Column 217,
Line 6, "SEQ ID NO1" should read --SEQ ID NO:1--.

Signed and Sealed this

Eighth Day of August, 2006

JON W. DUDAS
*Director of the United States Patent and Trademark Office*